United States Patent
Brown et al.

(10) Patent No.: US 12,227,521 B2
(45) Date of Patent: Feb. 18, 2025

(54) CGRP ANTAGONIST COMPOUNDS

(71) Applicant: Nxera Pharma UK Limited, Cambridge (GB)

(72) Inventors: Giles Albert Brown, Cambridge (GB); Miles Stuart Congreve, Cambridge (GB); Stephen Paul Watson, Cambridge (GB); Julie Cansfield, Cambridge (GB); Michael Alistair O'Brien, Cambridge (GB); Francesca Deflorian, Cambridge (GB); Gregory R. Ott, North Wales, PA (US); Nigel Alan Swain, Cambridge (GB); Andrew David Cansfield, Cambridge (GB)

(73) Assignee: Nxera Pharma UK Limited, Cambridge (GB)

( * ) Notice: Subject to any disclaimer, the term of this patent is extended or adjusted under 35 U.S.C. 154(b) by 663 days.

(21) Appl. No.: 17/617,851

(22) PCT Filed: Jun. 12, 2020

(86) PCT No.: PCT/GB2020/051429
§ 371 (c)(1),
(2) Date: Dec. 9, 2021

(87) PCT Pub. No.: WO2020/249970
PCT Pub. Date: Dec. 17, 2020

(65) Prior Publication Data
US 2022/0251110 A1   Aug. 11, 2022

(30) Foreign Application Priority Data
Jun. 12, 2019 (GB) .................... 1908430

(51) Int. Cl.
*C07D 498/22* (2006.01)
(52) U.S. Cl.
CPC ................. *C07D 498/22* (2013.01)
(58) Field of Classification Search
CPC .................................................. C07D 498/22
See application file for complete search history.

(56) References Cited

U.S. PATENT DOCUMENTS

2018/0009808 A1   1/2018   Christopher et al.
2018/0092899 A1   4/2018   Liu et al.

FOREIGN PATENT DOCUMENTS

| WO | 2006/044504 A1 | 4/2006 |
|---|---|---|
| WO | 2009/080682 A1 | 7/2009 |
| WO | 2010/139717 A1 | 12/2010 |
| WO | 2012/064910 A1 | 5/2012 |
| WO | 2012/064911 A1 | 5/2012 |
| WO | 2017/072721 A1 | 5/2017 |
| WO | 2018/178938 A1 | 10/2018 |
| WO | 2019/093284 A1 | 5/2019 |

OTHER PUBLICATIONS

Paone et al., Calcitonin gene-related peptide receptor antagonists for the treatment of migraine: a patent review. Expert Opin. Ther. Pat. Dec. 2009;19(12):1675-713.
Yasuda et al., Practical Asymmetric Synthesis of a Calcitonin Gene-Related Peptide (CGRP) Receptor Antagonist Ubrogepant. Org Process Res Dev. 2017;21(11):1851-1858.
International Search Report and Written Opinion for Application No. PCT/GB2020/051429, dated Jul. 29, 2020, 9 pages.

*Primary Examiner* — Susanna Moore
(74) *Attorney, Agent, or Firm* — Haley Guiliano LLP; Karen Mangasarian; Mihaela D. Danca

(57) ABSTRACT

The disclosures herein relate to novel compounds of Formula (1a): and salts thereof, wherein W, Z, L, $R^1$ and $R^2$ are defined herein, and their use in treating, preventing, ameliorating, controlling or reducing the risk of disorders associated with CGRP receptors.

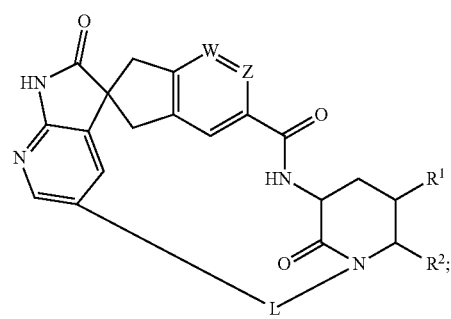

(1a)

31 Claims, No Drawings

CGRP ANTAGONIST COMPOUNDS

CROSS-REFERENCE TO RELATED APPLICATIONS

This application is a 35 U.S.C. § 371 national stage filing of International Application No. PCT/GB2020/051429, filed on Jun. 12, 2020, which claims priority to United Kingdom Application No. 1908430.0, filed on Jun. 12, 2019, the entire contents of each of which are incorporated herein by reference.

This application relates to novel compounds and their use as calcitonin gene-related peptide (CGRP) receptor antagonists. Compounds described herein may be useful in the treatment or prevention of diseases in which CGRP receptors are involved. Compounds described herein may be useful in the treatment or prevention of cerebrovascular or vascular disorders such as migraine. The application is also directed to pharmaceutical compositions comprising these compounds and the manufacture and use of these compounds and compositions in the prevention or treatment of such diseases in which CGRP receptors are involved.

BACKGROUND OF THE INVENTION

Migraine is a highly disabling neurovascular disorder characterized by attacks of moderate to severe headache that are often associated with nausea, vomiting, photophobia, and phonophobia. The attacks can last from 4 to 72 h, and the average attack frequency is 1 or 2 per month. About 20-30% of migraine patients experience transient focal neurologic symptoms known as aura, which are usually visual and can precede or accompany the headache. Migraine afflicts about 11% of adults worldwide and results in a significant socioeconomic burden, in terms of both quality of life and lost productivity.

Whilst the pathomechanism of migraine is still unclear, one of the leading hypotheses is based on activation of the trigeminovascular system (TS). Several neuropeptides participate in this activation, calcitonin gene-related peptide (CGRP) playing a crucial role among them. CGRP exerts various biological effects through the peripheral and central nervous system (CNS). The functional CGRP-receptor (CGRP-R) complex has been well characterized, and novel therapeutic approaches target CGRP itself and its receptors. This invention relates to the development of CGRP receptor antagonists (CGRP-RA).

CGRP, a 37-amino acid neuropeptide derived from the gene encoding calcitonin, is formed from the alternative splicing of the calcitonin/CGRP gene located on chromosome 11. In humans, CGRP has two isoforms: α- and β-CGRP. The β-isoform differs from the α-isoform in the amino acids located at positions 3, 22 and 25. The chemical structure of CGRP involves a disulphide bridge between residues 2 and 7 and an amidated C-terminus. The cyclic cysteine2-cysteine7 motif has a basic role in receptor activation. In the human trigeminal ganglia (TRIG), CGRP-immunoreactive neurons account for up to 50% of all neurons. It has been demonstrated through an in situ hybridization technique that 40% of all nerve cell bodies contain CGRP mRNA and CGRP.

The functional CGRP-R consists of three proteins: i) Calcitonin Receptor Like Receptor (known as CRLR, CAL-CRL or CLR) is a seven-transmembrane spanning protein, which forms the ligand binding site with; ii) RAMP1, determining the specificity of the receptor; and iii) the CGRP-R component protein (RCP) couples the receptor to intracellular signal transduction pathways and to adenylyl cyclase.

Blockade of CGRP function as a treatment for migraine has been clinically validated for both antibody and small molecule agents. For example, antibody agents Erenumab (Aimovig), which targets the CGRP receptor, and Fremanezumab (Ajovy) and Galcanezumab (Emgality) which target the CGRP Protein are now approved medicines for treatment of migraine. Similarly small molecule antagonists of CGRP have also demonstrated efficacy against migraine. For example, both Ubrogepant and Rimegepant have demonstrated clinical efficacy and are now approved medicines for the treatment of migraine.

THE INVENTION

The present invention provides compounds having activity as calcitonin gene-related peptide (CGRP) receptor antagonists. Disclosed herein are novel compounds, and the first medical use of said compounds as CGRP receptor antagonists.

Accordingly, in one embodiment the invention provides a compound of Formula (1a):

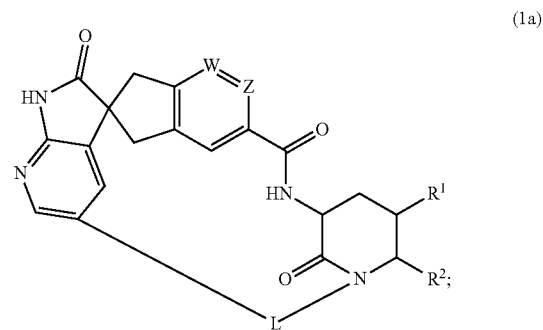

(1a)

or a salt thereof, wherein;
W is OH or N;
Z is OH or N;
$R^1$ is an aryl or heteroaryl group optionally substituted with one or more halo groups or $C_{1-3}$ alkyl groups which are themselves optionally substituted with one or more F atoms;
$R^2$ is H or $C_{1-3}$ alkyl optionally substituted with one or more F atoms;
and L is a $C_{4-15}$ linker group optionally substituted with one or more F atoms, wherein one, two or three, but not all, of the carbon atoms of the linker group may be optionally replaced by a heteroatom selected from O and N.

The compounds may be used as CGRP receptor antagonists. The compounds may be used in the manufacture of medicaments. The compounds or medicaments may be for use in treating, preventing, ameliorating, controlling or reducing the risk of diseases or disorders in which CGRP receptors are involved including cerebrovascular or vascular disorders such as migraine.

DETAILED DESCRIPTION OF THE INVENTION

The invention relates to novel compounds. The invention also relates to the use of novel compounds as antagonists of the CGRP receptor. The invention further relates to the use of novel compounds in the manufacture of medicaments for use as CGRP receptor antagonists.

The invention further relates to compounds, compositions and medicaments for the treatment of cerebrovascular or vascular disorders including migraine (with or without aura), chronic migraine, pure menstrual migraine, frequent episodic migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine, status migrainosus, cluster headache, dialysis headache, chronic headaches of unknown origin, tension/stress induced headaches, allergy induced headaches, paroxysmal hemicrania, osteoarthritis and associated osteoporotic fracture pain, hot flashes associated with menopause or medically induced menopause due to surgery or drug treatment, hemicrania continua, cyclic vomiting syndrome, opiate withdrawal syndrome, morphine tolerance, neurodegenerative disease, epilepsy, allergic rhinitis, rosacea, dental pain, earache, middle ear inflammation, sunburn, joint pain associated with osteoarthritis and rheumatoid arthritis and gout, cancer pain, neuropathic pain (including but not limited to cancer pain in all its various forms including of unexplained origin), dystonic pain, inflammatory pain, post-operative incision pain, sciatica, fibromyalgia, trigeminal neuralga, diabetic neuropathy, complex regional pain syndrome, Behçet's disease, endometriosis pain, back pain, phantom limb pain, menstrual period pain, pain associated with labour, pain resulting from burns to skin, or visceral pain associated with inflammatory bowel disease (including Crohn's disease, ileitis and ulcerative colitis), gastro-esophageal reflux disease, dyspepsia, irritable bowel syndrome, renal colic, cystitis, gout, pancreatitis and prostatitis.

The compounds, compositions and medicaments of the invention may also be beneficial in the treatment of inflammatory and immune associated disorders including chronic fatigue syndrome, skin diseases, neurogenic cutaneous redness, skin rosaceousness, erythema, bronchial hyperreactivity, asthma, mast cell activation syndrome, mastocytosis, mast cell degranulation disorder, vascular disorders, shock, sepsis, non-insulin dependent diabetes mellitus, and infectious diseases including those of a respiratory and gastrointestinal origin.

In one embodiment the invention provides a compound of Formula (1a):

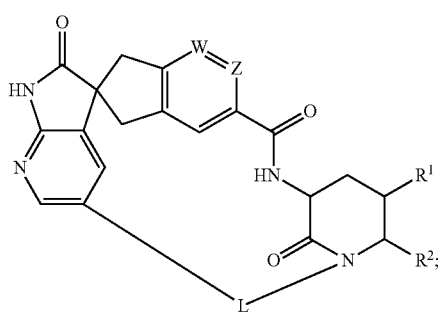

(1a)

or a salt thereof, wherein;
W is OH or N;
Z is OH or N;

$R^1$ is an aryl or heteroaryl group optionally substituted with one or more halo groups or $C_{1-3}$ alkyl groups which are themselves optionally substituted with one or more F atoms;

$R^2$ is H or $C_{1-3}$ alkyl optionally substituted with one or more F atoms; and L is a $C_{4-15}$ linker group optionally substituted with one or more F atoms, wherein one, two or three, but not all, of the carbon atoms of the linker group may be optionally replaced by a heteroatom selected from O and N.

Particular compounds include compounds of Formula (2a):

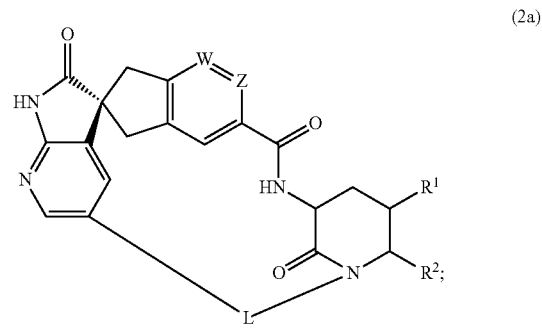

(2a)

or a salt thereof wherein W, Z, L, R and R are as defined above.

Particular compounds include compounds of Formula (3a):

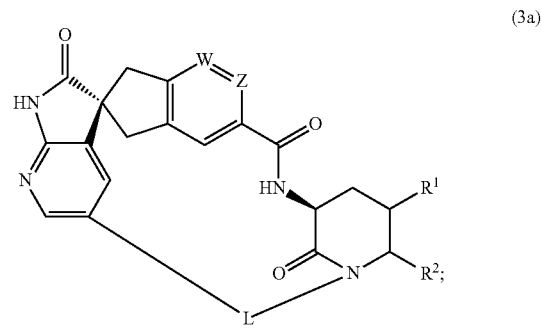

(3a)

or salts thereof, wherein W, Z, L, $R^1$ and $R^2$ are as defined above.

Particular compounds include compounds of Formula (4a):

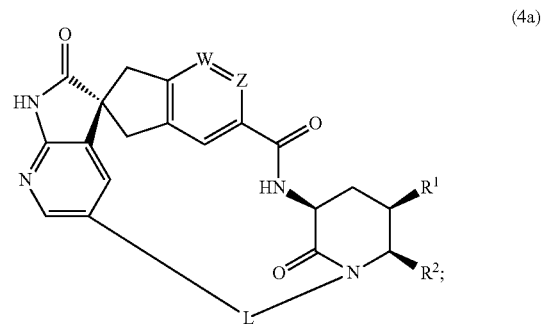

(4a)

or salts thereof, wherein W, Z, L, R¹ and R² are as defined above.

In the compounds herein, the ring system formed by W, Z and the atoms to which they are attached can be selected from the group consisting of an indan ring system, a pyrindan, 4-azaindan, 2,3-cyclopentenopyridine or 6,7-Dihydro-5H-cyclopenta[b]pyridine ring system, a 2-pyrindan, 5-azaindan or 6,7-Dihydro-5H-cyclopenta[c]pyridine ring system and a 4,5-diazaindan ring system.

The ring system formed by W, Z and the atoms to which they are attached can be selected from the group consisting of:

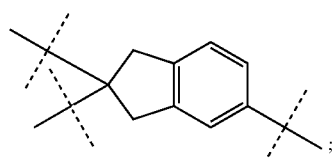

;

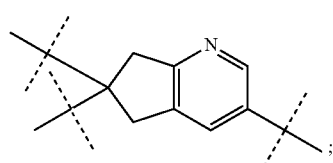

;

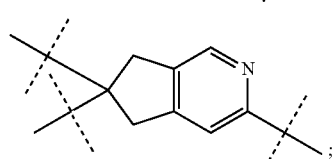

;

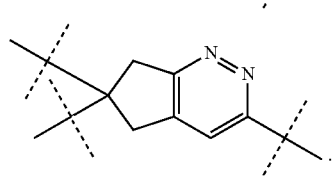

.

In the compounds herein, W can be N. W can be CH.

In the compounds herein, Z can be N. Z can be CH.

In the compounds herein, W can be N and Z can be CH. W can be CH and Z can be N. W and Z can both be CH. W and Z can both be N.

Particular compounds include compounds of Formula (1b), (1c), (1d) and (1e):

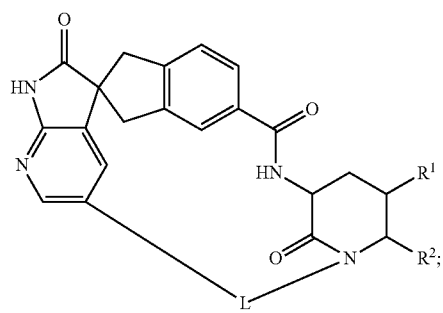

(1b)

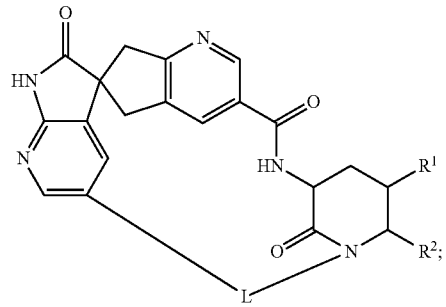

(1c)

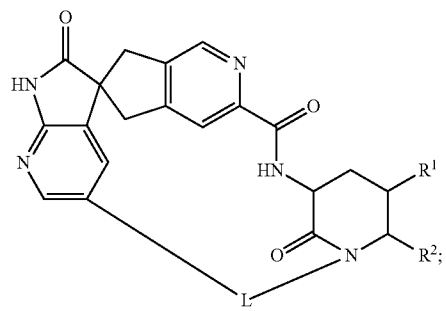

(1d)

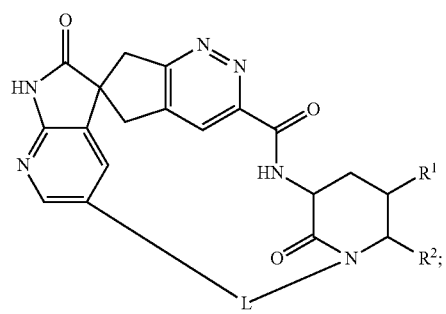

(1e)

or salts thereof, wherein L, R and R are as defined above.

Particular compounds include compounds of Formula (2b), (2c), (2d) and (2e):

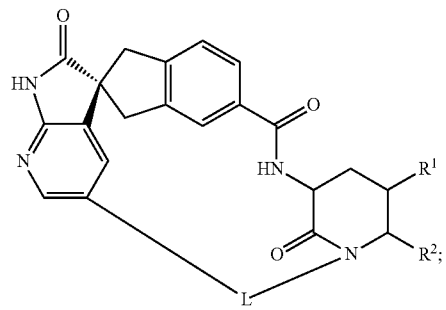

(2b)

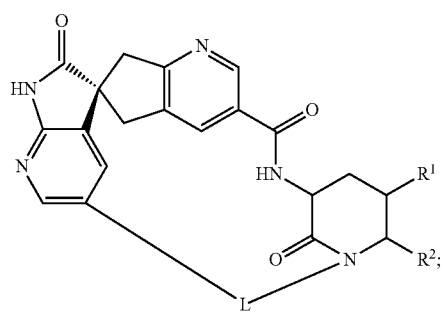
(2c)
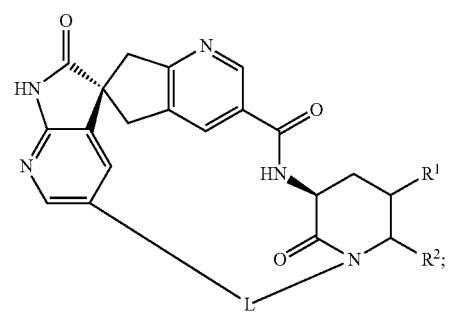
(3c)
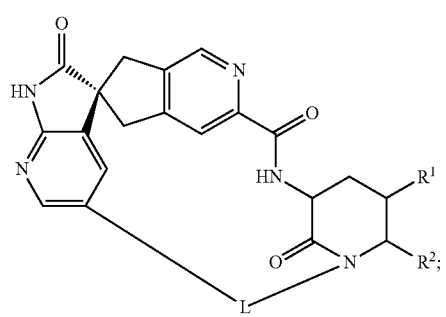
(2d)
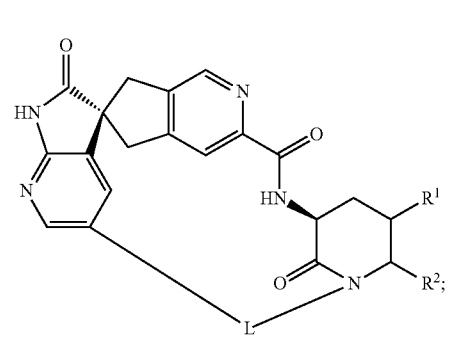
(3d)
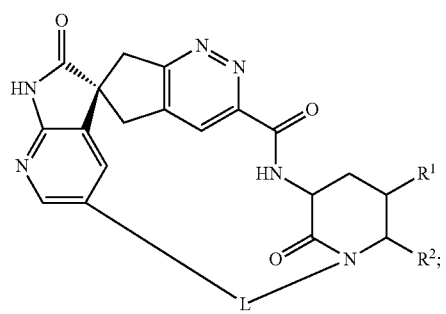
(2e)
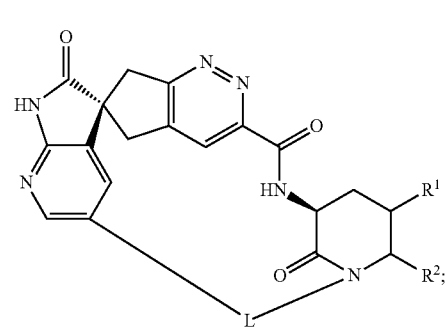
(3e)
or salts thereof, wherein L, $R^1$ and $R^2$ are as defined above.
Particular compounds include compounds of Formula (3b), (3c), (3d) and (3e):
or salts thereof, wherein L, $R^1$ and $R^2$ are as defined above.
Particular compounds include compounds of Formula (4b), (4c), (4d) and (4e):
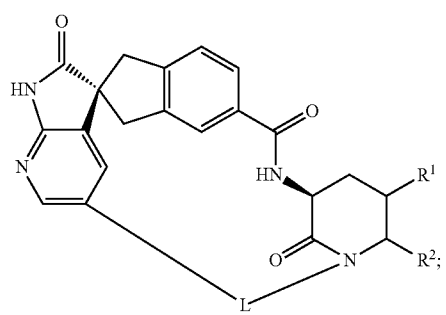
(3b)
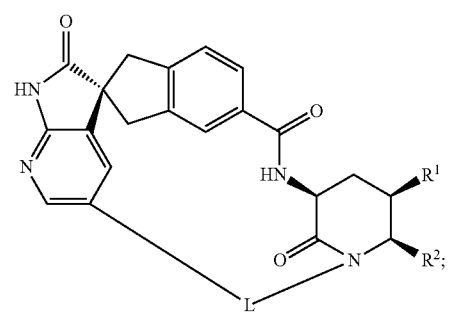
(4b)

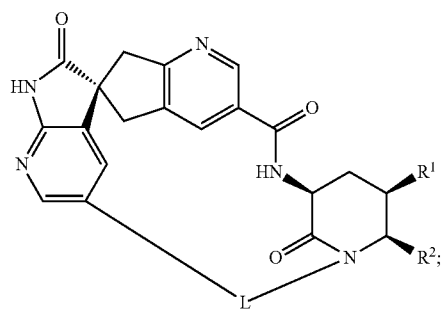
(4c)
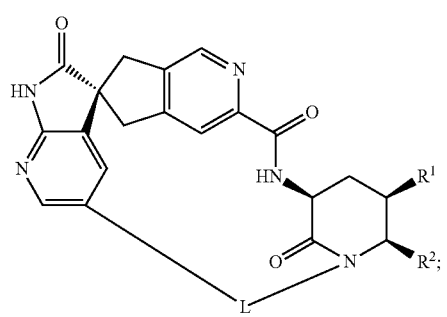
(4d)
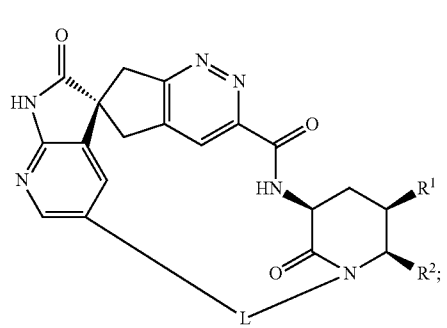
(4e)
or salts thereof, wherein L, $R^1$ and $R^2$ are as defined above.
Particular compounds may also include compounds of Formula (5a) to (5g):
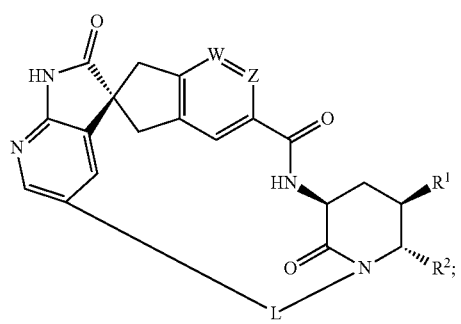
(5a)
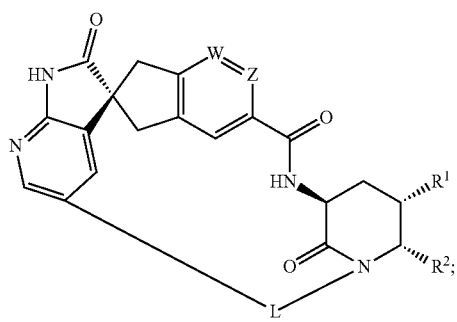
(5b)
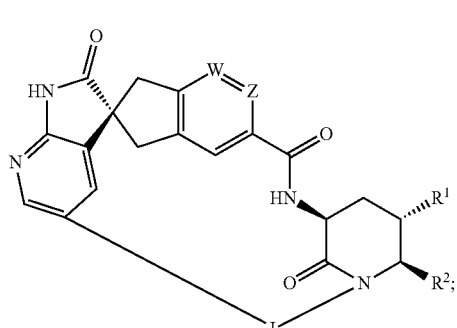
(5c)
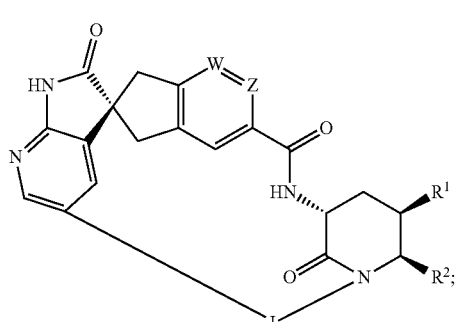
(5d)
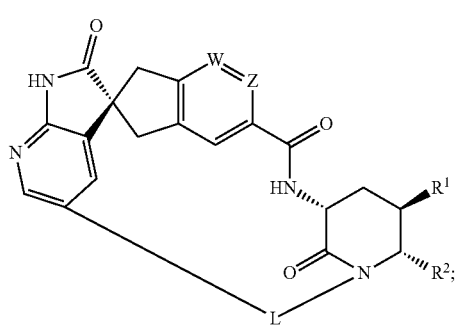
(5e)
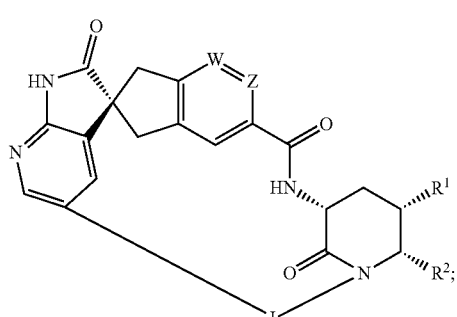
(5f)

(5g)

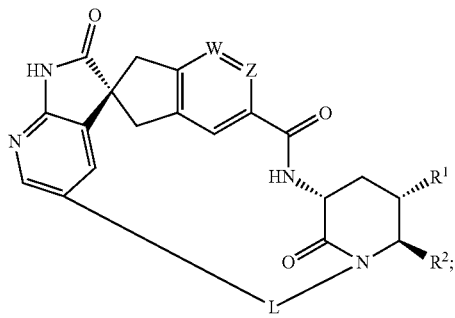

or salts thereof, wherein L, W, Z, $R^1$ and $R^2$ are as defined above.

In the compounds herein, $R^1$ can be an aryl group optionally substituted with one or more halo groups or $C_{1-3}$ alkyl groups which are themselves optionally substituted with one or more F atoms. $R^1$ can be a heteroaryl group optionally substituted with one or more halo groups or $C_{1-3}$ alkyl groups which are themselves optionally substituted with one or more F atoms. $R^1$ can be a phenyl ring optionally substituted with one or more F atoms or $C_{1-3}$ alkyl groups which are themselves optionally substituted with one or more F atoms. $R^1$ can be a phenyl ring optionally substituted with 1-5 F atoms. $R^1$ can be a phenyl ring. $R^1$ can be a phenyl ring substituted with 1-5 F atoms. $R^1$ can be a phenyl ring substituted with 1-3 F atoms.

In the compounds herein, $R^2$ can be H. $R^2$ can be alkyl optionally substituted with one or more F atoms. $R^2$ can be $C_{1-3}$ alkyl. $R^2$ can be $C_{1-3}$ alkyl optionally substituted with one or more F atoms. $R^2$ can be methyl. $R^2$ can be methyl optionally substituted with one or more F atoms.

In the compounds herein, L can be a $C_{4-15}$ linker group optionally substituted with one or more F atoms. L can be a $C_{4-15}$ linker group optionally substituted with 1-3 F atoms. L can be a $C_{4-15}$ linker group substituted with 1-3 F atoms. L can be a $C_{4-15}$ linker group. L can be a $C_{4-15}$ linker group wherein one, two or three, but not all, of the carbon atoms of the linker group is replaced by a heteroatom selected from O and N. L can be a $C_{6-12}$ linker group, wherein one, two or three, but not all, of the carbon atoms of the linker group may be optionally replaced by a heteroatom selected from O and N. L can be a $C_{4-15}$ linker group, wherein one, two or three, but not all, of the carbon atoms of the linker group may be optionally replaced by O. L can be a $C_{6-12}$ linker group, wherein one, two or three, but not all, of the carbon atoms of the linker group may be optionally replaced by O. L can be partially unsaturated. L can be monounsaturated. L can be polyunsaturated. L can contain a double bond. L can be saturated. L can be substituted with one or more F atoms.

L can be a linker group of the formula:

wherein "r" indicates the point of attachment to the pyridine ring and "a" indicates the point of attachment to V; X and Y can be independently selected from a bond, O, $CH_2$, NH and NMe; b, c, d and e are independently 1, 2 or 3 and the dotted line indicates that a single or double bond may be present.

L can selected from the group consisting of:
—$CHCHCH_2OCH_2CH_2OCH_2CH_2$—;
—$CHCHCH_2OCH_2CH_2OCH_2CH_2OCH_2CH_2$—;
—$CH_2CH_2CH_2OCH_2CH_2OCH_2CH_2$—;
—$CH_2CH_2CH_2OCH_2CH_2OCH_2CH_2OCH_2CH_2$—;
—$CHCHCH_2OCH_2CH_2CH_2CH_2CH_2$—;
—$CHCHCH_2OCH_2CH_2N(CH_3)CH_2CH_2$—;
—$CHCHCH_2OCH_2CH_2NHCH_2CH_2$—;
—$CHCHCH_2CH_2CH_2CH_2N(CH_3)CH_2CH_2$—;
—$CHCHCH_2N(CH_3)CH_2CH_2CH_2CH_2CH_2$—;
—$CH_2CH_2CH_2N(CH_3)CH_2CH_2CH_2CH_2CH_2$—;
—$CHCHCH_2CH_2CH_2CH_2NHCH_2CH_2$—;
—$CHCHCH_2N(CH_3)CH_2CH_2N(CH_3)CH_2CH_2$—;
—$CHCHCH_2OCH_2CH_2OCH_2CH_2CH_2$—;
—$CHCHCH_2OCH_2CH_2CH_2OCH_2CH_2$—;
—$CHCHCH_2CH_2OCH_2CH_2OCH_2CH_2$—;
—$CHCHCH_2CH_2OCH_2CH_2CH_2CH_2$—;
—$CHCHCH_2CH_2CH_2OCH_2CH_2CH_2$—
and
—$CHCHCH_2OCH_2CH_2CH_2CF_2CH_2$—.

The compound can be selected from the group consisting of:

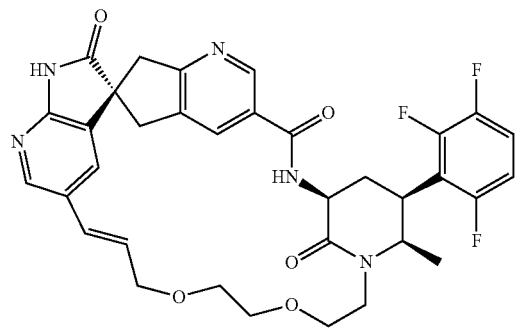

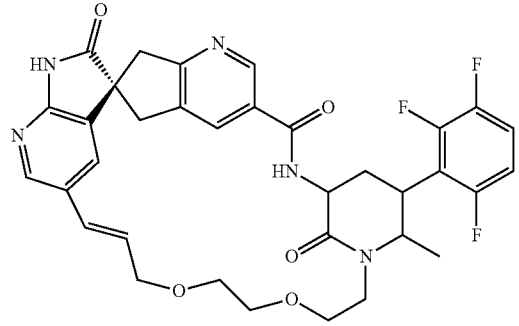

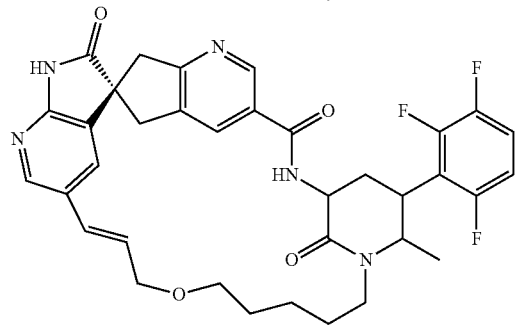 [SMILES: CC1C(c2c(F)ccc(F)c2F)CC2NC(=O)c3cnc4c(c3)C[C@@]3(C4)C(=O)Nc4ncc(cc43)/C=C/CCOCCCCN1C2=O]

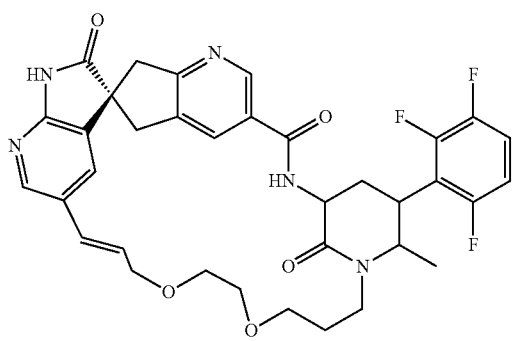
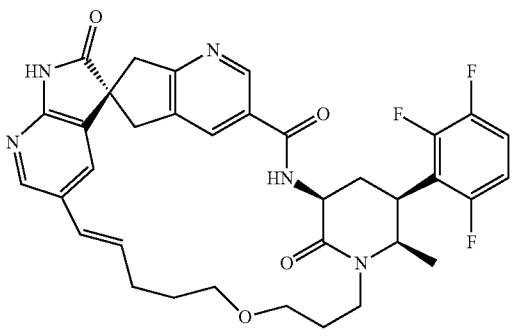
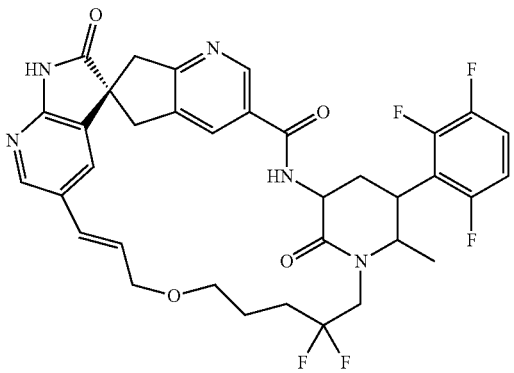
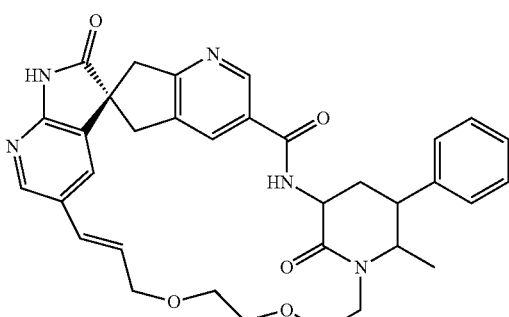
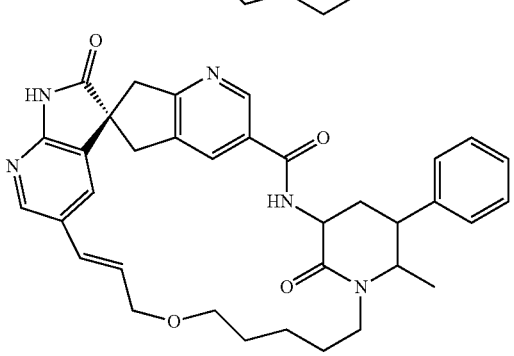
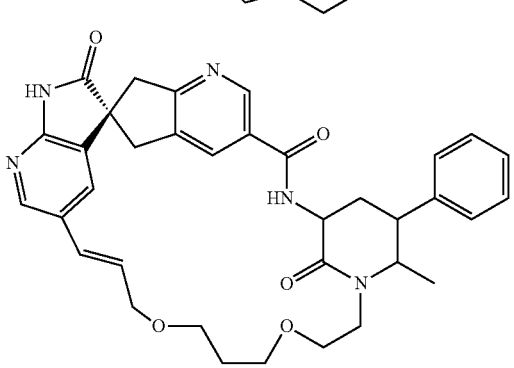

-continued
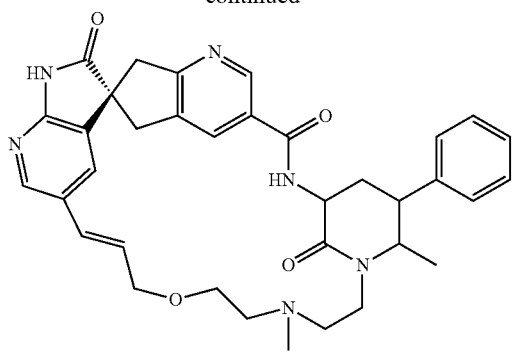
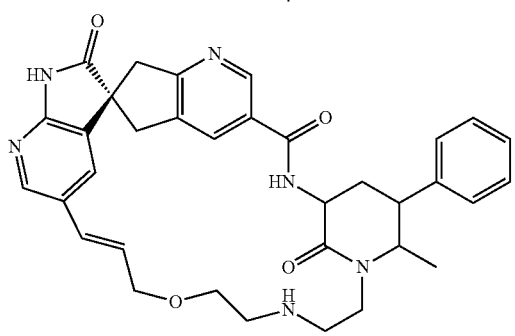
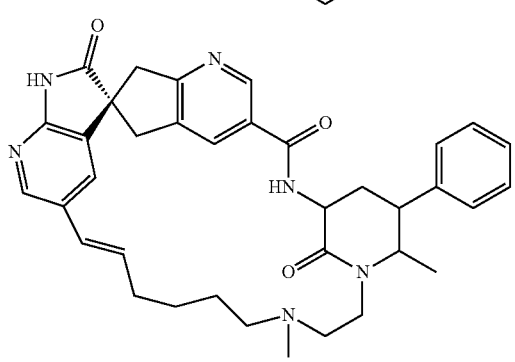
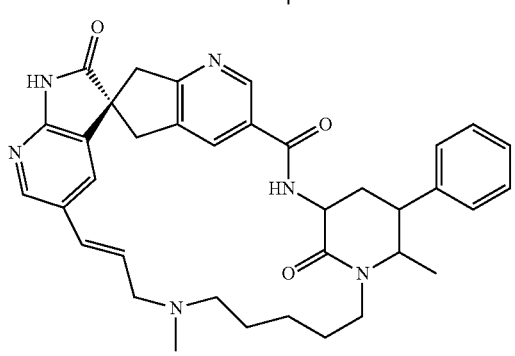
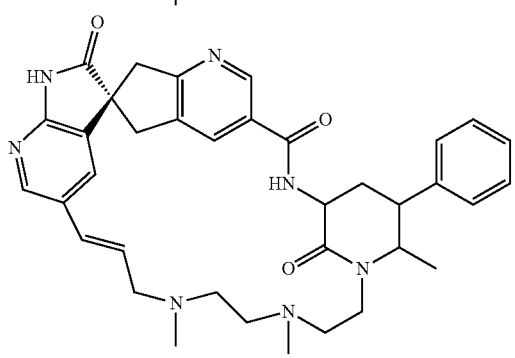
-continued
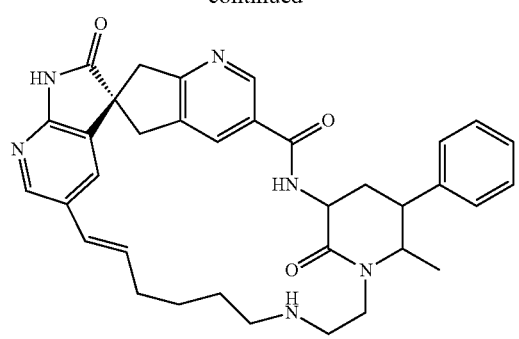
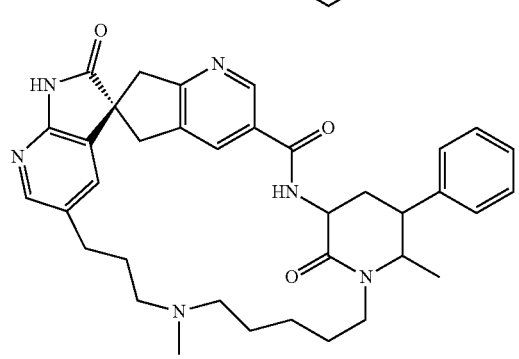
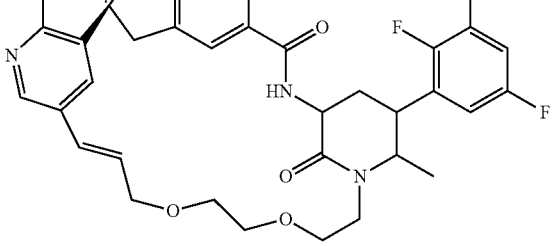
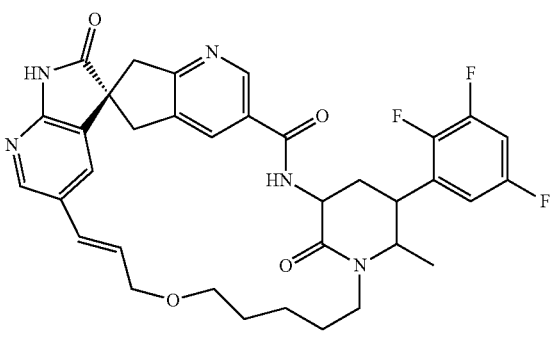
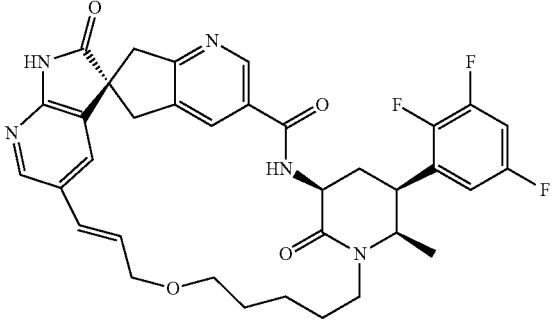

17
-continued
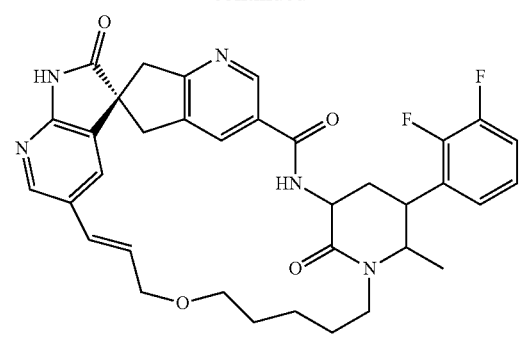
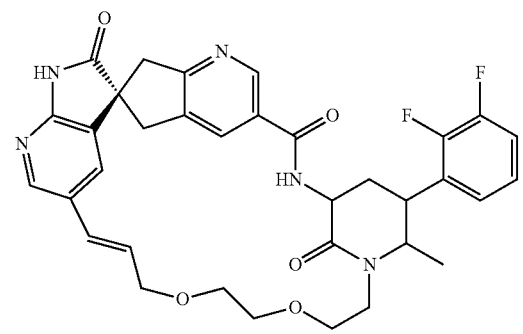
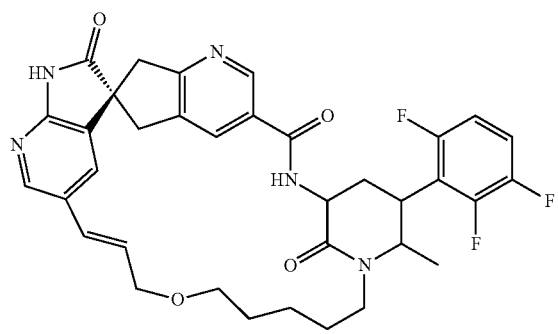
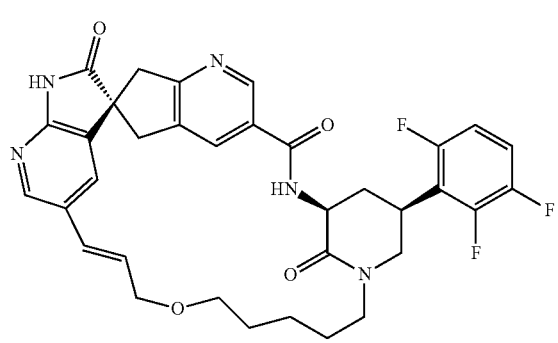
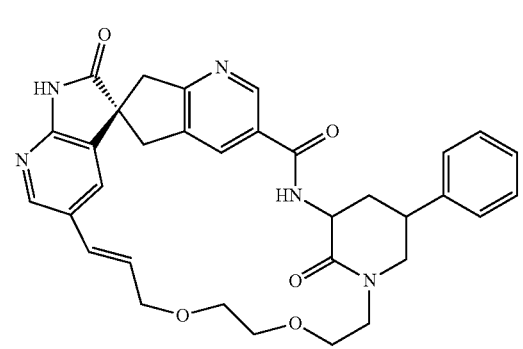
18
-continued
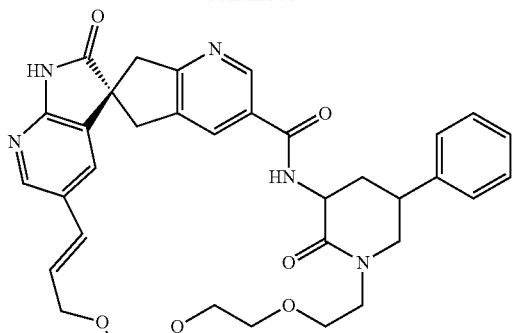
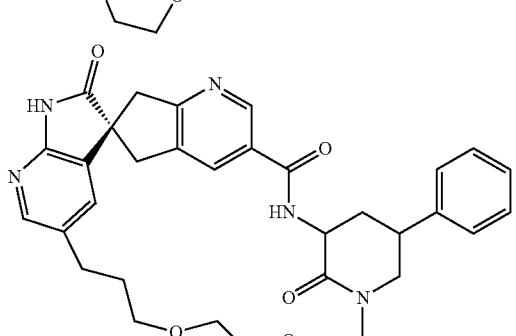
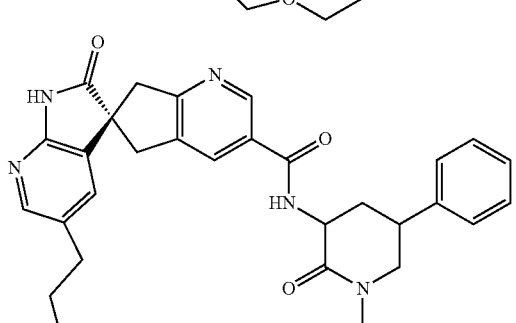
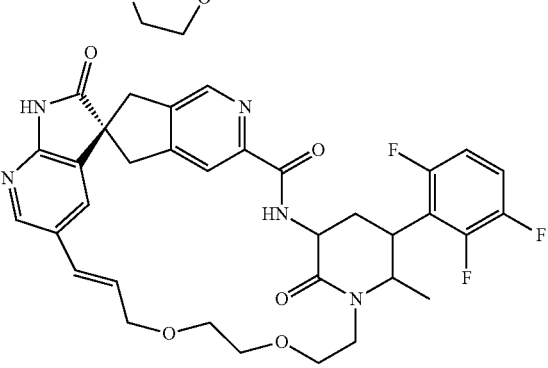
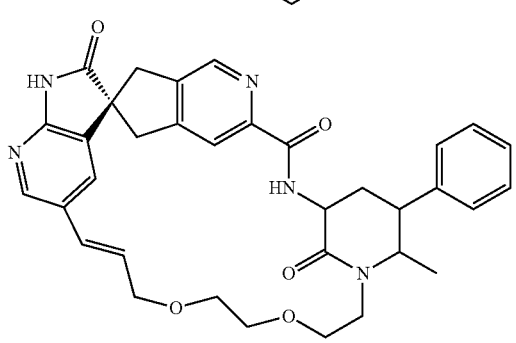

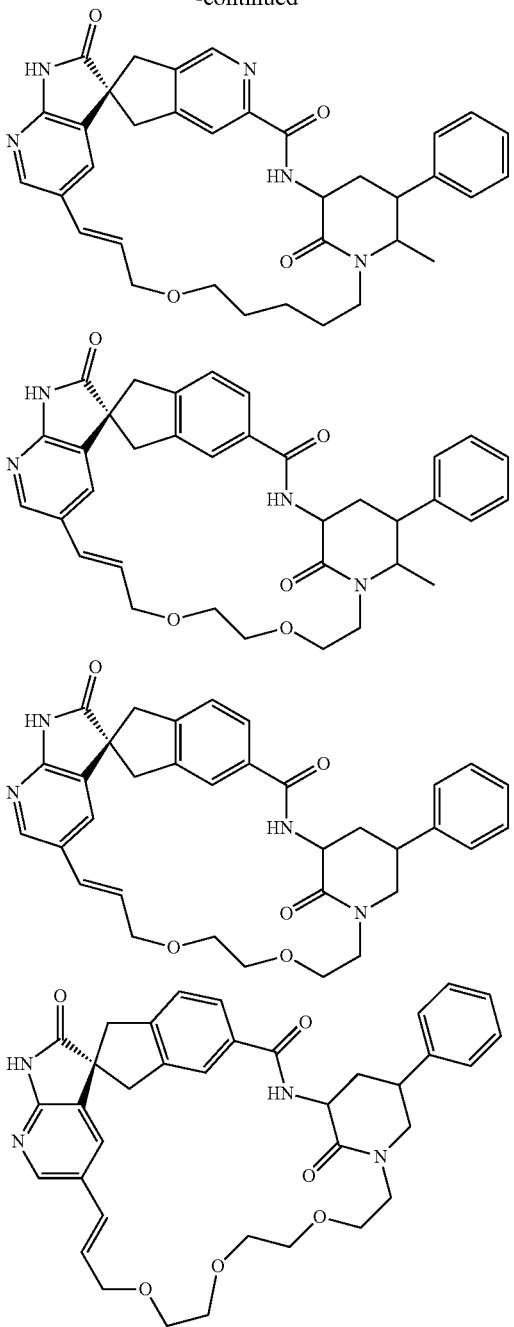

and salts thereof.

The compound can be selected from the group consisting of:
(1S,22E)-13-methyl-12-(2,3,6-trifluorophenyl)-17,20-dioxa-5,9,14,26,28-pentazahexacyclo[22.5.2.11,4.13,7.110, 14.027,30]tetratriaconta-3,5,7(33),22,24(31),25,27(30)-heptaene-8,29,32-trione;
(1S,10S,12S,13R,22E)-13-methyl-12-(2,3,6-trifluorophenyl)-17,20-dioxa-5,9,14,26,28-pentazahexacyclo[22.5.2.11,4.13,7.110,14.027,30]tetratriaconta-3,5,7(33), 22,24(31),25,27(30)-heptaene-8,29,32-trione;
(1S,22E)-13-methyl-12-(2,3,6-trifluorophenyl)-20-oxa-5,9, 14,26,28-pentazahexacyclo[22.5.2.11,4.13,7.110,14.027, 30]tetratriaconta-3,5,7(33),22,24(31),25,27(30)-heptaene-8,29,32-trione;
(1S,23E)-13-methyl-12-(2,3,6-trifluorophenyl)-18,21-dioxa-5,9,14,27,29-pentazahexacyclo[23.5.2.11,4.13,7.110, 14.028,31]pentatriaconta-3,5,7(34),23,25(32),26,28(31)-heptaene-8,30,33-trione;
(1S,23E)-13-methyl-12-(2,3,6-trifluorophenyl)-17,20-dioxa-5,9,14,27,29-pentazahexacyclo[23.5.2.11,4.13,7.110, 14.028,31]pentatriaconta-3,5,7(34),23,25(32),26,28(31)-heptaene-8,30,33-trione;
(1S,22E)-13-methyl-12-(2,3,6-trifluorophenyl)-19-oxa-5,9, 14,26,28-pentazahexacyclo[22.5.2.11,4.13,7.110,14.027, 30]tetratriaconta-3,5,7(33),22,24(31),25,27(30)-heptaene-8,29,32-trione;
(1S,23E)-13-methyl-12-(2,3,6-trifluorophenyl)-17,21-dioxa-5,9,14,27,29-pentazahexacyclo[23.5.2.11,4.13,7.110, 14.028,31]pentatriaconta-3,5,7(34),23,25(32),26,28(31)-heptaene-8,30,33-trione;
(1S,22E)-13-methyl-12-(2,3,6-trifluorophenyl)-18-oxa-5,9, 14,26,28-pentazahexacyclo[22.5.2.11,4.13,7.110,14.027, 30]tetratriaconta-3,5,7(33),22,24(31),25,27(30)-heptaene-8,29,32-trione;
(1S,22E)-16,16-difluoro-13-methyl-12-(2,3,6-trifluorophenyl)-20-oxa-5,9,14,26,28-pentazahexacyclo[22.5.2.11, 4.13,7.110,14.027,30]tetratriaconta-3,5,7(33),22,24(31), 25,27(30)-heptaene-8,29,32-trione;
(1S,22E)-13-methyl-12-phenyl-17,20-dioxa-5,9,14,26,28-pentazahexacyclo[22.5.2.11,4.13,7.110,14.027,30]tetratriaconta-3,5,7(33),22,24(31),25,27(30)-heptaene-8,29, 32-trione;
(1S,22E)-13-methyl-12-phenyl-17,20-dioxa-9,14,26,28-tetrazahexacyclo[22.5.2.11,4.13,7.110,14.027,30]tetratriaconta-3,5,7(33),22,24(31),25,27(30)-heptaene-8,29,32-trione;
(1S,23E)-13-methyl-12-phenyl-17,21-dioxa-5,9,14,27,29-pentazahexacyclo[23.5.2.11,4.13,7.110,14.028,31]pentatriaconta-3,5,7(34),23,25(32),26,28(31)-heptaene-8,30, 33-trione;
(1S,22E)-13,17-dimethyl-12-phenyl-20-oxa-5,9,14,17,26, 28-hexazahexacyclo[22.5.2.11,4.13,7.110,14.027,30]tetratriaconta-3,5,7(33),22,24(31),25,27(30)-heptaene-8,29, 32-trione;
(1S,22E)-13-methyl-12-phenyl-20-oxa-5,9,14,17,26,28-hexazahexacyclo[22.5.2.11,4.13,7.110,14.027,30]tetratriaconta-3,5,7(33),22,24(31),25,27(30)-heptaene-8,29, 32-trione;
(1S,22E)-13,17-dimethyl-12-phenyl-5,9,14,17,26,28-hexazahexacyclo[22.5.2.11,4.13,7.110,14.027,30]tetratriaconta-3,5,7(33),22,24(31),25,27(30)-heptaene-8,29, 32-trione;
(1S,22E)-13,20-dimethyl-12-phenyl-5,9,14,20,26,28-hexazahexacyclo[22.5.2.11,4.13,7.110,14.027,30]tetratriaconta-3,5,7(33),22,24(31),25,27(30)-heptaene-8,29, 32-trione;
(1S,22E)-13,17,20-trimethyl-12-phenyl-5,9,14,17,20,26,28-heptazahexacyclo[22.5.2.11,4.13,7.110,14.027,30]tetratriaconta-3,5,7(33),22,24(31),25,27(30)-heptaene-8,29, 32-trione;
(1S,22E)-13-methyl-12-phenyl-5,9,14,17,26,28-hexazahexacyclo[22.5.2.11,4.13,7.110,14.027,30]tetratriaconta-3,5,7(33),22,24(31),25,27(30)-heptaene-8,29,32-trione;
(1 S)-13,20-dimethyl-12-phenyl-5,9,14,20,26,28-hexazahexacyclo[22.5.2.11,4.13,7.110,14.027,30]tetratriaconta-3,5,7(33),24(31),25,27(30)-hexaene-8,29,32-trione;
(1S,22E)-13-methyl-12-(2,3,5-trifluorophenyl)-17,20-dioxa-5,9,14,26,28-pentazahexacyclo[22.5.2.11,4.13,7.110, 14.027,30]tetratriaconta-3,5,7(33),22,24(31),25,27(30)-heptaene-8,29,32-trione;

(1S,22E)-13-methyl-12-(2,3,5-trifluorophenyl)-20-oxa-5,9, 14,26,28-pentazahexacyclo[22.5.2.1¹,⁴.1³,⁷.1¹⁰,¹⁴.0²⁷, ³⁰]tetratriaconta-3,5,7(33),22,24(31),25,27(30)-heptaene-8,29,32-trione;

(1S,22E)-13-methyl-12-(2,3-difluorophenyl)-20-oxa-5,9, 14,26,28-pentazahexacyclo[22.5.2.1¹,⁴.1³,⁷.1¹⁰,¹⁴.0²⁷, ³⁰]tetratriaconta-3,5,7(33),22,24(31),25,27(30)-heptaene-8,29,32-trione;

(1S,22E)-12-(2,3-difluorophenyl)-13-methyl-17,20-dioxa-5,9,14,26,28-pentazahexacyclo[22.5.2.1¹,⁴.1³,⁷.1¹⁰, 14.0²⁷,³⁰]tetratriaconta-3,5,7(33),22,24(31),25,27(30)-heptaene-8,29,32-trione;

(1S,22E)-12-(2,3,6-trifluorophenyl)-20-oxa-5,9,14,26,28-pentazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29, 32-trione;

(1S,22E)-12-phenyl-17,20-dioxa-5,9,14,26,28-pentazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29,32-trione;

(1S,25E)-12-phenyl-17,20,23-trioxa-5,9,14,29,31-pentazahexacyclo[25.5.2.1¹,⁴.1³,⁷.1¹⁰,¹⁴.0³⁰,³³]heptatriaconta-3,5,7(36),25,27(34),28,30(33)-heptaene-8,32,35-trione;

(1 S)-12-phenyl-17,20-dioxa-5,9,14,26,28-pentazahexacyclo[22.5.2.1¹,⁴.1³,⁷.1¹⁰,¹⁴.0²⁷,³⁰]tetratriaconta-3,5,7 (33),24(31),25,27(30)-hexaene-8,29,32-trione;

(1 S)-12-phenyl-17,20,23-trioxa-5,9,14,29,31-pentazahexacyclo[25.5.2.1¹,⁴.1³,⁷.1¹⁰,¹⁴.0³⁰,³³]heptatriaconta-3,5, 7(36),27(34),28,30(33)-hexaene-8,32,35-trione;

(1S,22E)-13-methyl-12-(2,3,6-trifluorophenyl)-17,20-dioxa-6,9,14,26,28-pentazahexacyclo[22.5.2.1¹,⁴.1³,⁷.1¹⁰, 14.0²⁷,³⁰]tetratriaconta-3,5,7(33),22,24(31),25,27(30)-heptaene-8,29,32-trione;

(1S,22E)-13-methyl-12-phenyl-17,20-dioxa-6,9,14,26,28-pentazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29, 32-trione;

(1S,22E)-13-methyl-12-phenyl-20-oxa-6,9,14,26,28-pentazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29,32-trione;

(1R,22E)-13-methyl-12-phenyl-17,20-dioxa-9,14,26,28-tetrazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29,32-trione;

(1R,22E)-12-phenyl-17,20-dioxa-9,14,26,28-tetrazahexacyclo[22.5.2.1¹,⁴.1³,⁷.1¹⁰,¹⁴.0²⁷,³⁰]tetratriaconta-3,5,7 (33),22,24(31),25,27(30)-heptaene-8,29,32-trione;

(1R,22E)-12-phenyl-17,20-dioxa-9,14,26,28-tetrazahexacyclo[22.5.2.1¹,⁴.1³,⁷.1¹⁰,¹⁴.0²⁷,³⁰]tetratriaconta-3,5,7 (33),22,24(31),25,27(30)-heptaene-8,29,32-trione;

(1R,25E)-12-phenyl-17,20,23-trioxa-9,14,29,31-tetrazahexacyclo[25.5.2.1¹,⁴.1³,⁷.1¹⁰,¹⁴.0³⁰,³³]heptatriaconta-3,5,7(36),25,27(34),28,30(33)-heptaene-8,32,35-trione;

(1S,10S,12S,13R,22E)-13-methyl-12-(2,3,6-trifluorophenyl)-18-oxa-5,9,14,26,28-pentaazahexacyclo[22.5.2.1¹, 4.1³,⁷.1¹⁰,¹⁴.0²⁷,³⁰]tetratriaconta-3(33),4,6,22,24,26, 30-heptaene-8,29,32-trione;

(1S,10S,12S,13R,22E)-13-methyl-12-(2,3,5-trifluorophenyl)-20-oxa-5,9,14,26,28-pentaazahexacyclo[22.5.2.1¹, 4.1³,⁷.1¹⁰,¹⁴.0²⁷,³⁰]tetratriaconta-3(33),4,6,22,24,26, 30-heptaene-8,29,32-trione;

(1S,10S,12S,22E)-12-(2,3,6-trifluorophenyl)-20-oxa-5,9, 14,26,28-pentaazahexacyclo[22.5.2.1¹,⁴.1³,⁷.1¹⁰, 14.0²⁷,³⁰]tetratriaconta-3(33),4,6,22,24,26,30-heptaene-8,29,32-trione;

and salts thereof.

Further embodiments of the invention include methods of treatment comprising administering an effective therapeutic amount of a compound of Formula (1a) as a CGRP receptor antagonist. The treatment using a compound of Formula (1a) may be in the treatment of cerebrovascular or vascular disorders including migraine (with or without aura), chronic migraine, pure menstrual migraine, frequent episodic migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine, status migrainosus, cluster headache, dialysis headache, chronic headaches of unknown origin, tension/stress induced headaches, allergy induced headaches, paroxysmal hemicrania, osteoarthritis and associated osteoporotic fracture pain, hot flashes associated with menopause or medically induced menopause due to surgery or drug treatment, hemicrania continua, cyclic vomiting syndrome, opiate withdrawal syndrome, morphine tolerance, neurodegenerative disease, epilepsy, allergic rhinitis, rosacea, dental pain, earache, middle ear inflammation, sunburn, joint pain associated with osteoarthritis and rheumatoid arthritis and gout, cancer pain, neuropathic pain (including but not limited to cancer pain in all its various forms including of unexplained origin), dystonic pain, inflammatory pain, postoperative incision pain, sciatica, fibromyalgia, trigeminal neuralga, diabetic neuropathy, complex regional pain syndrome, Behçet's disease, endometriosis pain, back pain, phantom limb pain, menstrual period pain, pain associated with labour, pain resulting from burns to skin, or visceral pain associated with inflammatory bowel disease (including Crohn's disease, ileitis and ulcerative colitis), gastroesophageal reflux disease, dyspepsia, irritable bowel syndrome, renal colic, cystitis, gout, pancreatitis and prostatitis.

The compounds of Formula (1a) may also be used in the treatment of inflammatory and immune associated disorders including chronic fatigue syndrome, skin diseases, neurogenic cutaneous redness, skin rosaceousness, erythema, bronchial hyperreactivity, asthma, mast cell activation syndrome, mastocytosis, mast cell degranulation disorder, vascular disorders, shock, sepsis, non-insulin dependent diabetes mellitus, and infectious diseases including those of a respiratory and gastrointestinal origin.

The compounds of the invention may be used alone or in combination with any other therapy or standard of care for any of the above indications.

Certain novel compounds of the invention show particularly high activities as CGRP receptor antagonists.

Definitions

In this application, the following definitions apply, unless indicated otherwise.

The term "treatment", in relation to the uses of any of the compounds described herein, including those of Formula (1a) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

Terms such as "alkyl" as in "$C_{1-3}$ alkyl", "heteroaryl", "aryl" and "halo" are all used in their conventional sense (e.g. as defined in the IUPAC Gold Book), unless indicated otherwise. "Optionally substituted" as applied to any group means that the said group may if desired be substituted with one or more substituents, which may be the same or different.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, Ind., USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of Formula (1a) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and cosolvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the Formula (1a) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient.

Pharmaceutical compositions according to the invention may be, for example, in unit dose form, such as in the form of ampoules, vials, suppositories, pre-filled syringes, dragees, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the Formula (1a) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

Methods for the Preparation of Compounds of the Formula (1a)

Compounds of Formula (1a) can be prepared in accordance with synthetic methods well known to the skilled person and as described herein. The invention provides a process for the preparation of a compound as defined in Formula (1a) above.

EXAMPLES

The invention will now be illustrated, but not limited, by reference to the following examples.

Examples 1-1 to 10-2

The compounds of Examples 1-1 to 10-2 shown in Table 1 below have been prepared. The compounds were either obtained as mixtures of stereoisomers or as individual isomers. Stereochemistry of Example 1-1, 1-7, 3-2 and 5-1 Isomer 1 were confirmed by X-ray crystallography. Full stereochemical configuration of remaining examples and isomers have not been confirmed.

TABLE 1

Example compounds

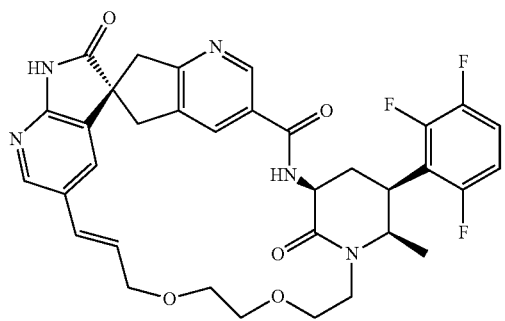 [SMILES: C[C@@H]1[C@H](c2c(F)ccc(F)c2F)C[C@@H]2NC(=O)c3cnc4c(c3)C[C@@]3(C4)C(=O)Nc4ncc(cc43)/C=C/COCCOCCN1C2=O]

Example 1-1
Isomer 1

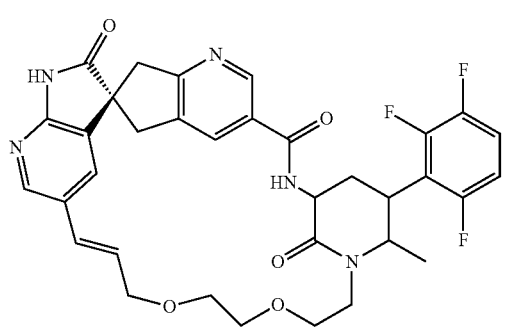 [SMILES: CC1C(c2c(F)ccc(F)c2F)CC2NC(=O)c3cnc4c(c3)C[C@@]3(C4)C(=O)Nc4ncc(cc43)/C=C/COCCCCCN1C2=O]

Example 1-1
Isomer 2/3

TABLE 1-continued

Example compounds

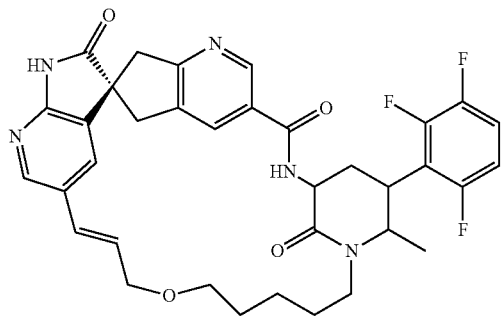

Example 1-2

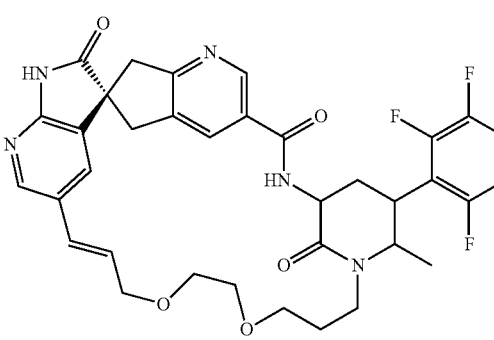

Example 1-3

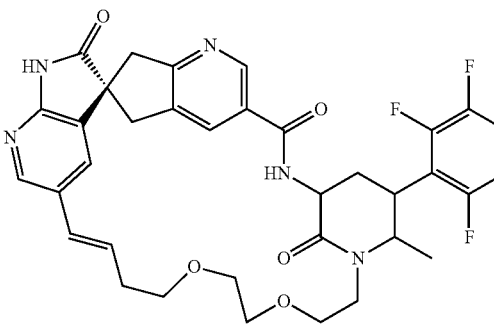

Example 1-4

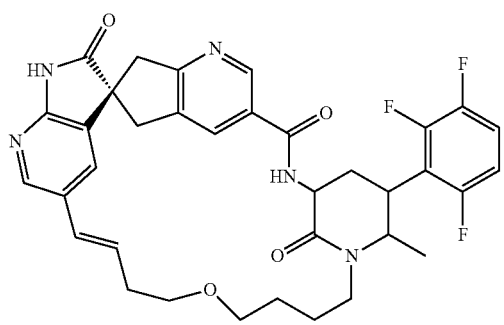 [SMILES: CC1C(c2c(F)ccc(F)c2F)CC2NC(=O)c3cnc4c(c3)C[C@@]3(C4)C(=O)Nc4ncc(cc43)/C=C/CCOCCCCN1C2=O]

Example 1-5

TABLE 1-continued
Example compounds
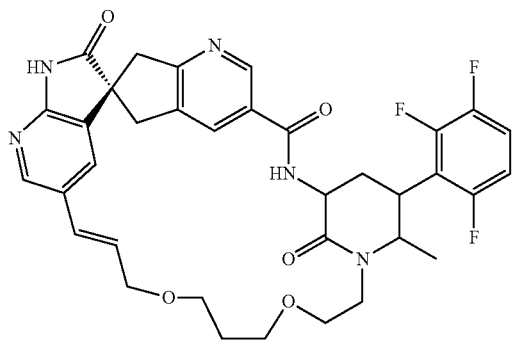 [SMILES: CC1C(c2c(F)ccc(F)c2F)CC2NC(=O)c3cnc4c(c3)C[C@@]3(C4)C(=O)Nc4ncc(cc43)/C=C/COCCCOCCN1C2=O]
Example 1-6
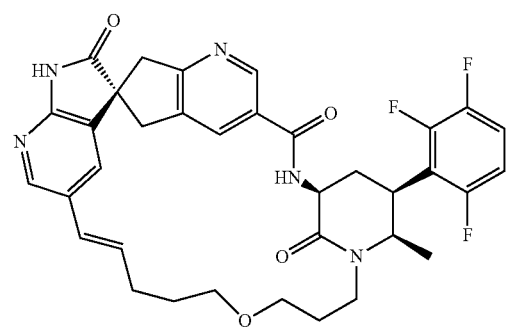 [SMILES: C[C@@H]1[C@H](c2c(F)ccc(F)c2F)C[C@@H]2NC(=O)c3cnc4c(c3)C[C@@]3(C4)C(=O)Nc4ncc(cc43)/C=C/CCCOCCCN1C2=O]
Example 1-7
Isomer 1
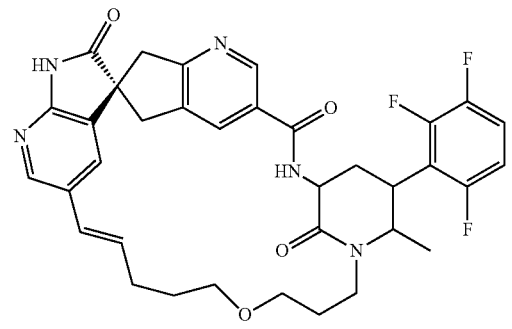 [SMILES: CC1C(c2c(F)ccc(F)c2F)CC2NC(=O)c3cnc4c(c3)C[C@@]3(C4)C(=O)Nc4ncc(cc43)/C=C/CCCOCCCN1C2=O]
Example 1-7
Isomer 2/3
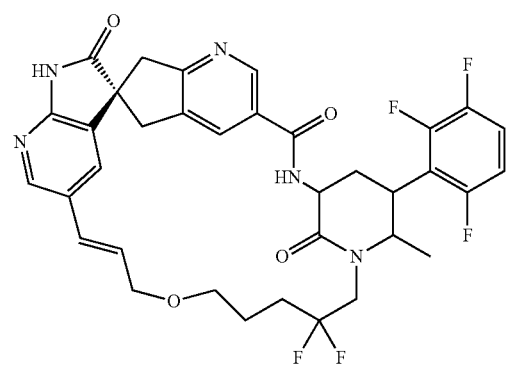 [SMILES: CC1C(c2c(F)ccc(F)c2F)CC2NC(=O)c3cnc4c(c3)C[C@@]3(C4)C(=O)Nc4ncc(cc43)/C=C/COCCCC(F)(F)CN1C2=O]
Example 1-8
TABLE 1-continued
Example compounds
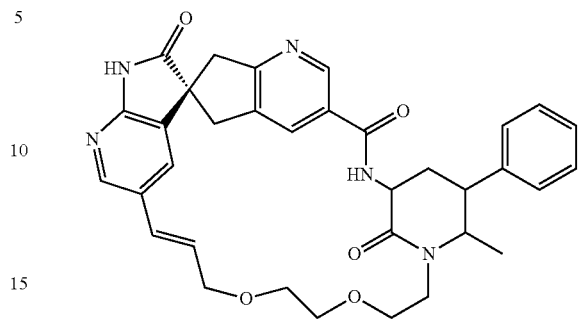
Example 2-1
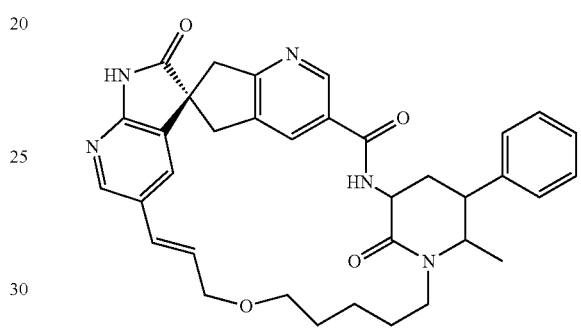
Example 2-2
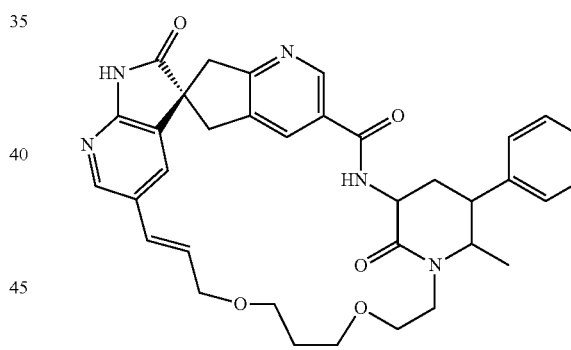
Example 2-3
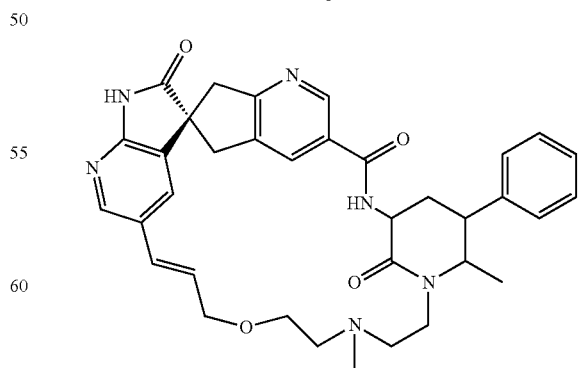
Example 2-4

TABLE 1-continued
Example compounds
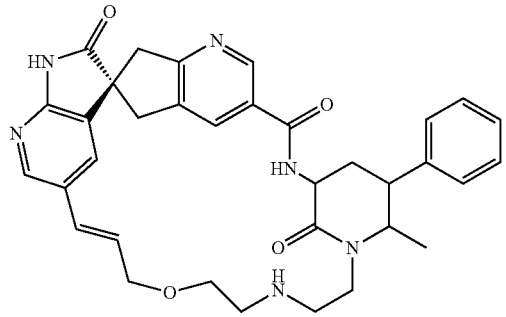
Example 2-5
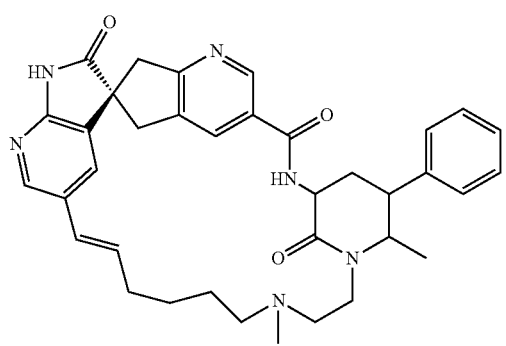 [SMILES: CC1C(c2ccccc2)CC2NC(=O)c3cnc4c(c3)C[C@@]3(C4)C(=O)Nc4ncc(cc43)/C=C/CCCCN(C)CCN1C2=O]
Example 2-6
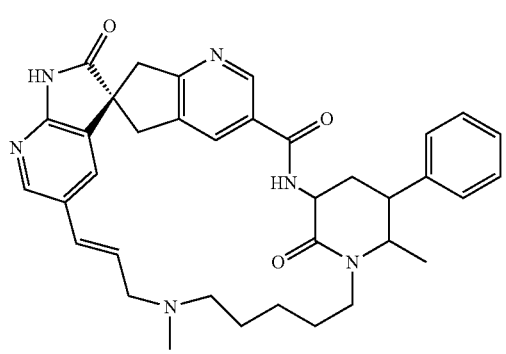 [SMILES: CC1C(c2ccccc2)CC2NC(=O)c3cnc4c(c3)C[C@@]3(C4)C(=O)Nc4ncc(cc43)/C=C/CN(C)CCCCCN1C2=O]
Example 2-7
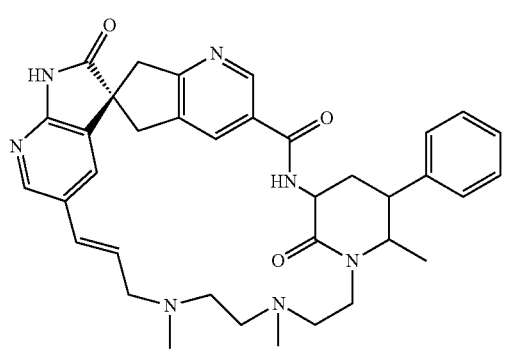 [SMILES: CC1C(c2ccccc2)CC2NC(=O)c3cnc4c(c3)C[C@@]3(C4)C(=O)Nc4ncc(cc43)/C=C/CN(C)CCN(C)CCN1C2=O]
Example 2-8
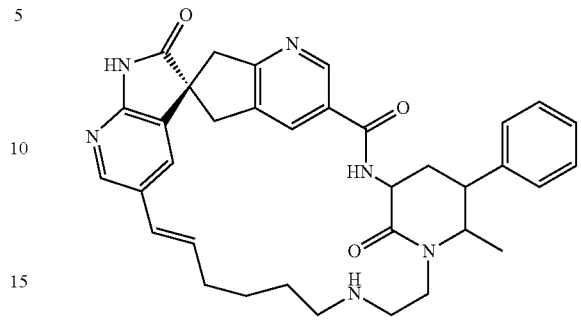
Example 2-9
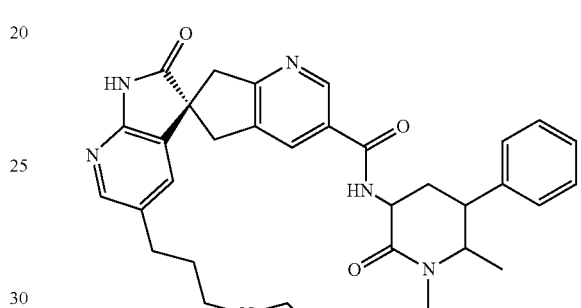
Example 2-10
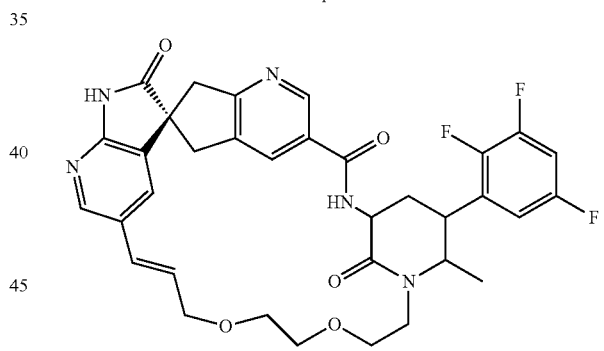
Example 3-1
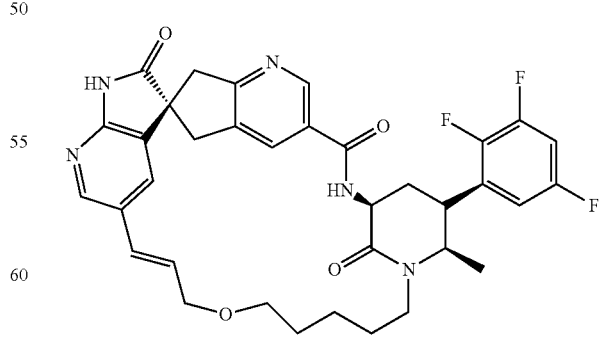
Example 3-2
Isomer 1

TABLE 1-continued
Example compounds
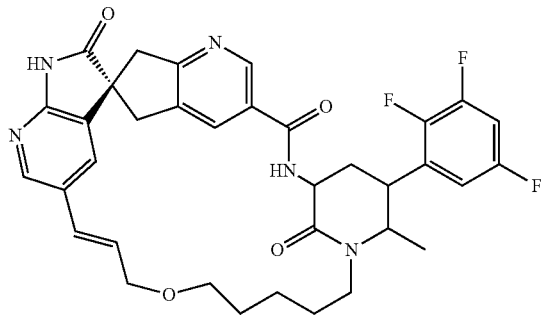 [SMILES: CC1C(c2cc(F)cc(F)c2F)CC2NC(=O)c3cnc4c(c3)C[C@@]3(C4)C(=O)Nc4ncc(cc43)/C=C/COCCCCCN1C2=O]
Example 3-2
Isomer 2/3
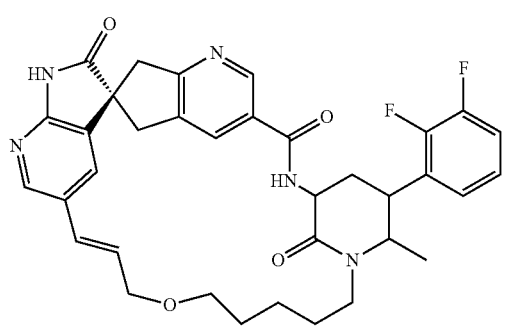 [SMILES: CC1C(c2cccc(F)c2F)CC2NC(=O)c3cnc4c(c3)C[C@@]3(C4)C(=O)Nc4ncc(cc43)/C=C/COCCCCCN1C2=O]
Example 4-1
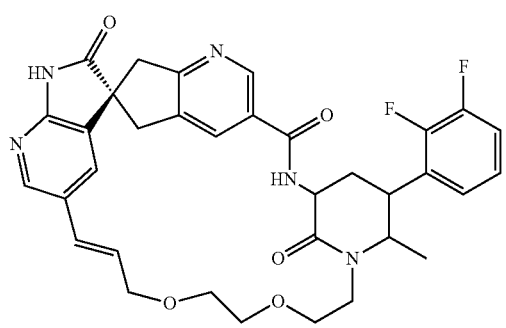 [SMILES: CC1C(c2cccc(F)c2F)CC2NC(=O)c3cnc4c(c3)C[C@@]3(C4)C(=O)Nc4ncc(cc43)/C=C/COCCOCCN1C2=O]
Example 4-2
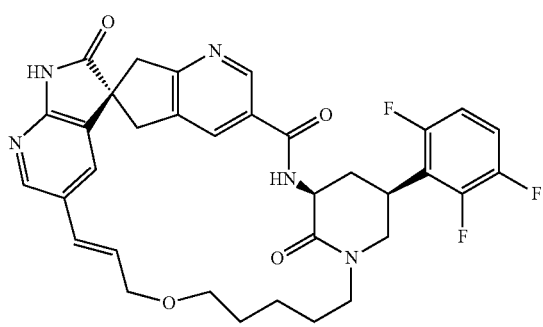 [SMILES: O=C1N[C@H]2C[C@@H](c3c(F)ccc(F)c3F)CN(CCCCCOC/C=C/c3cnc4c(c3)[C@@]3(Cc5cc1cnc5C3)C(=O)N4)C2=O]
Example 5-1
Isomer 1
TABLE 1-continued
Example compounds
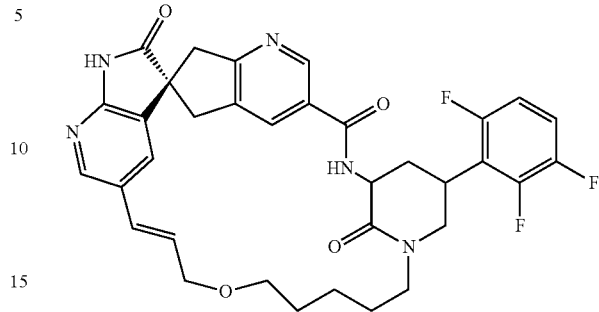
Example 5-1
Isomer 2/3
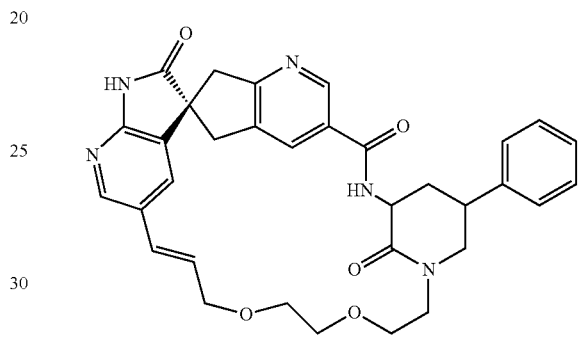
Example 6-1
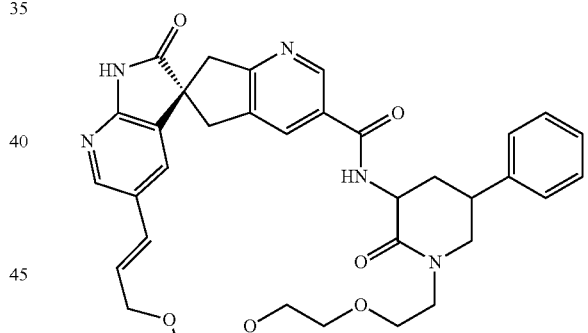
Example 6-2
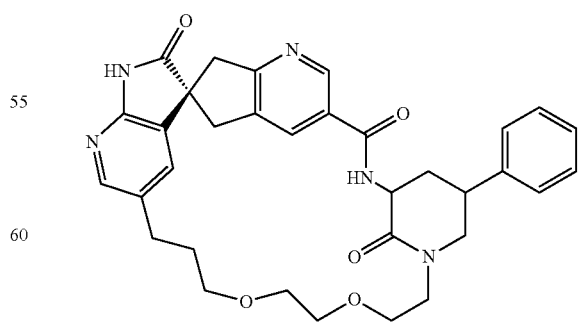
Example 6-3

TABLE 1-continued

Example compounds

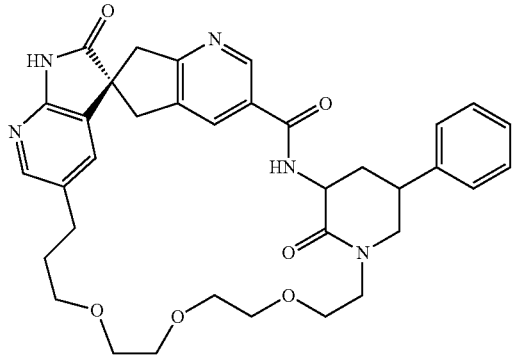 [SMILES: O=C1NC2CC(c3ccccc3)CN(CCOCCOCCOCCCc3cnc4c(c3)[C@@]3(Cc5cc1cnc5C3)C(=O)N4)C2=O]

Example 6-4

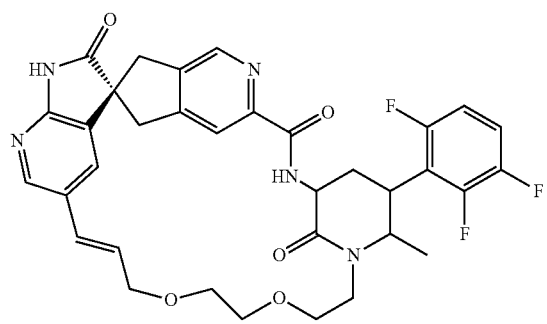 [SMILES: CC1C(c2c(F)ccc(F)c2F)CC2NC(=O)c3cc4c(cn3)C[C@]3(C4)C(=O)Nc4ncc(cc43)/C=C/COCCOCCN1C2=O]

Example 7-1

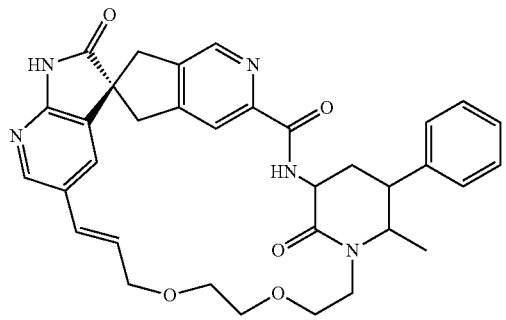 [SMILES: CC1C(c2ccccc2)CC2NC(=O)c3cc4c(cn3)C[C@]3(C4)C(=O)Nc4ncc(cc43)/C=C/COCCOCCN1C2=O]

Example 8-1

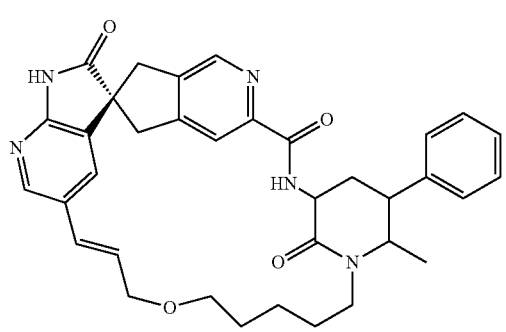 [SMILES: CC1C(c2ccccc2)CC2NC(=O)c3cc4c(cn3)C[C@]3(C4)C(=O)Nc4ncc(cc43)/C=C/COCCCCCN1C2=O]

Example 8-2

TABLE 1-continued

Example compounds

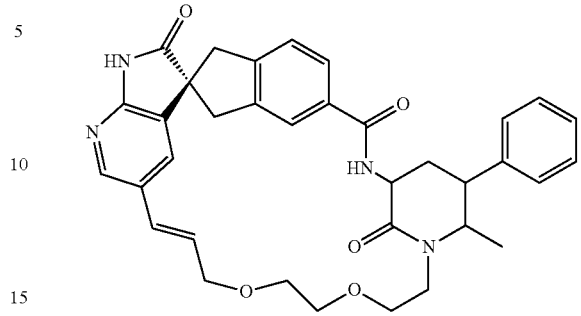

Example 9-1

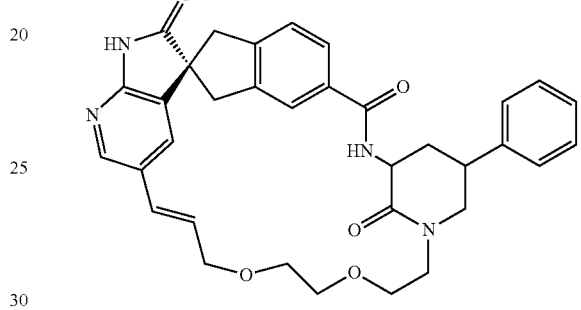

Example 10-1

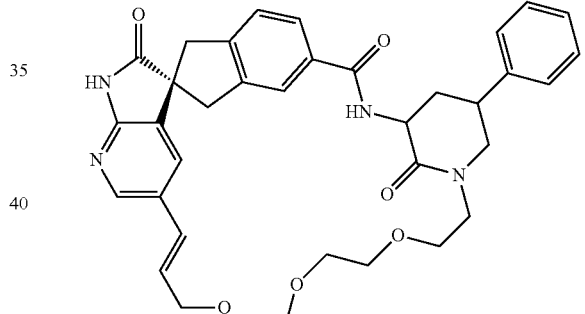

Example 10-2

General Information

NMR

NMR spectra were recorded on Bruker DPX 300 MHz equipped with a 5 mm BBI probe, Bruker AV400 MHz equipped with a 5 mm PABBO probe, Bruker DRX 500 MHz equipped with a 5 mm PABBI probe or Bruker Avance III 600 spectrometer equipped with a 5 mm RT BBI probe. The samples were recorded at 25° C. using DMSO-d, CDCl$_3$ or MeOD-d4 as a solvent and TMS as the internal standard.

HPLC

LC/MS System: Waters Acquity UPLC coupled with SQD mass spectrometer system Software used: FractionLynx and MassLynx v4.1

Method 1. Ammonium Bicarbonate Generic Analytical UPLC Open Access LC/MS 12 Minute Method LC Conditions Column: Acquity UPLC BEH C18 (50 mm×2.1 mm i.d., 1.7 μm packing diameter)

Column temperature: 40° C.
Solvents: A=10 mM aqueous solution of $NH_4HCO_3$ (adjusted to pH 10 with ammonia)
B=Acetonitrile
Injection Volume: 2 μl
The Gradient Table:

| Time (min) | Flow Rate (mL/min) | % A | % B |
|---|---|---|---|
| 0.0 | 0.9 | 97 | 3 |
| 10.0 | 0.9 | 0 | 100 |
| 11.5 | 0.9 | 0 | 100 |
| 12.00 | 0.05 | 97 | 3 |

Stop time: 12 min
UV Conditions
  PDA Range: 210 nm-450 nm
  The UV detection was a summed signal from wavelength of 210 nm to 450 nm
  Acquisition Rate: 40 Hz
MS Conditions
  Ionization Mode: Alternate-scan Positive and Negative Electrospray ($ES^+/ES^-$)
  Scan Range: 100 to 1500 AMU
  Scan Time: 0.15 seconds
Inter Scan Delays:
  MS inter-scan: 0.02 seconds
  Polarity/Mode switch inter-scan: 0.02 seconds

Method 2. Generic Basic Analytical UPLC Open Access

LC/MS 8 minute Method—MS range 100-1500, ES+/ES− Mode
LC Conditions
  Column: Acquity UPLC BEH C18 (2.1 mm×100 mm, 1.7 μm)
  Column temperature: 40° C.
  Solvents: A—Water+0.05% of Ammonia
    B—Acetonitrile+0.05% of Ammonia
  Injection volume: 2 μl
  Equilibration time: 1 min
Gradient Table:

| Time (min) | Flow Rate (mL/min) | % A | % B |
|---|---|---|---|
| 0.00 | 0.6 | 97 | 3 |
| 0.50 | 0.6 | 97 | 3 |
| 7.00 | 0.6 | 3 | 97 |
| 7.50 | 0.6 | 3 | 97 |
| 7.60 | 0.6 | 97 | 3 |
| 8.00 | 0.6 | 97 | 3 |

Stop time: 8 min
UV Conditions
  PDA Range: 210 nm-400 nm
  Resolution: 1.2 nm
  Acquisition Rate: 40 Hz
MS Conditions
  Ionization Mode: Electrospray Positive and Negative ($ES^+/ES^-$)
  Scan Range: 100 to 1500 Da
  Scan Time: 0.15 seconds
Method 3. Generic Basic Analytical UPLC Open Access LC/MS 4 minute Method—MS Range 100-1500, ES+/ES− Mode LC Conditions
  Column: Acquity UPLC BEH C18 (2.1 mm×50 mm, 1.7 μm)
  Column temperature: 40° C.
  Solvents: A—Water+0.05% of Ammonia
    B—Acetonitrile+0.05% of Ammonia
  Injection volume: 2 μl
  Equilibration time: 1 min
Gradient Table:

| Time (min) | Flow Rate (mL/min) | % A | % B |
|---|---|---|---|
| 0.00 | 0.9 | 97 | 3 |
| 3.50 | 0.9 | 3 | 97 |
| 3.90 | 0.9 | 3 | 97 |
| 3.91 | 0.9 | 97 | 3 |
| 4.00 | 0.9 | 97 | 3 |

Stop time: 4 min
UV Conditions
  PDA Range: 210 nm-400 nm
  Resolution: 1.2 nm
  Acquisition Rate: 40 Hz
MS Conditions
  Ionization Mode: Electrospray Positive and Negative ($ES^+/ES^-$)
  Scan Range: 100 to 1500 Da
  Scan Time: 0.15 s For preparative purification HPLC Waters Mass Directed Autopurification System was used. The system is composed of Waters Sample Manager 2767, Waters System Fluid Organizer, Waters Binary Gradient Module 2545, Waters 515 HPLC Pump, Waters Photodiode Array Detector 2998 and Waters Micromass ZQ MS detector. Software used: FractionLynx and MassLynx v4.1.

General HPLC method parameters: gradient mobile phase of 0.1% formic acid in $H_2O$ and $CH_3CN$ or 10 mM aqueous solution of $NH_4HCO_3$ (adjusted to pH 10 with ammonia) and $CH_3CN$. Column XBridge 30×150 mm, 5 μm.

PDA detector settings: wavelength: 210-400 nm, resolution: 1.2 nm, sampling rate: 1.0 points/sec, filter response: 1.

MS detector settings: MS scan: centroid, ionization mode: ES+ and ES−, mass range: 105-1500, scan time: 1.0 s, inter-scan delay: 0.1 s, capillary: 3.00 kV, cone: 30 V, extractor: 3.00 V, RF Lens: 0.2 V, source temp.: 150° C., desolvation temp.: 350° C., cone gas flow: 50 L/h, desolvation gas flow: 700 L/h, LM 1 resolution: 15.0, HM 1 resolution: 15.0, ion energy 1: 1.0 and multiplier: 650 V.

Scheme 1. General Synthesis of Examples

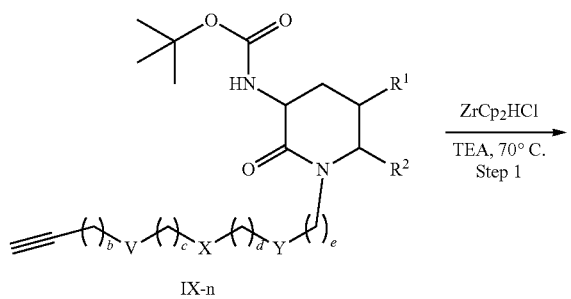

IX-n

-continued

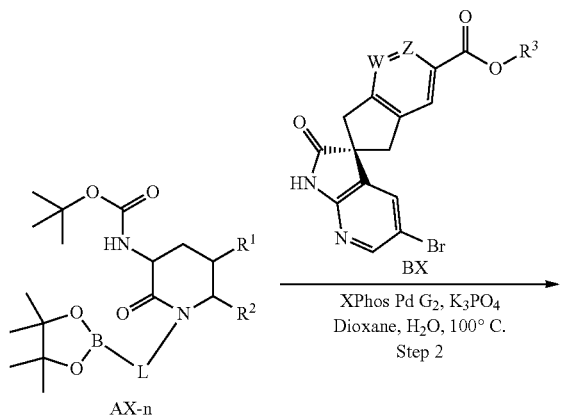

AX-n

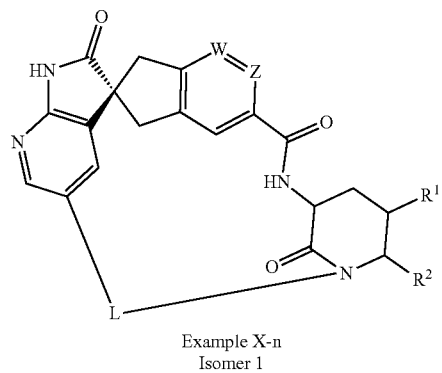

Example X-n
Isomer 1

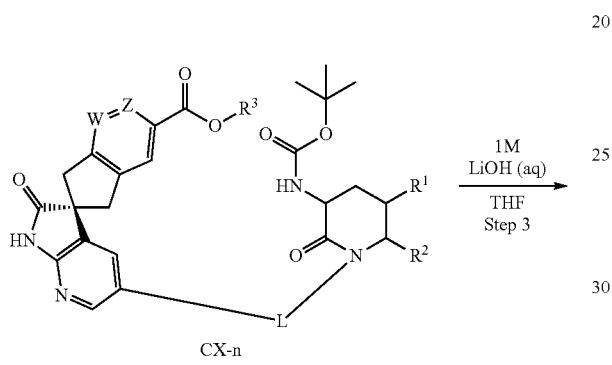

CX-n

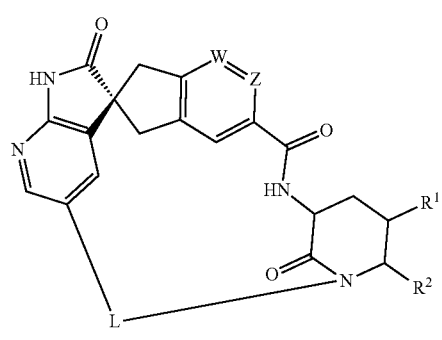

Example X-n
Isomer 2 or 3

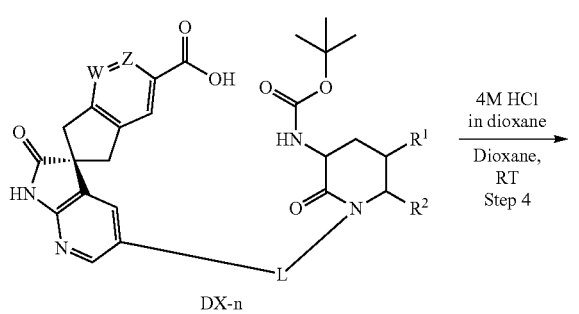

DX-n

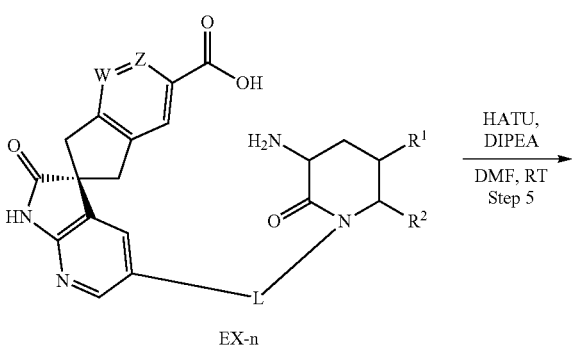

EX-n

In Scheme 1, b, c, d, e, L, V, W, X, Y, Z, $R^1$ and $R^2$ are as defined above and $R^3$ is selected from methyl, ethyl and isopropyl. An alkynyl N-Boc aminopiperidinone of type IX-n or IX-n*, (IX-n indicates enriched single enantiomer all cis piperidone IX-n* indicates all cis enriched racemic piperidone) is converted to 4,4,5,5-tetramethyl-1,3,2-dioxaborolan-2-yl-N-Boc aminopiperidinones of type AX-n by reaction for example with pinacolborane, TEA and $ZrCp_2HCl$ for 3 h at 70° C., and for a further 1 h after a second addition of pinacolborane (step 1). The resulting boronate can be coupled to a bromopyridyl-arylester of type BX, which is a single enantiomer, using a catalyst such as XPhos-Pd-G2 in, for example, water and dioxane at 100° C. for 2 h with $K_3PO_4$, (step 2) to afford an arylester-N-Boc-amino piperidinone intermediate of type CX-n. Hydrolysis of intermediate type CX-n with, for example, lithium hydroxide aq. in THF at room temperature, (step 3) affords an arylcarboxylic acid-N-Boc-amino piperidinone of type DX-n, Boc de-protection of which, with for example, 4M HCl in dioxane water at room temperature, (step 4) affords an aminopiperidone-arylcarboxylic acid of type EX-n. Macro lactamisation of aminopiperidinone-arylcarboxylic acid EX-n, with for example, HATU and DIPEA in DMF at room temperature, (step 5) affords examples of this invention (Example X-n) as one or more isomers.

Scheme 2 Synthesis of Example 1-1
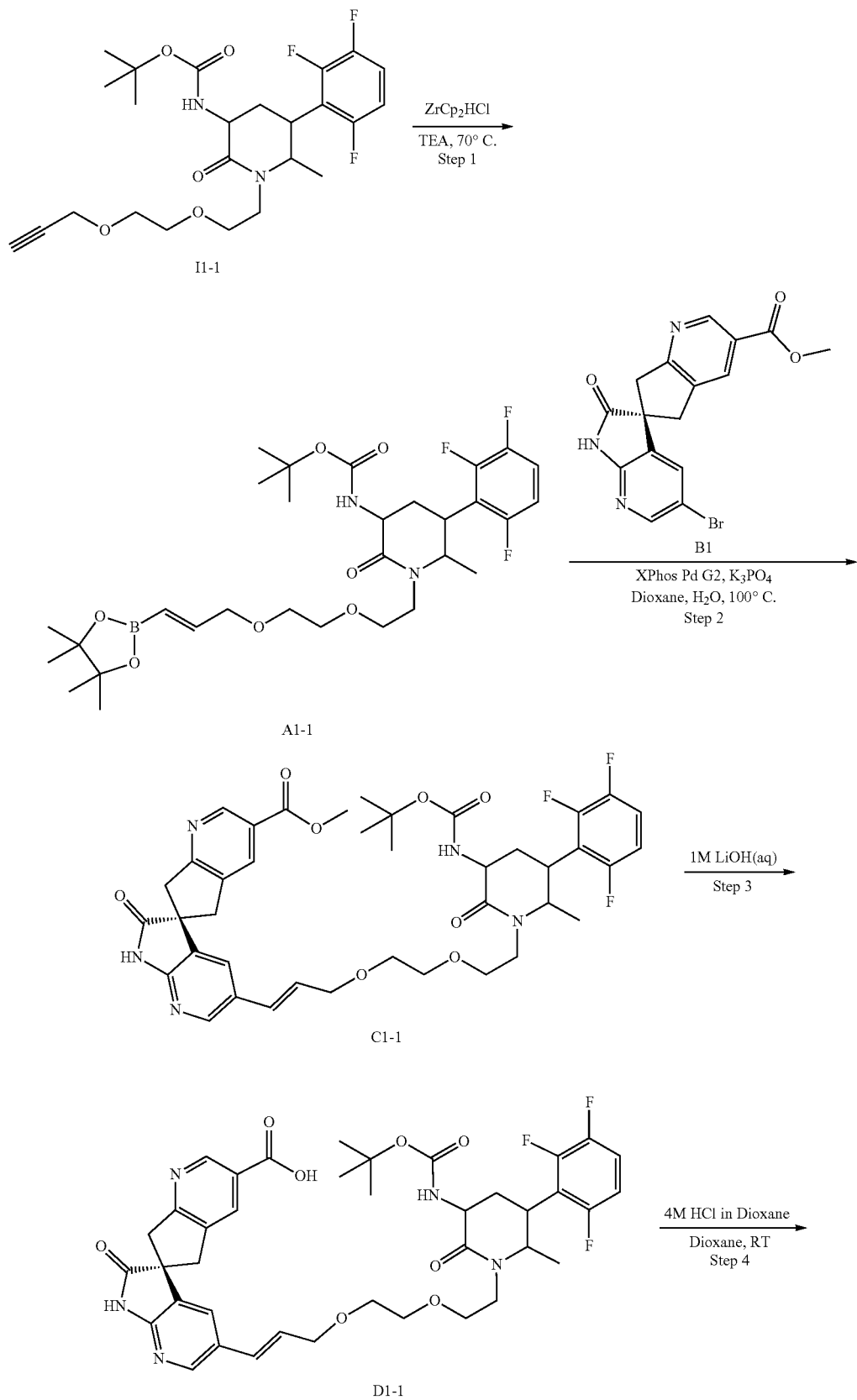

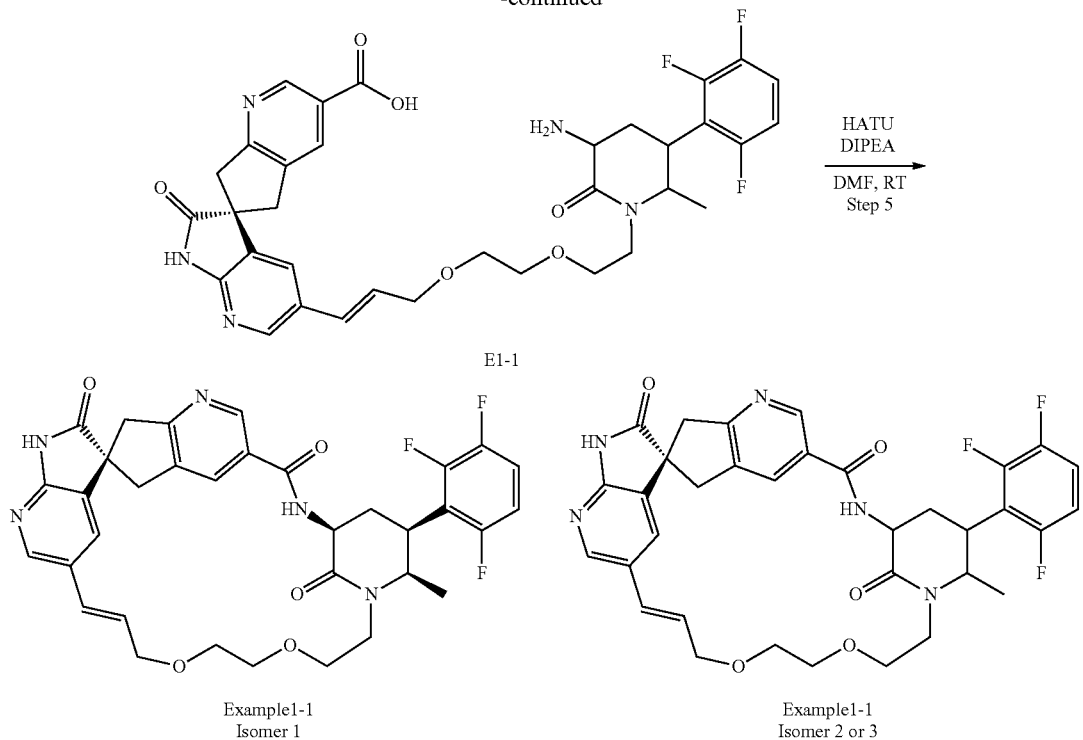

Example1-1
Isomer 1

Example1-1
Isomer 2 or 3

Experimental Procedure for Synthesis of Example 1-1 Isomers 1 and 2

Step 1. Synthesis of Tert-butyl N-[6-methyl-2-oxo-1-[2-[2-[(E)-3-(4,4,5,5-tetramethyl-1,3,2-dioxaborolan-2-yl)allyloxy]ethoxy]ethyl]-5-(2,3,6-trifluorophenyl)-3-piperidyl]carbamate (A1-1*)

Into a vial containing compound I1-1* (435 mg, 0.898 mmol), pinacolborane (146 μL, 1.0 mmol), TEA (15.2 μL, 0.109 mmol), and ZrCp$_2$HCl (29.4 mg, 0.988 mmol) were added. The vial was sealed and the suspension stirred at 70° C. After 3 hours additional pinacolborane (146 μL, 1.0 mmol) was added and stirring continued for 1 hour. The reaction mixture was quenched with sat. NH$_4$Cl (20 mL) and extracted with DCM (3×10 mL). The combined organic layers were washed with brine (10 mL), dried over Na$_2$SO$_4$ and concentrated under reduced pressure to afford desired crude product A1-1* (776 mg) which was used as is in the next reaction step. LC-MS (ES+): 613.3 [M+H]$^+$.

Step 2. Synthesis of Methyl (3S)-5-[(E)-3-[2-[2-[5-(tert-butoxycarbonylamino)-2-methyl-6-oxo-3-(2,3,6-trifluorophenyl)-1-piperidyl]ethoxy]ethoxy]prop-1-enyl]-2-oxo-spiro[1H-pyrrolo[2,3-b]pyridine-3,6'-5,7-dihydrocyclopenta[b]pyridine]-3'-carboxylate (Intermediate C1-1)

To a suspension of compound B-1 (183 mg, 0.49 mmol) and compound A1-1* (776 mg, crude material) in degassed dioxane (1.90 mL), a solution of K$_3$PO$_4$ (312 mg, 0.098 mmol) in degassed water (520 μL) was added. Then XPhos Pd G2 (77.1 mg, 0.098 mmol) was added and the reaction mixture degassed for an additional 5 minutes, sealed and heated at 100° C. for 2 hours. The reaction mixture was diluted with DCM (30 mL) washed with sat. NaHCO$_3$ (4×10 mL) and sat. NaCl (10 mL), dried over Na$_2$SO$_4$ and concentrated under reduced pressure to afford the crude product (676 mg) as a brown oil. The crude material was loaded and purified on a silica column (Interchim 25 g, 15 μm, SiO$_2$) using Interchim PuriFlash 450 instrument with a flowrate of 20 mL/min starting with DCM (100%) and going to 100% [DCM/MeOH (20:1)] in 20 CVs. Hold 100% for 10 CVs. The appropriate fractions were collected, the solvent removed to yield the desired product C1-1 (159 mg, 42%).

LC-MS (ES+): 780.4 [M+H]$^+$.

Step 3. Synthesis of (3S)-5-[(E)-3-[2-[2-[5-(tert-butoxycarbonylamino)-2-methyl-6-oxo-3-(2,3,6-trifluorophenyl)-1-piperidyl]ethoxy]ethoxy]prop-1-enyl]-2-oxo-spiro[1H-pyrrolo[2,3-b]pyridine-3,6'-5,7-dihydrocyclopenta[b]pyridine]-3'-carboxylic acid (Intermediate D1-1)

To a solution of compound C1-1 (159 mg, 0.204 mmol) in THF (3.0 mL), LiOH (1.0 N in H$_2$O, 815 μL, 0.815 mmol) was added. The reaction mixture was stirred at room temperature for 25 minutes. The reaction mixture was concentrated under reduced pressure and dissolved in water (15 mL). The solution was carefully washed with diethylether (2×10 mL). The pH value of the aq. layer was adjusted to 3.5 using 1 N HCl and extracted with DCM (4×10 mL). The combined organic layers were dried over Na$_2$SO$_4$ and concentrated under reduced pressure to afford the desired product D1-1 (130 mg, 83%).

LC-MS (ES+): 766.3 [M+H]$^+$.

Step 4. Synthesis of (3S)-5-[(E)-3-[2-[2-[5-amino-2-methyl-6-oxo-3-(2,3,6-trifluorophenyl)-1-piperidyl]ethoxy]ethoxy]prop-1-enyl]-2-oxo-spiro[1H-pyrrolo[2,3-b]pyridine-3,6'-5,7-dihydrocyclopenta[b]pyridine]-3'-carboxylic Acid (Compound E1-1)

To the solution of compound D1-1 (130 mg, 0.169 mmol) in dioxane (3.38 mL), HCl (4.0 M in dioxane, 1.69 mL, 6.79 mmol) was added. The reaction mixture was stirred at room temperature for 1.5 hours. The reaction mixture was concentrated to yield the desired product E1-1 (145.2 mg) which was used as is in the next reaction step.

LC-MS (ES+): 666.3 [M+H]$^+$.

Step 5. Synthesis of (1S,10S,12S,13R, 22E)-13-methyl-12-(2,3,6-trifluorophenyl)-17,20-dioxa-5,9,14,26,28-pentazahexacyclo[22.5.2.11,4.13,7.110,14.027,30]tetratriaconta-3,5,7(33),22,24(31),25,27(30)-heptaene-8,29,32-trione (Example 1-1 Isomer 1) and (1S,22E)-13-methyl-12-(2,3,6-trifluorophenyl)-17,20-dioxa-5,9,14,26,28-pentazahexacyclo[22.5.2.11,4.13,7.110,14.027,30]tetratriaconta-3,5,7(33),22,24(31),25,27(30)-heptaene-8,29,32-trione (Example 1-1 Isomer 2)

To a solution of DIPEA (60 µL, 0.34 mmol) and HATU (96.4 mg, 0.25 mmol) in dry DMF (28 mL) a solution of compound E1-1 (145 mg, 0.169 mmol) and DIPEA (120 µL, 0.68 mmol) in dry DMF (14 mL) was added dropwise over period of 2 minutes. The reaction was quenched by adding DCM (50 mL) and a mixture of sat. NaHCO$_3$/H$_2$O 1:1 (100 mL), layers were separated, and the aqueous layer extracted with DCM (3×20 mL). The combined organic layers were dried over Na$_2$SO$_4$ and concentrated under reduced pressure to afford the crude product (145 mg). The crude material was dissolved in EtOAc (70 mL). This solution was washed with sat. NaHCO$_3$ (3×15 mL). The organic layer was dried under Na$_2$SO$_4$ and concentrated under reduced pressure to afford 82.6 mg of the crude product as a yellow solid. The crude material was loaded and purified on a silica column (Interchim 4 g, 15 µm, SiO$_2$) using Interchim PuriFlash 450 instrument with a flowrate of 7 mL/min starting with DCM (100%). Hold DCM (100%) for 5 CV and going to 60% [DCM/MeOH (10:1)] in 10 CVs. Increasing to 75% [DCM/MeOH (10:1)] in 20 CVs and after that to 100% [DCM/MeOH (10:1)] in 10 CVs. The appropriate fractions were collected, the solvent removed to yield the desired products Example 1-1 Isomer 1 (29.9 mg, 27%) and Example 1-1 Isomer 2 (32.4 mg, 30%).

Data for Isomer 1:

LC-MS (ES+): 648.1 [M+H]$^+$, R$_t$=4.65 min (Method 1)

$^1$H NMR (600 MHz, DMSO-d$_6$): δ=1.14 (d, J=6.4 Hz, 3H), 2.17 (dd, J=11.7, 7.3 Hz, 1H), 2.84 (ddd, J=13.6, 8.0, 5.8 Hz, 1H), 2.89-2.98 (m, J=13.3, 11.7, 11.7, 3.5, 3.5 Hz, 1H), 3.00 (d, J=16.0 Hz, 1H), 3.15 (d, J=15.6 Hz, 1H), 3.41-3.53 (m, 5H), 3.59-3.65 (m, 2H), 3.62-3.67 (m, J=16.3 Hz, 1H), 3.77-3.84 (m, 1H) 3.84-3.92 (m, 2H), 3.98 (t, J=5.5 Hz, 2H), 4.67 (ddd, J=11.4, 9.2, 7.0 Hz, 1H), 5.65 (dt, J=16.1, 6.1 Hz, 1H), 6.43 (d, J=16.0 Hz, 1H), 6.49 (d, J=2.0 Hz, 1H), 7.17 (dddd, J=9.1, 4.0, 1.8 Hz, 1H), 7.48 (qd, J=9.1, 5.4 Hz, 1H), 8.01 (d, J=1.8 Hz, 1H), 8.09 (s, 1H), 8.66 (d, J=9.2 Hz, 1H), 8.82 (s, 1H), 11.40 (s, 1H) ppm.

$^{13}$C NMR (151 MHz, DMSO-d$_6$): δ=15.8, 26.5, 35.6, 40.5, 44.2, 49.1, 51.1, 54.5, 58.2, 69.5, 69.7, 71.8, 71.8, 112.1, 117.1, 118.5, 123.3, 126.1, 126.6, 127.6, 130.2, 130.3, 132.4, 135.3, 147.2, 148.9, 156.0, 157.0, 165.3, 167.0, 168.4, 178.7 ppm.

Data for Isomer 2:

LC-MS (ES+): 648.1 [M+H]$^+$, R$_t$=4.68 min (Method 1)

$^1$H NMR (600 MHz, DMSO-d$_6$): δ=1.15 (d, J=6.4 Hz, 3H), 2.14 (dd, J=11.9, 6.8 Hz, 1H), 2.81 (td, J=9.2, 3.7 Hz, 1H), 2.87-2.98 (m, J=13.6, 11.9, 11.5, 3.5, 3.5 Hz, 1H), 3.05 (d, J=16.1 Hz, 1H), 3.06 (d, J=15.2 Hz, 1H), 3.32-3.36 (m, 1H), 3.42-3.48 (m, 3H), 3.50 (d, J=15 Hz, 1H), 3.62 (d, J=16.3,1H) 3.63 (quin, J=6.4, 6.0 Hz, 1H), 3.67-3.74 (m, 1H), 3.82-3.95 (m, 4H), 4.04 (ddd, J=11.6, 4.0, 1.5 Hz, 1H), 4.65 (ddd, J=11.5, 8.7, 7.5 Hz, 1H), 5.70 (ddd, J=16.0, 8.8, 4.1 Hz, 1H), 6.47 (d, J=16.3 Hz, 1H), 6.64 (d, J=1.8 Hz, 1H), 7.12-7.20 (m, J=9.4, 9.4, 3.9, 1.7 Hz, 1H), 7.47 (qd, J=9.4, 4.9 Hz, 1H), 8.00 (d, J=2.0 Hz, 1H), 8.12 (s, 1H), 8.65 (d, J=9.2 Hz, 1H), 8.83 (s, 1H), 11.42 (s, 1H) ppm.

$^{13}$C NMR (151 MHz, DMSO-d$_6$): δ=15.8, 26.6, 35.5, 41.0, 43.9, 49.1, 50.9, 54.5, 58.3, 68.7, 69.8, 72.0, 72.1, 112.1, 116.6, 118.6, 123.2, 125.9, 126.4, 128.2, 129.3, 130.3, 131.0, 134.7, 147.5, 148.6, 149.1, 156.0, 157.0, 165.5, 166.5, 168.3, 178.7 ppm.

Examples 1-2, 1-3, 1-4, 1-5, 1-6, 1-7, 1-8, 2-1, 2-2, 2-3, 3-1, 3-2, 4-1, 4-2, 5-1, 7-1, 8-1, 8-2 and 9-1 were synthesized using the same experimental procedures as for the synthesis of Isomers 1 and 2 of Example 1-1 and starting from Intermediate IX-n and BX as stated in Table 2.

In Example 2-2 where synthesis starts with intermediate B2, step 2 of the synthesis described in scheme 2. was not used (hydrolysis of esters).

TABLE 2
Examples synthesis according to Scheme 2
| Starting material | | Intermediate BX | Example | Structure | Final products | | | |
|---|---|---|---|---|---|---|---|---|
| Intermediate IX-n | Structure IX-n | | | | Q | Example | Q | Structure |
| I1-1 4.34 g, | 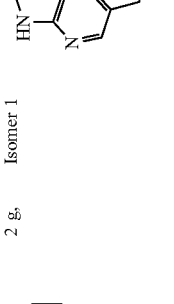 | B1 2 g, | Example 1-1 Isomer 1 | 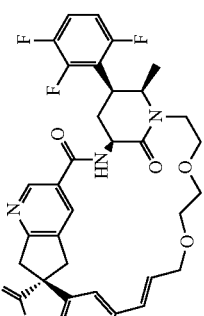 | 517 mg, | Example 1-1 Isomer 3 | 50.6 mg, | 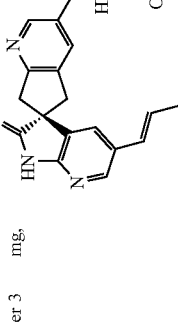 |
| I1-2* 440 mg, |  | B1 160 mg | Example 1-2 Isomer 1 | 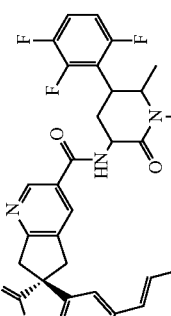 | 9.60 mg, | Example 1-2 Isomer 2 | 9.24 mg, | 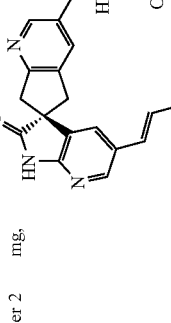 |
| I1-3* 300 mg, | 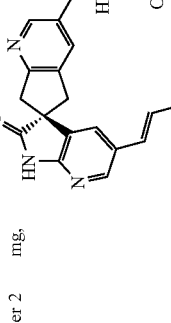 | B1 150 mg, | Example 1-3 Isomer 1 | 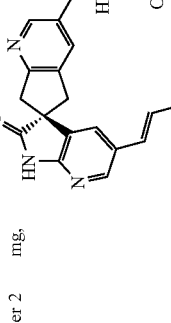 | 16.5 mg, | Example 1-3 Isomer 2 | 21.5 mg, | 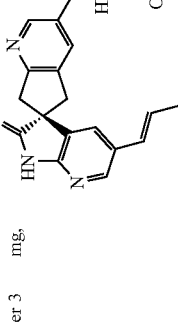 |

TABLE 2-continued

Examples synthesis according to Scheme 2

| Starting material | | Intermediate BX | Example | Final products | | | |
|---|---|---|---|---|---|---|---|
| Intermediate IX-n | Structure | | | Q | Example | Q | Structure |
| I1-4* 310 mg, | [structure] | B1 155 mg, | Example 1-4 Isomer 1 | 19 mg, | Example 1-4 Isomer 2 | 12.2 mg, | [structure] |
| I1-5* 333.0 mg, | [structure] | B1 172 mg, | Example 1-5 Isomer 1 | 19 mg, | Example 1-5 Isomer 2 | 19 mg, | [structure] |
| I1-6* 355.2 mg, | [structure] | B1 172.7 mg, | Example 1-6 Isomer 1 | 36.1 mg, | Example 1-6 Isomer 2 | 33.1 mg, | [structure] |

TABLE 2-continued

Examples synthesis according to Scheme 2

| Starting material | | | Intermediate BX | Example | Final products | | |
|---|---|---|---|---|---|---|---|
| Intermediate IX-n | Structure | | | | Structure | Example | Q |
| I1-7* 400 mg, | (structure) | | B1 170 mg, | Example 1-7 Isomer 1 | (structure) 19.2 mg, | Example 1-7 Isomer 2 | 21.1 mg, |
| I1-7 1.93 g, | (structure) | | B1 1.2 g, | Example 1-7 Isomer 1 | (structure) 212 mg | Example 1-7 Isomer 3 | 17.2 mg, |
| I1-8* 247 mg, | (structure) | | B1 130 mg, | Example 1-8 Isomer 1 | (structure) 9.4 mg, | Example 1-8 Isomer 2 | 17 mg, |

TABLE 2-continued

Examples synthesis according to Scheme 2

| Starting material | | Intermediate BX | Example | Final products | | | |
|---|---|---|---|---|---|---|---|
| Intermediate IX-n | Structure | | | Structure | Q | Example | Q |
| I2-1 234.1 mg, | [structure] | B3 140.8 mg, | Example 2-1 Isomer 1 | [structure] | 26.2 mg, | — | — |
| I2-2* 373 mg, | [structure] | B2 207 mg, | Example 2-2 Isomer 1 | [structure] | 12.8 mg, | Example 2-2 Isomer 2 | 12.2 mg, |
| I2-3 171.8 mg, | [structure] | B3 100 mg, | Example 2-3 Isomer 1 | [structure] | 40.4 mg, | — | — |

TABLE 2-continued

Examples synthesis according to Scheme 2

| Starting material | | Intermediate BX | Example | Final products | | | |
|---|---|---|---|---|---|---|---|
| Intermediate IX-n | Structure | | | Structure | Q | Example | Q |
| I3-1* 400 mg, | | B1 200 mg, | Example 3-1 Isomer 1 | | 68.7 mg, | Example 3-1 Isomer 2 | 23.3 mg, |
| I3-2* 400 mg, | | B1 180 mg, | Example 3-2 Isomer 1 | | 33 mg, | Example 3-2 Isomer 2 | 30 mg, |
| I3-2 3.32 g, | | B1 1.45 g, | Example 3-2 Isomer 1 | | 259.1 mg, | Example 3-2 Isomer 3 | 41.3 mg, |
| I4-1* 400 mg, | | B1 170 mg, | Example 4-1 Isomer 1 | | 26.85 mg, | Example 4-1 Isomer 2 | 27.95 mg, |

TABLE 2-continued

Examples synthesis according to Scheme 2

| Starting material | | Intermediate BX | Example | Final products | | |
|---|---|---|---|---|---|---|
| Intermediate IX-n | Structure | | | Structure | Example | Q |
| I4-2* 400 mg, | (structure) | B1 180 mg, | Example 4-2 Isomer 1 | (structure) | Example 4-2 Isomer 2 | 27.2 mg, 19.5 mg, |
| I5-1* 395.0 mg, | (structure) | B1 210 mg, | Example 5-1 Isomer 1 | (structure) | Example 5-1 Isomer 2 | 27.0 mg, 23.6 mg, |
| I5-1 5.0 g, | (structure) | B1 2.5 g, | Example 5-1 Isomer 1 | (structure) | Example 5-1 Isomer 3 | 727 mg, 57.6 mg, |

TABLE 2-continued

Examples synthesis according to Scheme 2

| Starting material | | Intermediate | | Final products | | | |
|---|---|---|---|---|---|---|---|
| Intermediate IX-n | Structure | diate BX | Example | Q | Example | Q | Structure |
| I1-1* 424.6 mg, | | B5 165 mg, | Example 7-1 Mixture of 2 isomers | 28.5 mg, | — | — | — |
| I2-1 234.1 mg, | | B5 78.4 mg, | Example 8-1 Isomer 1 | 6.45 mg, | — | — | — |
| I2-2 373 mg, | | B5 57.0 mg, | Example 8-2 Isomer 1 | 10 mg, | — | — | — |

TABLE 2-continued

Examples synthesis according to Scheme 2

| Starting material | | Intermediate BX | Final products | | | | |
|---|---|---|---|---|---|---|---|
| Intermediate IX-n | Structure IX-n | | Example | Structure | Q | Example | Q |
| I2-1* 234.1 mg, | [structure] | B6 272 mg, | Example 9-1 Isomer 1 mixture | [structure] | 41.8 mg, | Example 9-1 Isomer 2 mixture | 34.0 mg, |

IX-n indicates enriched single enantiomer all cis piperidone.
IX-n* indicates all cis enriched racemic piperidone.

TABLE 3

LC-MS and NMR data for Examples of Table 2

| Example | Analytical Data |
| --- | --- |
| Example 1-1 Isomer 3 | LC-MS (ES+): 648.4 [M + H]⁺, R$_t$ = 3.49 min (Method 2)<br>¹H NMR (600 MHz, DMSO-d$_6$): δ =1.08 (d, J = 6.4 Hz, 3 H), 1.98 (br. s., J = 13.4, 2.0, 1.0 Hz, 1 H), 2.78 (ddd, J = 13.4, 7.5, 5.7 Hz, 1H), 3.04 (d, J = 16.1 Hz, 1H), 3.05 (d, J = 15.6 Hz, 1H), 3.07-3.16 (m, 13.4, 13.4, 7.2, 3.5, 3.5 Hz 1 H ), 3.42-3.46 (m, 1H), 3.47-3.51 (m, 4 H), 3.59 (d, J = 16.1 Hz, 1H), 3.69-3.77 (m, 3 H), 3.92 (dd, 12.1, 8.8 Hz, 1 H), 3.97-4.04 (m, 1 H), 4.06 (ddd, J = 11.7, 4.0, 1.5 Hz, 1 H), 4.17 (dt, J = 13.9, 3.8, 2.8 Hz, 1 H), 4.88 (ddd, J = 8.6, 7.2, 1.0 Hz, 1 H), 5.84 (ddd, J = 16.0, 9.0, 4.1 Hz, 1 H), 6.48 (d, J = 16.3 Hz, 1 H), 6.79 (d, J = 2.0 Hz, 1 H), 7.13-7.20 (m, J = 9.6, 9.6, 4.0, 2.0 Hz, 1 H), 7.47 (qd, J = 9.3, 4.8 Hz, 1 H), 8.00 (d, J = 2.0 Hz, 1 H), 8.05 (s, 1 H), 8.71 (s, 1H), 8.89 (d, J = 9.0 Hz, 1 H), 11.40 (s, 1 H) ppm |
| Example 1-2 Isomer 1 | LC-MS (ES+): 646.5 [M + H]⁺, R$_t$ = 4.40 min (Method 1)<br>¹H NMR (500 MHz, DMSO-d$_6$) δ ppm 1.17-1.31 (m, 6 H), 1.32-1.40 (m, 1 H), 1.43-1.66 (m, 4 H), 2.16 (dd, J = 11.9, 6.7 Hz, 1 H), 2.71-2.86 (m, 1 H), 2.93-3.09 (m, 2 H), 3.16 (d, J = 15.9 Hz, 1 H), 3.23-3.30 (m, 1 H), 3.49 (d, J = 15.3 Hz, 1 H), 3.59-3.67 (m, 2 H), 3.68-3.80 (m, 1 H), 3.87 (d, J = 11.9 Hz, 1 H), 3.94-4.03 (m, 2 H), 4.60-4.67 (m, 1 H), 5.70 (dt, J = 16.1, 6.0 Hz, 1 H), 6.40 (d, J = 16.2 Hz, 1 H), 6.50 (d, J = 1.8 Hz, 1 H), 7.13-7.21 (m, 1 H), 7.43-7.53 (m, 1 H), 8.02 (d, J = 1.8 Hz, 1 H), 8.12 (s, 1 H), 8.75 (d, J = 8.9 Hz, 1 H), 8.85 (s, 1 H), 11.39 (br. s., 1 H) |
| Example 1-2 Isomer 2 | LC-MS (ES+): 646.6 [M + H]⁺, R$_t$ = 4.40 min (Method 1)<br>¹H NMR (500 MHz, DMSO-d$_6$) δ ppm 0.77-0.88 (m, 1 H), 1.20 (d, J = 6.1 Hz, 3 H), 1.23 (br. s., 2 H), 1.27-1.42 (m, 4 H), 1.50-1.64 (m, 1 H), 1.67-1.79 (m, 1 H), 2.13 (dd, J = 11.4, 7.2 Hz, 1 H), 2.64-2.80 (m, 1 H), 2.98 (q, J = 12.4 Hz, 1 H), 3.07 (d, J = 15.9 Hz, 2 H), 3.25-3.31 (m, 1 H), 3.43-3.56 (m, 1 H), 3.57-3.64 (m, 2 H), 3.78-3.95 (m, 3 H), 3.97-4.06 (m, 1 H), 4.58-4.66 (m, 1 H), 5.72-5.79 (m, 1 H), 6.46 (d, J = 16.2 Hz, 1 H), 6.69 (s, 1 H), 7.16 (t, J = 8.2 Hz, 1 H), 7.43-7.51 (m, 1 H), 7.97-8.02 (m, 1 H), 8.14 (s, 1 H), 8.70 (d, J = 8.9 Hz, 1 H), 8.85 (s, 1 H), 11.41 (br. s., 1 H) |
| Example 1-3 Isomer 1 | LC-MS (ES+): 662.1 [M + H]⁺, Rt = 3.57 min (Method 1)<br>¹H NMR (600 MHz, DMSO-d$_6$) δ ppm 1.19 (d, J = 6.4 Hz, 3 H), 1.73 (m, J = 13.2, 8.8, 4.3, 4.3 Hz, 1 H), 1.83-1.91 (m, 1 H), 2.14-2.18 (m, 1 H), 2.99 (d, J = 13.4 Hz, 1 H), 3.03-3.11 (m, 2 H), 3.15-3.19 (m, 1 H), 3.34-3.43 (m, 3 H), 3.43-3.51 (m, 5 H), 3.59-3.65 (m, 2 H), 3.85-3.89 (m, 1 H), 3.93-4.04 (m, 2 H), 4.56-4.61 (m, 1 H), 5.71 (ddd, J = 16.1, 7.3, 4.7 Hz, 1 H), 6.41 (d, J = 16.1 Hz, 1 H), 6.61 (d, J = 2.0 Hz, 1 H), 7.18 (t, J = 9.5 Hz, 1 H), 7.48 (qd, J = 9.4, 4.8 Hz, 1 H), 8.05 (d, J = 2.0 Hz, 1 H), 8.13 (s, 1 H), 8.80 (d, J = 8.8 Hz, 1 H), 8.84 (s, 1 H), 11.39 (br. s., 1 H) |
| Example 1-3 Isomer 2 | LC-MS (ES+): 662.1 [M +H ]⁺, Rt = 3.64 min (Method 1)<br>¹H NMR (600 MHz, DMSO-d$_6$) δ ppm 1.19 (d, J = 6.4 Hz, 3 H), 1.67-1.77 (m, 1 H), 1.80-1.89 (m, 1 H), 2.14 (dd, J = 12.0, 6.9 Hz, 1 H), 3.01-3.14 (m, 4 H), 3.34-3.44 (m, 3 H), 3.44-3.53 (m, 5 H), 3.58-3.65 (m, 2 H), 3.84-3.89 (m, 1 H), 3.91-3.96 (m, 1 H), 4.04-4.09 (m, 1 H), 4.50 (dt, J = 11.4, 7.9 Hz, 1 H), 5.82-5.87 (m, 1 H), 6.41 (d, J = 16.1 Hz, 1 H), 6.70 (d, J = 2.0 Hz, 1 H), 7.17 (t, J = 9.6 Hz, 1 H), 7.48 (qd, J = 9.3, 4.9 Hz, 1 H), 8.07 (d, J = 2.0 Hz, 1 H), 8.17 (s, 1 H), 8.81 (d, J = 8.4 Hz, 1 H), 8.93 (s, 1 H), 11.39 (s, 1 H) |
| Example 1-4 Isomer 1 | LC-MS (ES+): 662.0 [M + H]⁺, Rt = 4.07 min (Method 1)<br>¹H NMR (600 MHz, DMSO-d$_6$) δ ppm 1.16 (d, J = 6.4 Hz, 3 H), 2.17 (dd, J = 11.7, 7.0 Hz, 1 H), 2.25-2.36 (m, 1 H), 2.99-3.12 (m, 3 H), 3.14-3.20 (m, 1 H), 3.35-3.41 (m, 2 H), 3.42-3.45 (m, 2 H), 3.46-3.58 (m, 3 H), 3.59-3.68 (m, 4 H), 3.70-3.79 (m, 1 H), 3.86-3.94 (m, 1 H), 4.55-4.61 (m, 1 H), 5.60 (dt, J = 15.8, 7.2 Hz, 1 H), 6.33-6.37 (m, 1 H), 6.57 (d, J = 2.0 Hz, 1 H), 7.18 (t, J = 9.3 Hz, 1 H), 7.46-7.52 (m, 1 H), 7.94-7.97 (m, 1 H), 8.14 (s, 1 H), 8.80-8.85 (m, 1 H), 8.86 (s, 1 H), 11.36 (br. s., 1 H) |
| Example 1-4 Isomer 2 | LC-MS (ES+): 662.0 [M + H]⁺, Rt = 4.05 min (Method 1)<br>¹H NMR (500 MHz, DMSO-d$_6$) δ ppm 0.77-0.90 (m, 1 H), 1.16 (d, J = 6.4 Hz, 3 H), 2.14 (dd, J = 11.7, 6.9 Hz, 1 H), 2.22-2.38 (m, 2 H), 2.52-2.52 (m, 1 H), 3.01-3.17 (m, 4 H), 3.34-3.41 (m, 2 H), 3.43-3.51 (m, 4 H), 3.54-3.66 (m, 5 H), 3.69-3.79 (m, 1 H), 3.82-3.97 (m, 1 H), 4.48 (dt, J = 11.5, 7.7 Hz, 1 H), 5.64-5.73 (m, 1 H), 6.34 (d, J = 15.9 Hz, 1 H), 6.65 (d, J = 1.8 Hz, 1 H), 7.14-7.21 (m, 1 H), 7.48 (qd, J = 9.4, 4.9 Hz, 1 H), 7.96 (d, J = 2.1 Hz, 1 H), 8.19 (s, 1 H), 8.84 (d, J = 8.2 Hz, 1 H), 8.93 (s, 1 H), 11.35 (br. s., 1 H) |
| Example 1-5 Isomer 1 | LC-MS (ES+): 646.7 [M + H]⁺, Rt = 4.30 min (Method 1)<br>¹H NMR (600 MHz, DMSO-d$_6$) δ ppm 1.21 (d, J = 6.4 Hz, 3 H), 1.44-1.52 (m, 3 H), 1.67-1.74 (m, 1 H), 2.17 (dd, J = 12.2, 7.4 Hz, 1 H), 2.26-2.35 (m, 2 H), 2.81-2.87 (m, 1 H), 2.98-3.05 (m, 2 H), 3.17 (d, J = 15.8 Hz, 1 H), 3.28-3.31 (m, 1 H), 3.33-3.43 (m, 3 H), 3.49 (d, J = 15.6 Hz, 1 H), 3.58-3.65 (m, 2 H), 3.72 (dt, J = 13.8, 6.9 Hz, 1 H), 3.82-3.87 (m, 1 H), 4.58-4.63 (m, 1 H), 5.61 (dt, J = 15.8, 7.1 Hz, 1 H), 6.34 (d, J = 16.0 Hz, 1 H), 6.56 (d, J = 2.0 Hz, 1 H), 7.18 (t, J = 9.5 Hz, 1 H), 7.48 (qd, J = 9.3, 5.0 Hz, 1 H), 7.94 (d, J = 2.0 Hz, 1 H), 8.10 (s, 1 H), 8.77 (d, J = 9.0 Hz, 1 H), 8.83 (s, 1 H), 11.36 (br. s., 1 H) |
| Example 1-5 Isomer 2 | LC-MS (ES+): 646.6 [M + H]⁺, Rt = 4.36 min (Method 1)<br>¹H NMR (600 MHz, DMSO-d$_6$) δ ppm 1.23 (d, J = 6.2 Hz, 3 H), 1.36-1.44 (m, 1 H), 1.44-1.51 (m, 2 H), 1.70-1.78 (m, 1 H), 2.10-2.15 (m, 1 H), 2.26 (br. s., 1 H), 2.32-2.41 (m, 1 H), 2.68-2.78 (m, 1 H), 3.05-3.16 (m, 3 H), 3.19-3.28 (m, 2 H), 3.33-3.37 (m, 1 H), 3.41-3.52 (m, 2 H), 3.53-3.66 (m, 2 H), 3.79-3.89 (m, 2 H), 4.49-4.55 (m, 1 H), 5.74-5.80 (m, 1 H), 6.34 (d, J = 16.0 Hz, 1 H), 6.75 (d, J = 1.8 Hz, 1 H), 7.17 (t, J = 9.3 Hz, 1 H), 7.44-7.51 (m, 1 H), 7.95 (d, J = 1.7 Hz, 1 H), 8.16 (s, 1 H), 8.79 (d, J = 8.6 Hz, 1 H), 8.87 (s, 1 H), 11.37 (br. s., 1 H) |
| Example 1-6 Isomer 1 | LC-MS (ES+): 662.7 [M + H]⁺, Rt = 4.82 min (Method 1)<br>¹H NMR (600 MHz, DMSO-d$_6$) δ ppm 1.14 (d, J = 6.4 Hz, 3 H), 1.64-1.73 (m, 2 H), 2.14-2.19 (m, 1 H), 2.92-3.03 (m, 1 H), 3.03-3.08 (m, 2 H), 3.17 (d, J = 15.8 Hz, 1 H), 3.34-3.45 (m, 3 H), 3.47-3.56 (m, 3 H), 3.58-3.65 (m, 3 H), 3.76 (ddd, J = 12.8, 8.8, 3.8 Hz, 1 H), 3.87-3.98 (m, 3 H), 4.59-4.65 (m, 1 H), 5.69-5.76 (m, 1 H), 6.40 (d, J = 16.0 Hz, 1 H), 6.58 (d, J = 2.0 Hz, 1 H), 7.18 (t, J = 9.5 Hz, 1 H), 7.49 (qd, J = 9.4, 5.0 Hz, 1 H), 8.06 (d, J = 2.0 Hz, 1 H), 8.14 (s, 1 H), 8.77 (d, J = 9.0 Hz, 1 H), 8.86 (s, 1 H), 11.39 (s, 1 H) |
| Example 1-6 Isomer 2 | LC-MS (ES+): 662.6 [M + H]⁺, Rt = 4.84 min (Method 1)<br>¹H NMR (600 MHz, DMSO-d$_6$) δ ppm 1.14 (d, J = 6.4 Hz, 3 H), 1.63-1.77 (m, 2 H), 2.14 (dd, J = 11.3, 6.9 Hz, 1 H), 2.98-3.14 (m, 4 H), 3.34-3.44 (m, 3 H), 3.46-3.52 (m, 3 H), 3.55-3.65 (m, 3 H), 3.73 (ddd, J = 12.9, 8.6, 3.8 Hz, 1 H), 3.86-3.94 (m, 2 H), 3.96-4.02 (m, 1 H), 4.52 (dt, J = 11.4, 7.8 Hz, 1 H), 5.78-5.83 (m, 1 H), 6.41 (d, J = 16.1 Hz, 1 H), 6.67 (d, J = 2.0 Hz, 1 H), 7.17 (t, J = 9.5 Hz, 1 H), 7.45-7.51 (m, 1 H), 8.08 (d, J = 2.0 Hz, 1 H), 8.17 (s, 1 H), 8.80 (d, J = 8.4 Hz, 1 H), 8.92 (s, 1 H), 11.39 (s, 1 H) |
| Example 1-7 Isomer 1 | LC-MS (ES+): 646.0 [M + H]⁺, Rt = 5.00 min (Method 1)<br>¹H NMR (600 MHz, DMSO-d$_6$) δ ppm 1.15-1.27 (m, 3 H), 1.53 (dq, J = 13.5, 6.8 Hz, 1 H), 1.58-1.65 (m, 1 H), 1.69-1.80 (m, 2 H), 2.02-2.10 (m, 1 H), 2.14-2.21 (m, 2 H), 2.94-3.01 (m, 1 H), 3.01-3.09 (m, 1 H), 3.13 (d, J = 15.4 Hz, 1 H), 3.19-3.22 (m, 1 H), 3.22-3.31 (m, 2 H), 3.33-3.51 (m, 4 H), 3.60-3.68 (m, 2 H), 3.84-3.89 (m, 1 H), 4.52-4.57 (m, 1 H), 5.57 (ddd, J = 15.7, 8.4, 6.1 Hz, 1 H), 6.27 (d, J = 15.8 Hz, 1 H), 6.37 (d, J = 2.0 Hz, 1 H), 7.18 (t, J = 9.4 Hz, 1 H), 7.49 (qd, J = 9.4, 5.0 Hz, 1 H), 7.94 (d, J = 2.0 Hz, 1 H), 8.17 (s, 1 H), 8.76 (d, J = 8.8 Hz, 1 H), 8.88 (s, 1 H), 11.33 (br. s., 1 H) |

TABLE 3-continued

LC-MS and NMR data for Examples of Table 2

| Example | Analytical Data |
|---|---|
| Example 1-7 Isomer 2 | LC-MS (ES+): 646.0 [M + H]$^+$, Rt = 4.98 min (Method 1)<br>$^1$H NMR (600 MHz, DMSO-d$_6$) δ ppm 1.21 (d, J = 6.6 Hz, 3 H), 1.49-1.56 (m, 1 H), 1.65 (ddd, J = 12.7, 9.4, 6.4 Hz, 1 H), 1.72-1.81 (m, 2 H), 2.00-2.07 (m, 1 H), 2.12-2.19 (m, 2 H), 3.03-3.11 (m, 4 H), 3.25-3.32 (m, 2 H), 3.36-3.43 (m, 2 H), 3.49 (d, J = 15.6 Hz, 1 H), 3.52-3.58 (m, 1 H), 3.58-3.68 (m, 2 H), 3.84-3.89 (m, 1 H), 4.51-4.56 (m, 1 H), 5.64 (ddd, J = 15.5, 9.3, 5.7 Hz, 1 H), 6.29 (d, J = 15.8 Hz, 1 H), 6.61 (d, J = 2.0 Hz, 1 H), 7.15-7.20 (m, 1 H), 7.48 (qd, J = 9.3, 5.0 Hz, 1 H), 7.93 (d, J = 2.0 Hz, 1 H), 8.17 (s, 1 H), 8.74 (d, J = 8.6 Hz, 1 H), 8.88 (s, 1 H), 11.35 (s, 1 H) |
| Example 1-7 Isomer 3 | LC-MS(ES+): 646.4 [M + H]$^+$, Rt = 3.65 min (Method 2)<br>$^1$H NMR (600 MHz, DMSO-d$_6$): δ ppm 1.07 (d, J = 6.2 Hz, 3 H), 1.58-1.63 (m, 1 H), 1.66-1.79 (m, 2 H), 1.94-2.00 (m, 1 H), 2.03-2.10 (m, 1 H), 2.13-2.21 (m, 2 H), 2.77 (dt, J = 13.2, 4.4 Hz, 1 H), 3.04-3.10 (m, 2 H), 3.10-3.17 (m, 1 H), 3.26-3.40 (m, 4 H), 3.45 (d, J = 16.0 Hz, 1 H), 3.56 (d, J = 16.7 Hz, 1 H), 3.66-3.72 (m, 1 H), 3.88-3.94 (m, 1 H), 4.21-4.29 (m, 1 H), 4.90 (t, J = 8.1 Hz, 1 H), 5.76-5.84 (m, 1 H), 6.31 (d, J = 15.4 Hz, 1 H), 6.83 (d, J = 1.8 Hz, 1 H), 7.15-7.22 (m, 1 H), 7.44-7.52 (m, 1 H), 7.94 (d, J = 2.0 Hz, 1 H), 8.05 (s, 1 H), 8.76 (s, 1 H), 8.87 (d, J = 9.4 Hz, 1 H), 11.35 (s, 1 H) |
| Example 1-8 Isomer 1 | LC-MS (ES+): 682.7 [M + H]$^+$, Rt = 4.75 min (Method 1)<br>$^1$H NMR (600 MHz, DMSO-d$_6$) δ ppm 1.23 (d, J = 6.4 Hz, 3 H), 1.61-1.73 (m, 2 H), 1.87-2.06 (m, 2 H), 2.21 (dd, J = 11.5, 7.1 Hz, 1 H), 2.97-3.08 (m, 2 H), 3.14 (d, J = 15.4 Hz, 1 H), 3.28-3.33 (m, 2 H), 3.42-3.53 (m, 2 H), 3.65 (d, J = 16.0 Hz, 1 H), 3.73 (quin, J = 5.9 Hz, 1 H), 3.90-4.05 (m, 3 H), 4.09-4.19 (m, 1 H), 4.66-4.72 (m, 1 H), 5.60-5.70 (m, 1 H), 6.41-6.47 (m, 2 H), 7.18 (t, J = 9.6 Hz, 1 H), 7.49 (qd, J = 9.3, 4.9 Hz, 1 H), 7.99 (d, J = 2.0 Hz, 1 H), 8.15 (s, 1 H), 8.88 (s, 1 H), 8.96 (d, J = 8.8 Hz, 1 H), 11.39 (s, 1 H) |
| Example 1-8 Isomer 2 | LC-MS (ES+): 682.7 [M + H]$^+$, Rt = 1.86 min (Method 3)<br>$^1$H NMR (600 MHz, DMSO-d$_6$) δ ppm 1.23 (d, J = 6.4 Hz, 3 H), 1.53-1.61 (m, 1 H), 1.69 (d, J = 4.2 Hz, 1 H), 1.85-2.01 (m, 2 H), 2.16-2.20 (m, 1 H), 2.96-3.08 (m, 3 H), 3.20-3.26 (m, 1 H), 3.34-3.43 (m, 2 H), 3.46-3.53 (m, 1 H), 3.60-3.65 (m, 1 H), 3.69-3.74 (m, 1 H), 3.89-3.96 (m, 2 H), 4.06 (dt, J = 10.6, 1.9 Hz, 1 H), 4.17-4.27 (m, 1 H), 4.69-4.74 (m, 1 H), 5.65 (ddd, J = 16.1, 9.2, 3.9 Hz, 1 H), 6.46 (s, 1 H), 6.49 (s, 1 H), 6.63 (d, J = 2.0 Hz, 1 H), 7.15-7.20 (m, 1 H), 7.45-7.51 (m, 1 H), 7.99 (d, J = 2.2 Hz, 1 H), 8.13 (s, 1 H), 8.85 (s, 1 H), 8.92 (d, J = 8.8 Hz, 1 H), 11.41 (br. s., 1 H) |
| Example 2-1 Isomer 1 | LC-MS (ES+): 595.0 [M + H]$^+$, Rt = 4.54 min (Method 1)<br>$^1$H NMR (500 MHz, DMSO-d$_6$): δ ppm = 0.91 (d, J = 6.4 Hz, 3 H), 2.13 (dd, J = 11.3, 7.6 Hz, 1 H), 2.57 (q, J = 12.5 Hz, 1 H), 2.84 (ddd, J = 13.4, 7.9, 5.8 Hz, 1 H), 3.01 (d, J = 16.2 Hz, 1 H), 3.15 (d, J = 15.6 Hz, 1 H), 3.40-3.50 (m, 5 H), 3.52-3.58 (m, 1 H), 3.60-3.68 (m, 1 H), 3.67-3.73 (m, 1 H), 3.78-3.85 (m, 2 H), 3.91 (ddd, J = 13.4, 8.2, 5.3 Hz, 1 H), 3.96-4.01 (m, 2 H), 4.61-4.72 (m, 1 H), 5.65 (dt, J = 16.2, 6.1 Hz, 1 H), 6.43 (d, J = 16.2 Hz, 1 H), 6.50 (d, J = 1.8 Hz, 1 H), 7.25-7.30 (m, 1 H), 7.27 (d, J = 7.9 Hz, 2 H), 7.34-7.42 (m, 2 H), 8.01 (d, J = 1.8 Hz, 1 H), 8.10 (s, 1 H), 8.70 (d, J = 9.2 Hz, 1 H), 8.83 (s, 1 H), 11.40 (s, 1 H) |
| Example 2-2 Isomer 1 | LC-MS (ES+): 592.9 [M + H]$^+$, Rt = 4.83 min (Method 1)<br>$^1$H NMR (500 MHz, METHANOL-d$_4$) δ ppm 1.09 (d, J = 6.4 Hz, 3 H), 1.36-1.53 (m, 3 H), 1.55-1.61 (m, 1 H), 1.65 (dd, J = 11.9, 6.1 Hz, 1 H), 1.74-1.85 (m, 1 H), 2.21-2.36 (m, 1 H), 2.72 (q, J = 12.5 Hz, 1 H), 2.80-2.93 (m, 1 H), 3.05 (d, J = 16.2 Hz, 1 H), 3.15 (d, J = 15.9 Hz, 1 H), 3.36-3.48 (m, 2 H), 3.52-3.61 (m, 1 H), 3.69 (d, J = 15.6 Hz, 1 H), 3.75 (quin, J = 6.0 Hz, 1 H), 3.81 (d, J = 16.2 Hz, 1 H), 3.94-4.04 (m, 2 H), 4.04-4.11 (m, 1 H), 4.66-4.78 (m, 1 H), 5.88 (dt, J = 15.9, 6.2 Hz, 1 H), 6.39 (d, J = 15.9 Hz, 1 H), 6.79 (d, J = 1.8 Hz, 1 H), 7.25-7.34 (m, 3 H), 7.34-7.39 (m, 2 H), 7.94 (d, J = 1.8 Hz, 1 H), 8.22 (s, 1 H), 8.83 (s, 1 H) |
| Example 2-2 Isomer 2 | LC-MS (ES+): 592.9 [M + H]$^+$, Rt = 4.93 min (Method 1)<br>$^1$H NMR (500 MHz, METHANOL-d$_4$) δ ppm 1.07 (d, J = 6.7 Hz, 3 H), 1.36-1.52 (m, 4 H), 1.61-1.71 (m, 1 H), 1.85-1.98 (m, 1 H), 2.26 (dd, J = 11.9, 7.3 Hz, 1 H), 2.67 (q, J = 12.5 Hz, 1 H), 2.76-2.88 (m, 1 H), 3.11 (d, J = 16.2 Hz, 2 H), 3.37-3.47 (m, 2 H), 3.51-3.60 (m, 1 H), 3.64 (d, J = 15.6 Hz, 1 H), 3.71-3.77 (m, 1 H), 3.81 (d, J = 16.8 Hz, 1 H), 3.92-4.09 (m, 3 H), 4.72-4.81 (m, 1 H), 5.94 (ddd, J = 15.9, 9.2, 4.3 Hz, 1 H), 6.42 (d, J = 16.2 Hz, 1 H), 6.95 (d, J = 1.8 Hz, 1 H), 7.24-7.32 (m, 3 H), 7.32-7.39 (m, 2 H), 7.94 (d, J = 1.8 Hz, 1 H), 8.16 (s, 1 H), 8.96 (s, 1 H) |
| Example 2-3 Isomer 1 | LC-MS (ES+): 608.2 [M + H]$^+$, Rt = 4.81 min (Method 1)<br>$^1$H NMR (600 MHz, DMSO-d$_6$) δ ppm 0.90 (d, J = 6.4 Hz, 3 H), 1.65-1.72 (m, 2 H), 2.12 (dd, J = 11.6, 7.4 Hz, 1 H), 2.52-2.63 (m, 1 H), 3.02-3.08 (m, 2 H), 3.18 (d, J = 15.8 Hz, 1 H), 3.34-3.41 (m, 2 H), 3.42-3.48 (m, 1 H), 3.48-3.66 (m, 6 H), 3.67-3.73 (m, 1 H), 3.78 (ddd, J = 13.1, 8.8, 4.2 Hz, 1 H), 3.91-3.98 (m, 2 H), 4.60-4.65 (m, 1 H), 5.70-5.76 (m, 1 H), 6.40 (d, J = 16.1 Hz, 1 H), 6.59 (d, J = 2.0 Hz, 1 H), 7.25-7.30 (m, 3 H), 7.35-7.38 (m, 2 H), 8.06 (d, J = 2.0 Hz, 1 H), 8.14 (s, 1 H), 8.81 (d, J = 8.8 Hz, 1 H), 8.87 (s, 1 H), 11.40 (s, 1 H) |
| Example 3-1 Isomer 1 | LC-MS (ES+): 648.6 [M + H]$^+$, Rt = 4.71 min (Method 1)<br>$^1$H NMR (600 MHz, DMSO-d$_6$) δ ppm 1.00 (d, J = 6.6 Hz, 3 H), 2.06-2.13 (m, 1 H), 2.63 (q, J = 12.5 Hz, 1 H), 2.85 (ddd, J = 13.6, 8.1, 5.8 Hz, 1 H), 3.01 (d, J = 16.0 Hz, 1 H), 3.15 (d, J = 15.4 Hz, 1 H), 3.41-3.53 (m, 5 H), 3.62-3.65 (m, 1 H), 3.65 (d, J = 16.3 Hz, 1 H), 3.71 (quin, J = 5.7 Hz, 1 H), 3.80 (ddd, J = 9.2, 7.9, 5.5 Hz, 1 H), 3.85 (d, J = 13.6, 4.0, 2.0 Hz, 1 H), 3.90 (ddd, J = 13.4, 8.1, 5.2 Hz, 1 H), 3.99 (dt, J = 4.0, 2.1 Hz, 2 H), 4.68 (ddd, J = 11.3, 9.1, 7.6 Hz, 1 H), 5.66 (dt, J = 16.0, 6.2 Hz, 1 H), 6.43 (d, J = 16.1 Hz, 1 H), 6.49 (d, J = 1.8 Hz, 1 H), 7.00-7.08 (m, 1 H), 7.45-7.54 (m, 1 H), 8.02 (d, J = 2.0 Hz, 1 H), 8.10 (s, 1 H), 8.74 (d, J = 9.2 Hz, 1 H), 8.81 (s, 1 H), 11.40 (br. s., 1 H) |
| Example 3-1 Isomer 2 | LC-MS (ES+): 648.6 [M + H]$^+$, Rt = 4.74 min (Method 1)<br>$^1$H NMR (600 MHz, DMSO-d$_6$) δ ppm 1.00 (d, J = 6.6 Hz, 3 H), 2.03-2.08 (m, 1 H), 2.64 (q, J = 12.8 Hz, 1 H), 2.82 (ddd, J = 12.8, 8.3, 6.8 Hz, 1 H), 3.05 (d, J = 13.0 Hz, 1 H), 3.08 (d, J = 12.1 Hz, 1 H), 3.33-3.37 (m, 1 H), 3.39-3.49 (m, 3 H), 3.51 (d, J = 15.0 Hz, 1 H), 3.62 (d, J = 16.1 Hz, 1 H), 3.68-3.75 (m, 2 H), 3.83-3.94 (m, 4 H), 4.04 (ddd, J = 11.6, 4.0, 1.5 Hz, 1 H), 4.64 (ddd, J = 11.4, 8.8, 7.7 Hz, 1 H), 5.69 (ddd, J = 16.0, 8.8, 4.2 Hz, 1 H), 6.46 (d, J = 16.1 Hz, 1 H), 6.63 (d, J = 2.0 Hz, 1 H), 6.99-7.03 (m, 1 H), 7.47-7.52 (m, 1 H), 8.00 (d, J = 2.0 Hz, 1 H), 8.10 (s, 1 H), 8.72 (d, J = 8.8 Hz, 1 H), 8.85 (s, 1 H), 11.41 (s, 1 H) |
| Example 3-2 Isomer 1 | LC-MS (ESI+): 646.7 [M + H]$^+$, Rt = 4.54 min (Method 1)<br>$^1$H NMR (500 MHz, DMSO-d$_6$) δ ppm 1.05 (d, J = 6.4 Hz, 3 H), 1.22-1.30 (m, 3 H), 1.36 (td, J = 13.2, 7.2 Hz, 1 H), 1.40-1.51 (m, 2 H), 1.52-1.59 (m, 1 H), 1.59-1.67 (m, 1 H), 2.08 (dd, J = 11.1, 7.2 Hz, 1 H), 2.68 (q, J = 12.5 Hz, 1 H), 2.80 (dt, J = 12.8, 6.1 Hz, 1 H), 3.02 (d, J = 16.2 Hz, 1 H), 3.16 (d, J = 15.6 Hz, 1 H), 3.25-3.30 (m, 1 H), 3.33-3.40 (m, 1 H), 3.50 (d, J = 15.3 Hz, 1 H), 3.64 (d, J = 15.9 Hz, 1 H), 3.70 (quin, J = 6.4 Hz, 1 H), 3.78 (dt, J = 13.4, 6.6 Hz, 1 H), 3.84 (d, J = 13.4 Hz, 1 H), 3.94-4.00 (m, 2 H), 4.65 (ddd, J = 11.6, 8.9, 7.6 Hz, 1 H), 5.70 (dt, J = 16.0, 6.2 Hz, 1 H), 6.40 (d, J = 16.2 Hz, 1 H), 6.50 (d, J = 1.8 Hz, 1 H), 6.99-7.09 (m, 1 H), 7.45-7.52 (m, 1 H), 8.01 (d, J = 2.1 Hz, 1 H), 8.12 (s, 1 H), 8.82 (d, J = 8.9 Hz, 1 H), 8.84 (s, 1 H), 11.39 (br. s., 1 H) |
| Example 3-2 Isomer 2 | LC-MS (ESI+): 646.6 [M + H]$^+$, Rt = 4.55 min (Method 1)<br>$^1$H NMR (500 MHz, DMSO-d$_6$) δ ppm 1.06 (d, J = 6.4 Hz, 3 H), 1.25-1.32 (m, 2 H), 1.32-1.41 (m, 2 H), 1.58 (dt, J = 12.4, 6.1 Hz, 1 H), 1.73 (dd, J = 15.0, 7.6 Hz, 1 H), 2.05 (dd, J = 11.3, 7.3 Hz, 1 H), 2.68 (q, J = 12.8 Hz, 1 H), 2.75 (ddd, |

TABLE 3-continued

LC-MS and NMR data for Examples of Table 2

| Example | Analytical Data |
|---|---|
| | J = 12.2, 7.1, 5.6 Hz, 1 H), 3.07 (d, J = 8.2 Hz, 1 H), 3.10 (d, J = 7.6 Hz, 1 H), 3.27-3.31 (m, 2 H), 3.50 (d, J = 15.3 Hz, 1 H), 3.61 (d, J = 16.5 Hz, 1 H), 3.70 (quin, J = 5.9 Hz, 1 H), 3.79-3.86 (m, 2 H), 3.92 (dd, J = 12.8, 9.2 Hz, 1 H), 4.01 (d, J = 12.8 Hz, 1 H), 4.62 (ddd, J = 11.3, 8.5, 7.0 Hz, 1 H), 5.75 (ddd, J = 15.9, 9.1, 4.0 Hz, 1 H), 6.45 (d, J = 16.2 Hz, 1 H), 6.69 (d, J = 2.1 Hz, 1 H), 6.98-7.03 (m, 1 H), 7.49 (m, J = 9.5, 9.5, 6.7, 3.1 Hz, 1 H), 7.99 (d, J = 1.8 Hz, 1 H), 8.12 (s, 1 H), 8.77 (d, J = 8.9 Hz, 1 H), 8.86 (s, 1 H), 11.40 (br. s., 1 H) |
| Example 3-2 Isomer 3 | LC-MS(ES+): 646.4 [M + H]+, Rt = 3.88 min (Method 2)<br>$^1$H NMR (600 MHz, DMSO-$d_6$): δ ppm 0.91 (d, J = 6.6 Hz, 3 H), 1.29-1.62 (m, 6 H), 1.82 (d, J = 15.8 Hz, 1 H), 2.66-2.72 (m, 1 H), 2.86-2.94 (m, 1 H), 3.01-3.10 (m, 2 H), 3.27-3.31 (m, 2 H), 3.45 (d, J = 15.8 Hz, 1 H), 3.58 (d, J = 16.1 Hz, 1 H), 3.74-3.79 (m, 1 H), 3.90-3.97 (m, 2 H), 3.99-4.02 (m, 1 H), 4.09-4.16 (m, 1 H), 4.87-4.94 (m, 1 H), 5.81-5.89 (m, 1 H), 6.48 (d, J = 16.7 Hz, 1 H), 6.80 (d, J = 2.0 Hz, 1 H), 7.06 (br. s., 1 H), 7.47-7.52 (m, 1 H), 8.00 (d, J = 2.0 Hz, 1 H), 8.05 (s, 1 H), 8.74 (s, 1 H), 8.83 (d, J = 9.4 Hz, 1 H), 11.40 (s, 1 H) |
| Example 4-1 Isomer 1 | LC-MS (ES+): 628.25 [M + H]+, Rt = 4.47 min (Method 1)<br>$^1$H NMR (500 MHz, DMSO-$d_6$) δ ppm 1.03 (d, J = 6.7 Hz, 3 H), 1.22-1.28 (m, 1 H), 1.36 (dt, J = 13.4, 6.6 Hz, 1 H), 1.40-1.51 (m, 2 H), 1.52-1.60 (m, 1 H), 1.60-1.69 (m, 1 H), 2.04-2.11 (m, 1 H), 2.71 (q, J = 12.6 Hz, 1 H), 2.80 (dt, J = 13.1, 5.8 Hz, 1 H), 3.02 (d, J = 16.2 Hz, 1 H), 3.16 (d, J = 15.6 Hz, 1 H), 3.25-3.30 (m, 1 H), 3.34-3.41 (m, 1 H), 3.50 (d, J = 15.6 Hz, 1 H), 3.64 (d, J = 16.2 Hz, 1 H), 3.70 (quin, J = 5.8 Hz, 1 H), 3.78 (q, J = 6.7 Hz, 1 H), 3.83 (d, J = 15.6 Hz, 1 H), 3.93-4.04 (m, 2 H), 4.66 (ddd, J = 11.6, 8.9, 7.0 Hz, 1 H), 5.79 (dt, J = 16.1, 6.0 Hz, 1 H), 6.40 (d, J = 16.2 Hz, 1 H), 6.50 (d, J = 2.1 Hz, 1 H), 7.12 (t, J = 6.9 Hz, 1 H), 7.25 (td, J = 7.9, 6.5 Hz, 1 H), 7.38 (q, J = 8.5 Hz, 1 H), 8.02 (d, J = 1.8 Hz, 1 H), 8.13 (s, 1 H), 8.81 (d, J = 9.2 Hz, 1 H), 8.85 (s, 1 H), 11.39 (s, 1 H) |
| Example 4-1 Isomer 2 | LC-MS (ES+): 628.19 [M + H]+, Rt = 4.42 min (Method 1)<br>$^1$H NMR (500 MHz, DMSO-$d_6$) δ ppm 1.04 (d, J = 6.4 Hz, 3 H), 1.25-1.32 (m, 2 H), 1.32-1.40 (m, 2 H), 1.57 (dt, J = 12.4, 6.1 Hz, 1 H), 1.75 (dt, J = 15.6, 7.9 Hz, 1 H), 2.04 (dd, J = 11.3, 7.6 Hz, 1 H), 2.67-2.73 (m, 1 H), 2.73-2.79 (m, 1 H), 3.07 (d, J = 5.8 Hz, 1 H), 3.10 (d, J = 4.9 Hz, 1 H), 3.27-3.31 (m, 2 H), 3.50 (d, J = 15.3 Hz, 1 H), 3.61 (d, J = 16.2 Hz, 1 H), 3.69 (quin, J = 5.9 Hz, 1 H), 3.78-3.88 (m, 2 H), 3.92 (dd, J = 12.8, 9.5 Hz, 1 H), 4.01 (ddd, J = 13.0, 3.8, 1.0 Hz, 1 H), 4.63 (ddd, J = 11.3, 8.5, 7.0 Hz, 1 H), 5.75 (ddd, J = 15.9, 9.2, 4.3 Hz, 1 H), 6.46 (d, J = 15.9 Hz, 1 H), 6.69 (d, J = 1.8 Hz, 1 H), 7.09 (t, J = 7.1 Hz, 1 H), 7.24 (td, J = 7.6, 6.5 Hz, 1 H), 7.37 (q, J = 8.5 Hz, 1 H), 7.99 (d, J = 1.8 Hz, 1 H), 8.13 (s, 1 H), 8.76 (d, J = 8.9 Hz, 1 H), 8.87 (s, 1 H), 11.41 (br. s., 1 H) |
| Example 4-2 Isomer 1 | LC-MS (ES+): 630.63 [M + H]+, Rt = 3.76 min (Method 1)<br>$^1$H NMR (600 MHz, DMSO-$d_6$) δ ppm 0.98 (d, J = 6.4 Hz, 3 H), 2.09 (dd, J = 10.0, 9.7 Hz, 1 H), 2.67 (q, J = 12.6 Hz, 1 H), 2.85 (ddd, J = 14.3, 8.6, 5.2 Hz, 1 H), 3.01 (d, J = 16.0 Hz, 1 H), 3.16 (d, J = 15.4 Hz, 1 H), 3.41-3.54 (m, 5 H), 3.62-3.68 (m, 2 H), 3.71 (quin, J = 5.5 Hz, 1 H), 3.79-3.83 (m, 1 H), 3.82-3.88 (m, 1 H), 3.90 (s, 1 H), 3.96-4.03 (m, 2 H), 4.70 (dt, J = 11.2, 8.8 Hz, 1 H), 5.65 (dt, J = 16.2, 6.0 Hz, 1 H), 6.43 (d, J = 16.3 Hz, 1 H), 6.49 (d, J = 1.7 Hz, 1 H), 7.13 (t, J = 6.8 Hz, 1 H), 7.25 (q, J = 7.1 Hz, 1 H), 7.38 (q, J = 8.3 Hz, 1 H), 8.02 (d, J = 1.8 Hz, 1 H), 8.10 (s, 1 H), 8.72 (d, J = 9.2 Hz, 1 H), 8.83 (s, 1 H), 11.40 (s, 1 H) |
| Example 4-2 Isomer 2 | LC-MS (ES+): 630.62 [M + H]+, Rt = 3.81 min (Method 1)<br>$^1$H NMR (600 MHz, DMSO-$d_6$) δ ppm 0.98 (d, J = 6.6 Hz, 3 H), 2.05 (dd, J = 11.6, 7.4 Hz, 1 H), 2.68 (q, J = 12.6 Hz, 1 H), 2.82 (ddd, J = 12.7, 8.4, 5.8 Hz, 1 H), 3.05 (d, J = 10.1 Hz, 1 H), 3.08 (d, J = 9.4 Hz, 1 H), 3.34-3.36 (m, 1 H), 3.40-3.48 (m, 3 H), 3.51 (d, J = 15.2 Hz, 1 H), 3.63 (d, J = 16.1 Hz, 1 H), 3.68-3.74 (m, 2 H), 3.84 (ddd, J = 14.5, 4.6, 2.2 Hz, 1 H), 3.86-3.95 (m, 3 H), 4.04 (ddd, J = 11.7, 4.0, 1.7 Hz, 1 H), 4.66 (dt, J = 11.4, 8.1 Hz, 1 H), 5.68 (dt, J = 16.0, 8.9, 4.2 Hz, 1 H), 6.46 (d, J = 16.1 Hz, 1 H), 6.63 (d, J = 1.8 Hz, 1 H), 7.09 (t, J = 7.2 Hz, 1 H), 7.24 (td, J = 7.6, 6.0 Hz, 1 H), 7.38 (q, J = 8.4 Hz, 1 H), 8.00 (d, J = 2.0 Hz, 1 H), 8.11 (s, 1 H), 8.71 (d, J = 9.0 Hz, 1 H), 8.85 (s, 1 H), 11.41 (s, 1 H) |
| Example 5-1 Isomer 1 | LC-MS (ES+): 632.21 [M + H]+, Rt = 5.01 min (Method 1)<br>$^1$H NMR (500 MHz, DMSO-$d_6$): δ ppm 1.19-1.38 (m, 4 H), 1.59-1.70 (m, 2 H), 2.16-2.26 (m, 1 H), 2.61-2.68 (m, 1 H), 2.75 (q, J = 13.1 Hz, 1 H), 2.99 (d, J = 15.9 Hz, 1 H), 3.13 (d, J = 15.6 Hz, 1 H), 3.18-3.25 (m, 1 H), 3.25-3.30 (m, 1 H), 3.33-3.37 (m, 1 H), 3.49 (d, J = 15.6 Hz, 1 H), 3.63 (d, J = 15.9 Hz, 1 H), 3.68 (t, J = 11.6 Hz, 1 H), 3.75-3.84 (m, 1 H), 3.95 (ddd, J = 13.1, 4.3, 1.5 Hz, 1 H), 4.03 (dd, J = 13.7, 7.9 Hz, 1 H), 4.16 (td, J = 11.6, 3.7 Hz, 1 H), 4.55-4.67 (m, 1 H), 5.71 (ddd, J = 15.9, 7.9, 4.6 Hz, 1 H), 6.41 (d, J = 15.9 Hz, 1 H), 6.47 (d, J = 1.8 Hz, 1 H), 7.12-7.24 (m, 1 H), 7.41-7.53 (m, 1 H), 7.99 (d, J = 1.8 Hz, 1 H), 8.03 (s, 1 H), 8.75 (d, J = 7.9 Hz, 1 H), 8.76 (s, 1 H), 11.39 (s, 1 H) |
| Example 5-1 Isomer 2 | LC-MS (ES+): 632.26 [M + H]+, Rt = 5.05 min (Method 1)<br>$^1$H NMR (600 MHz, DMSO-$d_6$) δ ppm 1.14-1.24 (m, 1 H), 1.27-1.40 (m, 3 H), 1.52-1.62 (m, 2 H), 2.21 (m, J = 9.6, 6.9, 2.2, 2.2 Hz, 1 H), 2.61-2.67 (m, 2 H), 3.01 (d, J = 15.4 Hz, 1 H), 3.05 (d, J = 16.3 Hz, 1 H), 3.18 (q, J = 7.3 Hz, 1 H), 3.26 (ddd, J = 11.6, 4.8, 1.7 Hz, 1 H), 3.35 (dt, J = 8.4, 5.5 Hz, 1 H), 3.46 (d, J = 15.2 Hz, 1 H), 3.59 (d, J = 16.1 Hz, 1 H), 3.68 (t, J = 11.6 Hz, 1 H), 3.78 (m, J = 12.3, 12.3, 4.4, 3.0 Hz, 1 H), 3.91 (dd, J = 13.5, 8.7 Hz, 1 H), 4.07 (ddd, J = 12.8, 4.0, 2.0 Hz, 1 H), 4.14 (ddd, J = 13.9, 10.8, 2.9 Hz, 1 H), 4.71 (ddd, J = 11.7, 9.2, 7.2 Hz, 1 H), 5.78 (ddd, J = 16.1, 8.8, 3.9 Hz, 1 H), 6.45 (d, J = 16.5 Hz, 1 H), 6.72 (d, J = 2.0 Hz, 1 H), 7.16 (m, J = 9.7, 9.7, 3.7, 1.8 Hz, 1 H), 7.45 (qd, J = 9.4, 4.9 Hz, 1 H), 7.98 (d, J = 1.8 Hz, 2 H), 8.62 (d, J = 9.2 Hz, 1 H), 8.71 (t, J = 1.0 Hz, 1 H), 11.38 (s, 1 H) |
| Example 5-1 Isomer 3 | LC-MS(ES+): 632.40 [M + H]+, Rt = 3.67 min (Method 2)<br>$^1$H NMR (500 MHz, DMSO-$d_6$) δ ppm 1.15-1.21 (m, 1 H), 1.30-1.38 (m, 2 H), 1.39-1.45 (m, 1 H), 1.50-1.60 (m, 2 H), 1.99 (d, J = 13.7 Hz, 1 H), 2.59-2.67 (m, 2 H), 3.08 (d, J = 16.2 Hz, 1 H), 3.22-3.29 (m, 1 H), 3.34-3.39 (m, 1 H), 3.48-3.55 (m, 3 H), 3.59 (d, J = 16.5 Hz, 1 H), 3.87-3.94 (m, 1 H), 3.95-4.10 (m, 3 H), 4.83-4.94 (m, 1 H), 5.80-5.88 (m, 1 H), 6.46 (d, J = 16.2 Hz, 1 H), 6.82 (d, J = 1.8 Hz, 1 H), 7.14-7.21 (m, 1 H), 7.42-7.51 (m, 1 H), 8.00 (d, J = 1.8 Hz, 1 H), 8.06 (s, 1 H), 8.75 (s, 1 H), 8.92 (d, J = 9.2 Hz, 1 H), 11.41 (s, 1 H) |
| Example 7-1 Mixture of isomers | LC-MS (ES+): 648.24 [M + H]+, Rt = 4.93, 5.10 min (Method 1)<br>$^1$H NMR (600 MHz, DMSO-$d_6$) δ ppm 1.12 (d, J = 6.4 Hz, 3 H), 1.24 (d, J = 6.1 Hz, 3 H), 2.09-2.15 (m, 2 H), 2.86-2.95 (m, 2 H), 3.04 (q, J = 13.0 Hz, 1 H), 3.11-3.20 (m, 4 H), 3.36-3.41 (m, 1 H), 3.42-3.57 (m, 12 H), 3.59-3.68 (m, 4 H), 3.76-3.82 (m, 4 H), 3.82-3.94 (m, 3 H), 3.95-4.01 (m, 2 H), 4.01-4.08 (m, 2 H), 4.80 (td, J = 11.2, 6.1 Hz, 1 H), 5.53-5.63 (m, 2 H), 6.42 (t, J = 17.1 Hz, 2 H), 6.43 (d, J = 1.8 Hz, 1 H), 6.47 (d, J = 1.8 Hz, 1 H), 7.17 (t, J = 9.1 Hz, 2 H), 7.48 (m, J = 9.0, 9.0, 4.8, 4.8, 4.8, 4.8 Hz, 2 H), 7.98 (d, J = 1.8 Hz, 1 H), 8.01 (d, J = 1.8 Hz, 1 H), 8.05 (s, 1 H), 8.07 (s, 1 H), 8.61 (s, 1 H), 8.67 (s, 1 H), 8.81 (d, J = 10.3 Hz, 1 H), 9.14 (d, J = 7.2 Hz, 1 H), 11.33-11.44 (m, 2 H) |
| Example 8-1 Single isomer | LC-MS (ES+): 594.48 [M + H]+, Rt = 5.05 min (Method 1)<br>$^1$H NMR (500 MHz, DMSO-$d_6$) δ ppm 0.88 (d, J = 6.4 Hz, 3 H), 2.06 (dd, J = 11.4, 6.9 Hz, 1 H), 2.69 (q, J = 12.2 Hz, 1 H), 2.90 (ddd, J = 13.6, 7.9, 6.0 Hz, 1 H), 3.14 (d, J = 15.9 Hz, 1 H), 3.18 (d, J = 16.5 Hz, 1 H), 3.41-3.50 (m, 4 H), 3.54 (d, J = 15.3 Hz, 2 H), 3.58 (dd, J = 14.0, 3.7 Hz, 1 H), 3.61-3.72 (m, 2 H), 3.79 (ddd, J = 13.1, 8.2, 5.2 Hz, 1 H), 3.86 (td, J = 8.6, 5.0 Hz, 1 H), 3.92-4.03 (m, 2 H), 4.81 (ddd, J = 11.4, 10.7, 7.0 Hz, 1 H), 5.60 (dt, J = 16.2, 6.0 Hz, 1 H), 6.41 (d, J = 16.4 Hz, 1 H), 6.43 (d, J = 2.1 Hz, 1 H), 7.24-7.29 (m, 3 H), 7.37 (t, J = 7.6 Hz, 2 H), 8.01 (d, J = 1.8 Hz, 1 H), 8.06 (s, 1 H), 8.67 (s, 1 H), 8.81 (d, J = 10.4 Hz, 1 H), 11.38-11.41 (m, 1 H) |

TABLE 3-continued

LC-MS and NMR data for Examples of Table 2

| Example | Analytical Data |
|---|---|
| Example 8-2 Single isomer | LC-MS (ESI+): 592.24 [M + H]+, Rt = 5.02 min (Method 1)<br>$^1$H NMR (600 MHz, DMSO-$d_6$) δ ppm 0.92 (d, J = 6.6 Hz, 3 H), 1.18-1.31 (m, 1 H), 1.37 (s, 1 H), 1.48-1.58 (m, 3 H), 1.58-1.63 (m, 1 H), 2.06 (dd, J = 11.0, 7.0 Hz, 1 H), 2.72 (q, J = 12.1 Hz, 1 H), 2.87 (dt, J = 13.2, 6.8 Hz, 1 H), 3.16 (d, J = 16.0 Hz, 1 H), 3.19 (d, J = 16.5 Hz, 1 H), 3.28 (td, J = 8.6, 4.8 Hz, 1 H), 3.35-3.38 (m, 1 H), 3.53 (d, J = 16.0 Hz, 2 H), 3.57 (ddd, J = 14.3, 4.4, 2.2 Hz, 1 H), 3.61 (q, J = 6.2 Hz, 1 H), 3.68 (quin, J = 6.1 Hz, 1 H), 3.95 (ddd, J = 12.8, 5.5, 1.3 Hz, 1 H), 3.99 (ddd, J = 13.6, 6.2, 1.8 Hz, 1 H), 4.81 (ddd, J = 12.1, 10.2, 6.7 Hz, 1 H), 5.66 (dt, J = 16.1, 5.9 Hz, 1 H), 6.37 (dt, J = 16.1, 1.0 Hz, 1 H), 6.46 (d, J = 2.0 Hz, 1 H), 7.26 (t, J = 7.3 Hz, 1 H), 7.27 (d, J = 7.3 Hz, 2 H), 7.37 (t, J = 7.4 Hz, 2 H), 8.02 (d, J = 2.0 Hz, 1 H), 8.06 (s, 1 H), 8.68 (s, 1 H), 8.88 (d, J = 10.1 Hz, 1 H), 11.33-11.44 (m, 1 H) |
| Example 9-1 Mixture of diastereomers | LC-MS (ESI+): 594.04 [M + H]+, Rt = 5.04, 5.08 min (Method 1)<br>$^1$H NMR (500 MHz, DMSO-$d_6$): δ ppm 0.90 (d, J = 6.4 Hz, 3 H), 2.01-2.07 (m, 1 H), 2.55-2.64 (m, 1 H), 2.77-2.84 (m, 1 H), 2.98 (d, J = 15.0 Hz, 1 H), 3.05 (d, J = 15.6 Hz, 1 H), 3.30 (br. s., 1 H), 3.39-3.56 (m, 6 H), 3.65-3.75 (m, 2 H), 3.83-3.92 (m, 3 H), 4.00-4.05 (m, 1 H), 4.60-4.69 (m, 1 H), 5.58-5.66 (m, 1 H), 6.45 (d, J = 16.2 Hz, 1 H), 6.65 (d, J = 2.1 Hz, 1 H), 7.23-7.27 (m, 3 H), 7.34-7.36 (m, 2 H), 7.45 (d, J = 7.9 Hz, 1 H), 7.78 (d, J = 7.9 Hz, 1 H), 7.80 (s, 1 H), 7.98 (d, J = 1.8 Hz, 1 H), 8.48 (d, J = 8.9 Hz, 1 H), 11.35 (br. s., 1 H) |

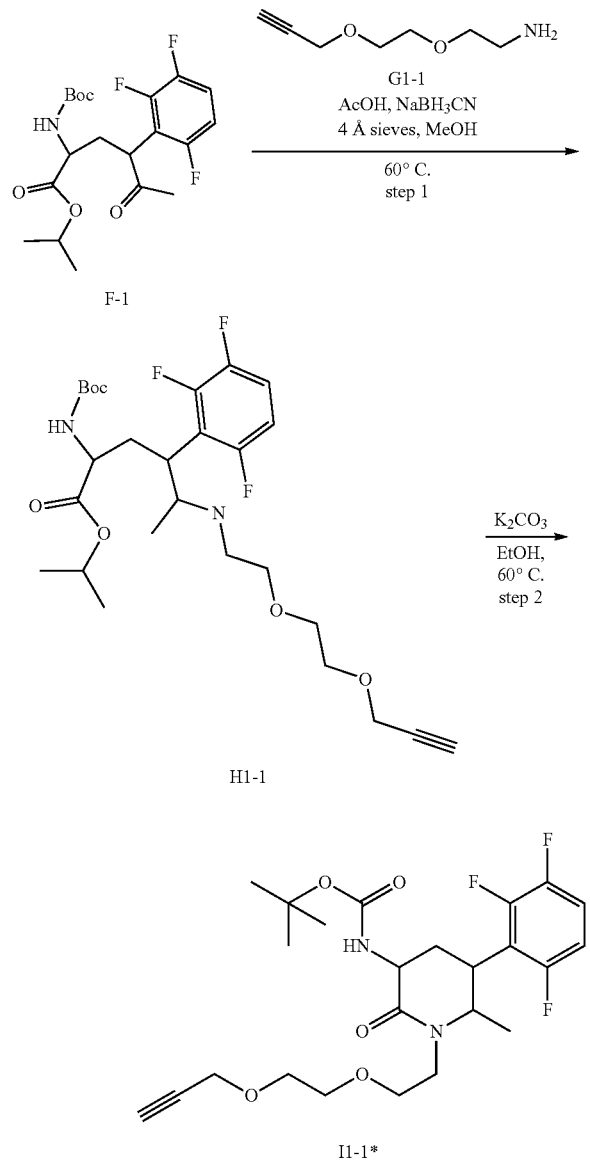

Scheme 3. Synthesis of Intermediate I1-1*

Experimental Procedure of Synthesis of Intermediate I1-1*

Step 1. Synthesis of Isopropyl 2-(tert-butoxycarbonylamino)-5-[2-(2-prop-2-ynoxyethoxy)ethylamino]-4-(2,3,6-trifluorophenyl)hexanoate (H1-1)

To compound F-1 (CAS 1488326-89-1) (1.75 g, 4.19 mmol), a solution of compound G1-1 (1.98 g, 9.16 mmol) in dry MeOH (17.8 mL), activated 4 Å molecular powdered sieves (3.6 g), glacial acetic acid (240 μL, 4.19 mmol), and NaCNBH$_3$ (144 mg, 9.17 mmol) were added. The mixture was heated at 60° C. overnight. The reaction mixture was filtered through a pad of Celite and the filtrate concentrated to yield m=4.42 g of the crude material. This crude product was dissolved in EtOAc (20 mL) and sat. NaHCO$_3$ (80 mL). The organic layer was separated, and the aq. layer extracted with EtOAc (3×15 mL). The combined organic layers were washed with brine (20 mL), dried over anhydrous Na$_2$SO$_4$ and concentrated to yield the desired product H1-1 (m=2.317 g) as a yellowish oil.

LC-MS (ES+): 545.3 [M+H]+.

Step 2. Synthesis of Tert-butyl N-[6-methyl-2-oxo-1-[2-(2-prop-2-ynoxyethoxy)ethyl]-5-(2,3,6-trifluorophenyl)-3-piperidyl]carbamate (I1-1*)

Into a solution of compound H1-1 (2.317 g, 4.25 mmol) in EtOH (65 mL), K$_2$CO$_3$ (1.94 g, 14 mmol) was added and the reaction mixture heated at 60° C. overnight. The mixture was concentrated and the residue dissolved in DCM (40 mL) and water (200 mL). The layers were separated, and the aqueous layer extracted with DCM (3×15 mL). The combined organic layer was dried and concentrated to give crude product (1.798 g). The crude material was loaded and purified on a silica column (Interchim 80 g, 15 μm, SiO$_2$) using Interchim PuriFlash 450 instrument with a flowrate of 30 mL/min starting with DCM (100%) and going to 40% DCM/MeOH (40/1) in 15 CVs. Hold 40% DCM/MeOH (40/1) for 15 CVs and increasing to 60% DCM/MeOH (40/1) in 10 CVs. The relevant fractions were collected, the solvent removed as appropriate to yield I1-1* (445 mg, 22.3%).

LC-MS (ES+): 485.2 [M+H]+.

Intermediates I1-1, I1-2*, I1-3*, I1-4*, I1-5*, I1-6*, I1-7*, I1-7, I2-2, I3-1* were Synthesized Using the Same Experimental Procedures as for the Synthesis of Intermediate I1-1* and Starting from Intermediates GX-n and F-X as Stated in Table 4.

Scheme 4. Synthesis of Intermediate I3-2*

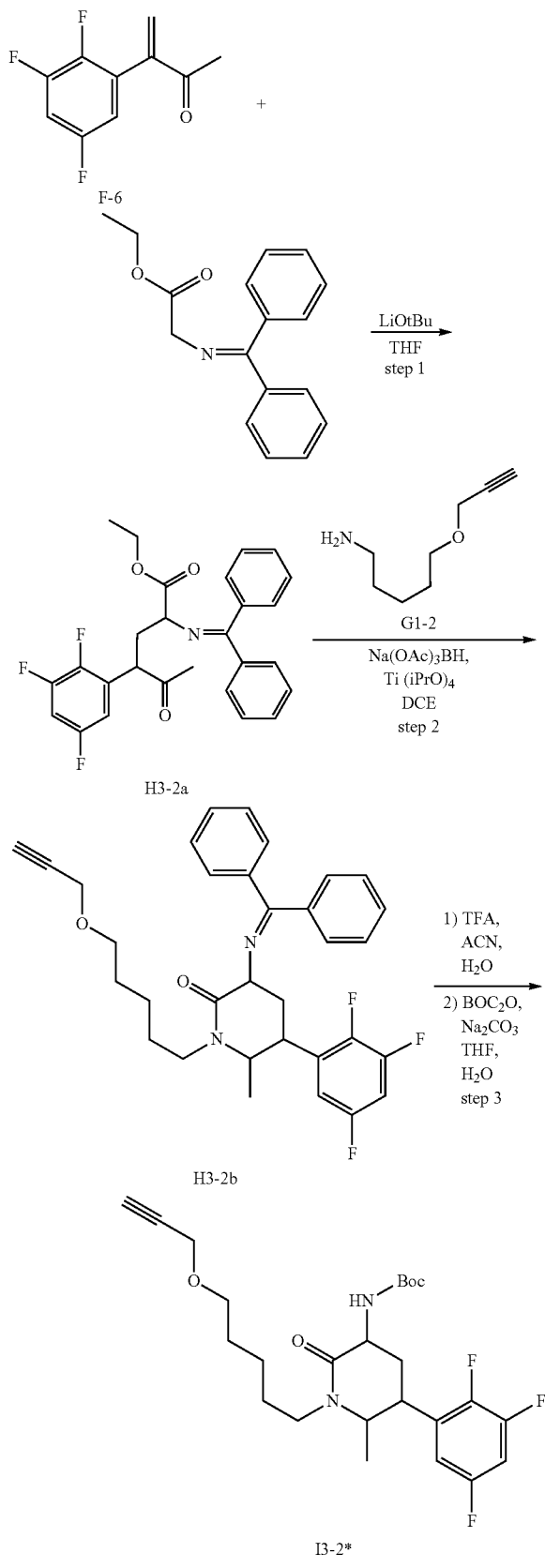

Experimental Procedure of Synthesis of Intermediate I3-2*

Step 1. Synthesis of Ethyl 2-(benzhydrylideneamino)-5-oxo-4-(2,3,5-trifluorophenyl)hexanoate (H3-2a)

3-(2,3,5-trifluorophenyl)but-3-en-2-one F-6 (2.00 g, 9.99 mmol) was dissolved in THF (12 mL), ethyl N-(diphenylmethylene)glycinate (2671 mg, 9.99 mmol) was added, the reaction mixture was purged with nitrogen and cooled down to 0° C. Then LiOtBu (881 mg, 11.0 mmol) was added portionwise and the reaction mixture was stirred at 0-10° C. for 3 hours. Reaction was quenched with cold water (10 mL) and extracted with MTBE (2×40 mL). Organics collected and washed with brine, dried and concentrated to give crude (4.7 g) that was purified by chromatography on an Interchim cartridge 40 g using EtOAc in cyclohexane 0-30% 20 CV to give ethyl 2-(benzhydrylideneamino)-5-oxo-4-(2,3,5-trifluorophenyl)hexanoate H3-2a (3.2 g, 57%) that was used in the next step as is.
LC-MS (ESI+): 468.5 [M+H]+.

Step 2. Synthesis of 3-(benzhydrylideneamino)-6-methyl-1-(5-prop-2-ynoxypentyl)-5-(2,3,5-trifluorophenyl)piperidin-2-one, (H3-2b)

H3-2a (2.780 g, 5.947 mmol) was dissolved in DCE (50 mL). The reaction mixture was cooled down to 0° C. and G1-2 (1602 mg, 9.019 mmol) was added followed by triethylamine (994.6 µL, 7.136 mmol) and titanium(IV) isopropoxide (2289 µL, 7.731 mmol). The reaction mixture was heated at 45° C. for 3 hours the reaction mixture was cooled down to 0° C. and Na(OAc)₃BH (4149 mg, 19.58 mmol) was added. The reaction mixture was heated at 40° C. for 3 hours then an additional amount of DCE (15 mL) and the reaction mixture was heated at 40° C. overnight. Reaction was quenched with brine (40 mL), the reaction mixture was filtered then filtrate was extracted with DCM (4×35 mL), organic layers were collected, washed with sat. NaHCO₃ (1×30 mL) dried and concentrated to give crude 3-(benzhydrylideneamino)-6-methyl-1-(5-prop-2-ynoxypentyl)-5-(2,3,5-trifluorophenyl)piperidin-2-one H3-2b (3.67 g, 100%) used as is.
LC-MS (ESI+): 547.7 [M+H]+.

Step 3. Synthesis of Tert-butyl N-[6-methyl-2-oxo-1-(5-prop-2-ynoxypentyl)-5-(2,3,5-trifluorophenyl)-3-piperidyl]carbamate (I3-2*)

H3-2b (3.67 g, 6.71 mmol) was dissolved in ACN/water (24.5/12.2 mL). After that TFA (1028 µL, 13.4 mmol) was added and the reaction mixture was stirred at rt until full deprotection, then THF (10.2 mL) and water (5.45 mL) were added into the reaction mixture, followed by Na₂CO₃ (2137 mg, 20.2 mmol) and Boc₂O (2200 mg, 10.1 mmol) and the reaction mixture was stirred for 2 hours then stored in the fridge. The reaction mixture was filtered through a pad of Celite, filtrate was diluted with DCM and water, layers were separated, aq. layer was extracted with DCM (2×30 mL). Organics collected, dried and concentrated to give crude (6.0 g) that was divided on two Interchim columns 40 g 25 µm, and purified using EtOAc in cyclohexane 0% 3 CV, 0-50% 30 CV to give tert-butyl N-[6-methyl-2-oxo-1-(5-prop-2-ynoxypentyl)-5-(2,3,5-trifluorophenyl)-3-piperidyl]carbamate I3-2* (520 mg, 16%).
LC-MS (ESI+): 483.6 [M+H]+.

Intermediates I4-1*, I4-2* and I3-1* were synthesized using the same Experimental Procedures as for the Synthesis of Intermediate I3-2* with Building Blocks as Detailed in Table 4.

TABLE 4

Structures and quantities of Intermediates for Scheme 3 and 4

| Starting material | | Intermediate 2/Q | Route | Intermediate 3/Q | Products | Analytical Data |
|---|---|---|---|---|---|---|
| Intermediate 1/Q | Structure | | | | Structure | |
| G1-1 20.8 g | CAS 944561-44-8 (propargyl-O-CH2CH2-O-CH2CH2-NH2) | F-1 20 g | Scheme 3 then SFC chiral separation of I1-1* | I1-1 3.44 g | Boc-NH piperidinone with 2,6-difluorophenyl and methyl, N-CH2CH2-O-CH2CH2-O-propargyl | 485.2 [M + H]+ SFC 1.59 min |
| G1-2 1.52 g | CAS 2411548-12-2 (propargyl-O-(CH2)4-NH2·HCl) | F-1 1.35 g | Scheme 3 | I1-2* 732 mg | Boc-NH piperidinone with 2,6-difluorophenyl and methyl, N-(CH2)4-O-propargyl | 483.5 [M + H]+ |
| G1-3 0.97 g | propargyl-O-CH2CH2-O-(CH2)3-NH2 | F-1 1.17 g | Scheme 3 | I1-3* 635 mg | Boc-NH piperidinone with 2,6-difluorophenyl and methyl, N-(CH2)3-O-CH2CH2-O-propargyl | 499.0 [M + H]+ |

TABLE 4-continued

Structures and quantities of Intermediates for Scheme 3 and 4

| Starting material | | Intermediate 2/Q | Route | Intermediate 3/Q | Products | Analytical Data |
|---|---|---|---|---|---|---|
| Intermediate 1/Q | Structure | | | | Structure | |
| G1-4 662 mg | H2N~~O~~O~~≡ HCl | F-1 600 mg | Scheme 3 | I1-4* 324 mg | [structure] | 499.1 [M + H]+ |
| G1-5 406 mg | H2N~~~O~~≡ CAS 1858472-14-6 US20190192668 | F-1 600 mg | Scheme 3 | I1-5* 333 mg | [structure] | 483.1 [M + H]+ |
| G1-6 571.0 mg | ≡~O~~O~~NH2 | F-1 600.0 mg | Scheme 3 | I1-6* 355.2 mg | [structure] | 499.1 [M + H]+ |

TABLE 4-continued
Structures and quantities of Intermediates for Scheme 3 and 4
| Starting material | | | | Intermediate 3/Q | Products | |
|---|---|---|---|---|---|---|
| Intermediate 1/Q | Structure | Intermediate 2/Q | Route | | Structure | Analytical Data |
| G1-7 650 mg | 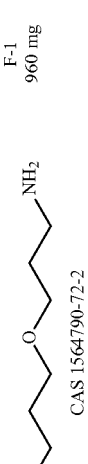 CAS 1564790-72-2 | F-1 960 mg | Scheme 3 | I1-7* 553 mg | 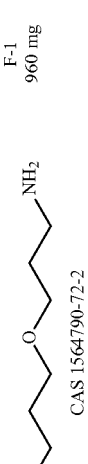 | 483.1 [M + H]+ |
| G1-7 15 g | 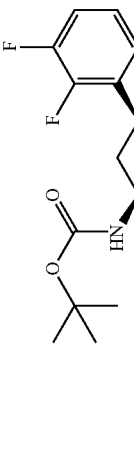 CAS 1564790-72-2 | F-1 18 g | Scheme 3 then SFC chiral separation of I1-7* | I1-1 1.93 g | 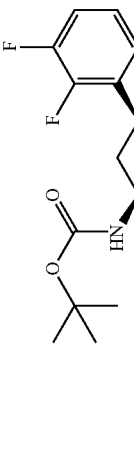 | 483.1 [M + H]+ SFC 1.52 min |
| G1-2 482 mg | 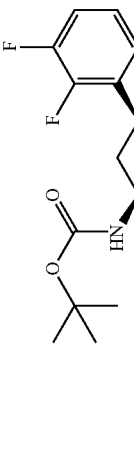 CAS 2411548-12-2 | F-3 649 mg CAS 1456803-33-0 | Scheme 3 | I2-2* 373 mg | 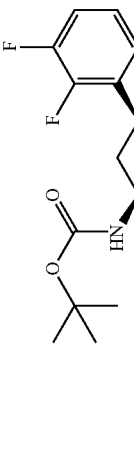 | 429.9 [M + H]+ |

TABLE 4-continued
Structures and quantities of Intermediates for Scheme 3 and 4
| Starting material | | Intermediate 2/Q | Route | Intermediate 3/Q | Products | Analytical Data |
|---|---|---|---|---|---|---|
| Intermediate 1/Q | Structure | | | | Structure | |
| G1-1 13.5 g | 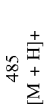 CAS 944561-44-8 | F-6 12 g | Scheme 4 | I3-1* 650 mg |  | 485 [M + H]+ |
| G1-2 16.5 g | 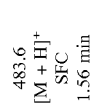 CAS 2411548-12-2 | F-5 20.5 g | Scheme 3 then SFC chiral separation of I3-2* | I3-2 3.32 g |  | 483.6 [M + H]+ SFC 1.56 min |
| G1-2 11 g |  CAS 2411548-12-2 | F-7 15 g | Scheme 4 | I4-1* 860 mg | 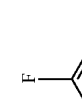 | 465.3 [M + H]+ |

TABLE 4-continued
Structures and quantities of Intermediates for Scheme 3 and 4
| Starting material | | | | | Products | |
|---|---|---|---|---|---|---|
| Intermediate 1/Q | Structure | Intermediate 2/Q | Route | Intermediate 3/Q | Structure | Analytical Data |
| G1-1 2.34 g | 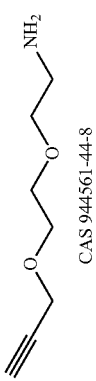 CAS 944561-44-8 | F-7 5.0 g | Scheme 4 | I4-2* 1.0 g | 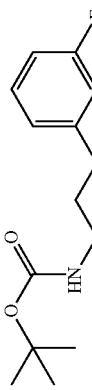 | 467.6 [M + H]+ |

SFC Preparative Methods for I1-1, I1-7 and I3-2

Instrument: Sepiatec Prep SFC 100 with Prep SFC 100 control software and UV/Vis detector.

Solvents: Primary mobile phase=$CO_2$

I1-1

Column: Phenomenex Lux Amylose-1, 5 μm, 250×21.2 mm at 40° C.

UV monitoring: 210 nm

Flow: 50 ml/min. Modifier: 20% MeOH with 0.2% $NH_3$.

I1-7

Column: Phenomenex Lux Amylose-1, 5 μm, 250×21.2 mm at 40° C.

UV monitoring: 210 nm

Flow: 50 ml/min. Modifier: 30% MeOH.

I3-2

Column: Phenomenex Lux Amylose-1, 5 μm, 250×21.2 mm at 40° C.

UV monitoring: 210 nm

Flow: 50 ml/min. Modifier: 30% MeOH.

Analytical SFC Method for I1-1, I1-7 and I3-2

Instrument: Waters Acquity UPC2 with Masslynx software, PDA detector and a QDa mass detector.

Column: Phenomenex Lux Amylose-1, 3 μm, 50×2 mm, 45° C., 1.5 ml/min

Solvents: Primary mobile phase=$CO_2$ with MeOH modifier

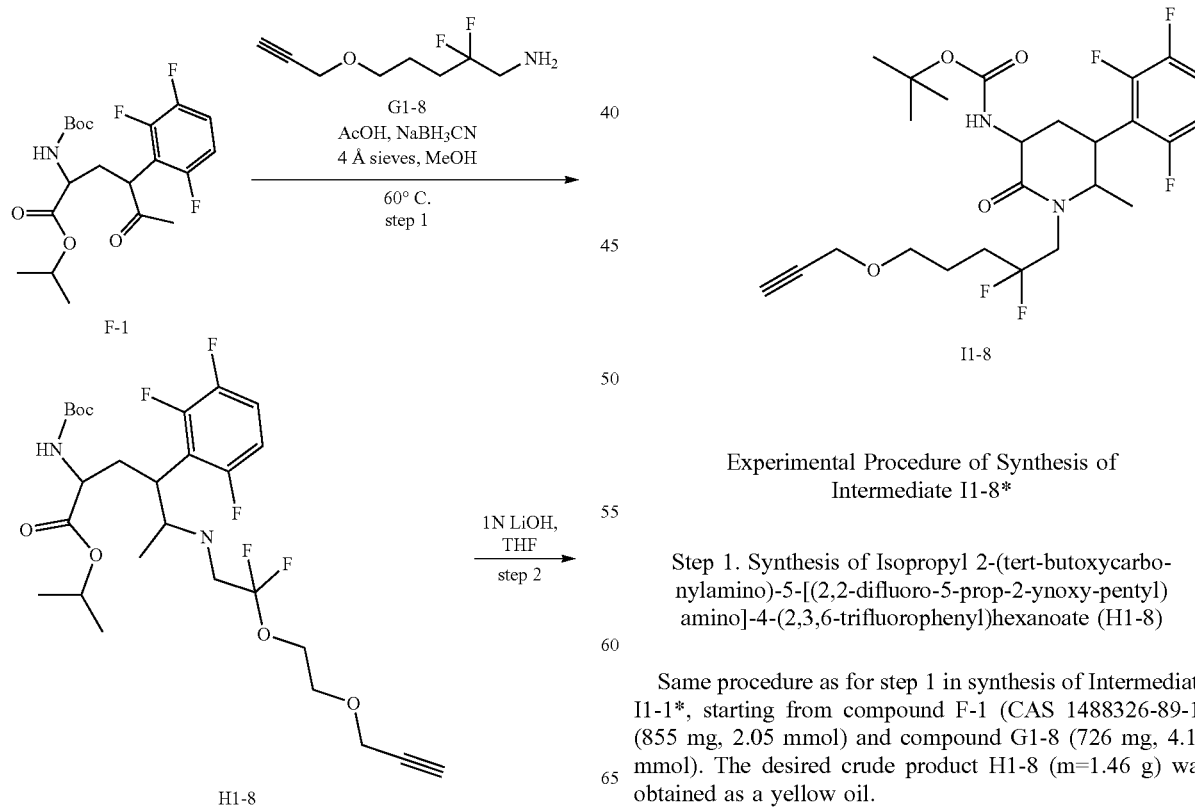

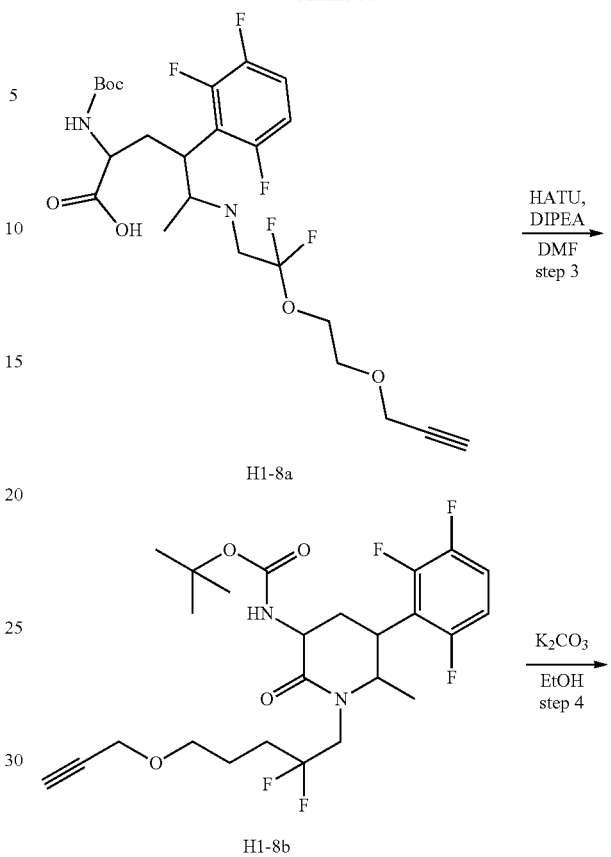

Experimental Procedure of Synthesis of Intermediate I1-8*

Step 1. Synthesis of Isopropyl 2-(tert-butoxycarbonylamino)-5-[(2,2-difluoro-5-prop-2-ynoxy-pentyl)amino]-4-(2,3,6-trifluorophenyl)hexanoate (H1-8)

Same procedure as for step 1 in synthesis of Intermediate I1-1*, starting from compound F-1 (CAS 1488326-89-1) (855 mg, 2.05 mmol) and compound G1-8 (726 mg, 4.10 mmol). The desired crude product H1-8 (m=1.46 g) was obtained as a yellow oil.

LC-MS (ES+): 579.1 [M+H]$^+$.

Step 2. Synthesis 2-(tert-butoxycarbonylamino)-5-[(2,2-difluoro-5-prop-2-ynoxy-pentyl)amino]-4-(2,3,6-trifluorophenyl)hexanoic Acid (H1-8a)

Same procedure as step 3 in synthesis of Example 1-1, starting with H1-8 ((1.1 g, 1.90 mmol). The desired product H1-8a (546 mg, 87%) was obtained and used as is in the next reaction step.
LC-MS (ES+): 537.0 [M+H]$^+$.

Step 3. Synthesis Tert-butyl N-[1-(2,2-difluoro-5-prop-2-ynoxy-pentyl)-6-methyl-2-oxo-5-(2,3,6-trifluorophenyl)-3-piperidyl]carbamate (H1-8b*)

Same procedure as step 5 in synthesis of Example 1-1, starting with H1-8a (504 mg, 0.940 mmol). The crude product H1-8b* (426 mg) was obtained as a sticky light orange solid.
LC-MS (ES+): 519.1 [M+H]$^+$.

Step 4. Synthesis Tert-butyl (1-(2,2-difluoro-5-prop-2-ynoxy-pentyl)-6-methyl-2-oxo-5-(2,3,6-trifluorophenyl)-3-piperidyl)carbamate (I1-8*)

Same procedure as step 2 in the synthesis of Intermediate I1-1* starting from H1-8b* (426 mg, 0.822 mmol). Desired product I1-8* was obtained (247 mg, 58%).
LC-MS (ES+): 519.0 [M+H]$^+$.

Scheme 6. Synthesis of Intermediate I2-1

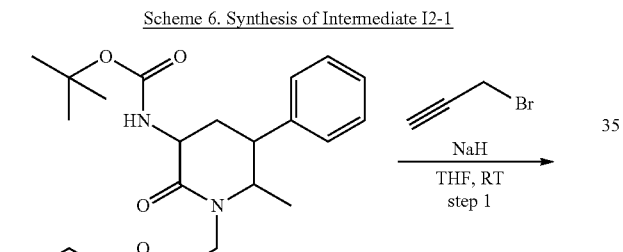

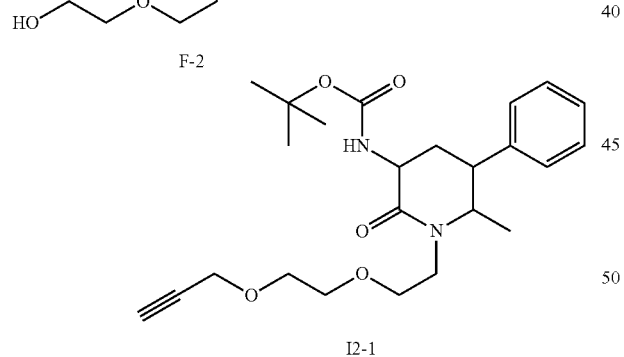

I2-1

Experimental Procedure of Synthesis of Intermediate I2-1

Step 1. Synthesis of Tert-butyl N-[6-methyl-2-oxo-5-phenyl-1-[2-(2-prop-2-ynoxyethoxy)ethyl]-3-piperidyl]carbamate (I2-1)

To the ice cooled solution of F-2 (658 mg, 1.67 mmol) in THF (8 mL), under argon, NaH (60% suspension in mineral oil, 74.3 mg, 1.86 mmol) was added portionwise. The resulted mixture was stirred at 0 C for 15 minutes upon which compound propargyl bromide (80% in toluene, 186 µL, 2.61 mmol) was added dropwise during 5 min. Stirring was continued at 0° C. for 5 minutes then at room temperature overnight. The reaction mixture was quenched with sat NH$_4$Cl (40 mL) and extracted with diethyl ether (3×20 mL). The combined organic layers were dried over Na$_2$SO$_4$ and concentrated under reduced pressure to afford crude product (723 mg). The crude material was loaded and purified on a silica column (Interchim 12 g, 15 µm, SiO$_2$) using Interchim PuriFlash 450 instrument with a flow of 20 mL/min starting with cyclohexane (100%) and going to 100% EtOAc in 20 CVs. Hold 100% EtOAc for 5 CVs The appropriate fractions were collected, the solvent removed to yield I2-1 (472 mg, 65.6%).
LC-MS (ES+): 431.8 [M+H]$^+$.

Scheme 7. Synthesis of Intermediate I2-2

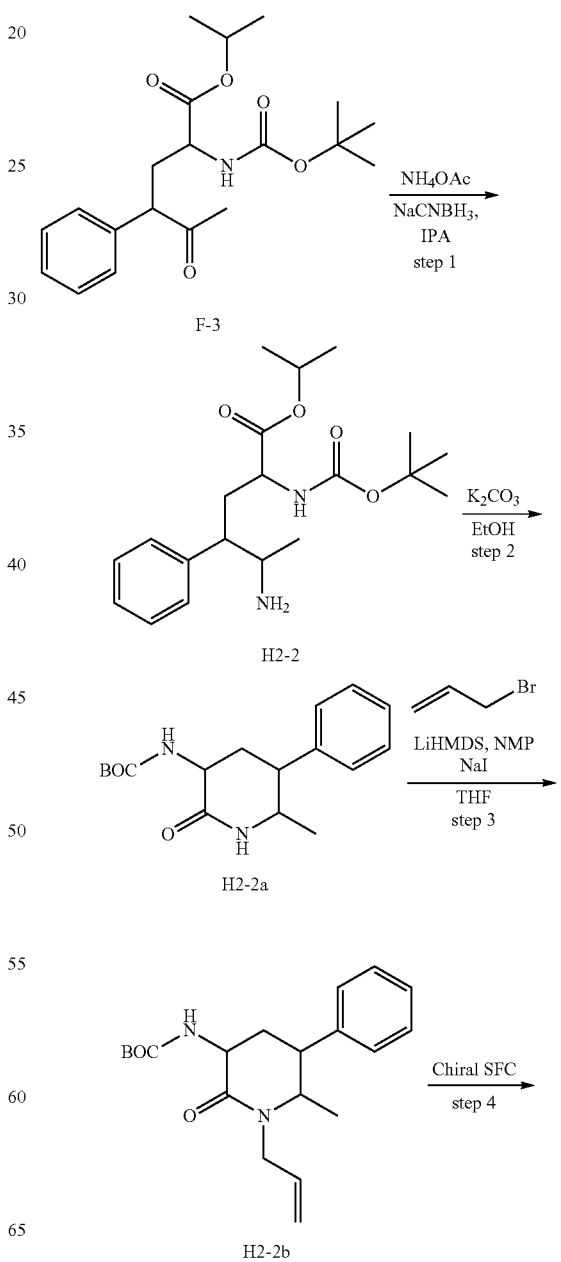

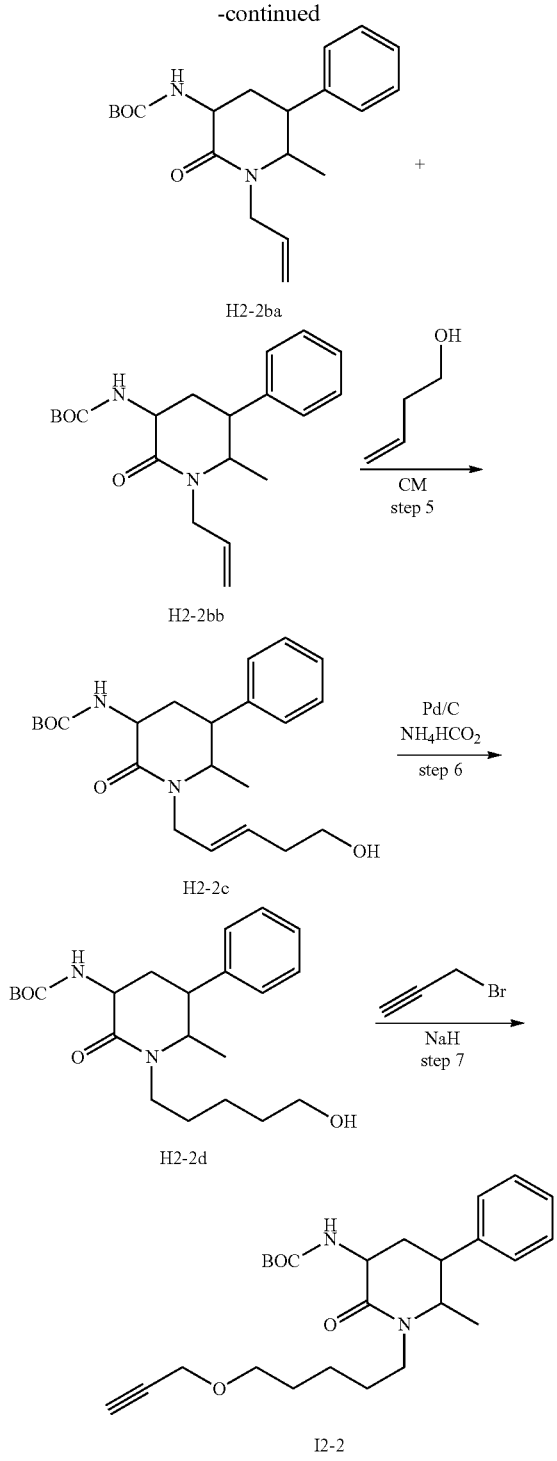

Experimental Procedures of Synthesis of Intermediate I2-2

Step 1. Synthesis of Isopropyl 5-amino-2-((tert-butoxycarbonyl)amino)-4-phenylhexanoate (H2-2)

To a stirred solution of isopropyl 2-((tert-butoxycarbonyl)amino)-5-oxo-4-phenylhexanoate, F-3 (CAS 1456803-33-0) (40 g, 110.19 mmol), NH$_4$OAc (84.84 g, 1.1 mol) and 4 Å molecular sieves (40 g) in IPA (1000 mL) at RT was added NaCNBH$_3$ (10.38 g, 165.28 mmol) and the resultant reaction mixture was stirred at RT for 12 h. The reaction mixture was filtered through Celite, and the filtrate was evaporated and diluted with 10% NaHCO$_3$ (aq) solution, extracted with 10% MeOH in DCM, dried over anhydrous Na$_2$SO$_4$ and concentrated in vacuo. The crude compound was purified by flash column chromatography using silica gel (230-400 mesh) and compound was eluted with 0-5% MeOH in DCM gradient to afford isopropyl 5-amino-2-((tert-butoxycarbonyl)amino)-4-phenylhexanoate H2-2 (20 g, 49%).

LC-MS (ESI+): 365.3 [M+H]$^+$.

Step 2. Synthesis of Tert-butyl (6-methyl-2-oxo-5-phenylpiperidin-3-yl)carbamate (H2-2a)

To a stirred solution of isopropyl 5-amino-2-((tert-butoxycarbonyl)amino)-4-phenylhexanoate H2-2 (20 g, 54.94 mmol) in EtOH (500 mL) was added K$_2$CO$_3$ (15.16 g, 109.89 mmol) at RT. The reaction mixture was stirred at 80° C. for 1 h and the reaction mixture was filtered through Celite. The filtrate was evaporated and diluted with water, extracted with EtOAc, dried over anhydrous Na$_2$SO$_4$, and concentrated in vacuo to obtain crude compound. The crude compound was purified by flash column chromatography using silica gel (230-400 mesh) and compound was eluted with 0-30% EtOAc in petroleum-ether gradient to afford tert-butyl (6-methyl-2-oxo-5-phenylpiperidin-3-yl)carbamate H2-2a (13 g, 77.8%).

LC-MS (ESI+): 249.2 [M+H-tBu]$^+$

Step 3. Synthesis of Tert-butyl (1-allyl-6-methyl-2-oxo-5-phenylpiperidin-3-yl)carbamate (H2-2b)

To a stirred solution of tert-butyl (6-methyl-2-oxo-5-phenylpiperidin-3-yl)carbamate H2-2a (8 g, 26.31 mmol) in THF:NMP (2:1) (100 ml) was dropwise added LiHMDS (28.94 ml, 28.94 mmol). The reaction mixture was allowed to stir and after 15 min allyl bromide (15.91 g, 131.55 mmol) and NaI (3.94 g, 26.31 mmol) were added. The resulting mixture was stirred at 0° C. for 2 h and then warmed to RT for an additional 18 h. The reaction mixture was diluted with water and extracted with EtOAc (2×500 mL), dried over anhydrous Na$_2$SO$_4$, concentrated to obtain crude compound, which was purified by flash column chromatography using silica gel (230-400 mesh) and compound was eluted with 0-20% EtOAc in petroleum-ether gradient to afford tert-butyl (1-allyl-6-methyl-2-oxo-5-phenylpiperidin-3-yl)carbamate H2-2b (7 g, 77.34%).

LC-MS (ESI+): 344.5 [M+H]$^+$.

Step 4 Preparative Chiral SFC:
Instrument: PICLab PREP 100
Solvents: Primary mobile phase=CO$_2$ Modifier: 30% MeOH
Column: YMC Cellulose-SC Sum, 250×30 mm, at 35° C.
UV monitoring: 210 nm
Flow: 80 g/min.
Product fractions combined and evaporated to give cis isomers 1.45 g H2-2ba Isomer 1 and 1.18 g H2-2b Isomer 2.

Step 5. Synthesis of Tert-butyl (E)-(1-(5-hydroxypent-2-en-1-yl)-6-methyl-2-oxo-5-phenylpiperidin-3-yl)carbamate (H2-2c)

tert-butyl (1-allyl-6-methyl-2-oxo-5-phenylpiperidin-3-yl)carbamate H2-2ba (1.0 g, 2.90 mmol) is dissolved in DCM (18.5 mL), reaction mixture was purged with argon then but-3-en-1-ol (628 mg, 8.71 mmol) was added followed by Ti(iPrO)4 (0.258 mL, 0.871 mmol) and the reaction mixture was stirred for 30 minutes at room temperature. Then Hoveyda-Grubbs 2nd gen (182 mg, 0.290 mmol) was added and RM was stirred rt, overnight (green colour was changed to red). RM was diluted with DCM (15 mL), sat NaHCO₃ was added (10 mL), layers were separated, aqueous layer was extracted with DCM, organics collected, dried and concentrated to get crude product that was purified by column chromatography (normal phase [Interchim cartridge 25 g, 25 μm, using DCM/MeOH=90/10 in DCM, 0-40%, 20 CV, 40-80% 20 CV, 100% 3 CV, 10 mL/min flow rate]), to get tert-butyl (E)-(1-(5-hydroxypent-2-en-1-yl)-6-methyl-2-oxo-5-phenylpiperidin-3-yl)carbamate H2-2c (520 mg, 46%) that was used in next step as is.

LC-MS (ESI+): 389.3 [M+H]⁺.

Step 6. Synthesis of Tert-butyl (1-(5-hydroxypentyl)-6-methyl-2-oxo-5-phenylpiperidin-3-yl)carbamate, H2-2d H2-2c (168 mg, 0.43 mmol) was dissolved in EtOH (6 mL) in a vial, the reaction mixture was purged with argon then Pd/C (16 mg) was added followed by ammonium formate (189 mg, 3 mmol) and the reaction mixture was heated at 70° C. for 2 hours. The reaction mixture was filtered through a pad of Celite, filtrate was concentrated to give crude. Crude was purified by column chromatography (normal phase [Biotage, Interchim cartridge 12 g, 25 um, 0-50%, 10 CV, 50-100% 20 CV, 100% 3 CV, 10 mL/min flow rate DCM/MeOH=9/1 in DCM, 20 mL/min flow rate]) to give tert-butyl (1-(5-hydroxypentyl)-6-methyl-2-oxo-5-phenylpiperidin-3-yl)carbamate H2-2d (123 mg, 74%).

LC-MS (ESI+): 391.3 [M+H]1.

1H NMR (600 MHz, DMSO-d₆): δ/ppm: =0.81 (d, J=6.5 Hz, 3H), 1.24-1.32 (m, 2H), 1.41-1.51 (m, 3H), 1.55-1.64 (m, 1H), 1.94-2.00 (m, 1H), 2.32-2.42 (m, 1H), 2.71-2.79 (m, 1H), 3.38-3.44 (m, 3H), 3.58-3.64 (m, 1H), 3.64-3.72 (m, 1H), 3.95-4.02 (m, 1H), 4.37 (t, J=5.0 Hz, 1H), 7.03 (d, J=4.9 Hz, 1H), 7.21-7.27 (m, 3H), 7.34 (t, J=8.7 Hz, 2H).

Step 7 Synthesis of Tert-butyl (6-methyl-2-oxo-5-phenyl-1-(5-(prop-2-yn-1-yloxy)pentyl)piperidin-3-yl)carbamate, I2-2

H2-2d (420 mg, 1.08 mmol) was dissolved in THF (3.4 mL), the reaction mixture was cooled down to 0° C. and purged with argon, then NaH (60.0%, 55.9 mg, 1.40 mmol), was added portion wise, the reaction mixture was stirred for 10 minutes then propargyl bromide (80.0%, 0.144 mL, 1.29 mmol) was added and the reaction mixture was stirred overnight at rt. The reaction mixture was quenched with sat. Aq NH₄Cl (5 mL) and EtOAc (15 mL), layers were separated, aqueous layer was extracted with EtOAc (2×10 mL), organics collected, dried and concentrated to give crude. Crude was purified by column chromatography (normal phase [Interchim cartridge, 25 g, 25 μm, eluting with DCM/MeOH=9/1 in MeOH 0-50%, 30 CV, 50% 3 CV, 20 mL/min flow rate]) to give tert-butyl (6-methyl-2-oxo-5-phenyl-1-(5-(prop-2-yn-1-yloxy)pentyl)piperidin-3-yl)carbamate, I2-2. (250 mg, 54%).

LC-MS (ESI+): 429.2 [M+H]⁺.

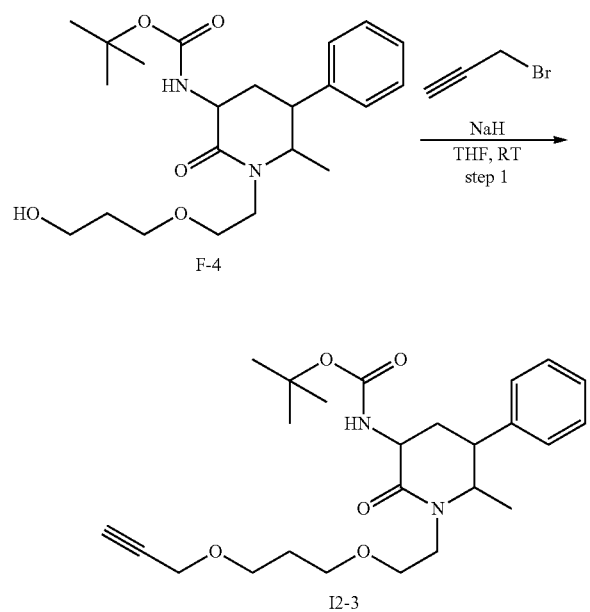

Experimental Procedure of Synthesis of Intermediate I2-3

Step 1. Synthesis of Tert-butyl N-[6-methyl-2-oxo-5-phenyl-1-[2-(3-prop-2-ynoxypropoxy)ethyl]-3-piperidyl]carbamate (I2-3)

Same procedure as synthesis of Intermediate I2-1 starting from F-4 (412.6 mg, 1.015 mmol). Desired product I2-3 was obtained (171.8 mg, 38.1%).

LC-MS (ES+): 445.1 [M+H]⁺.

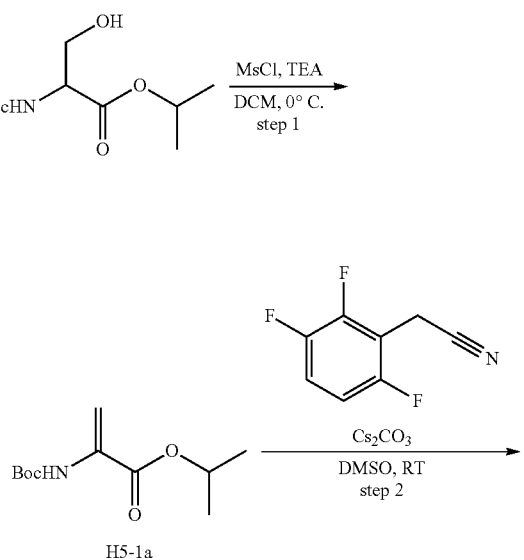

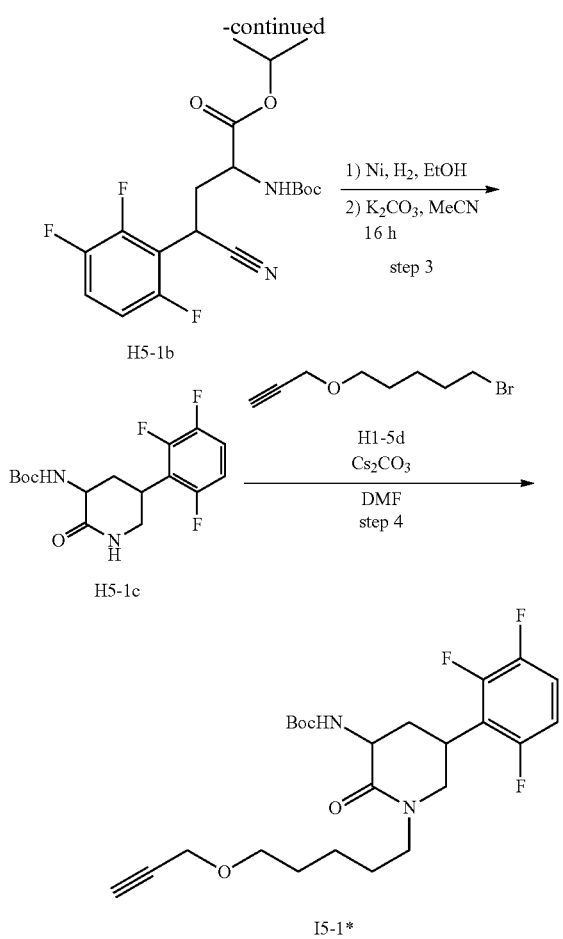

Experimental Procedure for Synthesis of Intermediates I5-1* and I5-1

Step 1 Synthesis of Isopropyl 2-((tert-butoxycarbonyl)amino)acrylate H5-1a

To a stirred solution of isopropyl (tert-butoxycarbonyl) serinate (50 g, 202.4 mmol) and TEA (84 mL, 607 mmol) in DCM (500 mL) at 0° C. was added methane sulfonyl chloride (23.38 mL, 303.3 mmol) dropwise and the resultant the reaction mixture was stirred at room temperature for 4 h. The reaction mixture was quenched with ice water (200 mL) and extracted with DCM (300 mL). Organic layer was separated, dried over anhydrous $Na_2SO_4$ and concentrated under reduced pressure to obtained crude material, which was purified by Biotage-Isolera using silica snap (230-400 mesh) and eluted with (0-10%) EtOAc in petroleum-ether gradient to afford isopropyl 2-((tert-butoxycarbonyl)amino) acrylate H5-1a as a colourless gum (45 g, 96%).

$^1$H NMR (400 MHz, DMSO-d6) δ: 8.36 (s, 1H), 5.60 (s, 1H), 5.46 (s, 1H), 5.0-4.94 (m, 1H), 1.42 (s, 9H), 1.24 (d, J=6.4 Hz, 6H)

Step 2 Synthesis of Isopropyl 2-((tert-butoxycarbonyl)amino)-4-cyano-4-(2,3,6-trifluorophenyl)butanoate H5-1b To a stirred solution of 2-(2,3,6-trifluorophenyl)acetonitrile (CAS 114152-21-5) (40 g, 233.91 mmol) and isopropyl 2-((tert-butoxycarbonyl)amino)acrylate H5-1a (53.56 g, 233.91 mmol) in DMSO (800 mL) at 0° C. was added $Cs_2CO_3$ (38.01 g, 116.95 mmol) portion wise and the resultant the reaction mixture was stirred at the same temperature for 10 min. After the completion of starting material, monitored by TLC, the reaction mixture was diluted with EtOAc (1 L) and washed with water (3×500 mL). Organic layer was separated, dried over anhydrous $Na_2SO_4$ and concentrated under reduced pressure to obtain crude mass. The crude compound was purified by flash column chromatography using silica gel (230-400 mesh) and eluted with (0-10%) EtOAc in petroleum-ether gradient to afford isopropyl 2-((tert-butoxycarbonyl)amino)-4-cyano-4-(2,3,6-trifluorophenyl)butanoate H5-1b as an off-white solid (85 g, 90%).

LC-MS (ESI+): 300.9 [M+H]$^+$.

Step 3 Synthesis of Tert-butyl (2-oxo-5-(2,3,6-trifluorophenyl)piperidin-3-yl)carbamate H5-1c To a stirred solution of isopropyl 2-((tert-butoxycarbonyl)amino)-4-cyano-4-(2,3,6-trifluorophenyl)butanoate H5-1b (85 g, 212 mmol) in ethanol (1.5 L) was added Raney Ni (90 g) (Raney Ni was washed with ethanol 200 mL and decanted) and the resultant reaction mixture was hydrogenated under 8 kg/cm$^2$ hydrogen pressure in an autoclave instrument at rt for 48 h. Reaction mixture was filtered through Celite pad, rinsed with EtOH (500 mL) and the filtrate was concentrated under reduced pressure. Residue obtained was dissolved in acetonitrile (1 L), potassium carbonate (47.8 g, 346 mmol) was added and the resultant reaction mixture was heated at 80° C. for 16 h. After the completion of starting material monitored by TLC, the reaction mixture concentrated under reduced pressure to remove EtOH. Residue obtained was partitioned between EtOAc (1 L) and with water (500 mL). Organic layer was separated, dried over anhydrous $Na_2SO_4$ and concentrated under reduced pressure to obtain crude compound which was purified by flash column chromatography using silica gel (230-400 mesh) eluted with (0-50%) EtOAc in petroleum-ether gradient to afford tert-butyl (2-oxo-5-(2,3,6-trifluorophenyl)piperidin-3-yl)carbamate H5-1c as a white solid (55 g, 75%).

LC-MS (ESI+): 245.1 [M+H-Boc]$^+$

Step 4 Synthesis of Tert-butyl (2-oxo-1-(5-(prop-2-yn-1-yloxy)pentyl)-5-(2,3,6-trifluorophenyl)piperidin-3-yl)carbamate I5-1*

To a stirred solution of tert-butyl (2-oxo-5-(2,3,6-trifluorophenyl)piperidin-3-yl)carbamate H5-1c (32 g, 93.02 mmol) and 1-bromo-5-(prop-2-yn-1-yloxy)pentane H5-1d (22.88 g, 111.6 mmol) in DMF (350 mL), $Cs_2CO_3$ (45.94 g, 139.5 mmol) was added and the resultant reaction mixture was stirred at 60° C. for 16 h. After the completion of starting material, monitored by TLC, the reaction mixture was partitioned between EtOAc (1 L) and water (3×500 mL). Organic layer was separated, dried over anhydrous $Na_2SO_4$ and concentrated under reduced pressure to give crude mass. Crude compound was purified by flash column chromatography using silica gel (230-400 mesh) and eluted with (0-20%) EtOAc in petroleum-ether gradient to afford tert-butyl (2-oxo-1-(5-(prop-2-yn-1-yloxy)pentyl)-5-(2,3,6-trifluorophenyl)piperidin-3-yl)carbamate I5-1* as a colourless gum (35 g, 80%).

Preparative Chiral SFC:
Instrument: PICLab PREP 100
Solvents: Primary mobile phase=$CO_2$ Modifier: 40% IPA Column: YMC Cellulose-SC 5 um, 250×30 mm, at 35° C.
UV monitoring: 210 nm Flow: 80 g/min.

Pure fractions were concentrated under reduced pressure and lyophilized to give products.

Isomer 1 (the first eluting peak) tert-butyl ((3S,5S)-2-oxo-1-(5-(prop-2-yn-1-yloxy)pentyl)-5-(2,3,6-trifluorophenyl)piperidin-3-yl)carbamate I5-1 as white solid 5.0 g Chiral SFC analytical YMC Cellulose-SC, 250×4.6 mm 5p at 35° C., 3 ml/min, 40% Methanol 35° C. Isomer-1 3.07 min $^1$H NMR (400 MHz, CDCL$_3$) δ 7.13-7.02 (m, 1H), 6.89-6.82 (m, 1H), 5.63-5.55 (m, 1H), 4.15 (d, J=2.4 Hz, 3H), 3.80-3.72 (m, 1H), 3.60-3.40 (m, 5H), 3.35-3.27 (m, 1H), 2.74-2.65 (m, 1H), 2.43 (t, J=2.4 Hz, 1H), 2.32-2.22 (m, 1H), 1.68-1.53 (m, 4H), 0.73 (s, 9H), 1.40-1.35 (m, 2H).

Experimental Procedure of Synthesis of Intermediate H5-1d

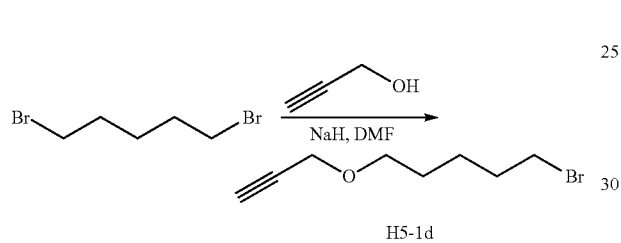

H5-1d

To a stirred solution of prop-2-yn-1-ol (20 g, 357.14 mmol) and 1,5-dibromopentane (163 g, 714 mmol) in DMF (120 mL) at 0° C. was added NaH (27.38 g, 714 mmol) portion wise and the resultant reaction mixture was stirred at room temperature for 15 h. The reaction mixture was quenched by the dropwise addition of water (500 mL) and extracted with EtOAc (2×500 mL). Combined organic layers were washed with brine solution (2×500 mL), dried over anhydrous Na$_2$SO$_4$ and concentrated under reduced pressure. The crude compound was purified by Biotage-Isolera using 340 g silica gel Snap cartridge (230-400 mesh) and eluted with (0-5%) EtOAc in petroleum-ether gradient to afford 1-bromo-5-(prop-2-yn-1-yloxy)pentane H5-1d as a colourless gum (90 g, 33.5%).

$^1$HNMR (400 MHz, DMSO-d6) δ: 4.16 (d, J=2.4 Hz, 2H), 3.55 (t, J=6.4 Hz, 2H), 3.44 (t, J=6.8 Hz, 2H), 2.45 (t, J=2.4 Hz, 1H), 1.95-1.85 (m, 2H), 1.70-1.60 (m, 2H), 1.57-1.50 (m, 2H)

Synthesis of Intermediates F-X

Scheme 10. Synthesis of intermediate F-2

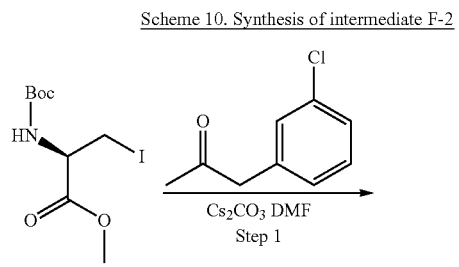

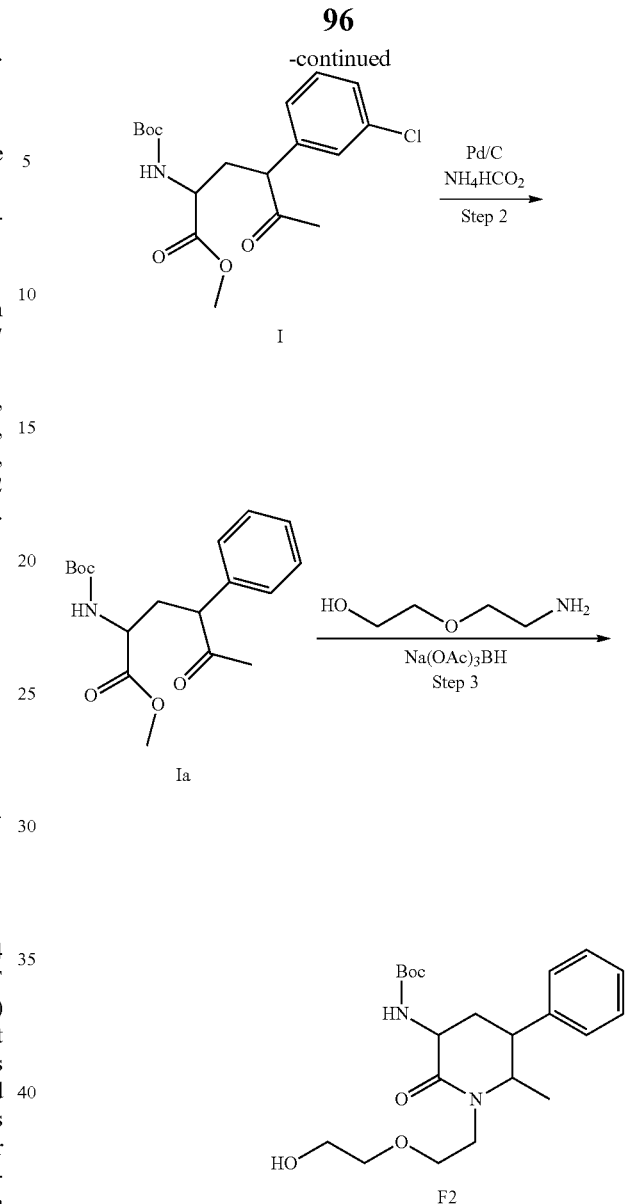

Experimental Procedure for Synthesis of F-2

Step-1 Synthesis of Methyl 2-(tert-butoxycarbonylamino)-4-(3-chlorophenyl)-5-oxo-hexanoate (I)

Into a solution of Boc-3-Iodo-D-Ala-OMe (6.0 g, 18 mmol) in dry DMF (40 mL), 3-chlorophenylacetone (3.36 g, 20. mmol) and cesium carbonate (6.5 g 20 mmol) were added and stirred at room temp. under argon for 45 min. Further 3-chlorophenylacetone (3.36 g, 20.18 mmol) and cesium carbonate (6.5 g 20 mmol) were added. The reaction mixture was stirred at room temp. under argon for 2.5 h. EtOAc (50 mL and water (200 mL) were added, and the layers separated. The organic layer was washed with NaHCO$_3$ (aq, sat.) (2×40 mL) and brine (40 mL), dried over anhydrous Na$_2$SO$_4$ and concentrated to afford the desired product I (5.98 g, 80%) used as is in the next step.

LC-MS (ES+): 392.6 [M+Na]$^+$.

Step-2 Synthesis of Methyl 2-(tert-butoxycarbonylamino)-5-oxo-4-phenylhexanoate (Ia)

A solution of 1 (5.97 g, 16.14 mmol) and ammonium formate (4.07 g, 64.56 mmol) in EtOH (42 mL) was degassed with argon in a ultrasonic bath for 15 min. Palladium on carbon (10%, 1.37 g, 1.29 mmol) was added and the mixture was stirred at 60° C. for 1.5 h. The reaction mixture was filtered through a pad of Celite. The Celite was washed with EtOH and the sample concentrated. The yellow residue was dissolved in EtOAc (100 mL) and the undissolved solids filtered off. The solvent was evaporated to afford the crude product 5 (5.1 g) as a sticky residue. The crude product was dry-loaded and purified on a silica column (Interchim 120 g, 15 µm, $SiO_2$) using an Interchim PuriFlash 450 instrument with a flowrate of 60 mL/min starting with cyclohexane (100%) and going to 100% cyclohexane/EtOAc (5/1) in 20 CVs. Hold 100% cyclohexane/EtOAc (5/1) for 10 CVs The appropriate fractions were collected, the solvent removed to yield the desired product Ia (3.1 g, 57.3%).

LC-MS (ES+): 358.6 $[M+Na]^+$.

Step-3 Synthesis of Tert-butyl N-[1-[2-(2-hydroxyethoxy)ethyl]-6-methyl-2-oxo-5-phenyl-3-piperidyl]carbamate (F-2)

Into a solution of 2-(2-aminoethoxy)ethanol (3.43 g, 32.6 mmol) in dry DCE (40 mL) was added a solution of Ia (2.73 g, 8.15 mmol) in dry DCE (40 mL), followed by acetic acid (1.4 mL, 24.45 mmol), 4 Å powdered molecular sieves (2 g) and sodium triacetoxyborohydride (6.91 g, 32.61 mmol). This mixture was stirred at room temp. under argon for 2 days. A new amount of 2-(2-aminoethoxy)ethanol (1.71 g, 16.3 mmol) was added followed by sodium triacetoxyborohydride (3.46 g, 16.3 mmol). The reaction was continued at room temp. for further 2 days. DCM (80 mL) and water (80 mL) were added with vigorous stirring. The organic layer was separated, washed with water (80 mL) and brine, dried over anhydrous $Na_2SO_4$, filtered and the solvent evaporated to afford the desired product F-2 (2.9 g, 90.6%) as a sticky yellow residue.

LC-MS (ES+): 393.7 $[M+H]^+$.

Scheme 11. Synthesis of Intermediate F-4

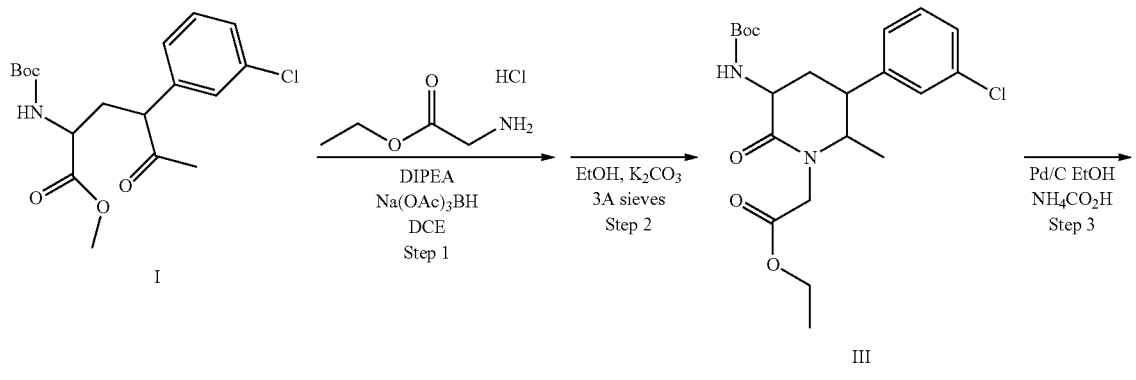

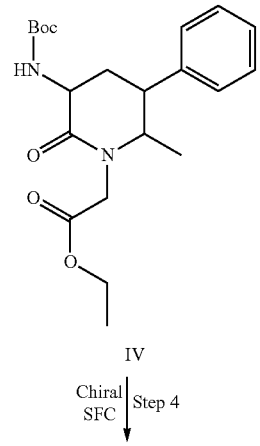

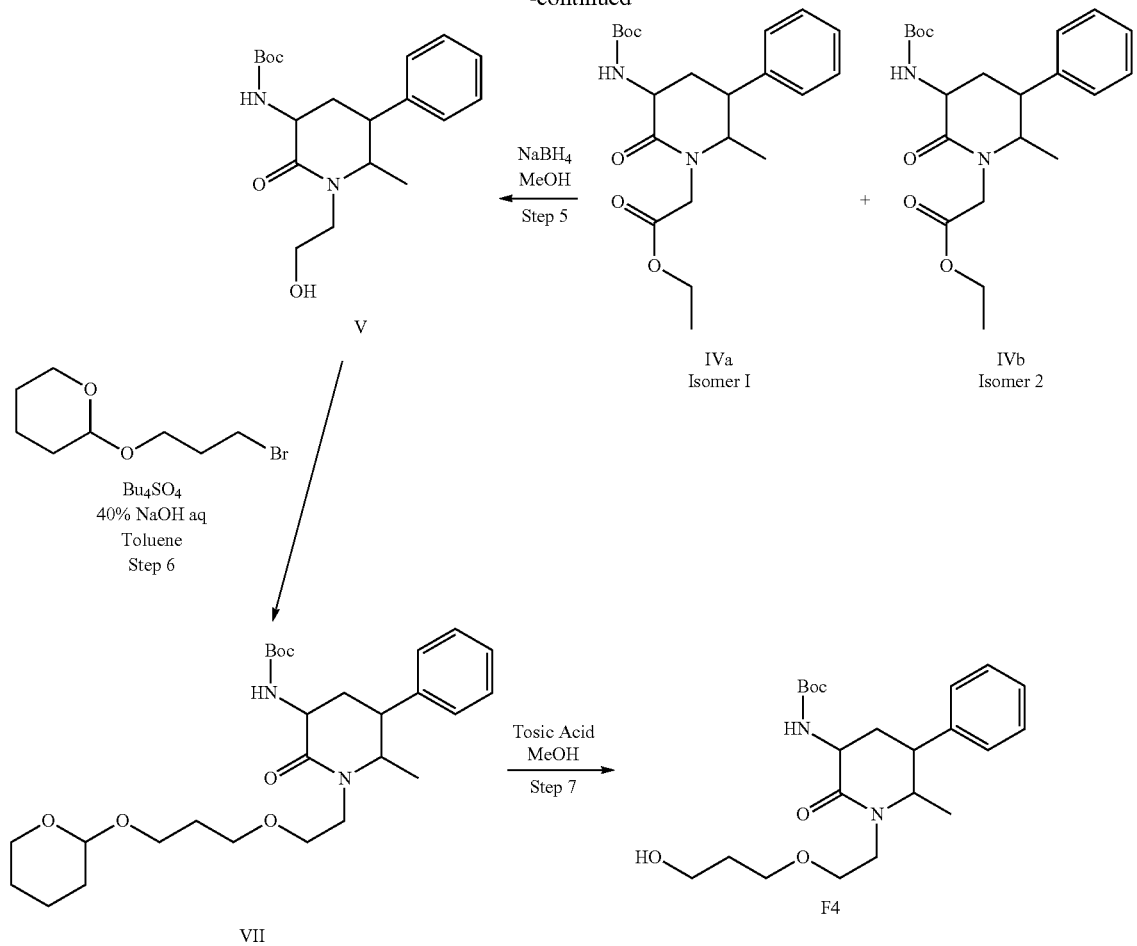

Experimental Procedure for Synthesis of Intermediate F-4

Step 1 and 2. Synthesis of Ethyl 2-[5-(tert-butoxycarbonylamino)-3-(3-chlorophenyl)-2-methyl-6-oxo-1-piperidyl]acetate (III)

1) Ethylaminoacetate hydrochloride (34.7 g, 249 mmol) was suspended in DCE (200 mL), DIPEA (43 ml, 248 mmol) was added dropwise and suspension was stirred for 15 minutes, then was added solution of I (23 g, 62 mmol) in DCE (250 mL) followed by acetic acid, 4 Å molecular sieves (0.25 g), Na(OAc)$_3$BH (52.7 g, 248 mmol) and the reaction mixture was stirred overnight at room temperature. LCMS showed traces of SM, and formation of intermediate M=457, in a mixture with final cyclized compound. An additional amount of ethylaminoacetate hydrochloride (2 eq), DIPEA (2 eq), and Na(OAc)$_3$BH (3 eq) were added and the was stirred for two additional days. LCMS showed completed reaction. The reaction mixture was diluted with DCM (200 mL), water was added (600 mL), molecular sieves were removed by filtration, layers were separated and organic layer was washed with water (3×500 mL), dried (Na$_2$SO$_4$) and concentrated to obtain intermediate (m=30.3 g).

2) Epimerisation step. Into a solution of product from step 1 (29.17 g, 68.65 mmol) in dry EtOH (400 mL), potassium carbonate (28.46 g, 205.95 mmol) and 3 Å molecular sieves (10 g) were added and stirred at 60° C. for 2 hours and overnight at RT. The reaction mixture was concentrated, and the residue dissolved in EtOAc (200 mL). The organic layer was carefully separated and the solid residue washed again with EtOAc (4×50 mL). The combined organic layer was washed with sat. NaHCO$_3$ (100 mL), brine (4×50 mL), dried over anhydrous Na$_2$SO$_4$, and evaporated to yield product III (23.85 g) that was used as is in the next reaction step.

Step 3. Synthesis of Ethyl 2-[5-(tert-butoxycarbonylamino)-2-methyl-6-oxo-3-phenyl-1-piperidyl]acetate (IV)

A solution of III (23.85 g, 56.12 mmol) and ammonium formate (17.69 g, 280.64 mmol) in ethanol (500 mL) was flushed with argon. To this solution 10% Palladium on Charcoal (4.77 g) was added and the reaction mixture heated at 60° C. for 30 min. The reaction mixture was filtered through a pad of Celite. The solvent was evaporated to yield m=20.20 g of crude product. It was dissolved in DCM and loaded on a Interchim (300 g, 50 μm, SiO$_2$) column and purified using a Interchim Puriflash 450 system with a flowrate of 120 ml/min starting with cyclohexane (100%) and going to 65% cyclohexane/EtOAc (1/1) in 15 CVs, hold 100% for 10 CVs. The fractions containing the desired product mixture were evaporated to yield m=4.87 g and m=10.89 g of crude material that was repurified on a Interchim (120 g, HC-15 μm, SiO$_2$) column using the same method as above (flowrate of 50 ml/min) to yield m=1.45 g of desired product mixture and m=7.69 g of crude material. Additional chromatography yielded batches of m=1.38 g, m=0.87 g and m=0.26 g of desired compound. All product batches combined and further dried to yield 8.2 g of product mixture.

Step 4. SFC Chiral

System DETAILS
  Column Details Lux C4 (21.2 mm×250 mm, 5 um)
  Column Temperature 40° C.
  Flow Rate 50 mL/min
  Detector Wavelength 215 nm
  Injection Volume 1500 uL (62 mg) in ethanol
  Isocratic Conditions 35:65 EtOH:$CO_2$ (0.1% v/v $NH_3$)
  Combined product fractions were concentrated, transferred to final vessels with DCM, further dried under nitrogen at 40° C. and then under vacuum for 16 hour at 40° C. to give IVa Isomer 1 3.7 g (enantiomeric excess 100%) and IVb Isomer 2 3.6 g (enantiomeric excess 98.6%)

Step 5. Synthesis of Tert-butyl N-[1-(2-hydroxy-ethyl)-6-methyl-2-oxo-5-phenyl-3-piperidyl]carbamate (V)

To a solution of IVa (1.0 g, 2.561 mmol) in dry MeOH (10.0 mL) cooled at 0° C., $NaBH_4$ (387.6 mg, 10.244 mmol) was added. The reaction mixture was stirred at room temperature for 90 minutes. Added new amount of $NaBH_4$ (193.8 mg, 5.122 mmol) and stirring was continued at 45° C. After 2 hours a new amount of $NaBH_4$ (193.8 mg, 5.122 mmol) was added and stirring at 45° C. continued. After 2 hours new amount of $NaBH_4$ (193.8 mg, 5.122 mmol) was added and stirring was continued at room temperature for 15 hours. To the reaction mixture sat. $NH_4Cl$ (50 mL) and DCM (25 mL) were added, the layers separated, and the aqueous layer extracted with DCM (2×25 mL). The combined organic layers were dried over $Na_2SO_4$ and concentrated under reduced pressure to afford the raw product (986.5 mg). The crude material was loaded and purified on a silica column (Interchim 25 g, 15 μm, $SiO_2$) using Interchim PuriFlash 450 instrument with a flowrate of 20 mL/min starting with DCM (100%) and going to 100% [DCM/MeOH (20:1)] in 20 CVs. Hold 100% for 10 CVs. The appropriate fractions were collected, the solvent removed to yield the desired product V (821.2 mg, 92.0%).
  LC-MS (ES+): 349.2 [M+H]$^+$.

Step 7. Synthesis of Tert-butyl N-[6-methyl-2-oxo-5-phenyl-1-[2-(3-tetrahydropyran-2-yloxypropoxy)ethyl]-3-piperidyl]carbamate (VI)

To a solution of V (700.0 mg, 2.009 mmol) and 2-(3-bromopropoxy)tetrahydropyran (458.1 μL, 2.566 mmol) in toluene (1.75 mL), NaOH (40% in water, 1.75 mL) and tetrabutylammonium hydrogensulfate (695.9 mg, 2.009 mmol) was added and the resultant reaction mixture was stirred at 43° C. for 3 hours. Added new amount of 2-(3-bromopropoxy)tetrahydropyran (229.1 μL, 1.284 mmol) and tetrabutylammonium hydrogensulfate (348.0 mg, 1.005 mmol) and stirring at 43° C. was continued. After 17 hours, new amount of 2-(3-bromopropoxy)tetrahydropyran (117.5 μL, 0.658 mmol) and tetrabutylammonium hydrogensulfate (178.9 mg, 0.517 mmol) was added and stirring at 43° C. was continued for 4 hours. The reaction mixture was diluted with water (30 mL) and extracted with EtOAc (3×20 mL). The combined organic layers were washed with sat. $NH_4Cl$ (2×15 mL) aq. and brine (25 mL), dried over $Na_2SO_4$ and concentrated under reduced pressure to afford the crude product (1.27 g). The crude material was loaded and purified on a silica column (Interchim 25 g, 15 μm, $SiO_2$) using Interchim PuriFlash 450 instrument with a flowrate of 20 mL/min starting with DCM (100%) and going to 70% [DCM/MeOH (20:1)] in 20 CVs. Hold 70% for 10 CVs. The clean fractions were collected, and the mixed fractions purified again. This process was repeated five times to give compound VI (598.8 mg, 60.1%).
  LC-MS (ES+): 491.1 [M+H]$^+$.

Step 8. Synthesis of Tert-butyl N-[1-[2-(3-hydroxy-propoxy)ethyl]-6-methyl-2-oxo-5-phenyl-3-piperidyl]carbamate (F-4)

To a solution of VI (597.2 mg, 1.217 mmol) in dry MeOH (10.7 mL), p-toluenesulfonic acid (11.0 mg, 0.061 mmol) was added. The reaction mixture was stirred at room temperature for 5 hours. The reaction mixture was quenched with a mixture of sat. $NaHCO_3/H_2O$ 1:1 (30 mL), and DCM (30 mL) and stirred for 10 minutes. The layers were separated, and the aqueous layer extracted with DCM (2×25 mL). The combined organic layers were washed with brine (25 mL), dried over $Na_2SO_4$ and concentrated under reduced pressure to afford the raw product (545.0 mg). The crude material was loaded and purified on a silica column (Interchim 25 g, 15 μm, $SiO_2$) using Interchim PuriFlash 450 instrument with a flowrate of 20 mL/min starting with DCM (100%) and going to 100% [DCM/MeOH (20:1)] in 20 CVs. Hold 100% for 10 CVs. The appropriate fractions were collected, the solvent removed to yield the desired product F-4 (412.6 mg, 83.4%).
  LC-MS (ES+): 407.2 [M+H]$^+$.

Scheme 12. Synthesis of Intermediate F-5

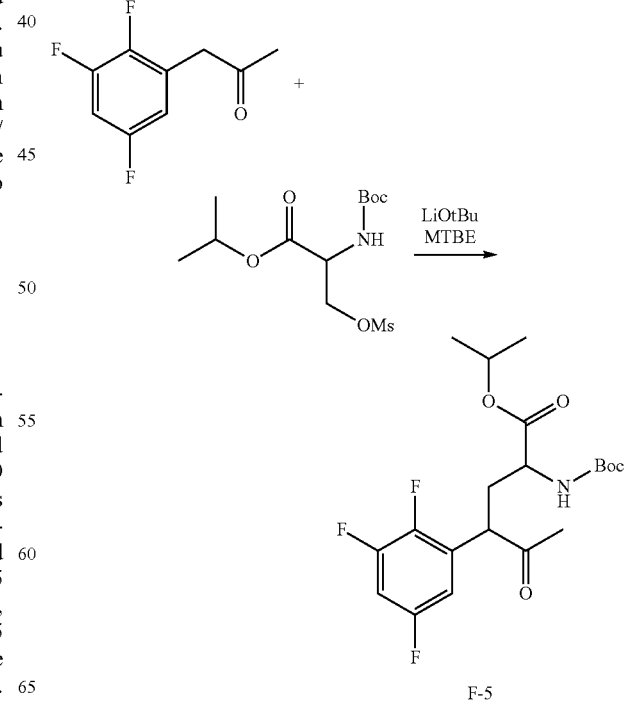

F-5

Experimental Procedure for Synthesis of Isopropyl 2-((Tert-butoxycarbonyl)amino)-5-oxo-4-(2,3,5-trifluorophenyl)hexanoate F-5

To a solution of isopropyl N-(tert-butoxycarbonyl)-O-(methylsulfonyl)serinate (35.9 g, 110.1 mmol) in dry MTBE (258 ml) molecular sieves (4 Å) and 1-(2,3,5-Trifluorophenyl)-2-propanone (CAS 1305323-99-2) (17.8 g, 94.8 mmol) were added and the solution was stirred at room temperature for 30 min. After that the mixture was cooled to 0° C. and lithium tert-butoxide (28.5 g, 355.4 mmol) was added in several portions. The reaction mixture was stirred at room temperature for 20 h. The reaction mixture was filtered through a pad of silica, washed with EtOAc (420 ml) and water (1 L) was added. The layers were separated, and the aqueous layer was extracted with EtOAc (3×315 mL). The combined organic layers were washed with sat. aq. NaHCO$_3$ (3×170 mL) and brine (3×170 mL), dried over anhydrous Na$_2$SO$_4$ and concentrated to yield the crude product which was loaded and purified on a silica column (Interchim, HP columns, 30 µm, SiO$_2$, loading: 0.05) using Interchim Puri-Flash 430 instrument starting with cyclohexane (100%) for 2 CVs and going to 30% [cyclohexane/EtOAc (5:1)] in 10 CVs. Increasing to 70% [cyclohexane/EtOAc (5:1)] in 15 CVs. Hold 70% [cyclohexane/EtOAc (5:1)] for 10 CVs. The appropriate fractions were collected, the solvent removed to yield the desired product F-5 (20.5 g, 51.8%).

LC-MS (ES+): 440.3 [M+Na]$^+$.

Scheme 13. Synthesis of Intermediate F-6

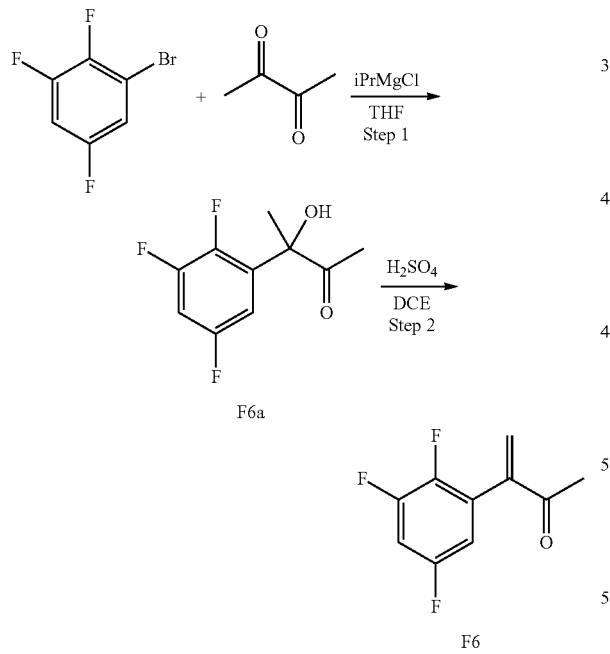

Experimental Procedure for Synthesis of 3-(2,3,5-trifluorophenyl)but-3-en-2-one F6

Step 1 Synthesis of 3-hydroxy-3-(2,3,5-trifluorophenyl)butan-2-one F6a

To a stirred solution of 1-bromo-2,3,5-trifluorobenzene (20.00 g, 95 mmol) in THF (200 mL) was added iPrMgCl-LiCl (1.3 M in THF) (80 mL, 104 mmol) dropwise at −20~−30° C. under nitrogen atmosphere. The mixture was stirred for 1 h at −20° C. under nitrogen atmosphere. The above mixture was added to a solution of diacetyl (9.42 g, 110 mmol) in THF (80 mL) at −20~−30° C. The resulting mixture was stirred for an additional 1.5 h at −10-20° C. The reaction was quenched with sat. NH$_4$Cl (aq.) at 0° C. The resulting mixture was extracted with EtOAc (2×200 mL). The combined organic layers were washed with brine (200 mL), dried over anhydrous Na$_2$SO$_4$. After filtration, the filtrate was concentrated under reduced pressure. This resulted in 3-hydroxy-3-(2,3,5-trifluorophenyl)butan-2-one F6a (20 g, 92 mmol) as a brown oil Step 2 Synthesis of 3-(2,3,5-trifluorophenyl)but-3-en-2-one F6

To a stirred mixture of H$_2$SO$_4$ (67.50 g, 0.7 mol) in DCE (500 mL) was added a solution of 3-hydroxy-3-(2,3,5-trifluorophenyl)butan-2-one F6a (50 g, 229 mmol) in DCE (100 mL) dropwise at 70° C. The resulting mixture was stirred for 0.5 h at 70° C. The mixture was allowed to cool down to 0-10° C. The reaction was quenched with Water/Ice. The resulting mixture was extracted with MTBE (2×300 mL). The combined organic layers were washed with brine (300 mL), dried over anhydrous Na$_2$SO$_4$. After filtration, the filtrate was concentrated under reduced pressure. The residue was purified by silica gel column chromatography, eluted with PE/EtOAc (100:1) to afford 3-(2,3,5-trifluorophenyl)but-3-en-2-one F6 (10.5 g, 53 mmol) as an orange solid.

LCMS (ES, m/z): 201 [M+H]$^+$.

1H NMR (300 MHz, Chloroform-d) δ 6.94 (dddd, J=10.0, 8.1, 6.1, 3.1 Hz, 1H), 6.75 (dddd, J=8.3, 4.7, 3.1, 2.1 Hz, 1H), 6.44 (s, 1H), 6.10 (s, 1H), 2.48 (s, 3H).

Scheme 14. Synthesis of Intermediate F-7

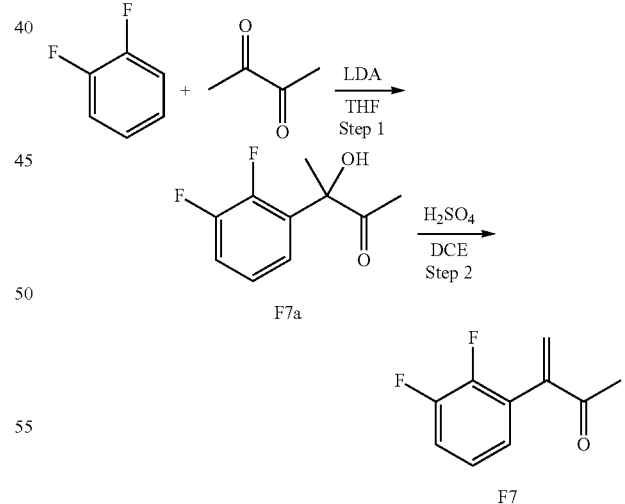

Experimental Procedure for Synthesis of 3-(2,3-difluorophenyl)but-3-en-2-one F-7

Step 1

To a stirred solution of 1,2-difluorobenzene (200 g, 1.75 mol) in THF (1 L) was added 2M LDA in (965.00 mL, 1.93 mol) dropwise at −40~−50° C. under nitrogen atmosphere. The mixture was stirred for 1 h at −30° C. and then added to a solution of diacetyl (173.5 g, 2.02 mol) in THF (1600 mL) at −70° C. The result mixture was stirred for 2 h at −10° C. The reaction was quenched with HOAc (126 g) and $H_2O$ (2 L). The resulting mixture was extracted with MTBE (3×1 L). The combined organic layers were washed with brine (500 mL), dried over anhydrous $Na_2SO_4$. After filtration, the filtrate was concentrated under reduced pressure. The residue was purified by silica gel column chromatography, eluted with PE/EtOAc (10:1) to afford 3-(2,3-difluorophenyl)-3-hydroxybutan-2-one F7a (230 g 1.15 mol) as a brown oil.

Step 2

To a stirred solution of 3-(2,3-difluorophenyl)-3-hydroxybutan-2-one F7a (70 g, 0.35 mol) in DCE (700 mL) was added $H_2SO_4$ (72.1 g, 0.74 mmol) dropwise at 30° C. under nitrogen atmosphere. The resulting mixture was stirred for 1 h at 40° C. under nitrogen atmosphere. The reaction was quenched with water at 0-10° C. DCE was removed under reduced pressure. The resulting mixture was extracted with MTBE (3×500 mL). The combined organic layers were washed with brine (300 mL), dried over anhydrous $Na_2SO_4$. After filtration, the filtrate was concentrated under reduced pressure. The residue was purified by silica gel column chromatography, eluted with PE/EtOAc (100:1) to afford 3-(2,3-difluorophenyl)but-3-en-2-one F-7 (18 g) as a brown oil.

LCMS (ES, m/z): 183 [M+H]$^+$.

$^1$H NMR (300 MHz, Chloroform-d) δ 7.25-6.91 (m, 3H), 6.40 (s, 1H), 6.06 (s, 1H), 2.46 (s, 3H).

Synthesis of Intermediates G1-X

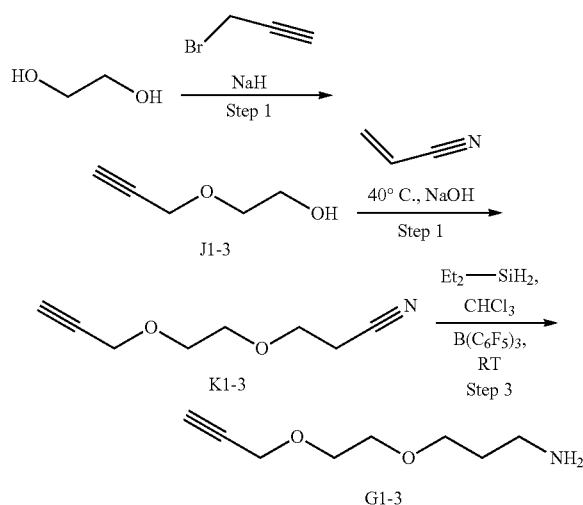

Scheme 15. Synthesis of Intermedate G1-3

Experimental Procedures for Synthesis of Intermediate G1-3

Step 1. Synthesis of 2-prop-2-ynoxyethanol (J1-3)

Into ethylene glycol (44.61 mL, 0.814 mol) a dispersion of NaH (8.13 g, 0.203 mol, 1 equiv., 60% in mineral oil) was carefully added in portions. After all the bubbling stopped, to the white suspension propargyl bromide (21.9 mL, 0.203 mol, 80% in toluene) was added. After the initial bubbling subsided the flask was sealed and the reaction stirred overnight at RT. DCM (20 mL) and water (200 mL) were added. The organic layer was separated and the aqueous layer extracted with with DCM/i-PrOH (1:1, 10×20 mL). The combined organic layers were dried over $Na_2SO_4$, filtered, and concentrated in vacuo to yield the desired product J1-3 (m=19.59 g) as a yellowish liquid. The product was used as is in the next step.

TLC (cyclohexane-EtOAc 1:1): rf=0.23

Step 2. Synthesis of 2-prop-2-ynoxyethanol (K1-3)

Into a flask containing compound J1-3 (18.5 g, 166 mmol) a freshly prepared solution of 2.5 M NaOH in water (1.99 mL) was added, followed by a dropwise addition of acrylonitrile (43.6 mL, 665 mmol), (very carefully so the temp did not exceed 45° C.). The reaction mixture was stirred at 45° C. overnight. Additional 2.5 M NaOH in water (2.0 mL) added and stirring continued at 45° C. over the weekend. Added a new amount of acrylonitrile (10 mL) and continued over the night. The reaction mixture was diluted with sat. $NaHCO_3$/water (1:1, 50 mL) and EtOAc (250 mL). The aqueous layer was separated and the organic layer washed with sat. $NaHCO_3$ (3×50 mL), dried over anhydrous $Na_2SO_4$ and concentrated to yield the crude product (m=27.3 g). The crude material was dry loaded and purified on a silica column (Interchim, 330 g, 50 µm, $SiO_2$) using an Interchim PuriFlash 430 instrument with a flowrate of 127 mL/min starting with cyclohexane (100%). Hold 100% cyclohexane for 2 CVs. Increasing to 60% [cyclohexane/EtOAc (1:1)] in 20 CVs. Hold 60% for 5 CVs. Increasing to 75% [cyclohexane:EtOAc (1:1)] in 10 CVs. Hold 75% for 5 CVs. Fractions containing the desired product were combined, the solvent removed to yield the desired product K1-3 (m=13.29 g, 52%).

TLC (cyclohexane-EtOAc 1:1): rf=0.54

Step 3. Synthesis of 3-(2-prop-2-ynoxyethoxy)propan-1-amine (G1-3)

A solution of tris(pentafluorophenyl)borane (369 mg, 70.56 mmoL) in chloroform (22.5 mL) was bubbled with argon for 5 minutes. To this solution diethylsilane (8.23 mL, 61.74 mmol) was added while bubbling argon through the solution. The reaction mixture was stirred briefly for 5 min after which a solution of compound K1-3 (2.7 g, 17.62 mmol) in dry $CHCl_3$ (5.94 mL) was added. The reaction stirred under argon for 15 minutes. The reaction mixture was concentrated under reduced pressure to afford the crude material (m=7.05 g). The crude product was loaded and purified on a silica column (Interchim 40 g, 15 µm, $SiO_2$) using an Interchim PuriFlash 430 instrument with a flowrate of 27 mL/min starting with DCM (100%) Hold 100% DCM for 2 CVs and increasing to 100% E-system (DCM/MeOH/$NH_4OH$) (90/9/1.5) in 10 CVs. Hold 100% E-system for 15 CVs. The desired fractions were combined, and the solvent removed to yield the desired product G1-3 (m=2.19 g, 79.1%) as a yellow oil.

$^1$H NMR (300 MHz, $CDCl_3$): δ=1.48 (s, 2H), 1.72 (quint, J=6.6 Hz, 2H), 2.40-2.41 (t, J=2.4 Hz, 1H), 2.78 (t, J=6.8 Hz, 2H), 3.53 (t, J=6.3 Hz, 2H), 3.56-3.62 (m, 2H), 3.63-3.70 (m, 2H), 4.18 (d, J=2.3 Hz, 2H) ppm Scheme 16. Synthesis of Intermediate G1-4

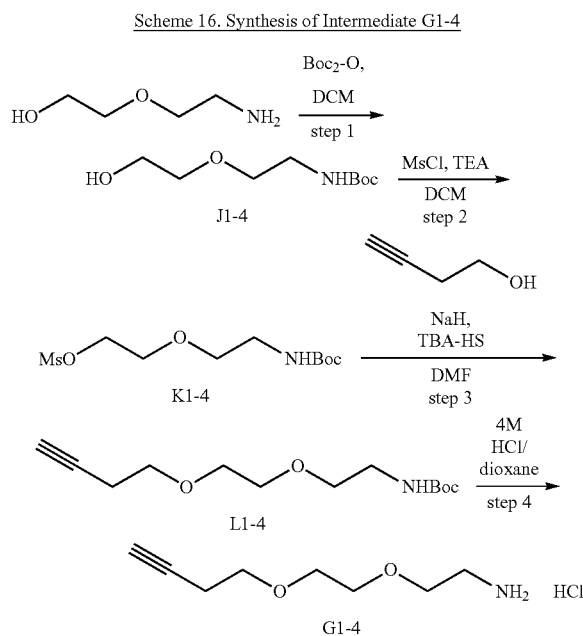

Experimental procedure for Synthesis of 2-(2-but-3-ynoxyethoxy)ethanamine, Hydrochloride (G1-4)

Step 1. Synthesis of Tert-butyl N-[2-(2-hydroxyethoxy)ethyl]carbamate (J1-4)

To a solution of compound 2-(2-aminoethoxy)ethanol (CAS 929-06-6) (5.00 g, 47.6 mmol) in dry DCM (125 mL) cooled at 0° C., Boc$_2$O (12.5 g, 57.1 mmol) was added portion wise. The reaction mixture was stirred at room temperature for 2 hours. The solvent was evaporated to yield the crude material (m=12.0 g). The crude product was loaded and purified on a silica column (Interchim 120 g, 15 µm, SiO$_2$) using an Interchim PuriFlash 430 instrument with a flowrate of 60 mL/min starting with cyclohexane (100%) and going to 100% cyclohexane/EtOAc (1/1) in 25 CVs. Hold 100% cyclohexane/EtOAc (1/1) for 5 CVs. The appropriate fractions were collected, the solvent removed to yield the desired product J1-4 (7.59 g, 78%).

LC-MS (ES+): 206.1 [M+H]$^+$.

Step 2. Synthesis of 2-[2-(tert-butoxycarbonylamino)ethoxy]ethyl Methanesulfonate (K1-4)

To a solution of compound J1-4 (4.10 g, 20.0 mmol) and methanesulfonyl chloride (1.78 mL, 23.0 mmol) in dry DCM (100 mL), triethylamine (3.34 mL, 24.0 mmol) was added slowly under an ice bath. The reaction mixture was stirred at room temperature for 75 minutes. The reaction mixture was quenched with NH$_4$Cl (aq. sat.) (150 mL), the organic layer separated, washed with brine (2×10 mL), dried over anhydrous Na$_2$SO$_4$, and concentrated to yield the desired product K1-4 (m=5.38 g, 95%).

LC-MS (ES+): 284.1 [M+H]$^+$.

Step 3. Synthesis of Tert-butyl N-[2-(2-but-3-ynoxyethoxy)ethyl]carbamate (L1-4)

Into a solution of but-3-yn-1-ol (2.9 mL, 38. mmoL) in dry DMF (60 mL) cooled at 0° C., NaH (840 mg, 21 mmol) was added portion wise. The reaction mixture was stirred at 0° C. for 10 minutes. After that a solution of K1-4 (5.38 g, 19.0 mmol) in dry DMF (5 mL) was added dropwise. The reaction mixture was allowed to warm to room temperature and was stirred for 24 hours. The reaction was cooled to 0° C. and tetrabutylammonium hydrogen sulphate (2.0 mL 55 wt. % in H$_2$O) was added. After 20 minutes NaH (160 mg, 4 mmol) was added in portions and the reaction continued at room temperature overnight. The reaction mixture was quenched with saturated NH$_4$Cl (360 mL) and DCM (50 mL). The layers were separated, and the aq. layer extracted with DCM (2×50 mL). The combined organic layer was concentrated to yield a solution of the crude product L1-4 in DMF.

LC-MS (ES+): 258.1 [M+H]$^+$.

Step 4. Synthesis of 2-(2-but-3-ynoxyethoxy)ethanamine, Hydrochloride (G1-4)

A DMF solution of compound L1-4 (4950 mg, 19.2 mmol—from step before) was cooled in an ice bath. Into this solution a 4 M HCl solution in dioxane (193 mL) was added dropwise over a period of 30 minutes. The reaction was stirred ice cooled for 2 hours, concentrated and the residue treated with n-hexane (4×30 ml) to yield the desired product G1-4 (m=2.86 g) as a HCl salt.

LC-MS (ES+): 158.0 [M+H]$^+$.

Scheme 17. Synthesis of Intermediate G1-6

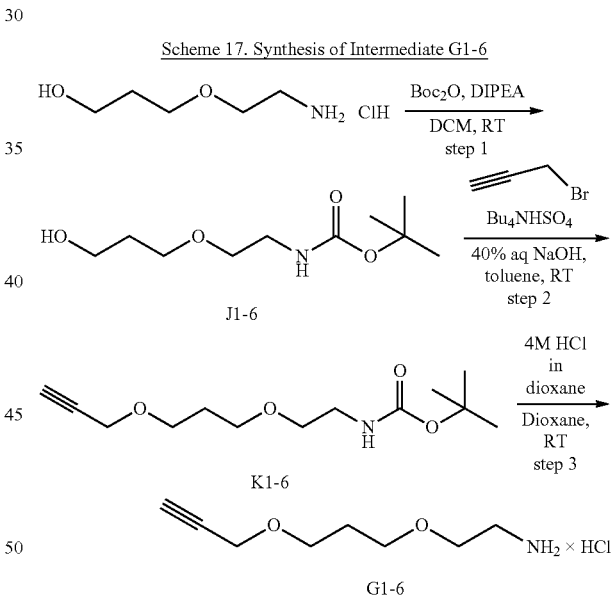

Experimental procedure for Synthesis of 2-(2-but-3-ynoxyethoxy)ethanamine, Hydrochloride (G1-6)

Step 1. Synthesis of Tert-butyl N-[2-(3-hydroxypropoxy)ethyl]carbamate (J1-6)

To a solution of compound 3-(2-aminoethoxy)propan-1-ol hydrochloride (CAS 947664-36-0) (1.0 g, 6.426 mmol) in DCM (11.3 mL), di-tert-butyl dicarbonate (3.09 g, 14.137 mmol) and DIPEA (1.23 mL, 7.068 mmol) were added. The reaction was stirred at room temperature overnight. The reaction mixture was poured into sat. NaHCO$_3$ (50 mL) and extracted with DCM (3×25 mL). The organic layer was washed with 10% citric acid (25 mL), brine (25 mL), dried over anhydrous MgSO$_4$ and concentrated to yield the crude material (2.81 g) as a colorless oil. The crude material was loaded and purified on a silica column (Interchim 40 g, 30 µm, SiO$_2$) using Interchim PuriFlash 450 instrument with a flowrate of 27 mL/min starting with cyclohexane (100%) for 2 CVs and going to 50% ethylacetate in 15 CVs. Hold 50% for 5 CVs. Increasing to 70% in 10 CVs. Hold 70% for 10 CVs. The appropriate fractions were collected, the solvent removed to yield the desired product J1-6 (1.12 g, 79.5%).

$^1$H NMR (300 MHz, CDCl$_3$): δ=1.42 (s, 9H), 1.81 (quint, J=5.7 Hz, 2H), 1.97 (br, 1H), 3.29 (m, 2H), 3.48 (t, J=5.0 Hz, 2H), 3.60 (t, J=5.7 Hz, 2H), 3.74 (t, J=5.6 Hz, 2H), 4.82 (br, 1H) ppm.

Step 2. Synthesis of Tert-butyl N-[2-(3-prop-2-ynoxypropoxy)ethyl]carbamate (K1-6)

To a solution of J1-6 (788.0 mg, 3.594 mmol) and propargyl bromide (445.3 µL, 4.133 mmol) in toluene (3.14 mL), NaOH (40% in water, 3.14 mL) and tetrabutylammonium hydrogensulfate (1.25 g, 3.594 mmol) was added and the resulted reaction mixture was stirred at room temperature for 6 hours. The reaction mixture was diluted with water (100 mL) and extracted with EtOAc (3×25 mL). The combined organic layers were washed with sat. NH$_4$Cl (2×50 mL) and brine (50 mL), dried over Na$_2$SO$_4$ and concentrated under reduced pressure to afford the crude product (842.6 mg). The crude material was loaded and purified on a silica column (Interchim 25 g, 15 µm, SiO$_2$) using Interchim PuriFlash 450 instrument with a flowrate of 20 mL/min starting with cyclohexane (100%) and going to 70% [cyclohexane/EtOAc (1:1)] in 20 CVs. Hold 70% for 10 CVs. The appropriate fractions were collected and the solvent removed to yield the desired product K1-6 (579.0 mg, 62.6%).

LC-MS (ES+): 280.1 [M+Na]$^+$.

$^1$H NMR (300 MHz, CDCl$_3$) δ=1.43 (s, 9H), 1.84 (quint, J=6.4 Hz, 2H), 2.42 (t, J=2.3 Hz, 1H), 3.21-3.35 (m, 2H), 3.46 (t, J=5.2 Hz, 2H), 3.51 (t, J=6.4 Hz, 2H), 3.59 (t, J=6.3 Hz, 2H), 4.13 (d, J=2.4 Hz, 2H), 4.89 (b.s., 1H) ppm.

Step 3. Synthesis of 2-(3-prop-2-ynoxypropoxy)ethanamine Hydrochloride (G1-6)

To the solution of compound K1-6 (747.4 mg, 2.904 mmol) in dioxane (8.22 mL), HCl (4.0 M in dioxane, 29.0 mL, 116.180 mmol) was added. The reaction mixture was stirred at room temperature for 3 hours. The reaction mixture was concentrated to yield the desired product G1-6 (595.0 mg) which was used as is in the next reaction step.

LC-MS (ES+): 407.2 [M+H]$^+$.

Scheme 18. Synthesis of Intermediate G1-7

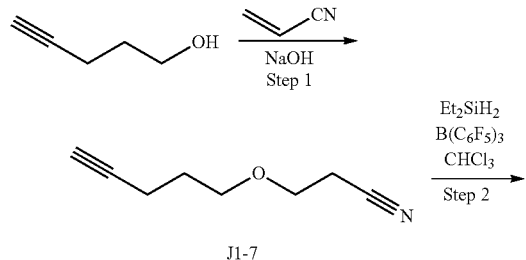

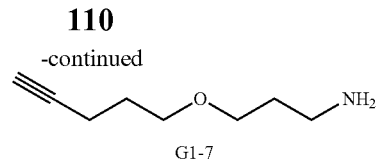

Experimental Procedure for Synthesis of 3-pent-4-ynoxypropan-1-amine (G1-7)

Step 1, Synthesis of 3-pent-4-ynoxypropanenitrile (J1-7)

Into a flask containing pent-4-yn-1-ol (CAS 5390-04-5) (10 g, 119 mmol) a freshly prepared solution of 2.5 N NaOH in water (1.43 mL) was added, followed by a dropwise addition of acrylonitrile (31.1 mL, 476 mmol), (very carefully so the temp did not exceed 45° C.). The reaction mixture was stirred at 45° C. overnight. The reaction mixture was diluted with sat. NaHCO$_3$/water (1:1, 100 mL) and EtOAc (250 mL). The aqueous layer was separated and the organic layer washed with sat. NaHCO$_3$ (3×50 mL), dried over anhydrous Na$_2$SO$_4$ and concentrated to yield the crude product (m=19.68 g) as a pale yellow oil. The crude material was dry loaded and purified on a silica column (Interchim, 330 g, 50 µm, SiO$_2$) using an Interchim PuriFlash 430 instrument with a flowrate of 100 mL/min starting with cyclohexane (100%). Hold 100% cyclohexane for 2 CVs. Increasing to 100% [cyclohexane/EtOAc (5:1)] in 20 CVs. Hold 100% for 5 CVs. Fractions containing the desired product were combined, the solvent removed to yield the desired J1-7 (m=10.42 g, 63.9%) TLC (cyclohexane-EtOAc 1:1): rf=0.5

Step 2, Synthesis of 3-pent-4-ynoxypropan-1-amine (G1-7)

A solution of tris(pentafluorophenyl)borane (427 mg, 0.816 mmoL) in chloroform (18.2 mL) was bubbled with argon for 1 minute. To this solution diethylsilane (8.78 mL, 65.7 mmol) was added followed by the immediate addition of a solution of 3-pent-4-ynoxypropanenitrile J1-7 (2.8 g, 20.4 mmol) in dry CHCl$_3$ (7.4 mL). The reaction was stirred for 30 minutes. The reaction mixture was concentrated under reduced pressure to afford the crude material. The crude product was loaded and purified on a silica column (Interchim 120 g, 15 µm, SiO$_2$)) using an Interchim PuriFlash 430 instrument with a flowrate of 37 mL/min starting with DCM (100%) Hold 100% DCM for 2 CVs and increasing to 100% E-system (DCM/MeOH/NH$_4$OH) (90/9/1.5) in 20 CVs. Hold 100% E-system for 10 CVs. The desired fractions were combined, and the solvent removed to yield the desired G1-7 (m=2.01 g, 70.1%) as a yellow oil.

TLC (DCM/MeOH/NH$_4$OH=90/9/1.5): rf=0.13

Scheme 19. Synthesis of Intermediate G1-8

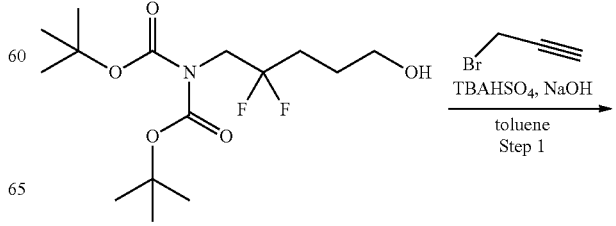

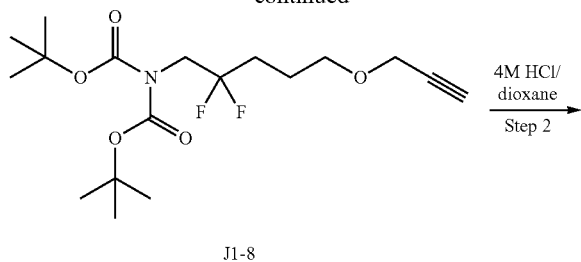

J1-8

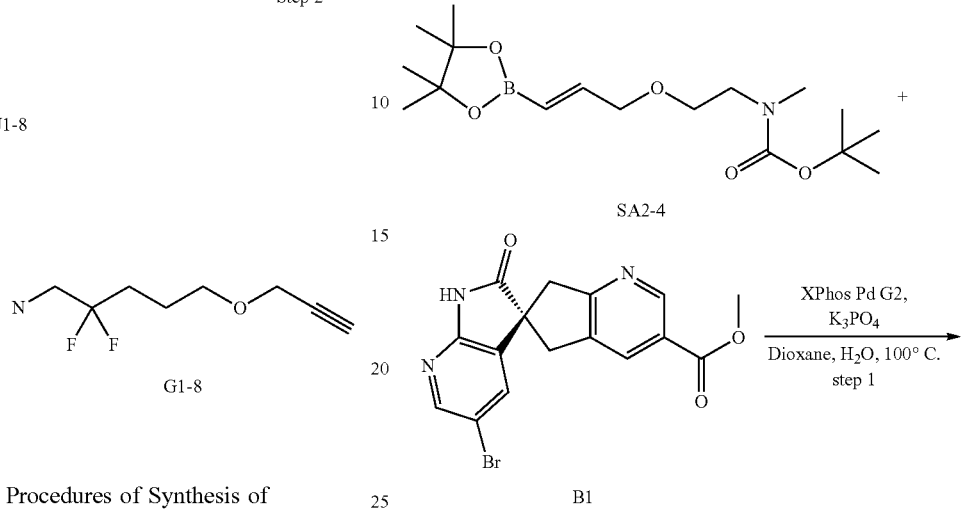

Experimental Procedures of Synthesis of 2,2-difluoro-5-prop-2-ynoxy-pentan-1-amine, G1-8

Step 1. Synthesis of Tert-butyl N-tert-butoxycarbonyl-N-(2,2-difluoro-5-prop-2-ynoxy-pentyl)carbamate (J1-8)

To a solution of compound tert-butyl N-tert-butoxycarbonyl-N-(2,2-difluoro-5-hydroxy-pentyl)carbamate (2.89 g, 8.52 mmol) and propargyl bromide (1.06 mL, 9.79 mmol) in toluene (7.46 mL), NaOH (40% in water, 7.43 mL) and tetrabuthyl ammonium hydrogen sulfate (2.95 g, 8.52 mmol) was added and the reaction mixture was stirred at room temperature over the night. The reaction mixture was diluted with water (200 mL) and extracted with EtOAc (3×50 mL). The combined organic layers were washed with sat. NH$_4$Cl (50 mL) aq. and brine (50 mL), dried over MgSO$_4$ and concentrated under reduced pressure to afford the raw product J1-8 (2.68 g) as a light orange oil.

TLC (cyclohexane-EtOAc 5:1): rf=0.38

Step 2. Synthesis of 2,2-difluoro-5-prop-2-ynoxy-pentan-1-amine (G1-8)

Into a flask, containing compound J1-8 (2.58 g, 6.84 mmol) a 4M HCl in dioxane (68.4 mL, 273 mmol) was added. The reaction was stirred fat RT over the night. The reaction mixture was concentrated and washed with toluene to yield the desired crude product (2.45 g) as a brown oil. The crude product was dry loaded and purified on a silica column (Interchim 40 g, 15 μm, SiO$_2$) using an Interchim PuriFlash 430 instrument with a flowrate of 26 mL/min starting with DCM (100%) Hold 100% DCM for 2 CVs and increasing to 80% E1-system (DCM/MeOH/NH$_4$OH) (90/9/0.5) in 20 CVs. Hold 80% E-system for 10 CVs. The desired fractions were combined, and the solvent removed to yield the desired product G1-8 (m=726 mg, 68%) as a yellow oil.

LC-MS (ES+): 178.0 [M+H]$^+$.

Final Examples with Different Synthetic Pathway than General Scheme 2

Scheme 20. Synthesis of Example 2-4

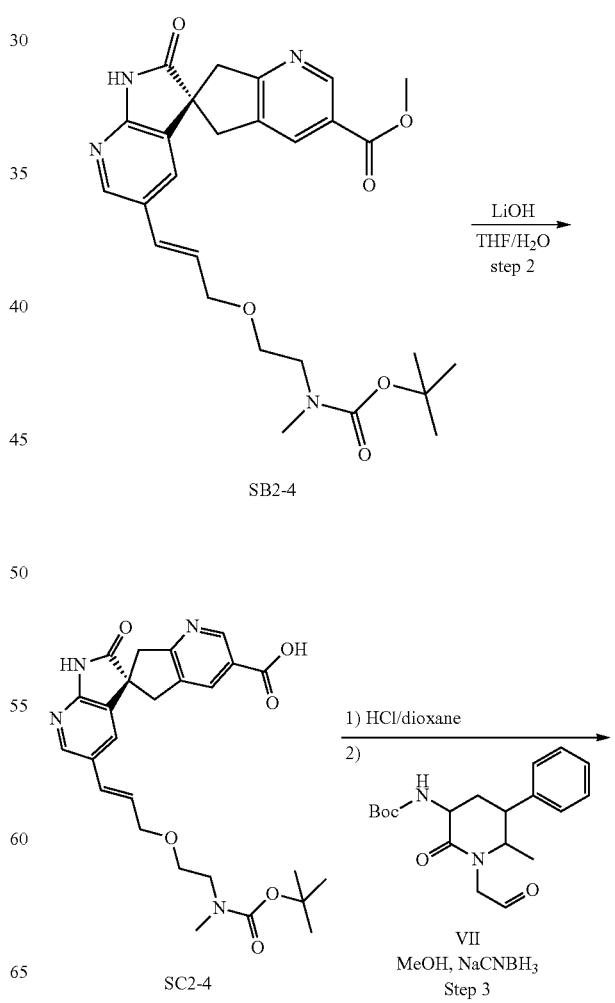

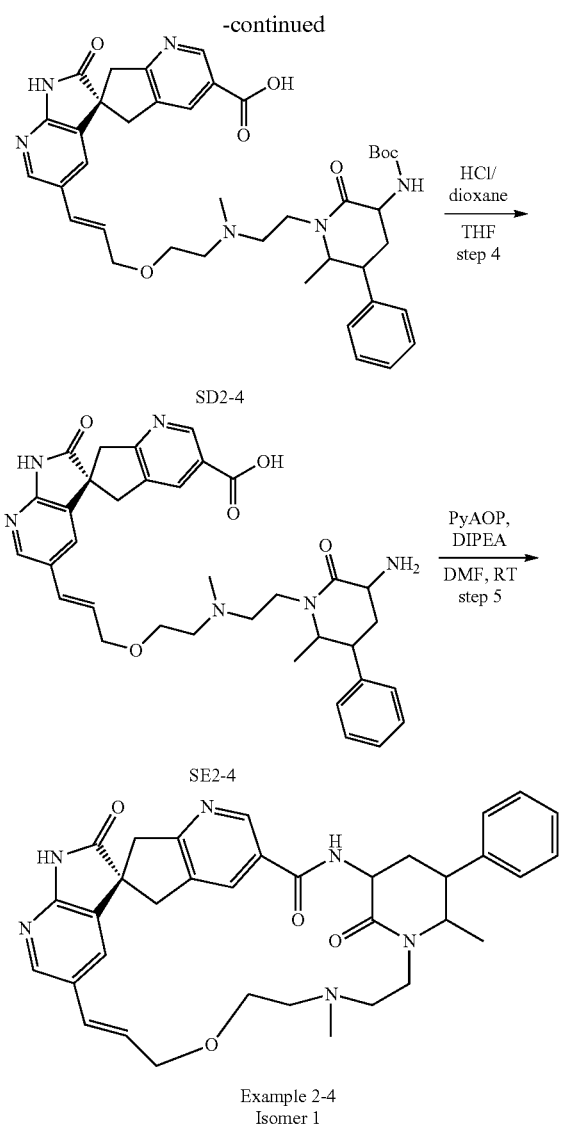

Example 2-4
Isomer 1

Experimental Procedures of Synthesis of Example 2-4

Step 1. Synthesis of Methyl (3S)-5-[(E)-3-[2-[tert-butoxycarbonyl(methyl)amino]ethoxy]prop-1-enyl]-2-oxo-spiro[1H-pyrrolo[2,3-b]pyridine-3,6'-5,7-dihydrocyclopenta[b]pyridine]-3'-carboxylate (SB2-4)

Synthesized using the same experimental procedures as described for synthesis of the Intermediate C1-1, starting from B-1 (300 mg, 0.8 mmol) and compound SA2-4 (410 mg, 1.2 mmol). The desired product was obtained SB2-4 (160 mg, 40%).

LC-MS (ESI+): 509.7 [M+H]$^+$.

Step 2. Synthesis of (3S)-5-[(E)-3-[2-[tert-butoxycarbonyl(methyl)amino]ethoxy]prop-1-enyl]-2-oxo-spiro[1H-pyrrolo[2,3-b]pyridine-3,6'-5,7-dihydrocyclopenta[b]pyridine]-3'-carboxylic Acid (SC2-4)

Methyl (3S)-5-[(E)-3-[2-[tert-butoxycarbonyl(methyl)amino]ethoxy]prop-1-enyl]-2-oxo-spiro[1H-pyrrolo[2,3-b]pyridine-3,6'-5,7-dihydrocyclopenta[b]pyridine]-3'-carboxylate (SB2-4) (110 mg, 0.22 mmol) was dissolved in THF/water (4/1 mL) and LiOH (16 mg, 0.66 mmol) was added. reaction mixture was stirred at room temperature and occasionally checked by UPLC until full conversion to product (3 hours). The reaction mixture was concentrated water was added (3 mL) and acidified to pH 4 by dropwise addition of HCl (aq, 0.2M). Product was extracted with DCM/iPrOH=2/1, organics collected dried and concentrated to give crude (3S)-5-[(E)-3-[2-[tert-butoxycarbonyl(methyl)amino]ethoxy]prop-1-enyl]-2-oxo-spiro[1H-pyrrolo[2,3-b]pyridine-3,6'-5,7-dihydrocyclopenta[b]pyridine]-3'-carboxylic acid, SC2-4 (84 mg, 78%). It was used in next step as is.

LC-MS (ESI+): 495.3 [M+H]$^+$.

Step 3. Synthesis of (3S)-5-[(E)-3-[2-[2-[5-(tert-butoxycarbonylamino)-2-methyl-6-oxo-3-phenyl-1-piperidyl]ethyl-methyl-amino]ethoxy]prop-1-enyl]-2-oxo-spiro[1H-pyrrolo[2,3-b]pyridine-3,6'-5,7-dihydrocyclopenta[b]pyridine]-3'-carboxylic Acid (SD2-4)

SC2-4 (84 mg, 0.17 mmol) was dissolved in THF (5 mL) the reaction mixture was cooled down to 0° C., then HCl in dioxane (5 mL, 4M) was added. The reaction mixture was stirred at rt until full consumption of starting material. The reaction mixture was concentrated, then suspended in MeOH (4 mL) and DIPEA (119 µL, 0.68 mmol) was added followed by VII (117 mg, 0.34 mmol) dissolved in DCM (4 mL), acetic acid (19 µL, 0.34 mmol) and NaCNBH$_3$ (16 mg, 0.255 mmol). The reaction mixture was stirred at rt for 2 hours then was added additional amount of NaCNBH$_3$ (16 mg, 0.255 mmol) and the reaction mixture was stirred for an additional 30 minutes. The reaction mixture was concentrated and redissolved in sat. NH$_4$Cl and DCM, layers were separated, aqueous layer was extracted with DCM (2*5 mL), organics collected, dried and concentrated to give crude product. Crude product was purified by column chromatography (normal phase [Biotage, Interchim cartridge 12 g, 25 um, 0% 3 CV, 0-100%, 20 CV DCM/MeOH/HCOOH=9/1/0.01 in DCM and then DCM/MeOH/AcOH=9/1/1 6 CV, 10 mL/min flow rate]) to give (3S)-5-[(E)-3-[2-[2-[5-(tert-butoxycarbonylamino)-2-methyl-6-oxo-3-phenyl-1-piperidyl]ethyl-methyl-amino]ethoxy]prop-1-enyl]-2-oxo-spiro[1H-pyrrolo[2,3-b]pyridine-3,6'-5,7-dihydrocyclopenta[b]pyridine]-3'-carboxylic acid, SD2-4 (180 mg, >100%, theoretically 123 mg). It was used in next step as is.

LC-MS (ESI+): 725.5 [M+H]$^+$.

Step 4. Synthesis of (3S)-5-[(E)-3-[2-[2-(6-amino-2-methyl-3-phenyl-1-piperidyl)ethyl-methyl-amino]ethoxy]prop-1-enyl]-2-oxo-spiro[1H-pyrrolo[2,3-b]pyridine-3,6'-5,7-dihydrocyclopenta[b]pyridine]-3'-carboxylic Acid; Tetrahydrochloride (SE2-4)

SD2-4 (180 mg, theor. 123 mg, 0.17 mmol) was dissolved in THF (4 mL) the reaction mixture was cooled down to 0° C. and HCl in dioxane (2 mL, 4M) was added. The reaction mixture was stirred at room temperature overnight. The reaction mixture was concentrated to give crude (3S)-5-[(E)-3-[2-[2-(5-amino-2-methyl-6-oxo-3-phenyl-1-piperidyl)ethyl-methyl-amino]ethoxy]prop-1-enyl]-2-oxo-spiro[1H-pyrrolo[2,3-b]pyridine-3,6'-5,7-dihydrocyclopenta[b]pyridine]-3'-carboxylic acid; tetrahydrochloride, SE2-4 (180 mg, theoretical yield 131 mg, 100%). It was used in next step as is

LC-MS (ESI+): 625.4 [M+H]$^+$. .

Step 5. Synthesis of (1S,22E)-13,17-dimethyl-12-phenyl-20-oxa-5,9,14,17,26,28-hexazahexacyclo[22.5.2.1¹,⁴.1³,⁷.1¹⁰,¹⁴.0²⁷,³⁰]tetratriaconta-3,5,7(33),22,24(31),25,27(30)-heptaene-8,29,32-trione, Example 2-4, Isomer 1

To a solution of PyAOP (134 mg, 0.255 mmol) and DIPEA (0.059 mL, 0.34 mmol) in DMF (30 mL) was added dropwise solution of 5-[(E)-3-[2-[2-(5-amino-2-methyl-6-oxo-3-phenyl-1-piperidyl)ethyl-methyl-amino]ethoxy]prop-1-enyl]-2-oxo-spiro[1H-pyrrolo[2,3-b]pyridine-3,6'-5,7-dihydrocyclopenta[b]pyridine]-3'-carboxylic acid; tetrahydrochloride, SE2-4 (180, theoretical yield 131 mg, 0.17 mmol) and DIPEA (0.118 mL, 0.68 mmol) in DMF (15 mL) over 20 minutes. The reaction mixture was stirred for 20 minutes then quenched with water (200 mL) and DCM (150 mL), layers were separated, aq. layer was extracted with DCM (3×60 mL), organics collected washed with aq. sat. NaHCO₃, dried and concentrated affording crude. Crude was purified by column chromatography (normal phase [Biotage, Interchim cartridge 12 g, 25 μm, 0-50%, 10 CV, 50-100% 20 CV, 100% 3 CV, DCM/MeOH/NH₄OH=90/10/1 in DCM, 10 mL/min flow rate]) to give Example 2-4, Isomer 1 (35 mg, 34%).

LC-MS (ESI+): 607.4 [M+H]⁺, $R_t$=4.52 min (Method 1)

¹H NMR (500 MHz, DMSO-d₆): δ ppm 0.92 (d, J=6.4 Hz, 3H), 2.09-2.17 (m, 1H), 2.25 (br. s., 3H), 2.54-2.61 (m, 1H), 3.01 (d, J=15.9 Hz, 1H), 3.15 (d, J=15.6 Hz, 1H), 3.44-3.53 (m, 3H), 3.56 (d, J=13.4 Hz, 1H), 3.65 (d, J=15.9 Hz, 1H), 3.71-3.76 (m, 1H), 3.93-4.03 (m, 2H), 4.57-4.69 (m, 1H), 5.62-5.72 (m, 1H), 6.41 (d, J=15.9 Hz, 1H), 6.47 (s, 1H), 7.23-7.30 (m, 3H), 7.33-7.41 (m, 2H), 8.01 (d, J=2.1 Hz, 1H), 8.15 (s, 1H), 8.73 (d, J=7.6 Hz, 1H), 8.88 (s, 1H), 11.40 (br. s., 1H) ppm.

¹³C NMR (126 MHz, DMSO-d₆): δ ppm 14.5, 26.4, 39.8, 41.2, 42.9, 43.7, 50.4, 54.1, 59.4, 68.8, 71.4, 122.8, 125.3, 126.0, 126.6, 127.5, 127.6, 128.3, 129.1, 129.8, 131.4, 134.9, 141.1, 146.9, 155.5, 165.1, 178.1.

Scheme 21. Synthesis of Intermediate SA2-4

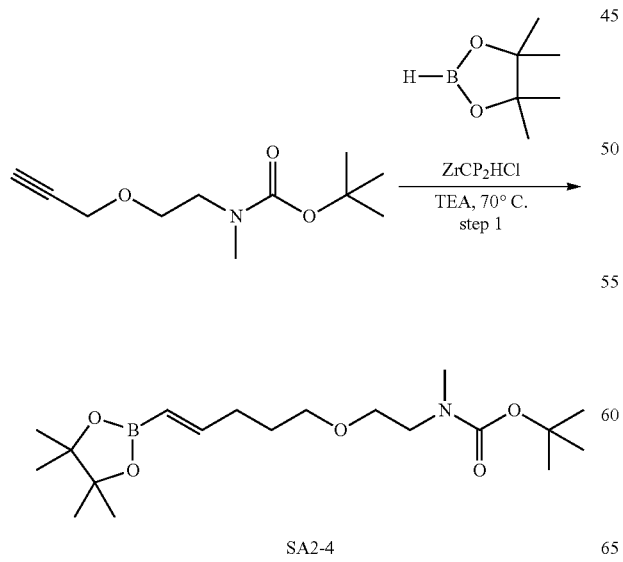

Experimental Procedures for Synthesis of Intermediate SA2-4

Synthesis of Tert-butyl N-methyl-N-[2-[(E)-3-(4,4,5,5-tetramethyl-1,3,2-dioxaborolan-2-yl)allyloxy]ethyl]carbamate (SA2-4)

Synthesized using the same experimental procedures as described in the synthesis of Intermediate A1-1*, starting from tert-butyl N-methyl-N-(2-prop-2-ynoxyethyl)carbamate (300 mg, 1.4 mmol). The desired product SA2-4 was obtained (430 mg) and used as is in the next reaction step.

LC-MS (ESI+): 242.7 [M+H-Boc]⁺

Scheme 22. Synthesis of Intermediate VII

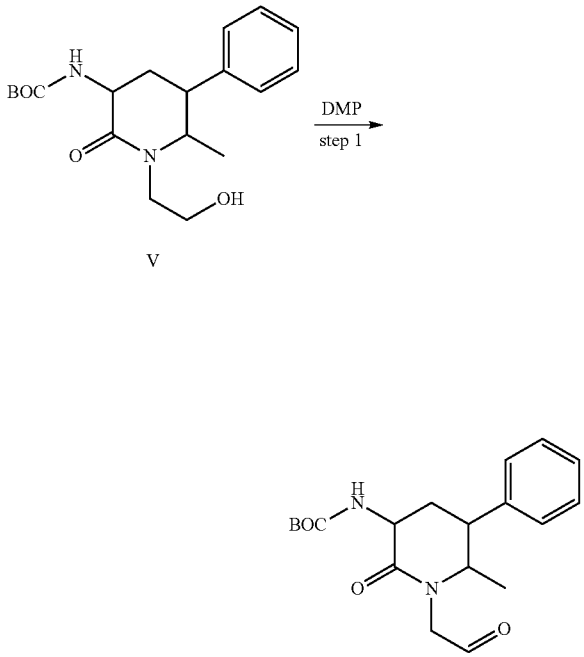

Experimental Procedures of Synthesis of Intermediate VII

Synthesis of Tert-butyl N-[6-methyl-2-oxo-1-(2-oxoethyl)-5-phenyl-3-piperidyl]carbamate (VII)

V (118 mg, 0.34 mmol) was dissolved in DCM (4 mL), the reaction mixture was cooled to 0° C. Dess Martin periodinane (216 mg, 0.51 mmol) was added and the reaction mixture was stirred at rt for 2 hours. Reaction was quenched by addition of sat. NaHCO₃/Na₂S₂O₃ (4/4 mL) mixture. Mixture was passed through the phase separator and product tert-butyl N-[6-methyl-2-oxo-1-(2-oxoethyl)-5-phenyl-3-piperidyl]carbamate (VII) was used as solution in DCM (theoretically 117 mg, 100%).

LC-MS (ESI+): 347.2 [M+H]⁺.

Scheme 23. Synthesis of Example 2-5, Isomer 1

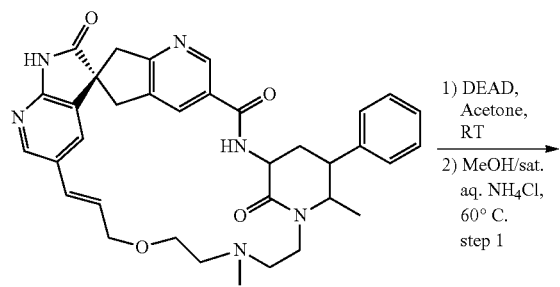

Example 2-4
Isomer 1

1) DEAD, Acetone, RT
2) MeOH/sat. aq. NH₄Cl, 60° C.
step 1

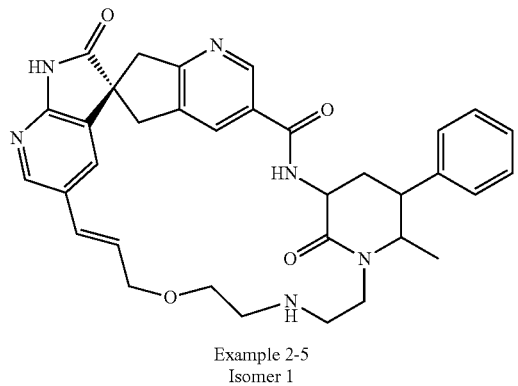

Example 2-5
Isomer 1

Experimental Procedures of Synthesis of Example 2-5

Step 1. Synthesis of (1S,22E)-13-methyl-12-phenyl-20-oxa-5,9,14,17,26,28-hexazahexacyclo[22.5.2.11,4.13,7.110,14.027,30]tetratriaconta-3,5,7(33),22,24(31),25,27(30)-heptaene-8,29,32-trione, Example 2-5, Isomer 1

Example 2-4, Isomer 1 (10 mg, 0.017 mmol) was dissolved in acetone (1 mL) and DEAD (40% in toluene, 23 μL, 0.050 mmol) was added slowly, the reaction mixture was stirred at rt overnight. The reaction mixture was concentrated and redissolved in MeOH/sat. aq. NH₄Cl (1/1 mL). The reaction mixture was heated at 60° C. for 1 hour. The reaction mixture was diluted with DCM, layers were separated, aq. layer was extracted with DCM (3×4 mL) organics collected, washed with aq. sat. NaHCO₃, dried and concentrated to give crude. Crude was purified by column chromatography (normal phase [Biotage, Interchim cartridge 4 g, 25 μm, 0-100%, 10 CV, 100% 20 CV, DCM/MeOH/NH₄OH=90/10/1 in DCM, 6 mL/min flow rate, to give Example 2-5, Isomer 1 (3.3 mg, 33%).

LC-MS (ESI+): 593.3 [M+H]⁺, $R_t$=4.25 min (Method 1)
¹H NMR (500 MHz, DMSO-d₆) δ ppm 0.89 (d, J=6.4 Hz, 3H), 2.11 (dd, J=11.0, 7.3 Hz, 1H), 2.51-2.60 (m, 1H), 2.66-2.79 (m, 2H), 2.97-3.11 (m, 2H), 3.12-3.19 (m, 1H), 3.26-3.31 (m, 1H), 3.40 (t, J=4.7 Hz, 2H), 3.47-3.53 (m, 1H), 3.61-3.72 (m, 2H), 3.72-3.76 (m, 2H), 3.84-4.16 (m, 3H), 4.42-5.12 (m, 1H), 5.60 (dt, J=16.2, 6.0 Hz, 1H), 6.39-6.47 (m, 1H), 6.50 (d, J=2.1 Hz, 1H), 7.22-7.33 (m, 1H), 7.33-7.40 (m, 1H), 7.99 (d, J=1.8 Hz, 1H), 8.18 (s, 1H), 8.87 (d, J=9.2 Hz, 1H), 8.92 (s, 1H), 11.40 (br. s., 1H)

Scheme 24. Synthesis of Examples 2-6, Isomer 1

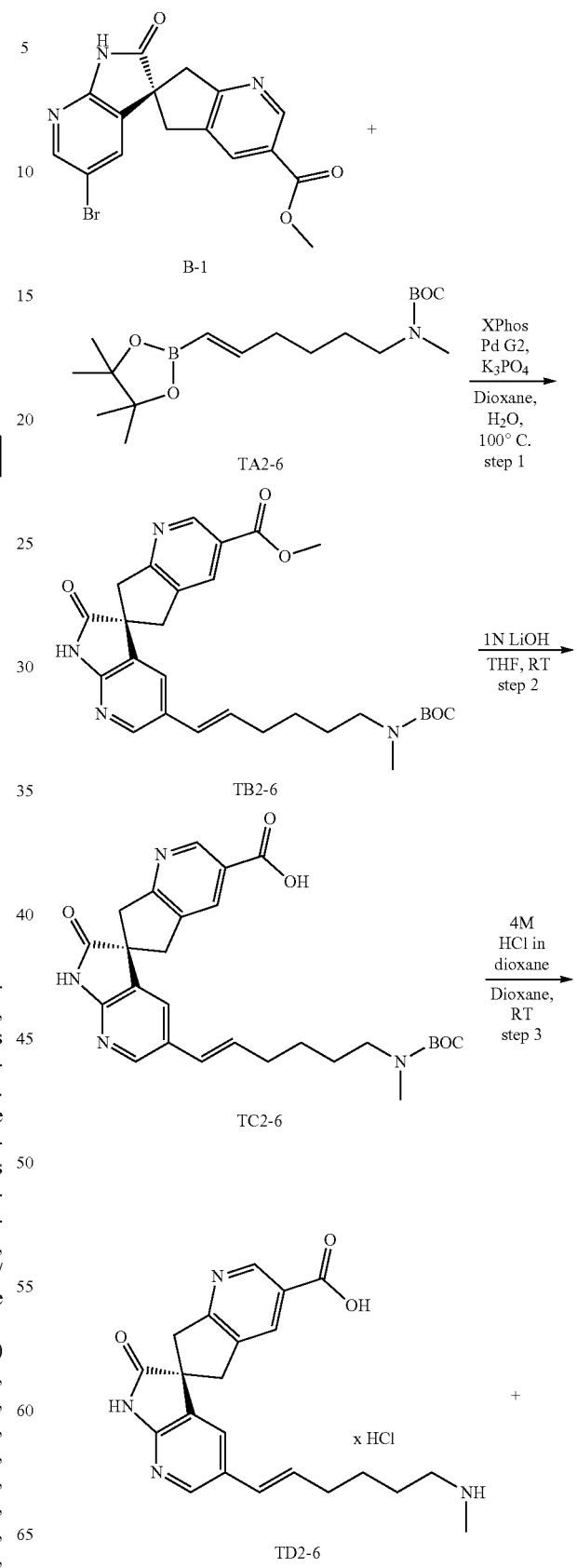

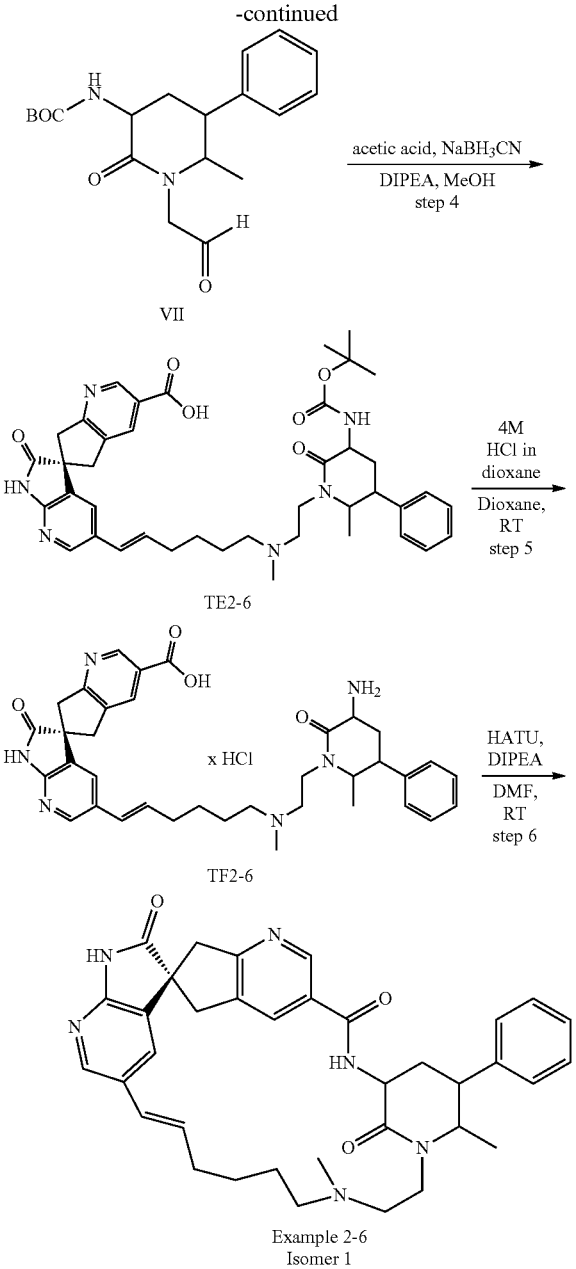

Experimental Procedures of Synthesis of Example 2-6, Isomer 1

Step 1. Synthesis of (3S)-5-[(E)-6-(methylamino)hex-1-enyl]-2-oxo-spiro[1H-pyrrolo[2,3-b]pyridine-3,6'-5,7-dihydrocyclopenta[b]pyridine]-3'-carboxylic Acid; Hydrochloride (TB2-6)

Synthesized using the same experimental procedures as described for synthesis of the Intermediate C1-1, starting from B-1 (600 mg, 1.60 mmol) and compound TA2-6 (841 mg, 2.4 mmol). The desired product was obtained TB2-6 (454 mg, 56%).

LC-MS (ES+): 507.2 [M+H]$^+$.

Step 2. Synthesis of (3S)-5-[(E)-6-[tert-butoxycarbonyl(methyl)amino]hex-1-enyl]-2-oxo-spiro[1H-pyrrolo[2,3-b]pyridine-3,6'-5,7-dihydrocyclopenta[b]pyridine]-3'-carboxylic Acid (TC2-6)

Synthesized using the same experimental procedures as described for synthesis of the Intermediate D1-1, starting from TB2-6 (200 mg, 0.395 mmol). The desired product TC2-6 was obtained (179 mg, 92%) and used as is in the next reaction step.

LC-MS (ES+): 493.2 [M+H]$^+$.

Step 3. Synthesis of (3S)-5-[(E)-6-(methylamino)hex-1-enyl]-2-oxo-spiro[1H-pyrrolo[2,3-b]pyridine-3,6'-5,7-dihydrocyclopenta[b]pyridine]-3'-carboxylic Acid (TD2-6)

Synthesized using the same experimental procedures as described for synthesis of the Intermediate E1-1, starting from TC2-6 (179 mg, 0.248 mmol). The desired fractions were combined, and the solvent removed to yield the desired product TD2-6 (197 mg, 98% yield as 4×HCl salt).

LC-MS (ES+): 393.4 [M+H]$^+$.

Step 4. Synthesis of (3S)-5-[(E)-6-[2-[5-(tert-butoxycarbonylamino)-2-methyl-6-oxo-3-phenyl-1-piperidyl]ethyl-methyl-amino]hex-1-enyl]-2-oxo-spiro[1H-pyrrolo[2,3-b]pyridine-3,6'-5,7-dihydrocyclopenta[b]pyridine]-3'-carboxylic Acid (TE2-6)

To a solution of crude compound TD2-6 (218 mg, 0.301 mmol) in MeOH (6 mL) and DIPEA (0.206 mL, 1.2 mmol), powdered molecular sieves (200 mg) and a solution of compound VII (crude in DCM 6 mL) was added followed by acetic acid (34.4 µL, 0.601 mmol) and NaCNBH$_3$ (28.3 mg, 0.451 mmol). The reaction mixture was stirred at RT for 90 minutes. Added a new amount of NaCNBH$_3$ (13 mg) and continued over the night. The reaction mixture was concentrated and the residue dissolved in sat. NH$_4$CL (20 mL) and DCM (10 mL). The layers were separated, and the aq. layer extracted with DCM/i-PrOH (1/1, 3×10 mL). The combined organic layer was dried and concentrated to yield the crude product (506 mg) as a yellowish solid. The crude material was dry loaded and purified on a silica column (Interchim 12 g, 15 µm, SiO$_2$) using an Interchim PuriFlash 450 instrument with a flowrate of 20 mL/min starting with DCM (100%) and going to 100% of DCM/MeOH/formic acid (10/2/1) in 20 CVs. Hold this 100% for further 20 CVs. The desired fractions were combined and the solvent removed to yield the desired product TE2-6 (179.7 mg, 82% yield).

LC-MS (ES+): 723.5 [M+H]$^+$.

Step 5. Synthesis of (3S)-5-[(E)-6-[2-[5-amino-2-methyl-6-oxo-3-phenyl-1-piperidyl]ethyl-methyl-amino]hex-1-enyl]-2-oxo-spiro[1H-pyrrolo[2,3-b]pyridine-3,6'-5,7-dihydrocyclopenta[b]pyridine]-3'-carboxylic Acid; Hydrochloride (TF2-6)

Synthesized using the same experimental procedures as described for synthesis of the Intermediate E1-1, starting from TE2-6 (179 mg, 0.248 mmol). 197 mg of desired product TF2-6 was obtained and was used in the next reaction step as is.

LC-MS (ES+): 623.4 [M+H]$^+$.

Step 6. Synthesis of (1S,22E)-13,17-dimethyl-12-phenyl-5,9,14,17,26,28-hexazahexacyclo[22.5.2.11,4.13,7.110,14.027,30]tetratriaconta-3,5,7(33),22,24(31),25,27(30)-heptaene-8,29,32-trione (Example 2-6, Isomer 1)

Synthesized using the same experimental procedures as described for synthesis of the Example 1-1 (step 4), starting from TF2-6 (191 mg, 0.248 mmol). The desired product was obtained Example 2-6, Isomer 1 (67 mg, 52%).

LC-MS (ESI+): 605.3 [M+H]$^+$, R$_t$=5.00 min (Method 1)

$^1$H NMR (600 MHz, DMSO-d$_6$) δ ppm 0.95 (d, J=6.2 Hz, 3H), 1.29-1.36 (m, 2H), 1.37-1.44 (m, 1H), 1.49 (br. s., 1H), 2.14 (d, J=6.8 Hz, 2H), 2.31-2.48 (m, 2H), 2.57-2.72 (m, 2H), 3.00 (d, J=16.0 Hz, 1H), 3.07-3.16 (m, 1H), 3.48-3.53 (m, 1H), 3.56-3.63 (m, 1H), 3.68 (br. s., 2H), 3.65 (d, J=16.0 Hz, 1H), 3.78 (br. s., 1H), 4.57 (br. s., 1H), 5.52-5.58 (m, 1H), 6.31 (d, J=15.8 Hz, 1H), 6.43 (br. s., 1H), 7.26-7.32 (m, 3H), 7.35-7.41 (m, 2H), 7.94 (d, J=2.0 Hz, 1H), 8.15-8.19 (m, 1H), 8.86 (br. s., 1H), 8.90 (s, 1H), 11.35 (s, 1H)

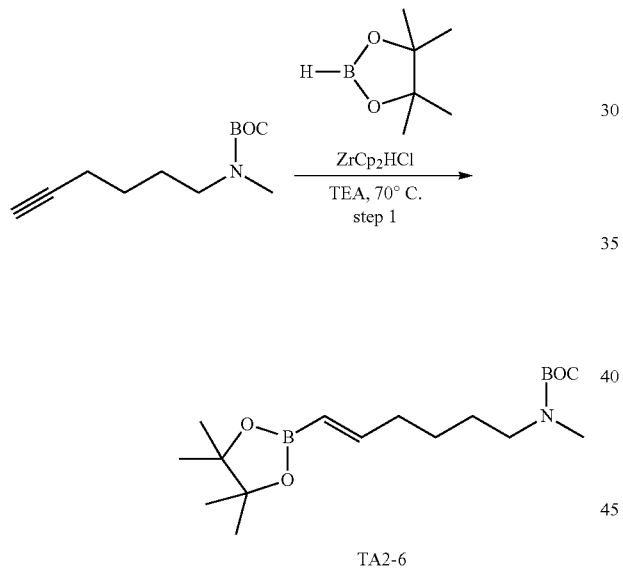

Scheme 25. Synthesis of Intermediate TA2-6

Experimental Procedures of Synthesis of Intermediate TA2-6

Step 1. Synthesis of Tert-butyl N-methyl-N-[(E)-6-(4,4,5,5-tetramethyl-1,3,2-dioxaborolan-2-yl)hex-5-enyl]carbamate (TA2-6)

Synthesized using the same experimental procedures as described in the synthesis of Intermediate A1-1, starting from tert-butyl N-hex-5-ynyl-N-methyl-carbamate (CAS 320367-00-8) (507 mg, 2.40 mmol). The desired product TA2-6 was obtained (776 mg) and used as is in the next reaction step.

TLC (cyclohexane/EtOAc; 5/1); rf=0.30.

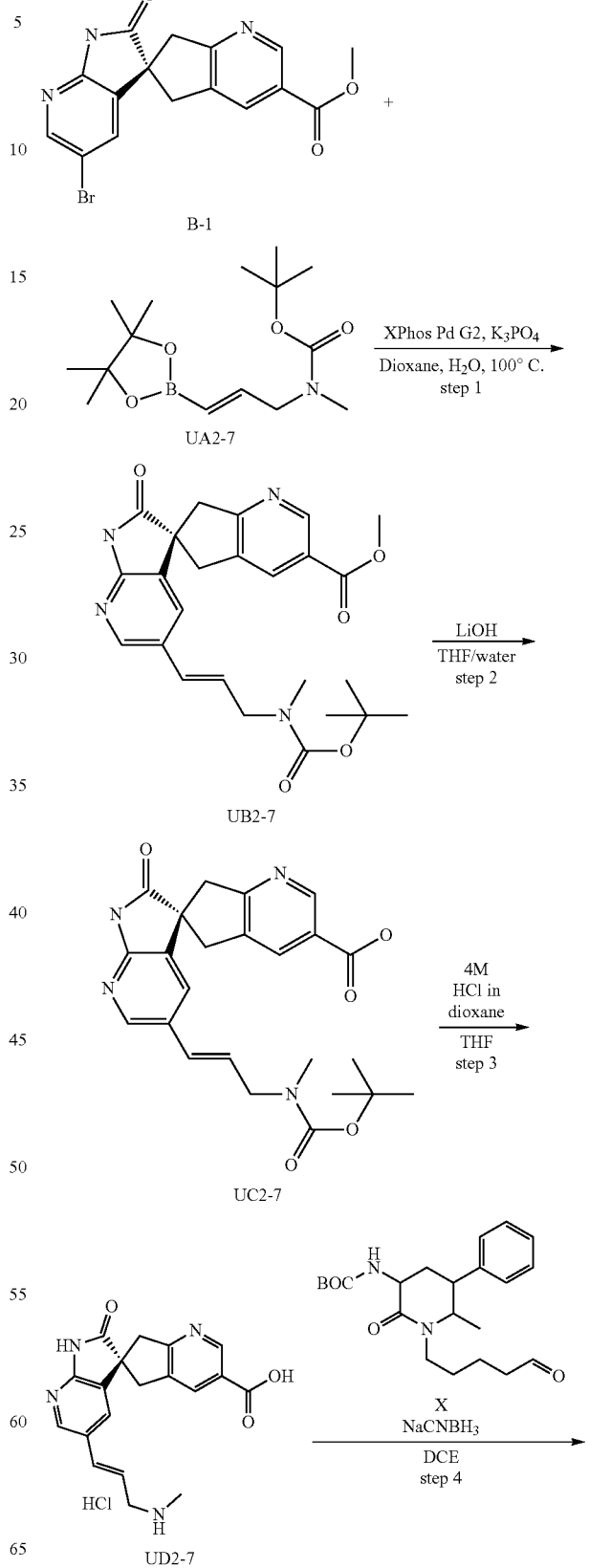

Scheme 26. Synthesis of Examples 2-7, Isomer 1

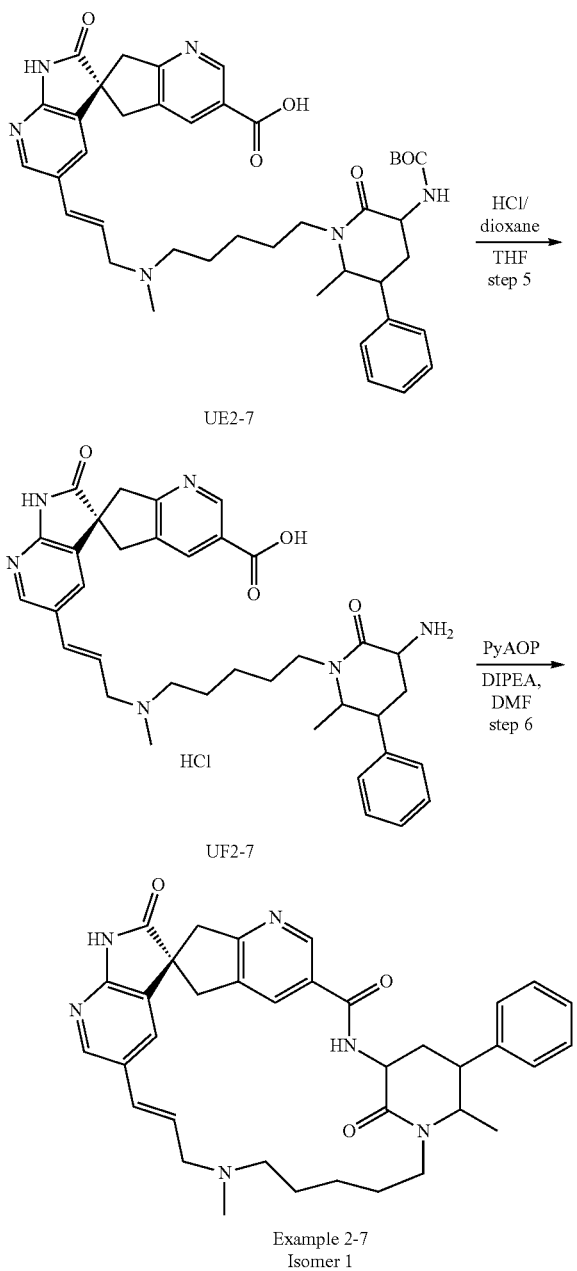 [SMILES: CC1C(c2ccccc2)CC(NC(=O)OC(C)(C)C)C(=O)N1CCCCCN(C)C/C=C/c1cnc2c(c1)[C@@]1(Cc3cc(C(=O)O)cnc3C1)C(=O)N2 ; CC1C(c2ccccc2)CC(N)C(=O)N1CCCCCN(C)C/C=C/c1cnc2c(c1)[C@@]1(Cc3cc(C(=O)O)cnc3C1)C(=O)N2 ; Cl ; CC1C(c2ccccc2)CC2NC(=O)c3cnc4c(c3)C[C@@]3(C4)C(=O)Nc4ncc(cc43)/C=C/CN(C)CCCCCN1C2=O]

UE2-7

UF2-7

Example 2-7
Isomer 1

Experimental Procedures of Synthesis of Example 2-7

Step 1. Synthesis of Methyl (3S)-5-[(E)-3-[tert-butoxycarbonyl(methyl)amino]prop-1-enyl]-2-oxo-spiro[1H-pyrrolo[2,3-b]pyridine-3,6'-5,7-dihydrocyclopenta[b]pyridine]-3'-carboxylate (UB2-7)

Synthesised using the same experimental procedures as described for synthesis of the Intermediate C1-1, starting from B-1 (300 mg, 0.8 mmol) and compound UA2-7 (356 mg, 1.2 mmol). The desired product was obtained UB2-7 (168 mg, 47%).

Step 2. Synthesis of (3S)-5-[(E)-3-[tert-butoxycarbonyl(methyl)amino]prop-1-enyl]-2-oxo-spiro[1H-pyrrolo[2,3-b]pyridine-3,6'-5,7-dihydrocyclopenta[b]pyridine]-3'-carboxylic Acid (UC2-7)

Synthesized using the same experimental procedures as described for synthesis of the Intermediate D1-1, starting from UB2-7 (110 mg, 0.24 mmol). The desired product UC2-7 was obtained (95 mg, 88%) and used as is in the next reaction step.

Step 3. Synthesis of (3S)-5-[(E)-3-(methylamino)prop-1-enyl]-2-oxo-spiro[1H-pyrrolo[2,3-b]pyridine-3,6'-5,7-dihydrocyclopenta[b]pyridine]-3'-carboxylic Acid (UD2-7)

Synthesized using the same experimental procedures as described for synthesis of the Intermediate E1-1, starting from UC2-7 (95 mg, 0.211 mmol). The desired fractions were combined and the solvent removed to yield the desired product UD2-7 (104 mg, 100% yield as 4×HCl salt).

Step 4. Synthesis of (3S)-5-[(E)-3-[5-[5-(tert-butoxycarbonylamino)-2-methyl-6-oxo-3-phenyl-1-piperidyl]pentyl-methyl-amino]prop-1-enyl]-2-oxo-spiro[1H-pyrrolo[2,3-b]pyridine-3,6'-5,7-dihydrocyclopenta[b]pyridine]-3'-carboxylic Acid (UE2-7)

UD2-7 (104 mg, 0.211 mmol) was dissolved in MeOH (4 mL) and DIPEA (147 µL, 0.84 mmol) was added followed by tert-butyl N-[-6-methyl-2-oxo-1-(5-oxopentyl)-5-phenyl-3-piperidyl]carbamate X (122 mg, 0.315 mmol) dissolved in DCM (4 mL), acetic acid (24 µL, 0.42 mmol) and NaCNBH$_3$ (27 mg, 0.42 mmol). The reaction mixture was stirred at rt for 1 hour. It was added additional amount of NaCNBH$_3$ (16 mg) and the reaction mixture was stirred for an additional 30 minutes. The reaction mixture was concentrated and redissolved in sat. NH$_4$Cl and DCM, layers were separated, organics collected, dried and concentrated. Crude was purified by column chromatography (normal phase [Biotage, Interchim cartridge 12 g, 25 µm DCM/MeOH/AcOH=9/2/2 in DCM, 0%, 3 CV, 0-100% 20 CV, 10 mL/min flow rate]) to give 5-[(E)-3-[5-[5-(tert-butoxycarbonylamino)-2-methyl-6-oxo-3-phenyl-1-piperidyl]pentyl-methyl-amino]prop-1-enyl]-2-oxo-spiro[1H-pyrrolo[2,3-b]pyridine-3,6'-5,7-dihydrocyclopenta[b]pyridine]-3'-carboxylic acid UE2-7 (100 mg, 66%). Used as is in the next step.

LC-MS (ESI+): 723.5 [M+H]$^+$.

Step 5. Synthesis of (3S)-5-[(E)-3-[5-(5-amino-2-methyl-6-oxo-3-phenyl-1-piperidyl)pentyl-methyl-amino]prop-1-enyl]-2-oxo-spiro[1H-pyrrolo[2,3-b]pyridine-3,6'-5,7-dihydrocyclopenta[b]pyridine]-3'-carboxylic Acid; Tetrahydrochloride, UF2-7

UE2-7 (100 mg, 0.139 mmol) was dissolved in THF (5 mL) the reaction mixture was cooled down to 0° C. and HCl in dioxane (4 mL, 4M) was added. The reaction mixture was stirred at room temperature 2 hours. The reaction mixture was concentrated to give crude 5-[(E)-3-[5-(5-amino-2-methyl-6-oxo-3-phenyl-1-piperidyl)pentyl-methyl-amino]prop-1-enyl]-2-oxo-spiro[1H-pyrrolo[2,3-b]pyridine-3,6'-5,7-dihydrocyclopenta[b]pyridine]-3'-carboxylic acid; tetrahydrochloride UF2-7 (107 mg, 100%). It was used in next step as is.

Step 6. Synthesis of Example 2-7, Isomer 1

To a solution of PyAOP (109 mg, 0.208 mmol) and DIPEA (0.048 mL, 0.278 mmol) in DMF (27 mL) was added dropwise solution of UF2-7 (107 mg, 0.139 mmol) and DIPEA (0.096 mL, 0.556 mmol) in DMF (12 mL) over 20 minutes. The reaction mixture was stirred for 20 minutes then quenched with water (100 mL) and DCM (60 mL), layers were separated, aq. layer was extracted with DCM (3×30 mL), organics collected washed with aq. sat. NaHCO$_3$, dried and concentrated affording crude. Crude was purified by column chromatography (normal phase [Biotage, Interchim cartridge 12 g, 25 μm, 0-50%, 10 CV, 50-100% 20 CV, 100% 3 CV, DCM/MeOH/NH$_4$OH=90/10/1 in DCM, 10 mL/min flow rate]) to give Example 2-7, Isomer 1 (16 mg, 19%) as a single diastereoisomer.

LC-MS (ESI+): 605.3 [M+H]$^+$, R$_t$=4.25 min (Method 1)

$^1$H NMR (500 MHz, DMSO-d$_6$) δ ppm 0.96 (d, J=6.4 Hz, 3H), 1.21-1.31 (m, 2H), 1.32-1.43 (m, 1H), 1.43-1.53 (m, 2H), 1.55-1.68 (m, 1H), 2.02 (br. s., 3H), 2.08-2.15 (m, 1H), 2.25 (br. s., 2H), 2.64 (q, J=12.7 Hz, 1H), 2.81 (dt, J=13.4, 6.6 Hz, 1H), 2.89 (br. s., 1H), 3.02 (d, J=16.2 Hz, 1H), 3.14 (d, J=11.9 Hz, 1H), 3.18 (d, J=15.9 Hz, 1H), 3.46-3.57 (m, 2H), 3.63 (d, J=16.2 Hz, 1H), 3.66-3.74 (m, 1H), 3.74-3.79 (m, 1H), 4.58-4.65 (m, 1H), 5.54-5.61 (m, 1H), 6.40 (d, J=15.9 Hz, 1H), 6.58 (d, J=1.8 Hz, 1H), 7.21-7.31 (m, 3H), 7.33-7.40 (m, 2H), 7.99 (d, J=1.8 Hz, 1H), 8.13 (s, 1H), 8.76 (d, J=8.9 Hz, 1H), 8.85 (s, 1H), 11.39 (s, 1H)

Scheme 27. Synthesis of Intermediate UA2-7

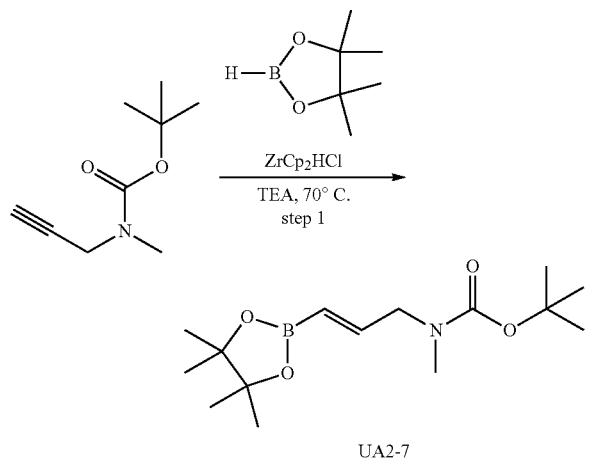

Experimental Procedures of Synthesis of Intermediate UA2-7

Step 1. Synthesis of Tert-butyl N-methyl-N-[(E)-3-(4,4,5,5-tetramethyl-1,3,2-dioxaborolan-2-yl)allyl]carbamate (UA2-7)

Synthesized using the same experimental procedures as described in the synthesis of Intermediate A1-1, starting from tert-butyl N-methyl-N-prop-2-ynyl-carbamate (204 mg, 1.2 mmol). The desired product UA2-7 was obtained (356 mg) and used as is in the next reaction step.

Scheme 28. Synthesis of intermediate X

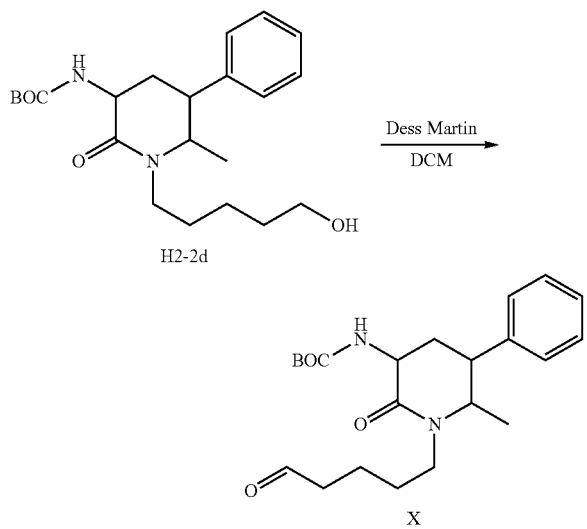

Experimental Procedures of Synthesis of Intermediate X

Synthesis of Tert-butyl (6-methyl-2-oxo-1-(5-oxopentyl)-5-phenyl-3-piperidyl)carbamate, X H2-2d (123 mg, 0.315 mmol) was dissolved in DCM (4 mL), the reaction mixture was cooled to 0° C. Dess Martin periodinane (200 mg, 0.472 mmol) was added and the reaction mixture was stirred at rt for 2 hours. Reaction was quenched by addition of sat. NaHCO$_3$/Na$_2$S$_2$O$_3$ (4/4 mL) aq. mixture. Mixture was passed through the phase separator and product tert-butyl (6-methyl-2-oxo-1-(5-oxopentyl)-5-phenyl-3-piperidyl)carbamate X was used as solution in DCM (theoretically 122 mg, 100%).

LC-MS (ESI+): 389.3 [M+H]$^+$.

Scheme 29. Synthesis of Example 2-8 Isomer 1

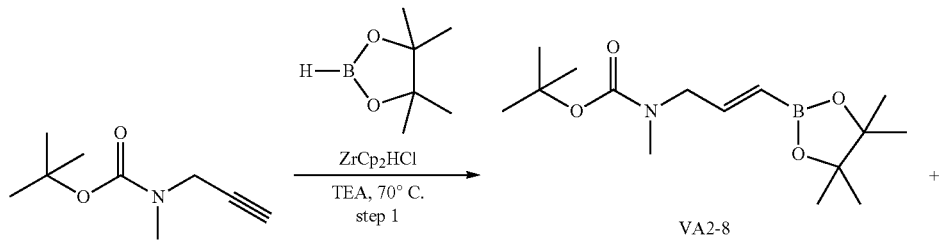

-continued
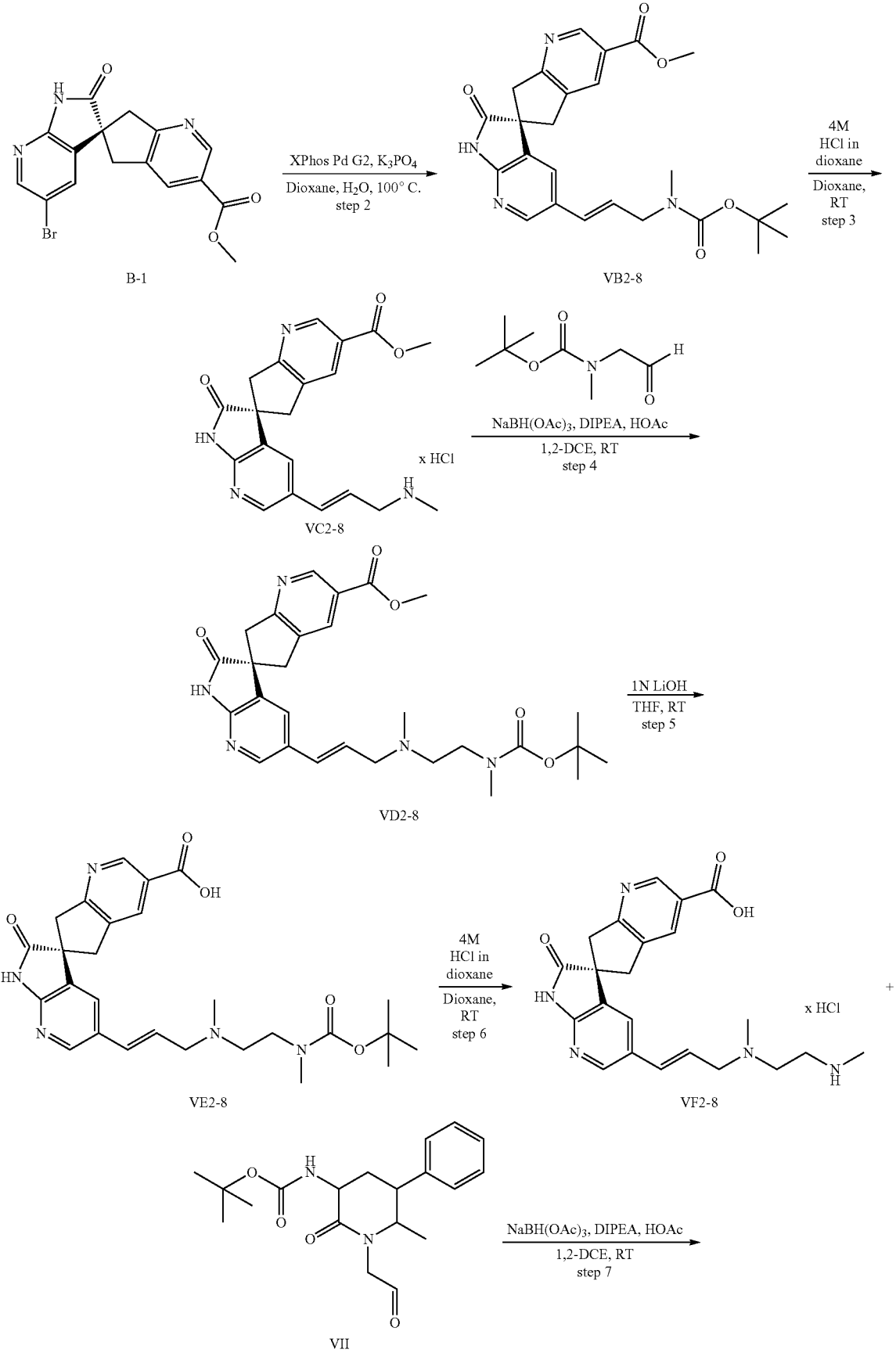

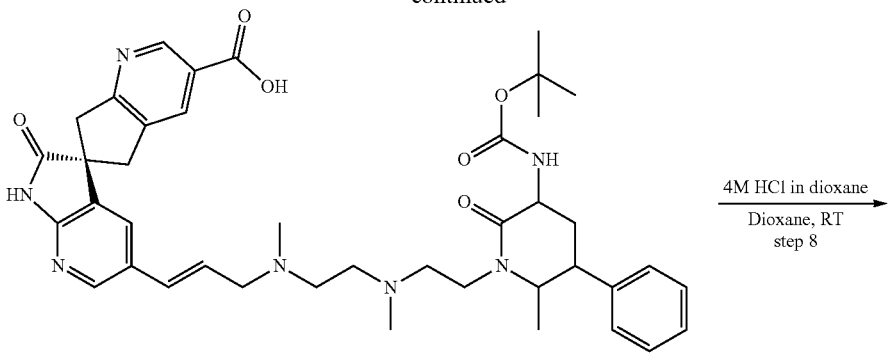

VG2-8

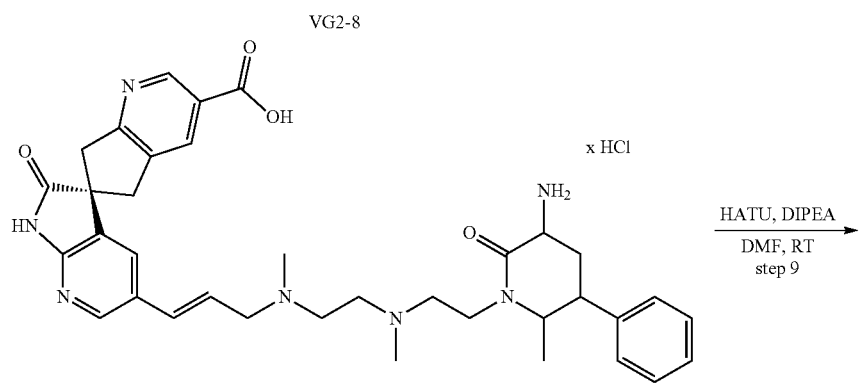

VH2-8

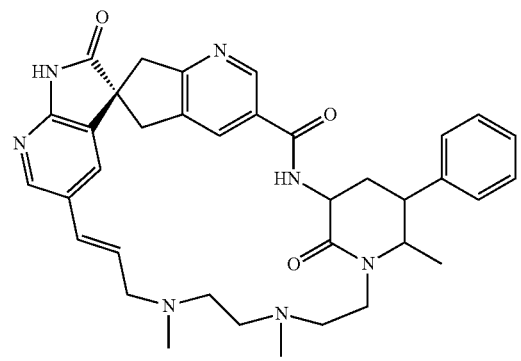

Example 2-8
Isomer 1

Step 1. Synthesis of Tert-butyl N-methyl-N-[(E)-3-(4,4,5,5-tetramethyl-1,3,2-dioxaborolan-2-yl)allyl]carbamate (VA2-8)

Synthesized using the same experimental procedures as described in step 3 of the synthesis of Intermediate A1-1, starting from (Methyl)(2-propyn-1-yl)carbamic acid tert-butyl ester (CAS 124045-51-8) (642.0 mg, 3.794 mmol). The desired product VA2-8 was obtained (776 mg) and used as is in the next reaction step.

LC-MS (ES+): 320.3 [M+Na]+.

Step 2. Synthesis of Methyl (3S)-5-[(E)-3-[tert-butoxycarbonyl(methyl)amino]prop-1-enyl]-2-oxo-spiro[1H-pyrrolo[2,3-b]pyridine-3,6'-5,7-dihydrocyclopenta[b]pyridine]-3'-carboxylate (VB2-8)

Synthesized using the same experimental procedure as described in the synthesis of Intermediate C1-1, starting from compound VA2-8 (800.0 mg, 2.138 mmol) and compound B-1 (1.16 g, 3.574 mmol). The desired product VB2-8 (448.0 mg, 45.1%).

LC-MS (ES+): 465.4 [M+H]+.

Step 3. Synthesis of Methyl (3S)-5-[(E)-3-(methylamino)prop-1-enyl]-2-oxo-spiro[1H-pyrrolo[2,3-b]pyridine-3,6'-5,7-dihydrocyclopenta[b]pyridine]-3'-carboxylate Hydrochloride (VC2-8)

Synthesized using the same experimental procedure as described in the synthesis of Intermediate E1-1, starting from compound VB2-8 (152.4 mg, 0.328 mmol). The desired product VC2-8 (172.6 mg) was obtained and used as is in the next reaction step.

LC-MS (ES+): 365.3 [M+H]+.

Step 4. Synthesis of Methyl (3S)-5-[(E)-3-[2-[tert-butoxycarbonyl(methyl)amino]ethyl-methyl-amino]prop-1-enyl]-2-oxo-spiro[1H-pyrrolo[2,3-b]pyridine-3,6'-5,7-dihydrocyclopenta[b]pyridine]-3'-carboxylate, (VD2-8)

To a suspension of compound VC2-8 (172.6 mg, 0.3281 mmol), DIPEA (233.3 μL, 1.312 mmol) and 4 Å molecular sieves in DCE (8.40 mL) was added a solution of tert-butyl (2-oxoethyl)carbamate (CAS 1189711-08-0) (3.7 mg, 0.656 mmol) in DCE (5.50 mL) followed by acetic acid (75.1 μL, 1.312 mmol) and sodium triacetoxyborohydride (278.2 mg, 1.312 mmol). The resulted mixture was left to stir at RT for 2 hours. The reaction mixture was filtered through pad of Celite pad and washed with DCM (3×10 mL). The filtrate was quenched with sat. NaHCO$_3$ (50 mL), layers were separated, and the aqueous layer additionally extracted with DCM (2×15 mL). The combined organic layers were washed with brine (50 mL), dried over anhydrous Na$_2$SO$_4$, and concentrated under reduced pressure to afford raw product (223.0 mg). The crude product was purified on an Interchim (12 g, 15 μm, SiO$_2$) column and using a flowrate of 20 mL/min starting with DCM (100%) and going to 100% [DCM/MeOH (10:1)] in 15 CVs. Hold 100% for 15 CVs. The appropriate fractions were collected, the solvent removed to yield the desired product VD2-8 (139.3 mg, 81.4%).

LC-MS (ESI+): 522.4 [M+H]$^+$.

Step 5. Synthesis of (3S)-5-[(E)-3-[2-[tert-butoxycarbonyl(methyl)amino]ethyl-methyl-amino]prop-1-enyl]-2-oxo-spiro[1H-pyrrolo[2,3-b]pyridine-3,6'-5,7-dihydrocyclopenta[b]pyridine]-3'-carboxylic Acid, (VE2-8)

Synthesized using the same experimental procedure as described in the synthesis of Intermediate D1-1, starting from compound VD2-8 (152.4 mg, 0.328 mmol). The desired product VE2-8 (135.6, 100.0%) was obtained and used as is in the next reaction step.

LC-MS (ESI+): 508.4 [M+H]$^+$.

Step 6. Synthesis of (3S)-5-[(E)-3-[methyl-[2-(methylamino)ethyl]amino]prop-1-enyl]-2-oxo-spiro[1H-pyrrolo[2,3-b]pyridine-3,6'-5,7-dihydrocyclopenta[b]pyridine]-3'-carboxylic Acid Hydrochloride (VF2-8)

Synthesized using the same experimental procedure as described in the synthesis of Intermediate E1-1, starting from compound VE2-8 (53.0 mg, 0.1045 mmol). The desired product VF2-8 (61.7 mg) was obtained and used in the next reaction step as is.

LC-MS (ES+): 408.3 [M+H]1.

Step 7. Synthesis of (3S)-5-[(E)-3-[2-[2-[5-(tert-butoxycarbonylamino)-2-methyl-6-oxo-3-phenyl-1-piperidyl]ethyl-methyl-amino]ethyl-methyl-amino]prop-1-enyl]-2-oxo-spiro[1H-pyrrolo[2,3-b]pyridine-3,6'-5,7-dihydrocyclopenta[b]pyridine]-3'-carboxylic Acid (VG2-8)

Synthesized using the same experimental procedure as described in the synthesis of Intermediate VD2-8, starting from compound VF2-8 (61.7 mg, 0.1045 mmol) and a solution of VII. 55.8 mg (72.3%) of the desired product VG2-8 (61.7 mg) was obtained.

LC-MS (ESI+): 738.7 [M+H]$^+$.

Step 8. Synthesis of (3S)-5-[(E)-3-[2-[2-(5-amino-2-methyl-6-oxo-3-phenyl-1-piperidyl)ethyl-methyl-amino]ethyl-methyl-amino]prop-1-enyl]-2-oxo-spiro[1H-pyrrolo[2,3-b]pyridine-3,6'-5,7-dihydrocyclopenta[b]pyridine]-3'-carboxylic Acid (VH2-8)

Synthesized using the same experimental procedure as described in the synthesis of Intermediate E1-1, starting from compound VG2-8 (55.8 mg, 0.0756 mmol). The desired product VH2-8 was obtained (64.8 mg) and used in the next reaction step as is.

LC-MS (ES+): 638.6 [M+H]$^+$.

Step 9. Synthesis of (1S, 22E)-13,17,20-trimethyl-12-phenyl-5,9,14,17,20,26,28-heptazahexacyclo[22.5.2.11,4.13,7.110,14.027,30]tetratriaconta-3,5,7(33),22,24(31),25,27(30)-heptaene-8,29,32-trione (Example 2-8, Isomer 1)

Synthesized using the same experimental procedure as described in the synthesis of Example 1-1, starting from compound VH2-8 (64.8 mg, 0.0756 mmol). 22.3 mg (52.9%) of desired product Example 2-8 was obtained.

LC-MS (ESI+): 620.6 [M+H]$^+$. R$_t$=3.53 min (Method 1)
$^1$H NMR (600 MHz, DMSO-d$_6$) δ ppm 0.92 (d, J=6.4 Hz, 3H), 2.03 (s, 3H), 2.07-2.16 (m, 1H), 2.20 (br. s., 3H), 2.30-2.36 (m, 1H), 2.36-2.45 (m, 2H), 2.45-2.48 (m, 1H), 2.56-2.68 (m, 2H), 2.90-3.12 (m, 5H), 3.12-3.22 (m, 1H), 3.48-3.52 (m, 1H), 3.56 (d, J=13.2 Hz, 1H), 3.61-3.69 (m, 2H), 3.70-3.76 (m, 1H), 4.56-4.64 (m, 1H), 5.55-5.62 (m, 1H), 6.39 (d, J=15.8 Hz, 1H), 6.51 (br. s., 1H), 7.24-7.31 (m, 3H), 7.37 (t, J=7.6 Hz, 2H), 7.99 (d, J=1.8 Hz, 1H), 8.18 (s, 1H), 8.75 (br. s., 1H), 8.90 (s, 1H), 11.38 (br. s., 1H)

Scheme 30. Synthesis of Example 2-9, Isomer 1

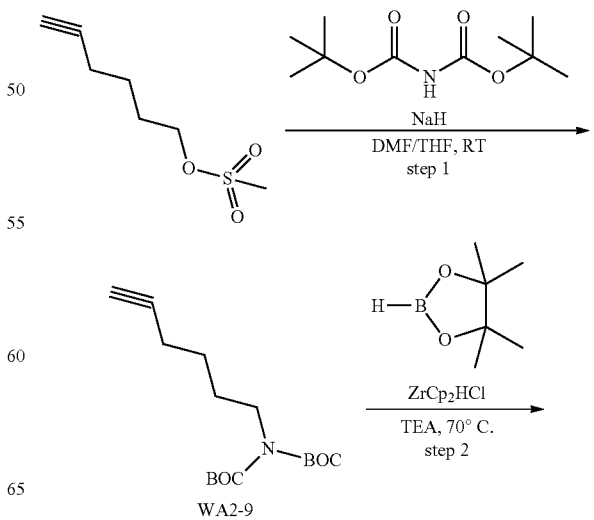

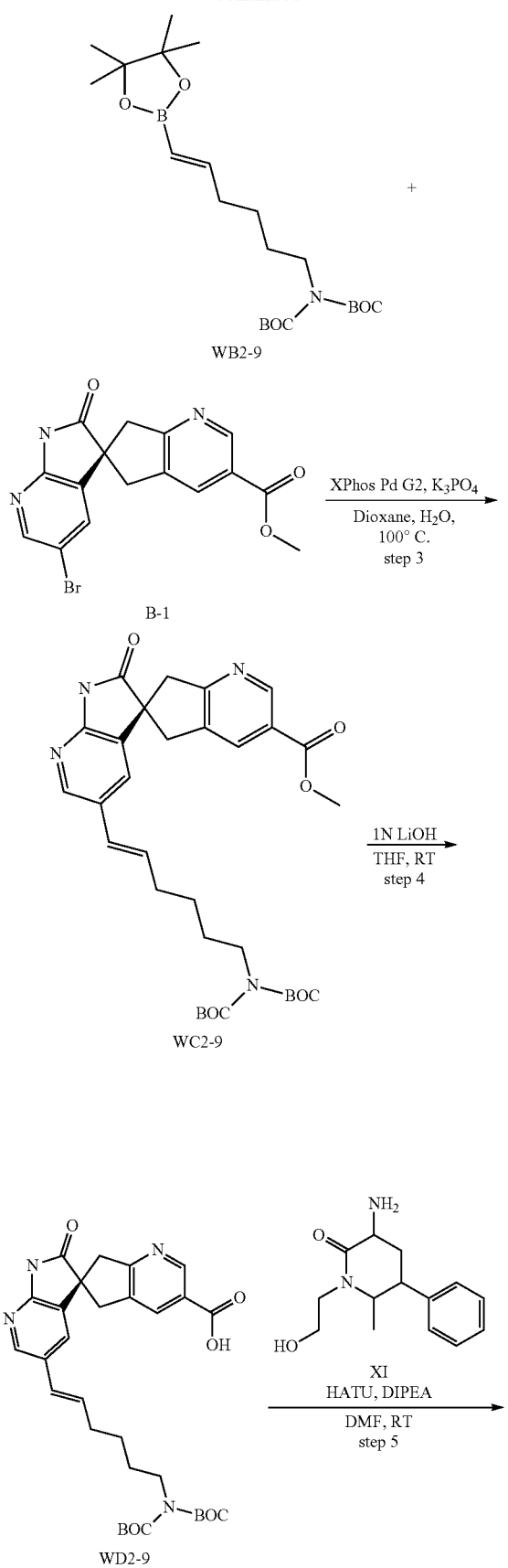
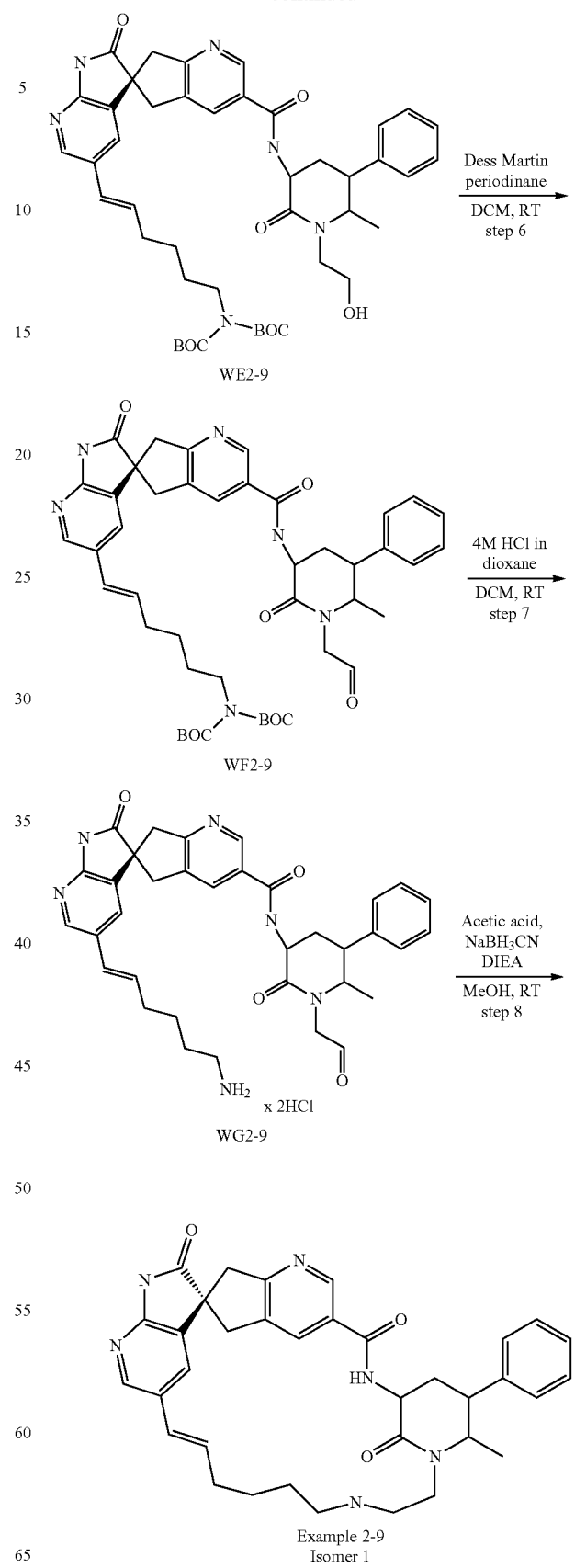

Experimental Procedures of Synthesis of Example 2-9

Step 1. Synthesis of Tert-butyl N-tert-butoxycarbonyl-N-hex-5-ynyl-carbamate (WA2-9)

To a suspension of compound NaH (79.5 mg, 2.0 mmol) in DMF (8.4 ml) was added a solution of tert-butyl N-tert-butoxycarbonylcarbamate (360 mg, 1.66 mmol) in THF (1.4 mL) in a dropwise fashion. The reaction mixture was stirred at RT for 1 h, then cooled in ice bath to 0° C. 5-Hexyn-1-ol 1-methanesulfonate (CAS 79496-61-0) (350 mg, 2.0 mmol) was added drop wise (dissolved in 0.2 ml of DMF). The stirring continued at RT for 16 h. The reaction mixture was quenched with sat. aq. $NH_4Cl$ (40 ml), extracted with EtOAc (3×30 ml), washed with water (30 ml) and brine (30 ml), dried under $MgSO_4$ and concentrated under reduced pressure to obtain crude product. The crude material was loaded and purified on a silica column (Interchim 12 g, 15 μm, $SiO_2$) using Interchim PuriFlash 430 instrument with a flowrate of 10 mL/min starting with cyclohexane (100%) and going to 10% of EtOAc/cyclohexane in 36 CVs. The appropriate fractions were collected, the solvent removed to yield the desired product WA2-9 (288 mg, Y=58%) as a colourless liquid.

LC-MS (ES+): 320.2 $[M+Na]^+$.

Step 2. Synthesis of Tert-butyl N-tert-butoxycarbonyl-N-[(E)-6-(4,4,5,5-tetramethyl-1,3,2-dioxaborolan-2-yl)hex-5-enyl]carbamate (WB2-9)

Synthesized using the same experimental procedures as described in the synthesis of Intermediate A1-1, starting from WA2-9 (288 mg, 0.97 mmol). The desired crude product WB2-9 (285 mg, yellow oil) was obtained and used as is in the next reaction step.

LC-MS (ES+): 426.4 $[M+H]^+$.

Step 3. Synthesis of Ditert-butyl 2-[(E)-6-[(3S)-3'-methoxycarbonyl-2-oxo-spiro[1H-pyrrolo[2,3-b]pyridine-3,6'-5,7-dihydrocyclopenta[b]pyridine]-5-yl]hex-5-enyl]propanedioate (WC2-9)

Synthesized using the same experimental procedures as described in the synthesis of Intermediate C1-1 starting from compound B1 (167 mg, 0.44 mmol) and compound WB2-9 (280.9 mg, 0.66 mmol). 158 mg (45.1%) of the desired product WC2-9 was obtained.

LC-MS (ES+): 593.4 $[M+H]^+$.

Step 4. Synthesis of (3S)-5-[(E)-6-[bis(tert-butoxycarbonyl)amino]hex-1-enyl]-2-oxo-spiro[1H-pyrrolo[2,3-b]pyridine-3,6'-5,7-dihydrocyclopenta[b]pyridine]-3'-carboxylic Acid (WD2-9)

Synthesized using the same experimental procedures as described in the synthesis of Intermediate D1-1 starting from compound WC2-9 (158 mg, 0.27 mmol). The desired product WD2-9 (86 mg, Y=55.8%, pale yellow solid) was obtained and used as is in the next reaction step.

LC-MS (ES+): 579.3 [M+H]1.

Step 5. Synthesis of Tert-butyl N-tert-butoxycarbonyl-N-[(E)-6-[(3S)-3'-[[1-(2-hydroxyethyl)-6-methyl-2-oxo-5-phenyl-3-piperidyl]carbamoyl]-2-oxo-spiro[1H-pyrrolo[2,3-b]pyridine-3,6'-5,7-dihydrocyclopenta[b]pyridine]-5-yl]hex-5-enyl]carbamate (WE2-9)

Synthesized using the same experimental procedure as described in the synthesis of Example 1-1, starting from compound WD2-9 (86 mg, 0.15 mmol) and compound XI (48.7 mg, 0.17 mmol). The desired product WE2-9 was obtained (74 mg, Y=61.6%) as an off-white solid.

LC-MS (ES+): 809.5 $[M+H]^+$.

Step 6. Synthesis of Tert-butyl N-tert-butoxycarbonyl-N-[(E)-6-[(3S)-3'-[[6-methyl-2-oxo-1-(2-oxoethyl)-5-phenyl-3-piperidyl]carbamoyl]-2-oxo-spiro[1H-pyrrolo[2,3-b]pyridine-3,6'-5,7-dihydrocyclopenta[b]pyridine]-5-yl]hex-5-enyl]carbamate (WF2-9)

A solution of compound WE2-9 (16 mg, 0.02 mmol) in DCM (0.3 mL) was cooled to 0° C., then Dess-Martin periodinane (12.6 mg, 0.03 mmol) was added and the reaction mixture stirred at RT for 5 hours. The reaction was quenched by adding 4 ml of a 1:1 mixture of sat. $NaHCO_3$/$Na_2S_2O_3$. The mixture was stirred for 10 minutes and then passed through a phase separator. The solution of the product WF2-9 in DCM was used as is in the next reaction step as is.

LC-MS (ES+): 829.4 $[M+Na]^+$.

Step 7. Synthesis of (3S)-5-[(E)-6-aminohex-1-enyl]-N-[6-methyl-2-oxo-1-(2-oxoethyl)-5-phenyl-3-piperidyl]-2-oxo-spiro[1H-pyrrolo[2,3-b]pyridine-3,6'-5,7-dihydrocyclopenta[b]pyridine]-3'-carboxamide; Dihydrochloride (WG2-9)

Synthesized using the same experimental procedure as described in the synthesis of Intermediate E1-1, starting from compound WF2-9 (16 mg, 0.019 mmol). The reaction mixture was concentrated to yield the desired product WG2-9 (21 mg) which was used as is in the next reaction step.

LC-MS (ES+): 607.3 [M+H]1.

Step 8. Synthesis of (1S,22E)-13-methyl-12-phenyl-5,9,14,17,26,28-hexazahexacyclo[22.5.2.11,4.13,7.110,14.027,30]tetratriaconta-3,5,7(33),22,24(31),25,27(30)-heptaene-8,29,32-trione (Example 2-9, Isomer 1)

To a solution of compound WG2-9 (21 mg, crude product) in methanol DIPEA (27 μL, 0.16 mmol) and powdered molecular sieves (40 mg) were added. The resulting brown mixture was stirred for 40 min at RT. Then acetic acid (2.3 μL, 0.04 mmol) and $NaBH_3CN$ (1.9 mg, 0.03 mmol) were added. The reaction mixture was stirred at RT for 2 h. The reaction mixture was concentrated, and the residue dissolved in sat. $NH_4Cl$ (20 mL) and DCM/i-PrOH 1:1 (10 mL). The layers were separated, and the aqueous layer extracted with DCM/i-PrOH 1:1 (3×10 mL). The combined organic layers were dried under MgSO4 and concentrated under reduced pressure to afford m=20 mg of the crude product. The crude material was loaded and purified on a silica column (Interchim 4 g, 15 μm, SiO$_2$) using Interchim PuriFlash 450 instrument with a flowrate of 8 mL/min starting with DCM (100%) and going to 100% DCM/MeOH/NH$_3$ (90:9:1.5) in 20 CVs. The appropriate fractions were collected, the solvent removed to yield the desired product Example 2-9, Isomer 1 (1 mg, 8.6%) as a white solid.

LC-MS (ES+): 591.5 [M+H]$^+$.

Scheme 31. Synthesis of Intermediate XI

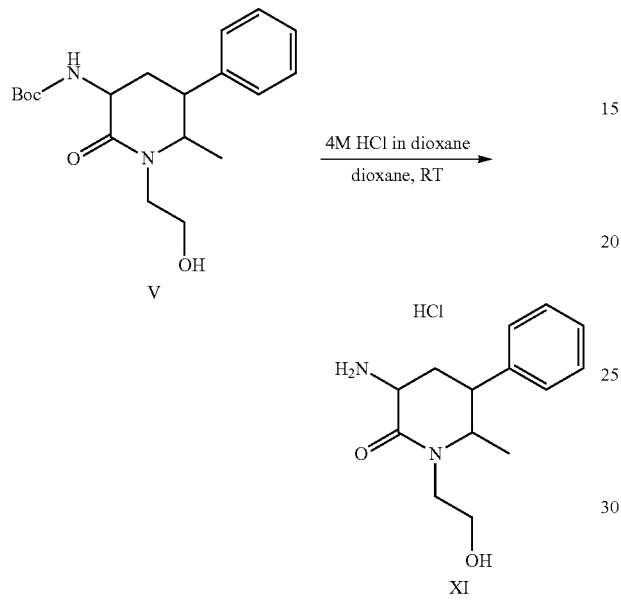

Experimental Procedures of Synthesis of Intermediate XI

Synthesis of 3-amino-1-(2-hydroxyethyl)-6-methyl-5-phenyl-piperidin-2-one Hydrochloride XI To the solution of compound V (145 mg, 0.4 mmol) in 1,4-dioxane (4.2 mL) HCl (4.0 M in dioxane, 4.2 ml, 0.02 mmol) was added. The reaction mixture was stirred at RT for 3 h. The reaction mixture was concentrated to yield the desired product XI (138 mg) which was used as is in the next reaction step.

LC-MS (ES+): 249.2 [M+H]$^+$.

Scheme 32. Synthesis of Example 2-10, Isomer 1

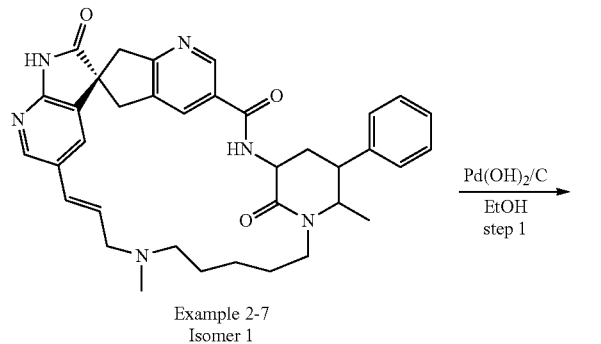

-continued

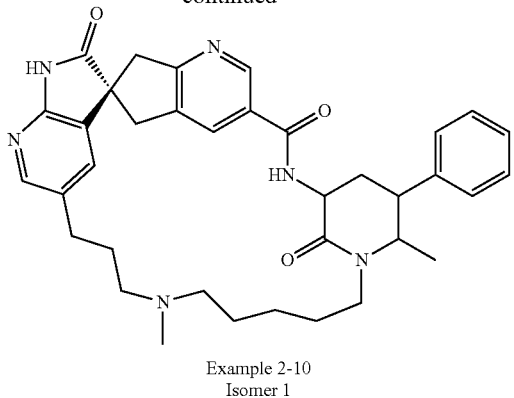

Example 2-10
Isomer 1

Step 1. Experimental Procedures of Synthesis of (1S)-13,20-dimethyl-12-phenyl-5,9,14,20,26,28-hexazahexacyclo[22.5.2.11,4.13,7.110,14.027,30] tetratriaconta-3,5,7(33),24(31),25,27(30)-hexaene-8, 29,32-trione (Example 2-10)

Example 2-7 (6.00 mg, 0.01 mmol) was dissolved in EtOH in a 5 mL flask, purged with argon, then Pd(OH)$_2$/C (2.0 mg) was added. reaction mixture was stirred and hydrogenated under a balloon filled with hydrogen till full reduction of double bond, monitored by UPLC MS. The reaction mixture was filtered through syringe filter, and concentrated to give crude (1 S)-13,20-dimethyl-12-phenyl-5,9,14,20,26,28-hexazahexacyclo[22.5.2.11,4.13,7.110, 14.027,30]tetratriaconta-3,5,7(33),24(31),25,27(30)-hexaene-8,29,32-trione (4.4 mg, 73%). Crude was purified by preparative HPLC to give final product Example 2-10, Isomer 1 (1.3 mg, Y=21%).

$^1$H NMR (500 MHz, METHANOL-d$_4$) δ ppm 1.11 (d, J=6.7 Hz, 3H), 1.32-1.49 (m, 4H), 1.49-1.68 (m, 4H), 1.68-1.81 (m, 1H), 2.24-2.30 (m, 2H), 2.31 (s, 3H), 2.36-2.47 (m, 2H), 2.56 (t, J=7.2 Hz, 2H), 2.82-2.95 (m, 2H), 3.04 (d, J=16.2 Hz, 1H), 3.11 (d, J=15.9 Hz, 1H), 3.54 (d, J=13.4 Hz, 1H), 3.67 (d, J=15.6 Hz, 1H), 3.73-3.82 (m, 2H), 3.97 (dt, J=13.9, 7.1 Hz, 1H), 4.48 (dd, J=11.4, 7.2 Hz, 1H), 6.57 (d, J=1.8 Hz, 1H), 7.25-7.32 (m, 3H), 7.37 (t, J=7.6 Hz, 2H), 7.91 (d, J=1.8 Hz, 1H), 8.16-8.20 (m, 1H), 8.78 (s, 1H)

Synthesis of Intermediates BX

Scheme 33. Synthesis of Intermediate B1

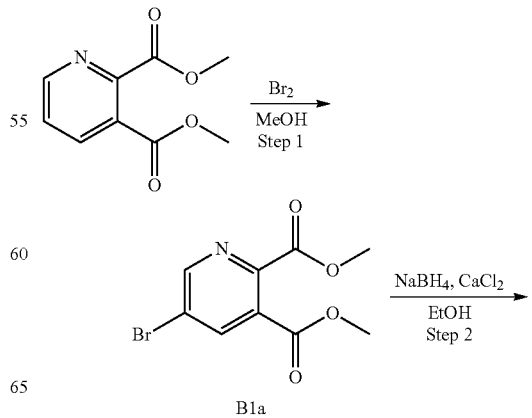

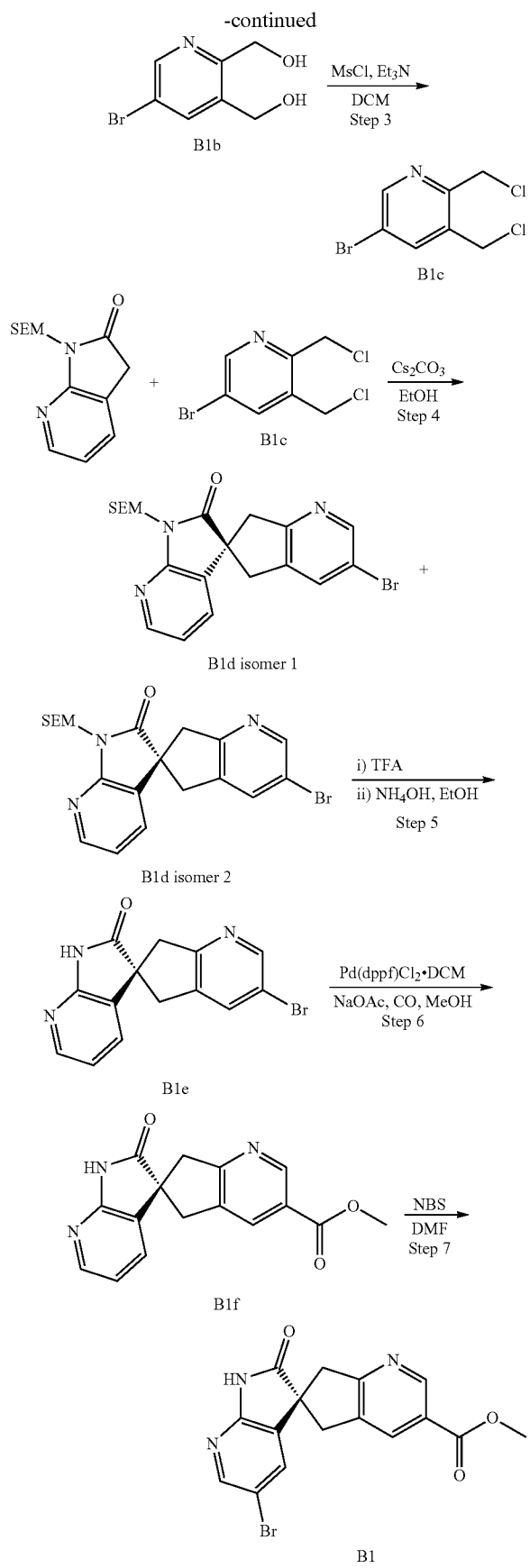

Experimental Procedure for Synthesis of methyl (S)-5'-bromo-2'-oxo-1',2',5,7-tetrahydrospiro[cyclopenta[b]pyridine-6,3'-pyrrolo[2,3-b]pyridine]-3-carboxylate B1

Step 1 Synthesis of Dimethyl 5-bromopyridine-2,3-dicarboxylate B1a

To a stirred solution of dimethyl pyridine-2,3-dicarboxylate (605-38-9) (100 g, 0.510 mol) in MeOH (500 mL) at 0° C. was added dropwise bromine (52.48 mL, 1.22 mol). The reaction mixture was then stirred at 55° C. overnight. The reaction mixture was quenched with ice cold $H_2O$ and extracted with EtOAc (2×1 L). The combined organic layers were washed with sat. NaCl (aq) (500 mL) and concentrated in vacuo. The resulting residue was purified by flash chromatography ($SiO_2$, petroleum ether-EtOAc) to give dimethyl 5-bromopyridine-2,3-dicarboxylate B1a (135 g, 96 LC-MS (ESI+): 274.0 $[M+H]^+$.

Step 2 Synthesis of (5-bromopyridine-2,3-diyl)dimethanol B1b

To a stirred solution dimethyl 5-bromopyridine-2,3-dicarboxylate B1a (135 g, 0.492 mol) in EtOH (2.5 L) at 0° C. was added portion wise sodium borohydride (112 g, 2.96 mol), followed by the dropwise addition of a solution of $CaCl_2$ (164 g, 1.48 mol) in EtOH (1.5 L) over a period of 40 mins. The temperature was maintained at 0° C. throughout the addition (exothermic reaction—efficient cooling was needed). The reaction mixture was then stirred at room temperature for 20 h and then re-cooled to 0° C. The reaction mixture was quenched with 2M HCl solution over a period of 30 mins to obtain a clear solution and was then allowed to warm to room temperature and stirred for 1 h. The reaction mixture was washed with EtOAc (1 L) and the organic layer was washed with further 1M HCL (0.2 L). The pH of the combined aqueous layers was adjusted to pH 7 using sat. $NaHCO_3$(aq) and then extracted with EtOAc (2×1 L). The combined organic layers were washed with sat. NaCl (aq) (500 mL) and concentrated in vacuo. The crude residue was triturated with MeOH to obtain a solid. The solid was collected by filtration to give (5-bromopyridine-2,3-diyl)dimethanol B1b (48 g, 45%).
LC-MS (ESI+): 218.0 $[M+H]^+$.

Step 3 Synthesis of 5-bromo-2,3-bis(chloromethyl)pyridine B1c

To a solution of (5-bromopyridine-2,3-diyl)dimethanol B1b (35 g, 0.160 mol) and $Et_3N$ (67 mL, 0.401 mol) in dry DCM (850 mL) at 0° C. was added methanesulfonyl chloride (31 mL, 0.481 mol). The reaction mixture was stirred at room temperature for 16 h and was then quenched with sat. $NH_4Cl$ (aq) (500 mL) and extracted with DCM (500 mL). The organic layer was washed with sat. NaCl (aq) (150 mL), dried ($Na_2SO_4$) and concentrated in vacuo to give 5-bromo-2,3-bis(chloromethyl)pyridine B1c (31.5 g, 77%).
LC-MS (ESI+): 255.9 $[M+H]^+$.

Step 4 Synthesis of (S)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one B1d Isomer 2

To a suspension of 1-((2-(trimethylsilyl)ethoxy)methyl)-1,3-dihydro-2H-pyrrolo[2,3-b]pyridin-2-one (CAS 879132-

48-6) (33 g, 0.125 mmol) and 5-bromo-2,3-bis(chloromethyl)pyridine B1c (44.6 g, 0.175 mol) in EtOH (900 mL) was added Cs₂CO₃ (113.75 g, 0.35 mol). The reaction mixture was stirred at room temperature for 16 h and was then quenched with ice cold H₂O (1 L) and extracted with EtOAc (2×1 L). The combined organic layers were washed with sat. NaCl (aq) (500 mL), dried (Na₂SO₄) and concentrated in vacuo. The resulting residue was purified by flash chromatography (SiO₂, petroleum ether-EtOAc) to give 3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one B1d.

Purified by Chiral SFC
  Instrument: PICLab PREP 400
  Solvents: Primary mobile phase=CO₂ Modifier: 35% MeOH
  Column: YMC Cellulose-SC 5 um, 250×30 mm, at 35° C.
  UV monitoring: 210 nm
  Flow: 120 g/min.
  To give
  (R)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one B1d isomer 1 (4.0 g) LC-MS (ESI+): 446.2 [M+H]⁺. SFC 2.34 min and
  (S)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one (3.5 g) B1d isomer 2 LC-MS (ESI+): 446.2 [M+H]⁺. SFC 3.25 min
  Chiral SFC analytical YMC Cellulose-SC, 250×4.6 mm 5p at 35° C., 3 ml/min, 40% Methanol 35° C.

Step 5 Synthesis of (S)-3-bromo-5,7-dihydrospiro[cyclopenta[b]pyridine-6,3'-pyrrolo[2,3-b]pyridin]-2'(1'H)-one B1e A suspension of (S)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one B1d isomer 2 (19 g, 42.6 mmol) in TFA (100 mL) was heated at 60° C. for 3 h and then concentrated in vacuo. The resulting residue was dissolved in EtOH (100 mL) and to this was then added NH₄OH (100 ml). The reaction mixture was stirred at room temperature for 2 h. The resulting precipitate was collected by filtration to give (S)-3-bromo-5,7-dihydrospiro[cyclopenta[b]pyridine-6,3'-pyrrolo[2,3-b]pyridin]-2'(1'H)-one B1e (10.2 g, 76%).
  LC-MS (ESI+): 316.0 [M+H]⁺.

Step 6 Synthesis of Methyl (S)-2'-oxo-1',2',5,7-tetrahydrospiro[cyclopenta[b]pyridine-6,3'-pyrrolo[2,3-b]pyridine]-3-carboxylate B1f A stirred solution of (S)-3-bromo-5,7-dihydrospiro[cyclopenta[b]pyridine-6,3'-pyrrolo[2,3-b]pyridin]-2'(1'H)-one B1e (10 g, 31.62 mmol) and sodium acetate (5.24 g, 63.3 mmol) in MeOH (150 mL) in a mini clave vessel was degassed with argon, followed by the addition of Pd(dppf)Cl₂.DCM (3.87 g, 4.74 mmol). The reaction mixture was heated at 100° C. for 16 h under 5 Kg/cm² pressure of CO gas. The reaction mixture was partitioned between EtOAc (600 mL) and H₂O (200 mL). The organic layer was washed with sat. NaCl (aq) (200 mL), dried (Na₂SO₄) and concentrated in vacuo. The resulting residue was purified by flash chromatography (SiO₂, petroleum ether-EtOAc) to give methyl (S)-2'-oxo-1',2',5,7-tetrahydrospiro[cyclopenta[b]pyridine-6,3'-pyrrolo[2,3-b]pyridine]-3-carboxylate B1f (5 g, 54%).
  LC-MS (ESI+): 296.1 [M+H]⁺.

Step 7 Synthesis of Methyl (S)-5'-bromo-2'-oxo-1',2',5,7-tetrahydrospiro[cyclopenta[b]pyridine-6,3'-pyrrolo[2,3-b]pyridine]-3-carboxylate B1

To a stirred solution of methyl (S)-2'-oxo-1',2',5,7-tetrahydrospiro[cyclopenta[b]pyridine-6,3'-pyrrolo[2,3-b]pyridine]-3-carboxylate B1f (5.0 g, 16.9 mmol) in DMF (50 mL) at 0° C. was added NBS (9.04 g, 50.8 mmol). The reaction mixture was stirred at room temperature for 3 h and was then quenched by ice cold H₂O. The resulting precipitate was collected by filtration, washed with cold H₂O, dried over high vacuum for 3 h to give methyl (S)-5'-bromo-2'-oxo-1',2',5,7-tetrahydrospiro[cyclopenta[b]pyridine-6,3'-pyrrolo[2,3-b]pyridine]-3-carboxylate B1 (4.7 g, 74%).
  LC-MS (ESI+): 374.0 [M+H]⁺.

Scheme 34. Synthesis of Intermediate B2

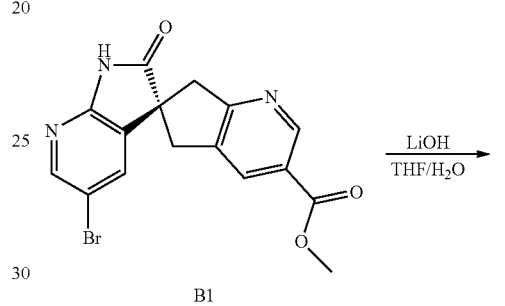

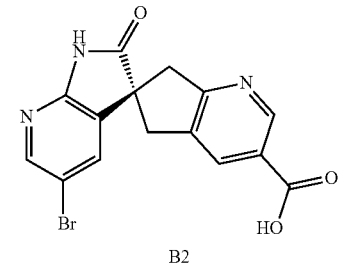

Experimental Procedure for Synthesis of (3S)-5-bromo-2-oxo-spiro[1H-pyrrolo[2,3-b]pyridine-3,6'-5,7-dihydrocyclopenta[b]pyridine]-3'-carboxylic Acid (B2)

To the solution of compound B1 (240 mg, 0.64 mmol) in THF (8.5 mL), LiOH (1.0 N in H₂O, 2.56 mL, 2.56 mmol) was added. The reaction mixture was stirred at room temperature for 40 minutes. The reaction mixture was concentrated under reduced pressure, diluted with water (20 mL) The pH value was adjusted to 3.5 using 1 N HCl, and extracted with a mixture of DCM/i-PrOH 1:1 (4×8 mL). The combined organic layers were dried over Na₂SO₄ and concentrated under reduced pressure to afford the desired product B2 (207 mg, 89%) which was used as is in the next reaction step.
  LC-MS (ES+): 360.4, 362.4 [M+H]⁺.

Scheme 35. Synthesis of Intermediate B3

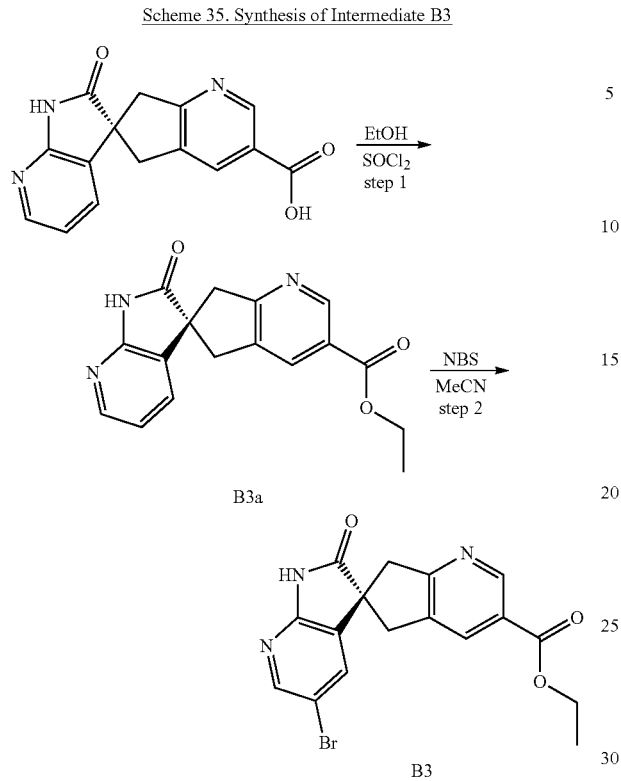

Experimental Procedures of Synthesis of Intermediate B3

Step 1. Synthesis of Ethyl (3S)-2-oxo-spiro[1H-pyrrolo[2,3-b]pyridine-3,6'-5,7-dihydrocyclopenta[b]pyridine]-3'-carboxylate A solution of (3S)-2-oxo-spiro[1H-pyrrolo[2,3-b]pyridine-3,6'-5,7-dihydrocyclopenta[b]pyridine]-3'-carboxylic acid (CAS 1375541-21-1) (1.023 g, 3.63 mmol) in dry EtOH (50 mL) was cooled to 0° C. Into this solution SOCl$_2$ (1.057 mL, 14.5 mmol) was added dropwise. The mixture was stirred at the 75° C. for 5 hours. The solvent was evaporated to yield ethyl (3S)-2-oxo-spiro[1H-pyrrolo[2,3-b]pyridine-3,6'-5,7-dihydrocyclopenta[b]pyridine]-3'-carboxylate (1.123 g, 100%). Product was used in next step as it is.
LC-MS (ES+): 310.1 [M+H]$^+$ Step 2. Synthesis of Ethyl (3S)-5-bromo-2-oxo-spiro[1H-pyrrolo[2,3-b]pyridine-3,6'-5,7-dihydrocyclopenta[b]pyridine]-3'-carboxylate B3

A suspension of ethyl (3S)-2-oxo-spiro[1H-pyrrolo[2,3-b]pyridine-3,6'-5,7-dihydrocyclopenta[b]pyridine]-3'-carboxylate (1.123 g, 0.363 mmol) in the dry ACN (20 mL) was cooled to 0° C. Into this solution NBS (1.292 g, 7.26 mmol) was added. The mixture was stirred at the RT ON. The reaction mixture was dropwise added into water (300 mL). The formed precipitation was filtered off, washed with water (50 mL) and dried overnight under vacuum at 45° C. to give ethyl (3S)-5-bromo-2-oxo-spiro[1H-pyrrolo[2,3-b]pyridine-3,6'-5,7-dihydrocyclopenta[b]pyridine]-3'-carboxylate B3 (1.4 g, 100%).
LC-MS (ES$^+$): 388 [M+H]$^+$ Scheme 36. Synthesis of Intermediate B4

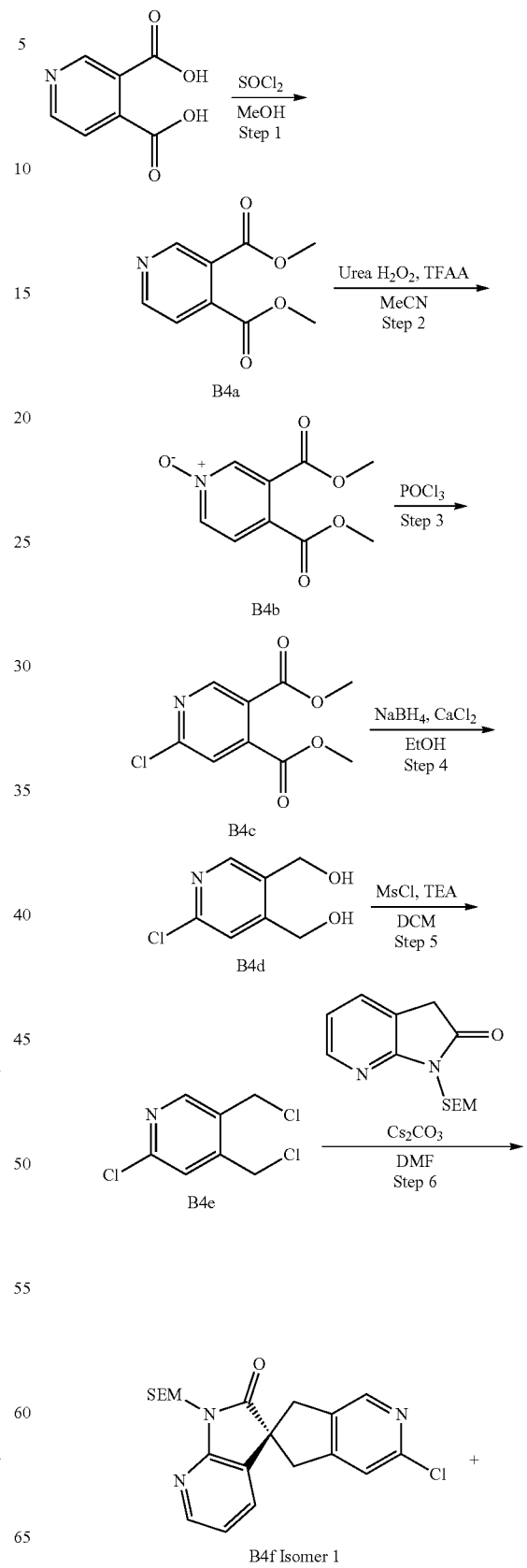

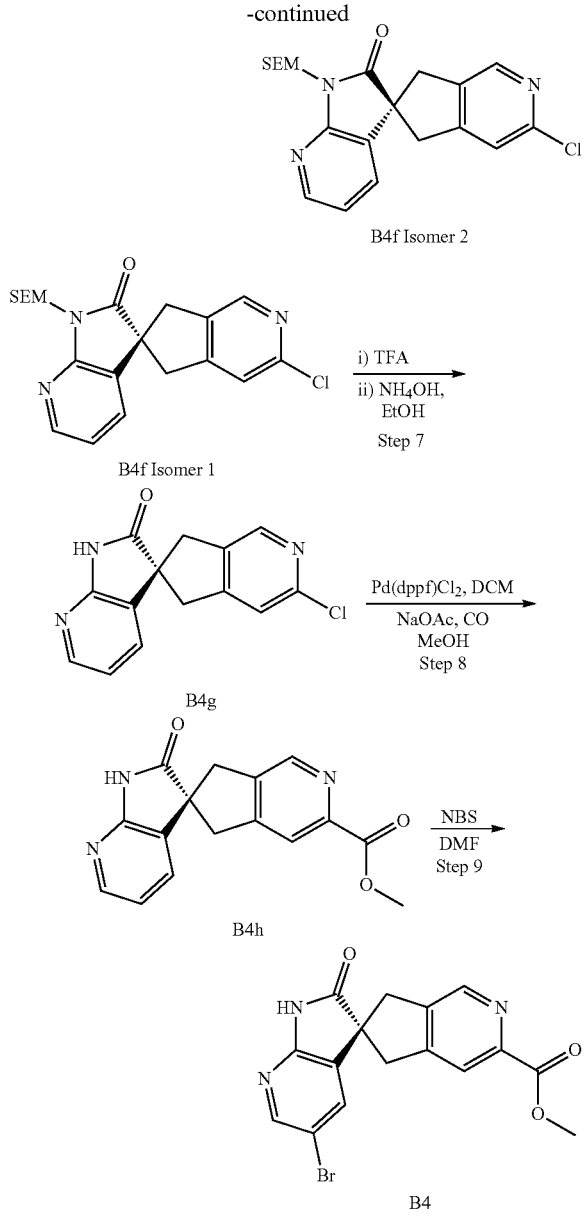

Experimental Procedures of Synthesis of Intermediate B4

Step 1 Synthesis of dimethyl pyridine-3,4-dicarboxylate B4a

To stirred solution of pyridine-3,4-dicarboxylic acid (CAS 490-11-9) (500 g, 2.99 mol) in MeOH (4 L) at 0° C. was added dropwise $SOCl_2$ (1.1 L, 15.0 mol). The reaction mixture was stirred at 70° C. for 16 h. The reaction mixture was then concentrated in vacuo and the resulting residue was quenched with saturated aqueous $NaHCO_3$ (2 L) and extracted with EtOAc (2×2 L). The combined organic layers were washed with brine (1 L), dried ($Na_2SO_4$) and concentrated in vacuo to give dimethyl pyridine-3,4-dicarboxylate B4a (380 g, 65%).

LC-MS (ESI+): 196.1 [M+H]$^+$.

Step 2 Synthesis of 3,4-bis(methoxycarbonyl)pyridine 1-oxide B4b

To a stirred solution of dimethyl pyridine-3,4-dicarboxylate B4a (380 g, 1.94 mol) and urea hydrogen peroxide (366 g, 3.89 mol) in MeCN (3.5 L) at 0° C. was added dropwise TFAA (548 mL, 3.89 mol). The reaction mixture was stirred at 0° C. for 2 h and was then quenched with saturated aqueous $NaHCO_3$ (1 L) (cautiously) and extracted with DCM (2×2 L). The combined organic layers were washed with brine (1 L), dried ($Na_2SO_4$) and concentrated in vacuo to give 3,4-bis(methoxycarbonyl)pyridine 1-oxide B4b (390 g, 95%).

LC-MS (ESI+): 212.0 [M+H]$^+$.

Step 3 Synthesis of Dimethyl 6-chloropyridine-3,4-dicarboxylate B4c

To a suspension of 3,4-bis(methoxycarbonyl)pyridine 1-oxide B4b (390 g, 1.84 mol) in toluene (3.5 L) at 0° C. was added $POCl_3$ (1.7 L, 18.4 mol) and the reaction mixture was then heated at 110° C. for 12 h. The reaction mixture was concentrated in vacuo and the resulting residue was poured into ice cold $H_2O$ (1 L), neutralized by the addition of saturated aqueous $NaHCO_3$ (~3.0 L) and extracted with EtOAc (2×2 L). The combined organic layers were washed with brine (2 L), dried ($Na_2SO_4$) and concentrated in vacuo. The crude was purified by flash chromatography ($SiO_2$, hexane-EtOAc) to give dimethyl 6-chloropyridine-3,4-dicarboxylate B4c (113 g, 27%).

LC-MS (ESI+): 230.0 [M+H]$^+$.

Step 4 Synthesis of (6-chloropyridine-3,4-diyl)dimethanol B4d

To a stirred solution of dimethyl 6-chloropyridine-3,4-dicarboxylate B4c (113 g, 0.49 mol) in EtOH (2.5 L) at 0° C. was added portion wise sodium borohydride (112 g, 2.95 mol), followed by the slow addition of a solution of $CaCl_2$ (164 g, 1.47 mmol) in EtOH (2.0 L) at 0° C. (over a period of 1.5 h, exothermic reaction-efficient cooling was needed). The reaction mixture was stirred at room temperature for 20 h and was then quenched by the addition of 4M HCl solution, over a period of 30 mins at 0° C., to obtain a clear solution. The reaction mixture was then stirred at room temperature for 1 h. The reaction mixture was washed with EtOAc (3 L) and the organic layer was washed with further 1M HCL (2.0 L). The pH of the combined aqueous layers was adjusted to pH 7 using saturated aqueous $NaHCO_3$ and then extracted with EtOAc (2×5 L). The combined organic layers were washed with brine (3.0 L), dried ($Na_2SO_4$) and concentrated in vacuo to give (6-chloropyridine-3,4-diyl) dimethanol B4d (90 g, crude).

LC-MS (ESI+): 174.0 [M+H]$^+$.

Step 5 Synthesis of 2-chloro-4,5-bis(chloromethyl)pyridine B4e

To a solution of (6-chloropyridine-3,4-diyl)dimethanol B4d (90 g, 0.518 mol) and $Et_3N$ (216 mL, 1.56 mol) in dry DCM (1.8 L) at 0° C. was added slowly methanesulfonyl chloride (80 mL, 1.04 mol). The reaction mixture was stirred at room temperature for 2 h and was then quenched with saturated aqueous $NaHCO_3$ (1 L) and extracted with DCM (1.0 L). The organic layer was washed with brine (1.5 L), dried ($Na_2SO_4$) and concentrated in vacuo to give 2-chloro-4,5-bis(chloromethyl)pyridine B4e (105 g, crude).

LC-MS (ESI+): 209.9 [M+H]$^+$.

Step 6 Synthesis of (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one B4f isomer 1

To a suspension of 1-((2-(trimethylsilyl)ethoxy)methyl)-1,3-dihydro-2H-pyrrolo[2,3-b]pyridin-2-one (CAS 879132-48-5) (132 g, 0.498 mol) and 2-chloro-4,5-bis(chloromethyl)pyridine B4e (105 g, 0.498 mol) in DMF (1.5 L) at room temperature was added $Cs_2CO_3$ (485 g, 1.49 mol). The reaction mixture was stirred for 16 h and was then quenched with ice cold $H_2O$ (2.0 L) and extracted with EtOAc (2×2 L). The combined organic layers were washed with brine (2×2 L), dried ($Na_2SO_4$) and concentrated in vacuo. This was then purified by flash chromatography ($SiO_2$, petroleum ether-EtOAc) to give 3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one B4f (60 g).
Purified by Chiral SFC
  Instrument: PICLab PREP 150
  Solvents: Primary mobile phase=$CO_2$ Modifier: 25% MeOH
  Column: YMC Cellulose-SC 5 um, 250×30 mm, at 35° C.
  UV monitoring: 210 nm
  Flow: 100 g/min.
  To give
  (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one B4f isomer 1 (20 g). LC-MS (ESI+): 402.1 [M+H]$^+$ SFC 3.14 min. and
  (R)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one B4f isomer 2 (19 g). LC-MS (ESI+): 402.1 [M+H]$^+$. SFC 3.73 min.
  Chiral SFC analytical YMC Cellulose-SC, 250×4.6 mm 5p at 35° C., 3 ml/min, 40% Methanol 35° C.

Step 7 Synthesis of (S)-3-chloro-5,7-dihydrospiro[cyclopenta[c]pyridine-6,3'-pyrrolo[2,3-b]pyridin]-2'(1'H)-one B4 g A suspension of (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one B4f (10 g, 0.024 mol) in TFA (70 mL) was heated at 60° C. for 1 h. The reaction mixture was concentrated in vacuo and dried under high vacuum. The resulting residue was dissolved in EtOH (70 mL) and to this was then added $NH_4OH$ (50 ml). The reaction mixture was stirred at 60° C. for 2 h. The resulting precipitate was collected by filtration, washed with $H_2O$ (100 mL) and dried under high vacuum to give (S)-3-chloro-5,7-dihydrospiro[cyclopenta[c]pyridine-6,3'-pyrrolo[2,3-b]pyridin]-2'(1'H)-one B4 g (6.2 g, 82%).
LC-MS (ESI+): 272.0 [M+H]$^+$.

Step 8 Synthesis of Methyl (S)-2'-oxo-1',2',5,7-tetrahydrospiro[cyclopenta[c]pyridine-6,3'-pyrrolo[2,3-b]pyridine]-3-carboxylate B4 h A stirred solution of (S)-3-chloro-5,7-dihydrospiro[cyclopenta[c]pyridine-6,3'-pyrrolo[2,3-b]pyridin]-2'(1'H)-one B4 g (6.2 g, 0.0228 mol) and sodium acetate (3.79 g, 0.457 mol) in MeOH (120 mL) was degassed with argon and to this was added Pd(dppf)$Cl_2$.DCM (2.8 g, 0.0034 mol). The reaction mixture was heated at 100° C. for 16 h in a mini clave vessel under 5 Kg/cm$^2$ pressure of CO gas. The reaction mixture was concentrated in vacuo and the resulting residue was purified by flash chromatography ($SiO_2$, petroleum ether-EtOAc). The solid obtained was triturated with MeOH (20 mL) and the solids were collected by filtration to give methyl (S)-2'-oxo-1',2',5,7-tetrahydrospiro[cyclopenta[c]pyridine-6,3'-pyrrolo[2,3-b]pyridine]-3-carboxylate B4 h (3.2 g, 48%).
LC-MS (ESI+): 296.2 [M+H]$^+$.

Step 9 Synthesis of Methyl (S)-5'-bromo-2'-oxo-1',2',5,7-tetrahydrospiro[cyclopenta[c]pyridine-6,3'-pyrrolo[2,3-b]pyridine]-3-carboxylate B4

To a stirred solution of methyl (S)-2'-oxo-1',2',5,7-tetrahydrospiro[cyclopenta[c]pyridine-6,3'-pyrrolo[2,3-b]pyridine]-3-carboxylate B4 h (2.4 g, 8.1 mmol) in DMF (25 mL) at 0° C. was added NBS (1.9 g, 10.5 mmol). The reaction mixture was stirred at room temperature for 5 h and was then quenched by the addition of ice-cold $H_2O$ (100 mL). The resulting precipitate was collected by filtration, washed with cold $H_2O$ and dried under high vacuum to give methyl (S)-5'-bromo-2'-oxo-1',2',5,7-tetrahydrospiro[cyclopenta[c]pyridine-6,3'-pyrrolo[2,3-b]pyridine]-3-carboxylate B4 (1.33 g, 44%).
LC-MS (ESI+): 374.0 [M+H]1.

Scheme 37. Synthesis of Intermediate B5

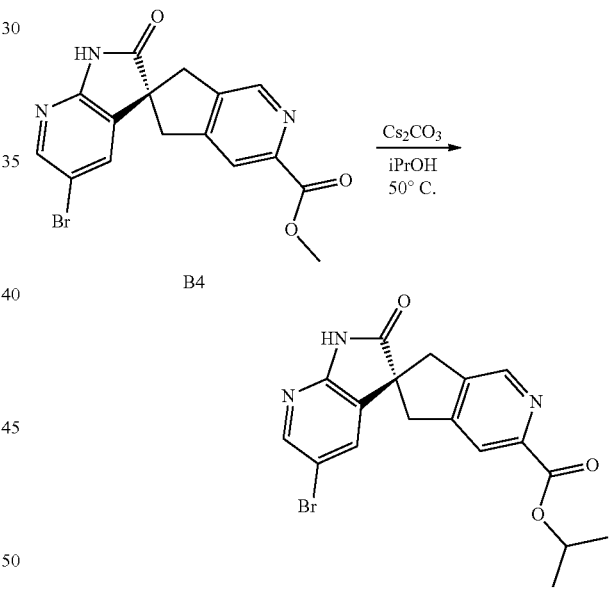

Synthesis of Isopropyl (3S)-5-bromo-2-oxo-spiro[1H-pyrrolo[2,3-b]pyridine-3,6'-5,7-dihydrocyclopenta[c]pyridine]-3'-carboxylate B5

To a suspension of B4 (1.175 g, 3.140 mmol) in a dry 2-propanol (78.0 mL), $Cs_2CO_3$ (413.5 mg, 1.256 mmol) was added. The resulting mixture was stirred at 50° C. for 13 hours. The reaction mixture was concentrated, water was added (50 mL) and extracted with EtOAc (3×25 mL). The combined organic extracts were washed with brine (50 mL), dried over $Na_2SO_4$ and concentrated under reduced pressure to afford raw product (1.17 g). The raw material was loaded and purified on a silica column (Interchim 25 g, 15 μm, SiO$_2$) using Interchim PuriFlash 450 instrument with a flowrate of 20 mL/min starting with DCM (100%) and going to 100% [DCM/MeOH (20:1)] in 30 CVs. Hold 100% for 10 CVs. The appropriate fractions were collected, the solvent removed to yield the desired product B5 (1.07 g, 84.7%).

LC-MS (ES+): 402.10, 404.10 [M+H]$^+$.

Scheme 38. Synthesis of intermediate B6

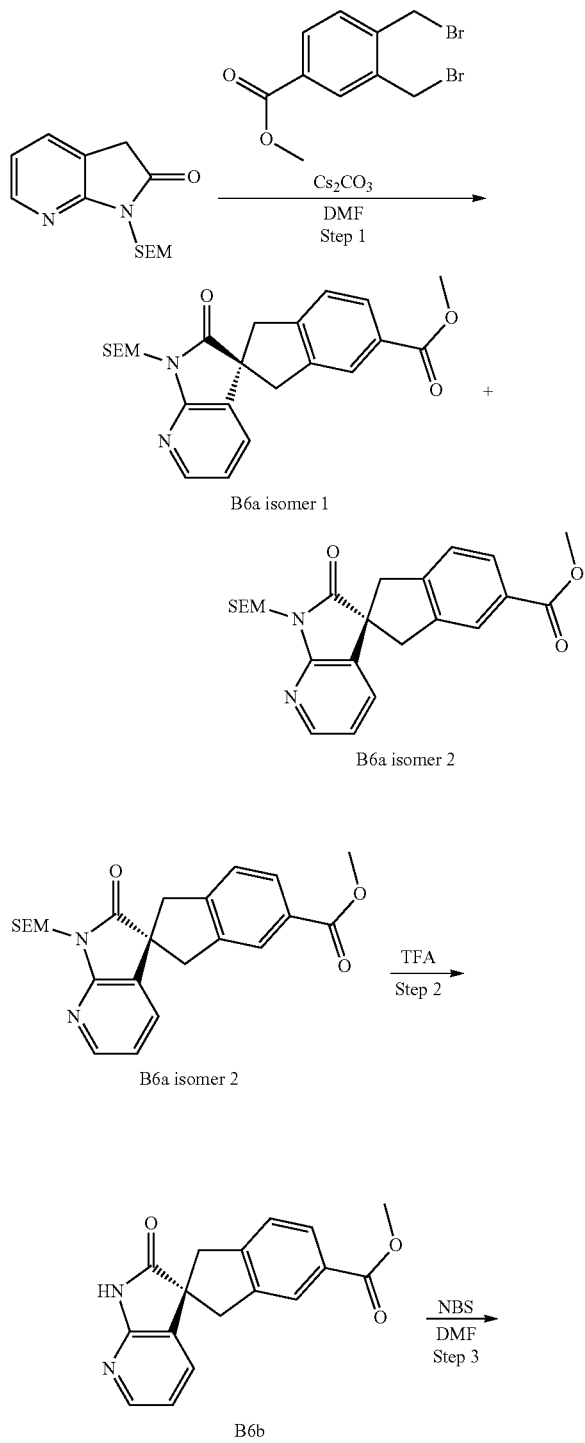

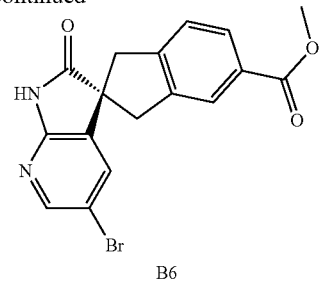

Step 1 Synthesis of Dimethyl pyridine-3,4-dicarboxylate B6a

To a suspension of 1-((2-(trimethylsilyl)ethoxy)methyl)-1,3-dihydro-2H-pyrrolo[2,3-b]pyridin-2-one (CAS 879132-48-6) (60 g, 0.22 mol) and methyl 3,4-bis(bromomethyl)benzoate (CAS 20896-23-5) (87.2 g, 0.27 mol) in DMF (1.5 L) was added Cs$_2$CO$_3$ (222 g, 0.68 mol). The reaction mixture was stirred at room temperature for 16 h and was then quenched with ice cold H$_2$O (5 L) and extracted with EtOAc (2×3 L). The combined organic layers were washed with brine (3 L), dried (Na$_2$SO$_4$) and concentrated in vacuo. The resulting residue was purified by flash chromatography (SiO$_2$, petroleum ether-EtOAc) to give methyl 2'-oxo-1'-((2-(trimethylsilyl)ethoxy)methyl)-1,1',2',3-tetrahydrospiro[indene-2,3'-pyrrolo[2,3-b]pyridine]-5-carboxylate B6a.
Purified by Chiral SFC
  Instrument: PICLab PREP 400
  Solvents: Primary mobile phase=CO$_2$ Modifier: 25% MeOH
  Column: YMC Amylose-C 5 um, 250×30 mm, at 35° C.
  UV monitoring: 210 nm
  Flow: 100 g/min.
  To give
  Methyl (S)-2'-oxo-1'-((2-(trimethylsilyl)ethoxy)methyl)-1,1',2',3-tetrahydrospiro[indene-2,3'-pyrrolo[2,3-b]pyridine]-5-carboxylate (B6a isomer 1) (11.5 g) LC-MS (ESI+): 425.1 [M+H]$^+$ SFC 1.52 min.
  and
  Methyl (R)-2'-oxo-1'-((2-(trimethylsilyl)ethoxy)methyl)-1,1',2',3-tetrahydrospiro[indene-2,3'-pyrrolo[2,3-b]pyridine]-5-carboxylate (B6a isomer 2) (9.8 g) LC-MS (ESI+): 425.1 [M+H]$^+$. SFC 2.02 min.
  Chiral SFC analytical YMC Amylose-C, 250×4.6 mm 5p at 35° C., 3 ml/min, 40% Methanol 35° C.

Step 2 Synthesis of Methyl (R)-2'-oxo-1,1',2',3-tetrahydrospiro[indene-2,3'-pyrrolo[2,3-b]pyridine]-5-carboxylate B6b A suspension of methyl (R)-2'-oxo-1'-((2-(trimethylsilyl)ethoxy)methyl)-1,1',2',3-tetrahydrospiro[indene-2,3'-pyrrolo[2,3-b]pyridine]-5-carboxylate B6a isomer 2 (9.8 g, 23.12 mmol) in TFA (100 mL) was heated at 60° C. for 2 h. The reaction mixture was concentrated in vacuo and dried over high vacuum. The crude mass was dissolved in MeOH (100 mL) and to this was then added DIPEA (9.8 g, 23.12 mmol). The reaction mixture was heated at 60° C. for 2 h. The resulting precipitate was collected by filtration and dried to give methyl (R)-2'-oxo-1,1',2',3-tetrahydrospiro[indene-2,3'-pyrrolo[2,3-b]pyridine]-5-carboxylate B6b (5.6 g, 84%).

LC-MS (ESI+): 295.1 [M+H]$^+$.

Step 3 Synthesis of Methyl (R)-5'-bromo-2'-oxo-1, 1',2',3-tetrahydrospiro[indene-2,3'-pyrrolo[2,3-b]pyridine]-5-carboxylate B6

To a stirred solution of methyl (R)-2'-oxo-1,1',2',3-tetrahydrospiro[indene-2,3'-pyrrolo[2,3-b]pyridine]-5-carboxylate (5.6 g, 19.04 mmol) in DMF (60 mL) at 0° C. was added NBS (10.17 g, 57.14 mmol). The reaction mixture was stirred at room temperature for 5 h and was then quenched with ice cold $H_2O$. The reaction mixture was stirred for 1 h and the resulting precipitate was collected by filtration, washed with ice cold $H_2O$ and dried under high vacuum. The solid was triturated with MeOH to give methyl (R)-5'-bromo-2'-oxo-1,1',2',3-tetrahydrospiro[indene-2,3'-pyrrolo[2,3-b]pyridine]-5-carboxylate B6 (6.0 g, 85%).

LC-MS (ESI+): 373.0 $[M+H]^+$

Biological Activity cAMP Functional Assay cAMP production following receptor activation was determined using the Homogeneous Time-Resolved Fluorescence (HTRF) cAMP dynamic-2 assay (Cisbio, France). The human neuroblastoma cell line SK-N-MC endogenously expressing the human CGRP receptor was seeded at a density of 12,500 cells/well in solid walled 96 well half area plates (Costar, Catalog Number 3688, Corning Life Sciences, Germany). After 16 h incubation at 37° C. media was removed and cells were incubated at 37° C. for 30 min in serum free media containing 500 μM IBMX (Tocris, Abingdon, UK, Catalog Number 2845) and increasing concentrations of test antagonist. Following this cells were challenged with an $EC_{80}$ concentration of human CGRP (0.3 nM) for a further 30 m at 37°) and then cAMP production was determined as manufacturer's instructions before plates were read on a PheraStar fluorescence plate reader (BMG LabTech, Germany). $IC_{50}$ values were derived from the inhibition curve. The $pIC_{50}$ values (where $pIC_{50}=-\log_{10} IC_{50}$) were converted to a functional $pK_b$ value using a modified Cheng-Prussoff equation where $K_d$=agonist $EC_{50}$ and L hot=agonist challenge concentration. The $pK_b$ values of certain compounds of the invention are detailed in Table 5.

TABLE 5

| CGRP $pK_b$ values | | |
|---|---|---|
| Example | isomer(s) | CGRP $pK_b$ |
| Example 1-1 | Isomer 1 | 11.2 |
| Example 1-1 | Isomer 2 | 9.3 |
| Example 1-1 | Isomer 3 | 9.3 |
| Example 1-2 | Isomer 1 | 11.3 |
| Example 1-2 | Isomer 2 | 9.3 |
| Example 1-3 | Isomer 1 | 11.1 |
| Example 1-3 | Isomer 2 | 9.3 |
| Example 1-4 | Isomer 1 | 11.1 |
| Example 1-4 | Isomer 2 | 9.9 |
| Example 1-5 | Isomer 1 | 11.6 |
| Example 1-5 | Isomer 2 | 7.7 |
| Example 1-6 | Isomer 1 | 11.1 |
| Example 1-6 | Isomer 2 | 8.9 |
| Example 1-7 | Isomer 1 | 11.4 |
| Example 1-7 | Isomer 2 | 8.9 |
| Example 1-7 | Isomer 3 | 9.1 |
| Example 1-8 | Isomer 1 | 11.3 |
| Example 1-8 | Isomer 2 | 9.2 |
| Example 2-1 | Single Isomer | 9.9 |
| Example 2-2 | Isomer 1 | 10.5 |
| Example 2-2 | Isomer 2 | 8.0 |
| Example 2-3 | Single Isomer | 10.6 |
| Example 2-4 | Single Isomer | 9.8 |

TABLE 5-continued

| CGRP $pK_b$ values | | |
|---|---|---|
| Example | isomer(s) | CGRP $pK_b$ |
| Example 2-5 | Single Isomer | 10.3 |
| Example 2-6 | Single Isomer | 10.2 |
| Example 2-7 | Single Isomer | 10.6 |
| Example 2-8 | Single Isomer | 10.0 |
| Example 2-9 | Single Isomer | 10.7 |
| Example 2-10 | Single Isomer | 10.5 |
| Example 3-1 | Isomer 1 | 11.1 |
| Example 3-1 | Isomer 2 | 8.2 |
| Example 3-2 | Isomer 1 | 11.4 |
| Example 3-2 | Isomer 2 | 8.9 |
| Example 4-1 | Isomer 1 | 11.9 |
| Example 4-1 | Isomer 2 | 9.7 |
| Example 4-2 | Isomer 1 | 11.1 |
| Example 4-2 | Isomer 2 | 9.2 |
| Example 5-1 | Isomer 1 | 10.8 |
| Example 5-1 | Isomer 2 | 8.8 |
| Example 5-1 | Isomer 3 | 8.9 |
| Example 6-1 | Isomer 1 | 6.3 |
| Example 6-1 | Isomer 2 | 8.5 |
| Example 6-2 | Isomer 1 | 7.5 |
| Example 6-2 | Isomer 2 | 8.9 |
| Example 6-3 | Single Isomer | 8.4 |
| Example 6-4 | Single Isomer | 8.3 |
| Example 7-1 | Mixture diastereomers | 9.7 |
| Example 8-1 | Single Isomer | 9.4 |
| Example 8-2 | Single Isomer | 9.6 |
| Example 9-1 | Mixture (Isomer 2) | 9.9 |
| Example 9-1 | Mixture (Isomer 1) | 7.9 |
| Example 10-1 | Isomer 1 | 7.6 |
| Example 10-1 | Isomer 2 | 6.9 |
| Example 10-2 | Mixture diastereomers | 7.9 |

The invention claimed is:

1. A compound of Formula (1 a):

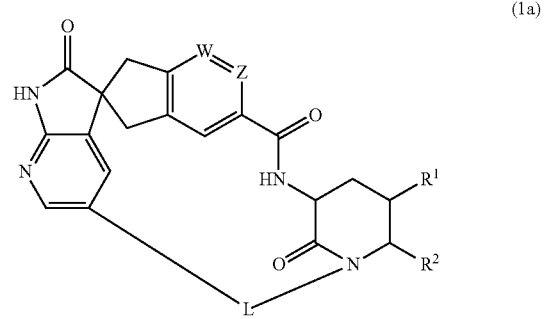

(1a)

or a salt thereof, wherein;

W is CH or N;

Z is CH or N;

$R^1$ is an aryl or heteroaryl group optionally substituted with one or more halo groups or $C_{1-3}$ alkyl groups which are themselves optionally substituted with one or more F atoms;

$R^2$ is H or $C_{1-3}$ alkyl optionally substituted with one or more F atoms;

and L is a $C_{4-15}$ linker group optionally substituted with one or more F atoms, wherein one, two or three, but not all, of the carbon atoms of the linker group may be optionally replaced by a heteroatom selected from O and N.

2. The compound according to claim 1, which is a compound of Formula (2a):

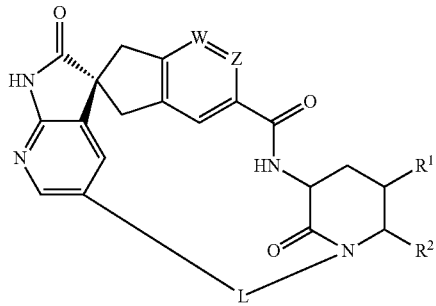

or a salt thereof.

3. The compound according to claim 1, which is a compound of Formula (3a):

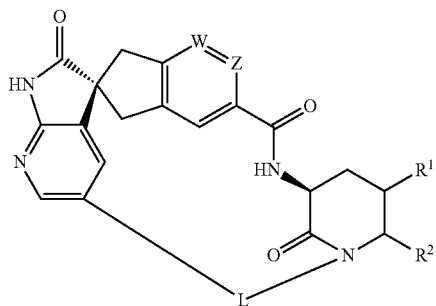

or a salt thereof.

4. The compound according to claim 1, which is a compound of Formula (4a):

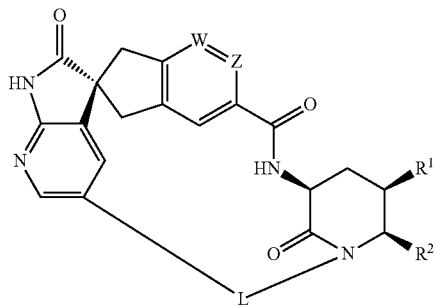

or a salt thereof.

5. The compound according to claim 1, or a salt thereof, wherein W is N and Z is CH.

6. The compound according to claim 1, or a salt thereof, wherein W is CH and Z is N.

7. The compound according to claim 1, or a salt thereof, wherein W and Z are both CH.

8. The compound according to claim 1, or a salt thereof, wherein $R^1$ is a phenyl ring optionally substituted with one or more F atoms or $C_{1-3}$ B alkyl groups which are themselves optionally substituted with one or more F atoms.

9. The compound according to claim 1, or a salt thereof, wherein $R^1$ is a phenyl ring optionally substituted with 1-5 F atoms.

10. The compound according to claim 1, or a salt thereof, wherein $R^2$ is H or methyl.

11. The compound according to claim 1, or a salt thereof, wherein $R^2$ is methyl.

12. The compound according to claim 1, or a salt thereof, wherein L is a linker group of the formula:

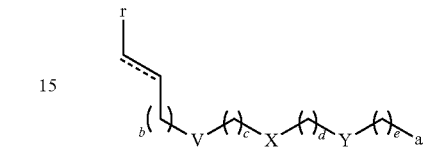

wherein "r" indicates the point of attachment to the pyridine ring and "a" indicates the point of attachment to N; V, X and Y are independently selected from a bond, O, $CH_2$, NH and NMe; b, c, d and e are independently 1, 2 or 3 and the dotted line indicates that a single or double bond may be present.

13. The compound according to claim 1, or a salt thereof, wherein L is selected from the group consisting of:
—CHCHCH$_2$OCH$_2$CH$_2$OCH$_2$CH$_2$—;
—CHCHCH$_2$OCH$_2$CH$_2$OCH$_2$CH$_2$OCH$_2$CH$_2$—;
—CH$_2$CH$_2$CH$_2$OCH$_2$CH$_2$OCH$_2$CH$_2$—;
—CH$_2$CH$_2$CH$_2$OCH$_2$CH$_2$OCH$_2$CH$_2$OCH$_2$CH$_2$—;
—CHCHCH$_2$OCH$_2$CH$_2$CH$_2$CH$_2$CH$_2$—;
—CHCHCH$_2$OCH$_2$CH$_2$N(CH$_3$)CH$_2$CH$_2$—;
—CHCHCH$_2$OCH$_2$CH$_2$NHCH$_2$CH$_2$—;
—CHCHCH$_2$CH$_2$CH$_2$CH$_2$N(CH$_3$)CH$_2$CH$_2$—;
—CHCHCH$_2$N(CH$_3$)CH$_2$CH$_2$CH$_2$CH$_2$CH$_2$—;
—CH$_2$CH$_2$CH$_2$N(CH$_3$)CH$_2$CH$_2$CH$_2$CH$_2$CH$_2$—;
—CHCHCH$_2$CH$_2$CH$_2$CH$_2$NHCH$_2$CH$_2$—;
—CHCHCH$_2$N(CH$_3$)CH$_2$CH$_2$N(CH$_3$)CH$_2$CH$_2$—;
—CHCHCH$_2$OCH$_2$CH$_2$OCH$_2$CH$_2$CH$_2$—;
—CHCHCH$_2$OCH$_2$CH$_2$CH$_2$OCH$_2$CH$_2$—;
—CHCHCH$_2$CH$_2$OCH$_2$CH$_2$OCH$_2$CH$_2$—;
—CHCHCH$_2$CH$_2$OCH$_2$CH$_2$CH$_2$CH$_2$—;
—CHCHCH$_2$CH$_2$CH$_2$OCH$_2$CH$_2$CH$_2$—
and
—CHCHCH$_2$OCH$_2$CH$_2$CH$_2$CF$_2$CH$_2$—.

14. The compound according to claim 1 which is selected from the group consisting of:

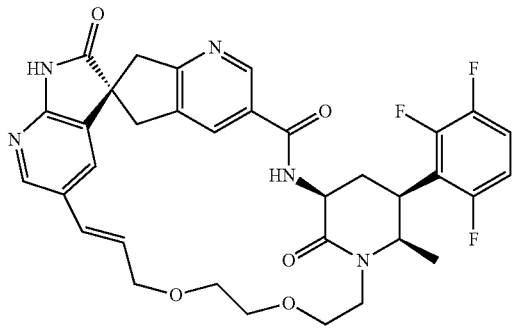

| 155 | 156 |
|---|---|
| 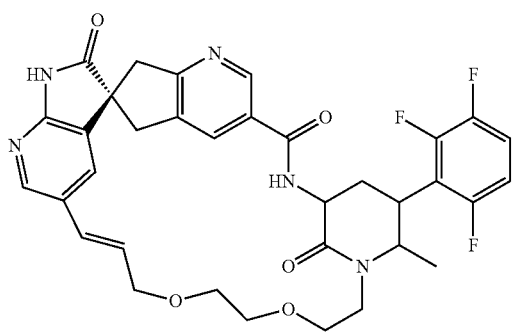 | 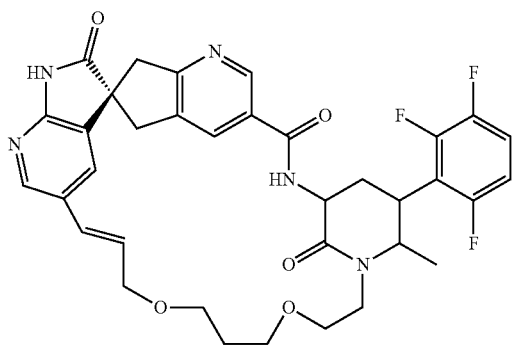 |
| 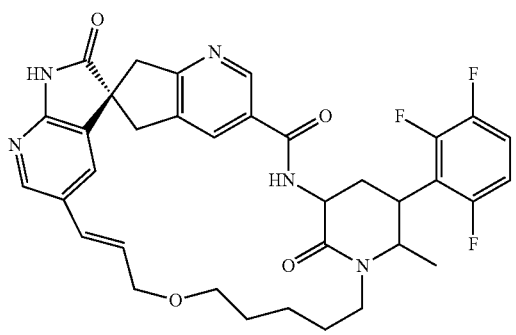 | 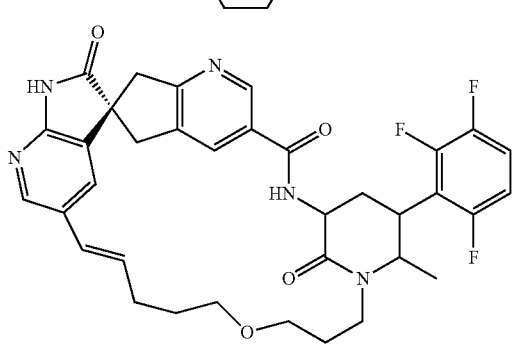 |
| 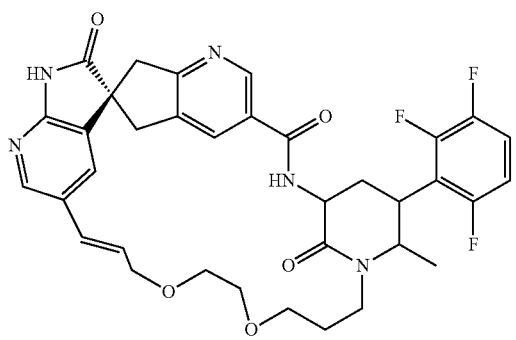 | 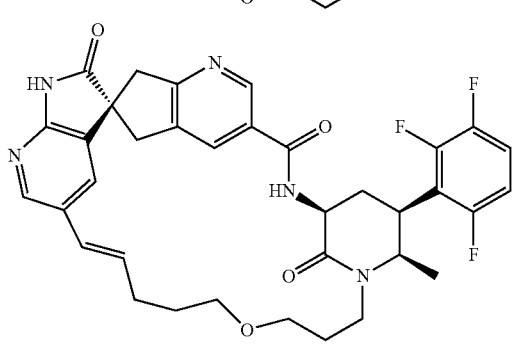 |
| 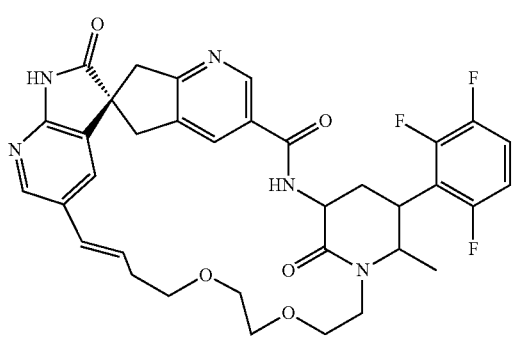 | 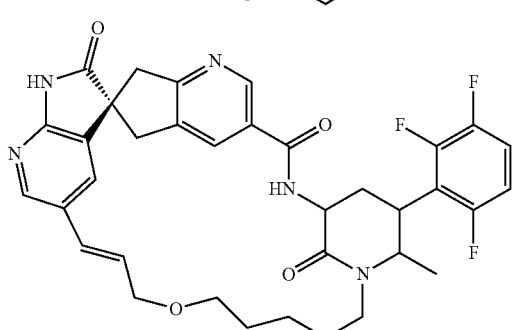 |
| 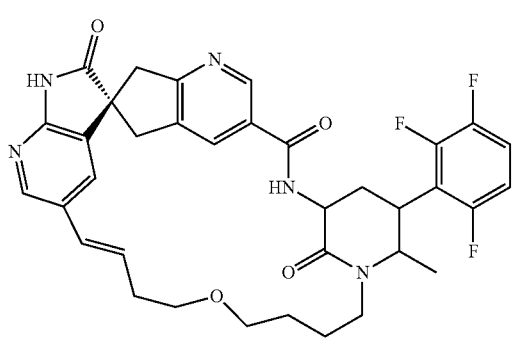 [SMILES: CC1C(c2c(F)ccc(F)c2F)CC2NC(=O)c3cnc4c(c3)C[C@@]3(C4)C(=O)Nc4ncc(cc43)/C=C/CCOCCCCN1C2=O] | 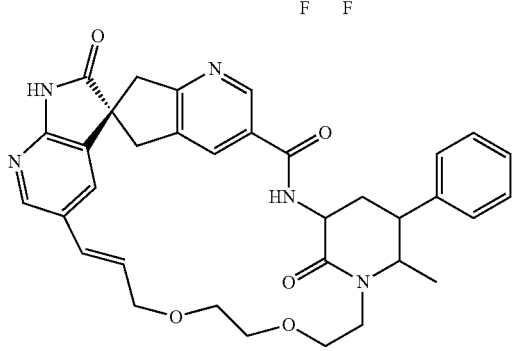 |

157
-continued
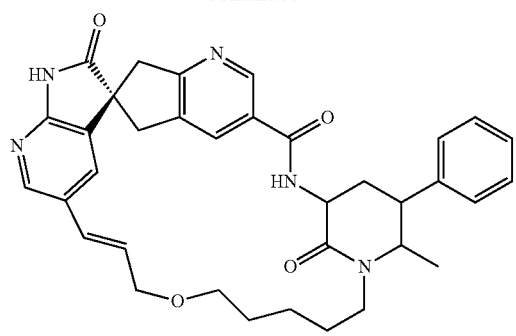
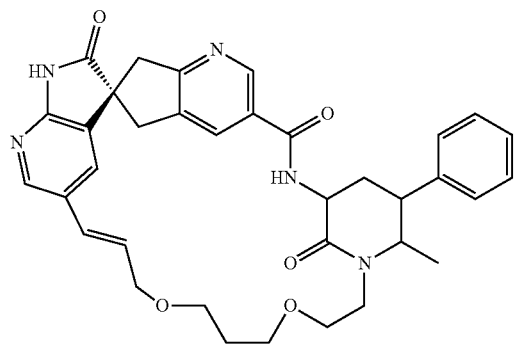
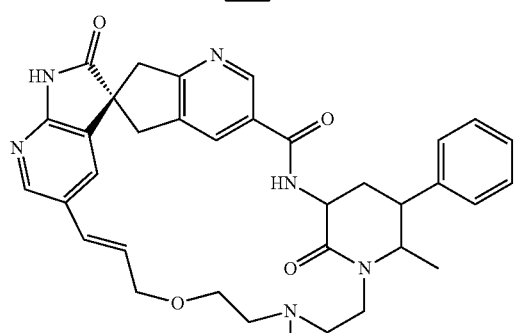
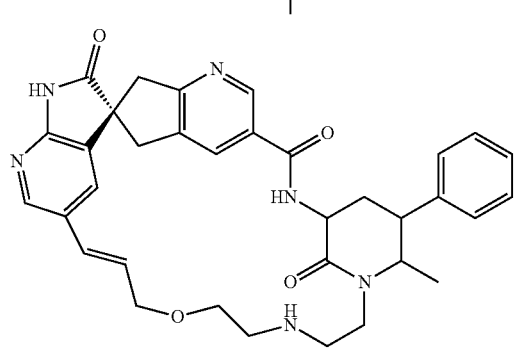
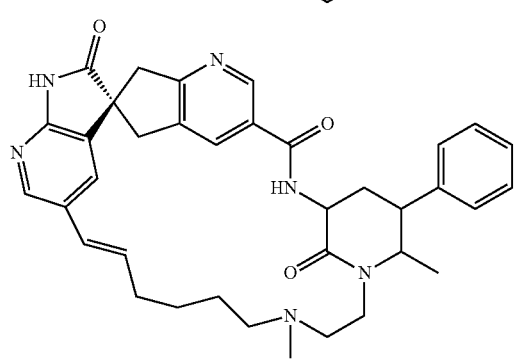
158
-continued
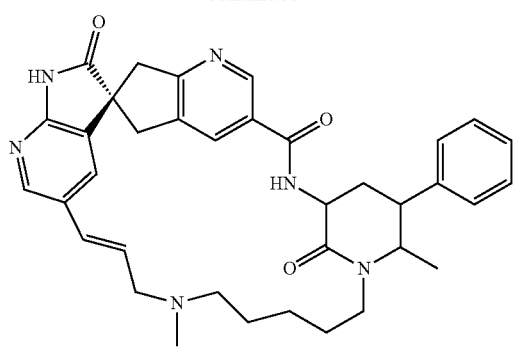
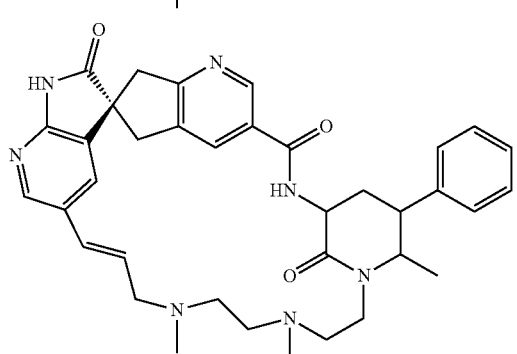
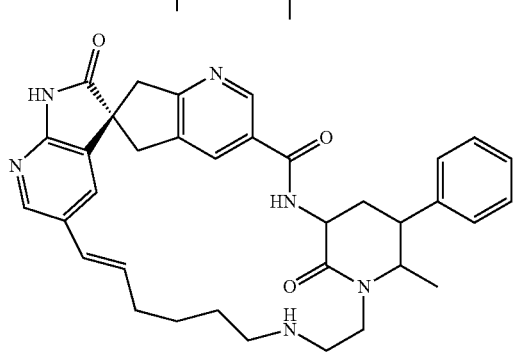
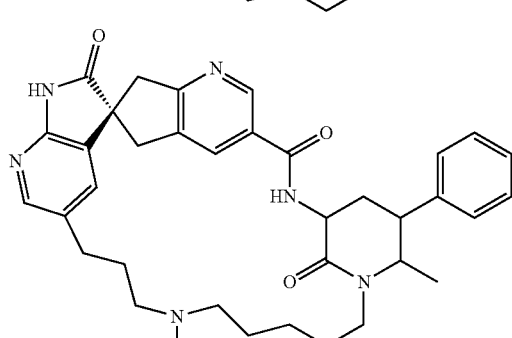
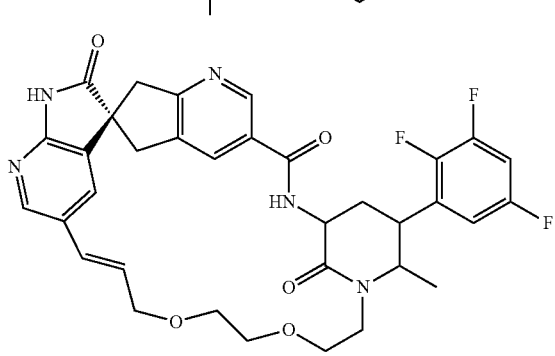

159
-continued
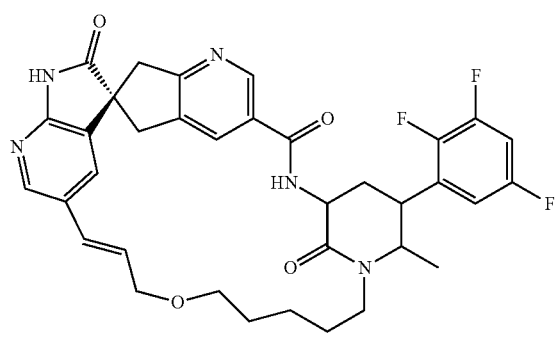
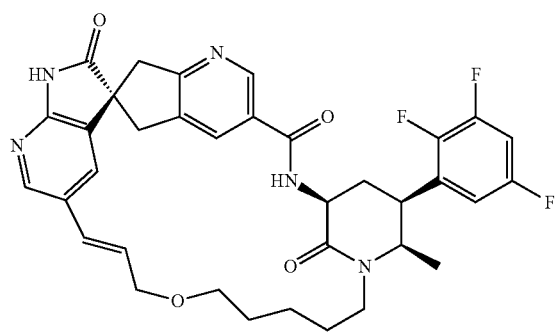
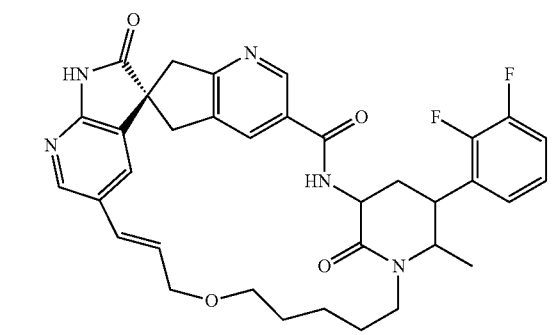
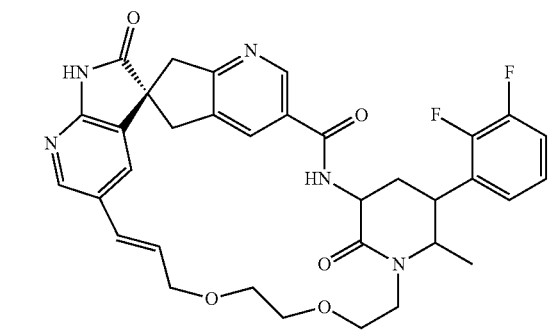
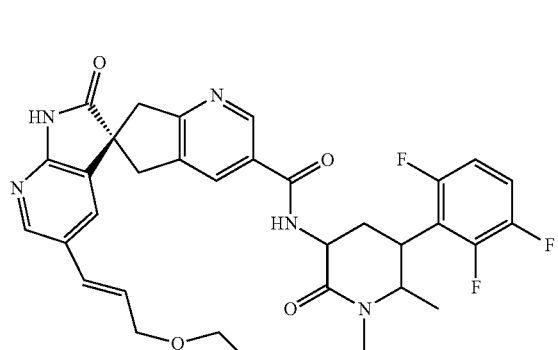
160
-continued
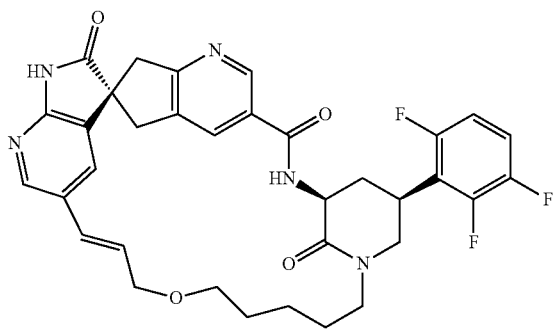
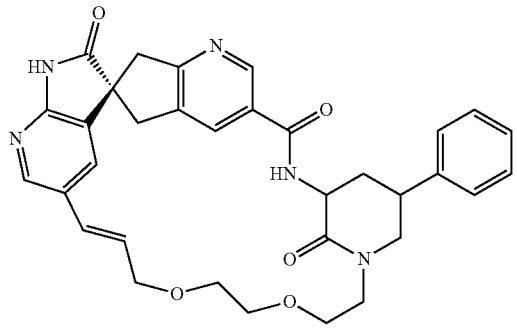
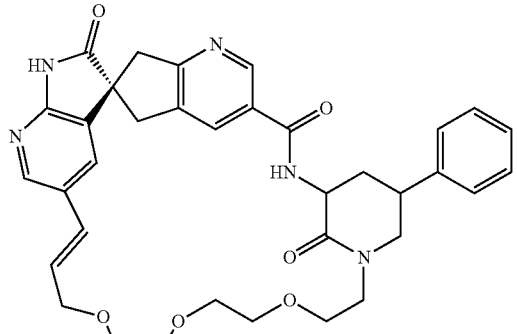
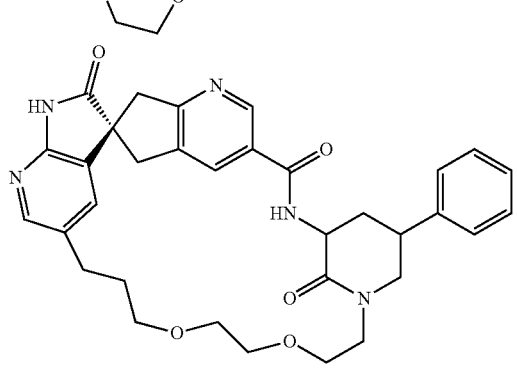
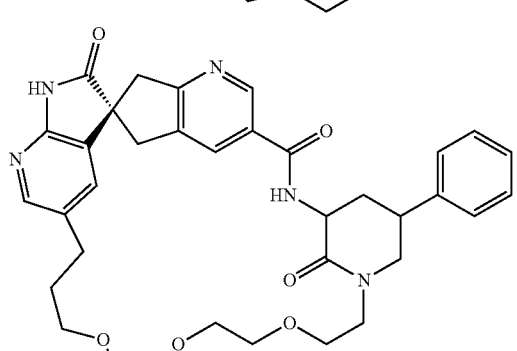

161
-continued

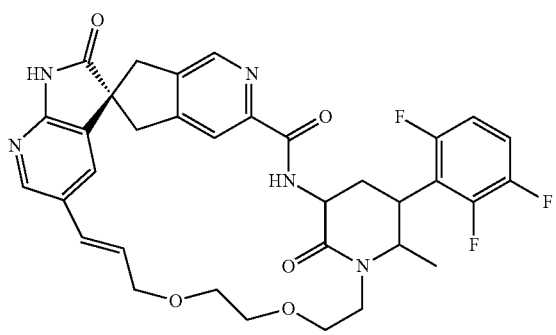

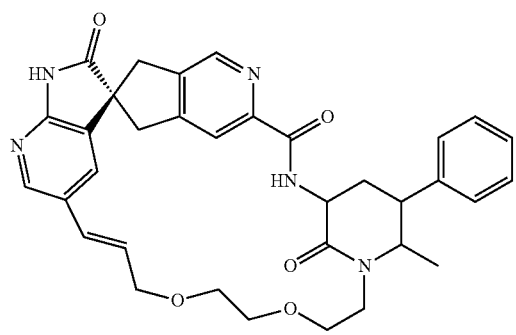

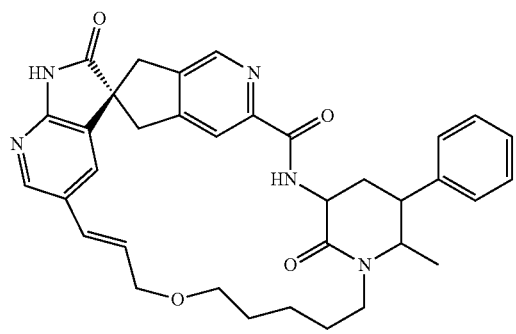

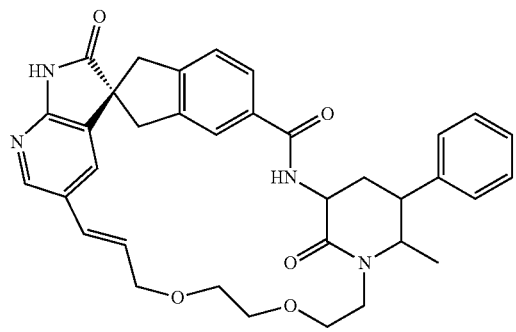

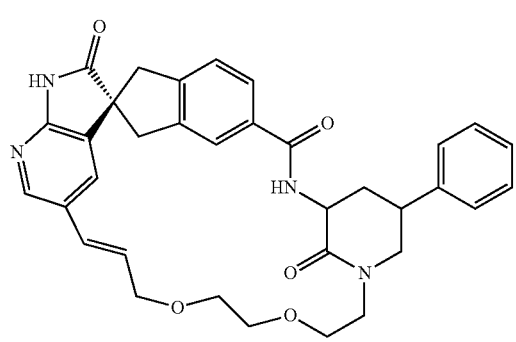

162
-continued

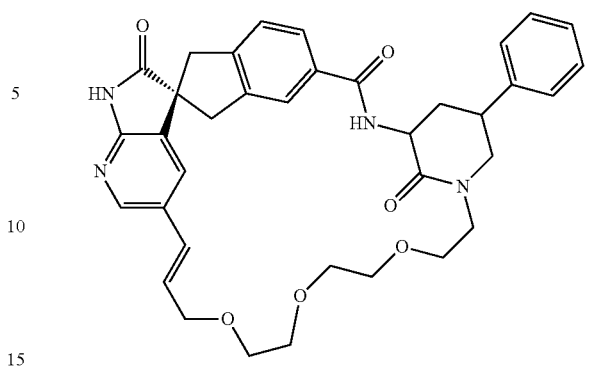

and salts thereof.

15. The compound according to claim 1, or a salt thereof, having CGRP receptor antagonist activity.

16. A pharmaceutical composition comprising a compound as defined in claim 1, or a salt thereof, and a pharmaceutically acceptable excipient.

17. The compound according to claim 14, wherein the compound is

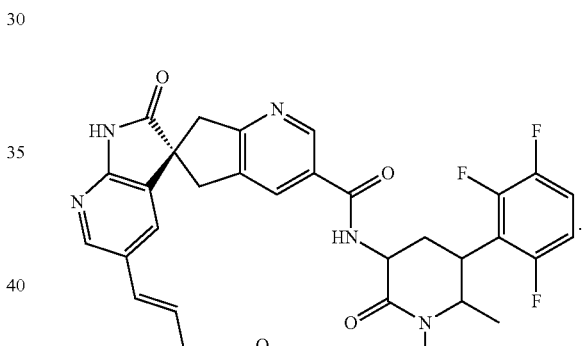

18. The compound according to claim 14, wherein the compound is a salt of

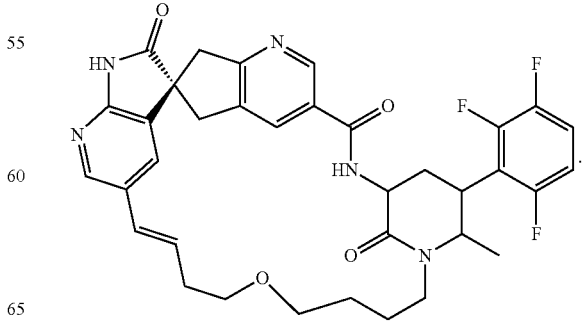

19. The compound according to claim 14, wherein the compound is

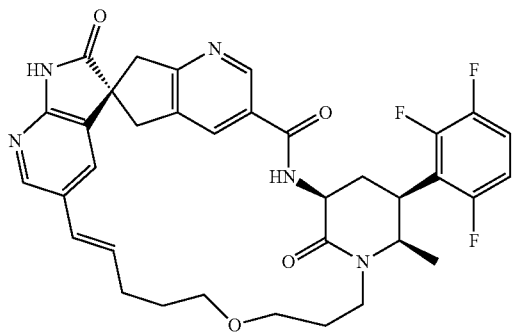

20. The compound according to claim 14, wherein the compound is a salt of

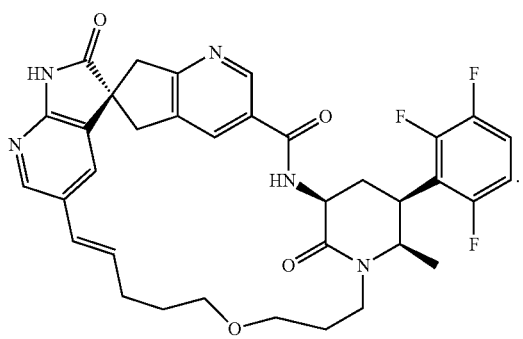 [SMILES: C[C@@H]1[C@H](c2c(F)ccc(F)c2F)C[C@@H]2NC(=O)c3cnc4c(c3)C[C@@]3(C4)C(=O)Nc4ncc(cc43)/C=C/CCCOCCCN1C2=O]

21. The compound according to claim 14, wherein the compound is

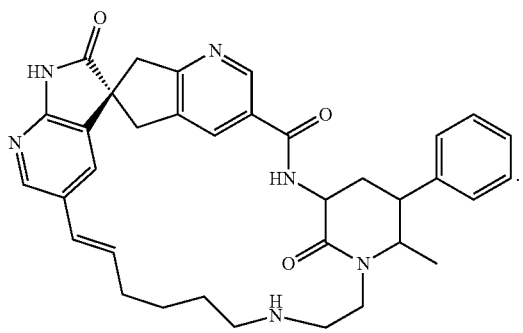 [SMILES: CC1C(c2ccccc2)CC2NC(=O)c3cnc4c(c3)C[C@@]3(C4)C(=O)Nc4ncc(cc43)/C=C/CCCCNCCN1C2=O]

22. The compound according to claim 14, wherein the compound is a salt of

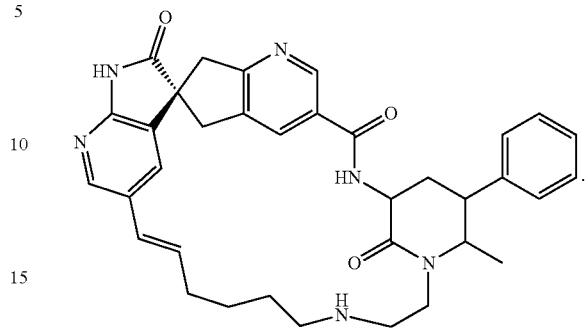

23. The compound according to claim 14, wherein the compound is

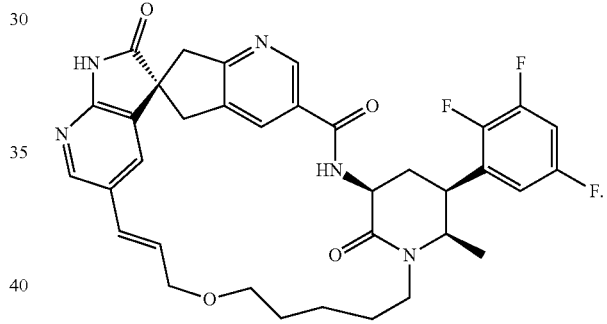

24. The compound according to claim 14, wherein the compound is a salt of

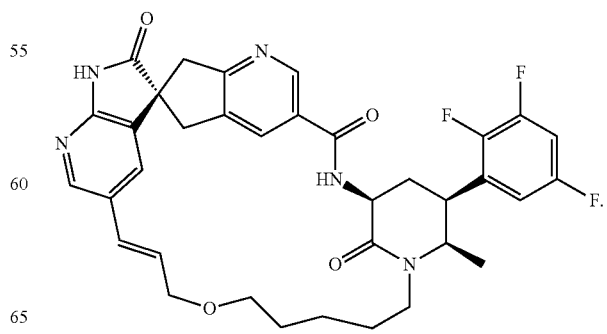

25. The compound according to claim 14, wherein the compound is

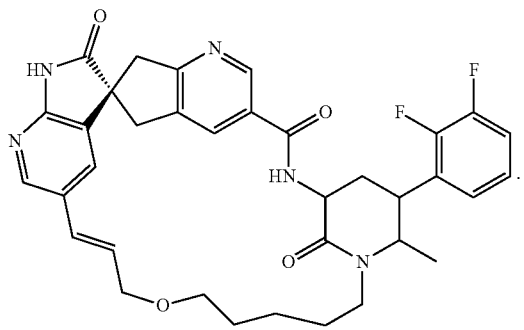 [SMILES: CC1C(c2cccc(F)c2F)CC2NC(=O)c3cnc4c(c3)C[C@@]3(C4)C(=O)Nc4ncc(cc43)/C=C/COCCCCCN1C2=O]

26. The compound according to claim 14, wherein the compound is a salt of

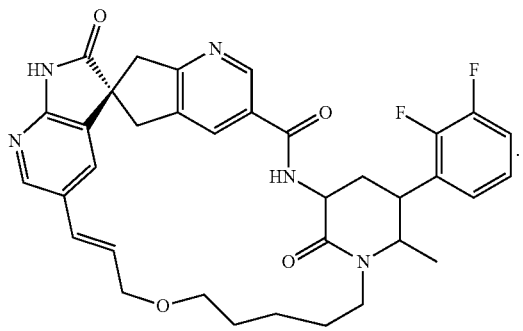 [SMILES: CC1C(c2cccc(F)c2F)CC2NC(=O)c3cnc4c(c3)C[C@@]3(C4)C(=O)Nc4ncc(cc43)/C=C/COCCCCCN1C2=O]

27. The compound according to claim 14, wherein the compound is

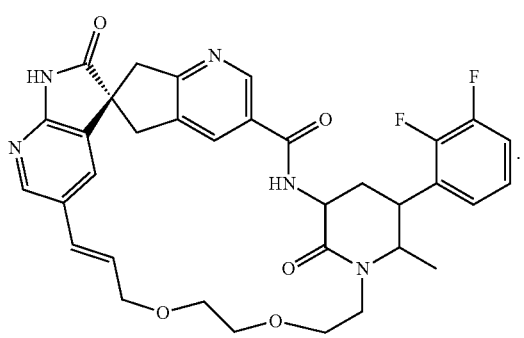 [SMILES: CC1C(c2cccc(F)c2F)CC2NC(=O)c3cnc4c(c3)C[C@@]3(C4)C(=O)Nc4ncc(cc43)/C=C/COCCOCCN1C2=O]

28. The compound according to claim 14, wherein the compound is a salt of

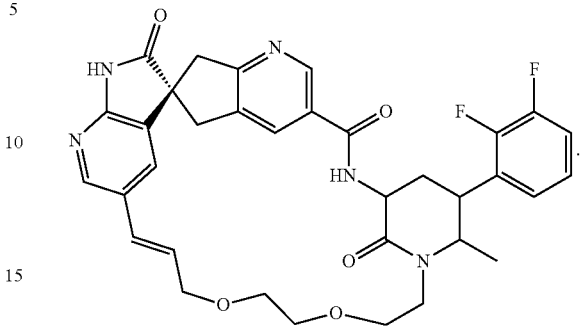

29. The compound according to claim 14, wherein the compound is

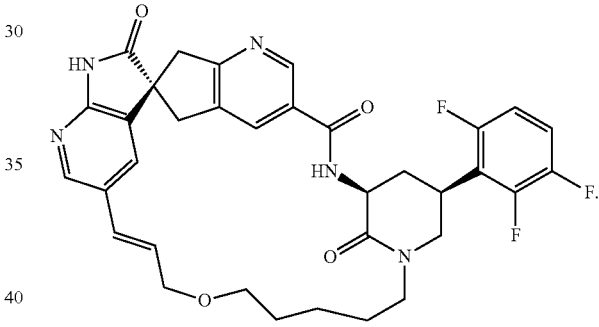

30. The compound according to claim 14, wherein the compound is a salt of

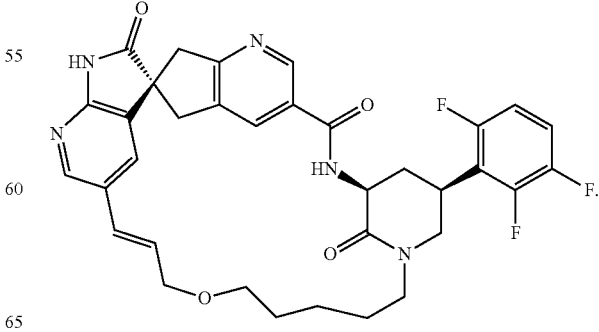

31. A pharmaceutical composition comprising a compound selected rom the group consisting of
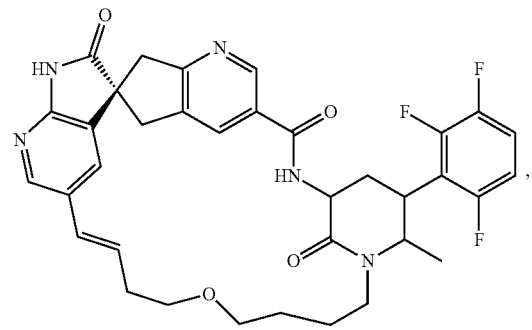
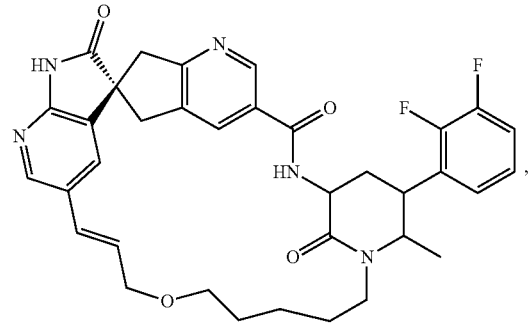
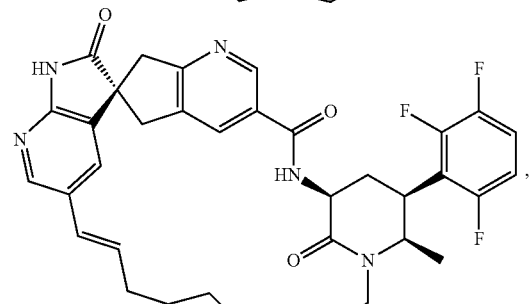
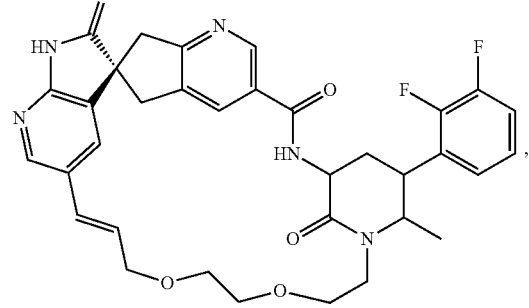
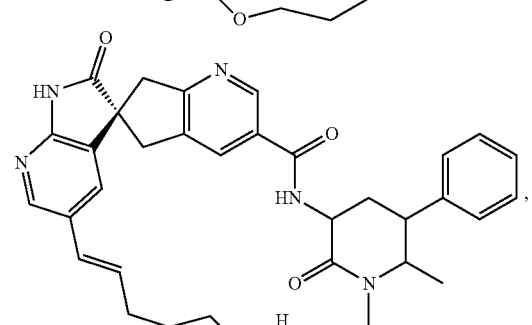
and
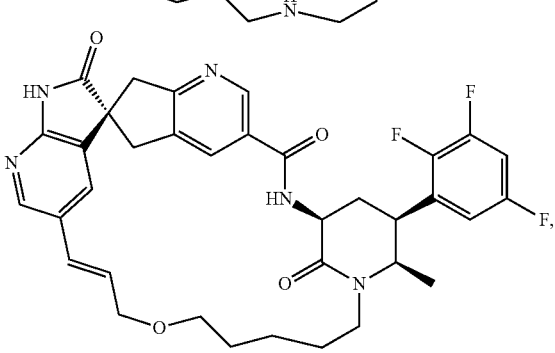
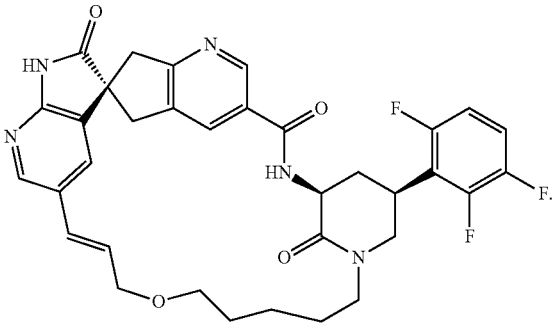 [SMILES: O=C1N[C@H]2C[C@@H](c3c(F)ccc(F)c3F)CN(CCCCCOC/C=C/c3cnc4c(c3)[C@@]3(Cc5cc1cnc5C3)C(=O)N4)C2=O]
* * * * *